US009734589B2

(12) United States Patent
Yu et al.

(10) Patent No.: US 9,734,589 B2
(45) Date of Patent: Aug. 15, 2017

(54) SYSTEMS, DEVICES, AND METHODS FOR TRACKING AND COMPENSATING FOR PATIENT MOTION DURING A MEDICAL IMAGING SCAN

(71) Applicant: Kineticor, Inc., Honolulu, HI (US)

(72) Inventors: Jeffrey N. Yu, Honolulu, HI (US); William Herman Alameida, Jr., Honolulu, HI (US); John Arthur Lovberg, San Diego, CA (US); Xiaojiang Jason Pan, San Diego, CA (US); Michael Engelmann, Pukalani, HI (US)

(73) Assignee: KinetiCor, Inc., Honolulu, HI (US)

( * ) Notice: Subject to any disclaimer, the term of this patent is extended or adjusted under 35 U.S.C. 154(b) by 71 days.

(21) Appl. No.: 14/806,521

(22) Filed: Jul. 22, 2015

(65) Prior Publication Data
US 2016/0035108 A1 Feb. 4, 2016

Related U.S. Application Data

(60) Provisional application No. 62/028,194, filed on Jul. 23, 2014.

(51) Int. Cl.
G06T 7/20 (2017.01)
A61B 5/00 (2006.01)
(Continued)

(52) U.S. Cl.
CPC .......... *G06T 7/2093* (2013.01); *A61B 5/0077* (2013.01); *A61B 5/055* (2013.01);
(Continued)

(58) Field of Classification Search
CPC ................... G06T 7/2093; G06T 7/204; G06T 2207/30204; G06T 7/292; G06T 7/248;
(Continued)

(56) References Cited

U.S. PATENT DOCUMENTS 3,811,213 A 5/1974 Eaves
4,689,999 A 9/1987 Shkedi
(Continued)

FOREIGN PATENT DOCUMENTS

CN 105392423 3/2016
DE 29519078 3/1996
(Continued)

OTHER PUBLICATIONS

Aksoy et al., "Hybrind Prospective and Retrospective Head Motion Correction to Mitigate Cross-Calibration Errors", NIH Publication, Nov. 2012.
(Continued)

*Primary Examiner* — Jon Chang
(74) *Attorney, Agent, or Firm* — Knobbe Martens Olson & Bear, LLP

(57) ABSTRACT

A motion tracking system for dynamic tracking of and compensation for motion of a patient during a magnetic resonance scan comprises a first camera positioned to view an optical marker along a first line of sight; a second camera positioned to view the optical marker along a second line of sight; and a computer system configured to analyze images generated by the first and second cameras to determine changes in position of the optical marker, and to generate tracking data for use by a magnetic resonance scanner to dynamically adjust scans to compensate for the changes in position of the optical marker, wherein the computer system is configured to dynamically adapt its image analysis to utilize images from all cameras that are currently viewing the optical marker.

15 Claims, 75 Drawing Sheets

(51) Int. Cl.
    *A61B 5/11*           (2006.01)
    *G06K 9/62*          (2006.01)
    *G06T 5/00*          (2006.01)
    *A61B 5/055*         (2006.01)
    *A61N 5/10*          (2006.01)
    *G06K 9/00*          (2006.01)
    *G06T 7/246*         (2017.01)
    *G06T 7/292*         (2017.01)
    *A61B 90/00*        (2016.01)

(52) U.S. Cl.
    CPC ............ *A61B 5/1127* (2013.01); *A61B 5/721* (2013.01); *A61N 5/1049* (2013.01); *G06K 9/00335* (2013.01); *G06T 7/248* (2017.01); *G06T 7/292* (2017.01); *A61B 2090/3937* (2016.02); *G06T 2207/30204* (2013.01)

(58) Field of Classification Search
    CPC ..... A61B 5/0077; A61B 5/055; A61B 5/1127; A61B 5/721; A61B 2090/3937; A61N 5/1049; G06K 9/00335
    USPC ........................................................ 382/131
    See application file for complete search history.

(56) References Cited

U.S. PATENT DOCUMENTS

| | | |
|---|---|---|
| 4,724,386 A | 2/1988 | Haacke et al. |
| 4,894,129 A | 1/1990 | Leiponen et al. |
| 4,923,295 A | 5/1990 | Sireul et al. |
| 4,953,554 A | 9/1990 | Zerhouni et al. |
| 4,988,886 A | 1/1991 | Palum et al. |
| 5,075,562 A | 12/1991 | Greivenkamp et al. |
| 5,318,026 A | 6/1994 | Pelc |
| 5,515,711 A | 5/1996 | Hinkle |
| 5,545,993 A | 8/1996 | Taguchi et al. |
| 5,615,677 A | 4/1997 | Pelc et al. |
| 5,687,725 A | 11/1997 | Wendt |
| 5,728,935 A | 3/1998 | Czompo |
| 5,802,202 A | 9/1998 | Yamada et al. |
| 5,835,223 A | 11/1998 | Zawemer et al. |
| 5,886,257 A | 3/1999 | Gustafson et al. |
| 5,889,505 A | 3/1999 | Toyama |
| 5,936,722 A | 8/1999 | Armstrong et al. |
| 5,936,723 A | 8/1999 | Schmidt et al. |
| 5,947,900 A | 9/1999 | Derbyshire et al. |
| 5,987,349 A | 11/1999 | Schulz |
| 6,031,888 A | 2/2000 | Ivan et al. |
| 6,044,308 A | 3/2000 | Huissoon |
| 6,057,680 A | 5/2000 | Foo et al. |
| 6,061,644 A | 5/2000 | Leis |
| 6,088,482 A | 7/2000 | He |
| 6,144,875 A | 11/2000 | Schweikard et al. |
| 6,236,737 B1 | 5/2001 | Gregson et al. |
| 6,246,900 B1 | 6/2001 | Cosman et al. |
| 6,279,579 B1 | 8/2001 | Riaziat et al. |
| 6,285,902 B1 | 9/2001 | Kienzle, III et al. |
| 6,289,235 B1 | 9/2001 | Webber |
| 6,292,683 B1 | 9/2001 | Gupta et al. |
| 6,298,262 B1 | 10/2001 | Franck et al. |
| 6,381,485 B1 | 4/2002 | Hunter et al. |
| 6,384,908 B1 | 5/2002 | Schmidt et al. |
| 6,390,982 B1 | 5/2002 | Bova et al. |
| 6,402,762 B2 | 6/2002 | Hunter et al. |
| 6,405,072 B1 | 6/2002 | Cosman |
| 6,421,551 B1 | 7/2002 | Kuth et al. |
| 6,467,905 B1 | 10/2002 | Stahl et al. |
| 6,474,159 B1 | 11/2002 | Foxlin et al. |
| 6,484,131 B1 | 11/2002 | Amorai-Moriya et al. |
| 6,490,475 B1 | 12/2002 | Seeley et al. |
| 6,501,981 B1 | 12/2002 | Schweikard et al. |
| 6,587,707 B2 | 7/2003 | Nehrke et al. |
| 6,621,889 B1 | 9/2003 | Mostafavi |
| 6,650,920 B2 | 11/2003 | Schaldach et al. |
| 6,662,036 B2 | 12/2003 | Cosman |
| 6,687,528 B2 | 2/2004 | Gupta et al. |
| 6,690,965 B1 | 2/2004 | Riaziat et al. |
| 6,711,431 B2 | 3/2004 | Sarin et al. |
| 6,731,970 B2 | 5/2004 | Schlossbauer et al. |
| 6,758,218 B2 | 7/2004 | Anthony |
| 6,771,997 B2 | 8/2004 | Schaffer |
| 6,794,869 B2 | 9/2004 | Brittain |
| 6,856,827 B2 | 2/2005 | Seeley et al. |
| 6,856,828 B2 | 2/2005 | Cossette et al. |
| 6,876,198 B2 | 4/2005 | Watanabe et al. |
| 6,888,924 B2 | 5/2005 | Claus et al. |
| 6,891,374 B2 | 5/2005 | Brittain |
| 6,892,089 B1 | 5/2005 | Prince et al. |
| 6,897,655 B2 | 5/2005 | Brittain et al. |
| 6,913,603 B2 | 7/2005 | Knopp et al. |
| 6,937,696 B1 | 8/2005 | Mostafavi |
| 6,959,266 B1 | 10/2005 | Mostafavi |
| 6,973,202 B2 | 12/2005 | Mostafavi |
| 6,980,679 B2 | 12/2005 | Jeung et al. |
| 7,007,699 B2 | 3/2006 | Martinelli et al. |
| 7,107,091 B2 | 9/2006 | Jutras et al. |
| 7,110,805 B2 | 9/2006 | Machida |
| 7,123,758 B2 | 10/2006 | Jeung et al. |
| 7,171,257 B2 | 1/2007 | Thomson |
| 7,176,440 B2 | 2/2007 | Cofer et al. |
| 7,191,100 B2 | 3/2007 | Mostafavi |
| 7,204,254 B2 | 4/2007 | Riaziat et al. |
| 7,209,777 B2 | 4/2007 | Saranathan et al. |
| 7,209,977 B2 | 4/2007 | Acharya et al. |
| 7,260,253 B2 | 8/2007 | Rahn et al. |
| 7,260,426 B2 | 8/2007 | Schweikard et al. |
| 7,295,007 B2 | 11/2007 | Dold |
| 7,313,430 B2 | 12/2007 | Urquhart et al. |
| 7,327,865 B2 | 2/2008 | Fu et al. |
| 7,348,776 B1 | 3/2008 | Aksoy et al. |
| 7,403,638 B2 | 7/2008 | Jeung et al. |
| 7,494,277 B2 | 2/2009 | Setala |
| 7,498,811 B2 | 3/2009 | Macfarlane et al. |
| 7,505,805 B2 | 3/2009 | Kuroda |
| 7,535,411 B2 | 5/2009 | Falco |
| 7,551,089 B2 | 6/2009 | Sawyer |
| 7,561,909 B1 | 7/2009 | Pai et al. |
| 7,567,697 B2 | 7/2009 | Mostafavi |
| 7,573,269 B2 | 8/2009 | Yao |
| 7,602,301 B1 | 10/2009 | Stirling et al. |
| 7,603,155 B2 | 10/2009 | Jensen |
| 7,623,623 B2 | 11/2009 | Raanes et al. |
| 7,657,300 B2 | 2/2010 | Hunter et al. |
| 7,657,301 B2 | 2/2010 | Mate et al. |
| 7,659,521 B2 | 2/2010 | Pedroni |
| 7,660,623 B2 | 2/2010 | Hunter et al. |
| 7,668,288 B2 | 2/2010 | Conwell et al. |
| 7,689,263 B1 | 3/2010 | Fung et al. |
| 7,702,380 B1 | 4/2010 | Dean |
| 7,715,604 B2 | 5/2010 | Sun et al. |
| 7,742,077 B2 | 6/2010 | Sablak et al. |
| 7,742,621 B2 | 6/2010 | Hammoud et al. |
| 7,742,804 B2 | 6/2010 | Faul et al. |
| 7,744,528 B2 | 6/2010 | Wallace et al. |
| 7,760,908 B2 | 7/2010 | Curtner et al. |
| 7,766,837 B2 | 8/2010 | Pedrizzetti et al. |
| 7,769,430 B2 | 8/2010 | Mostafavi |
| 7,772,569 B2 | 8/2010 | Bewersdorf et al. |
| 7,787,011 B2 | 8/2010 | Zhou et al. |
| 7,787,935 B2 | 8/2010 | Dumoulin et al. |
| 7,791,808 B2 | 9/2010 | French et al. |
| 7,792,249 B2 | 9/2010 | Gertner et al. |
| 7,796,154 B2 | 9/2010 | Senior et al. |
| 7,798,730 B2 | 9/2010 | Westerweck |
| 7,801,330 B2 | 9/2010 | Zhang et al. |
| 7,805,987 B1 | 10/2010 | Smith |
| 7,806,604 B2 | 10/2010 | Bazakos et al. |
| 7,817,046 B2 | 10/2010 | Coveley et al. |
| 7,817,824 B2 | 10/2010 | Liang et al. |
| 7,819,818 B2 | 10/2010 | Ghajar |
| 7,833,221 B2 | 11/2010 | Voegele |
| 7,834,846 B1 | 11/2010 | Bell |
| 7,835,783 B1 | 11/2010 | Aletras |

(56) References Cited

U.S. PATENT DOCUMENTS

| | | |
|---|---|---|
| 7,839,551 B2 | 11/2010 | Lee et al. |
| 7,840,253 B2 | 11/2010 | Tremblay et al. |
| 7,844,094 B2 | 11/2010 | Jeung et al. |
| 7,844,320 B2 | 11/2010 | Shahidi |
| 7,850,526 B2 | 12/2010 | Zalewski et al. |
| 7,860,301 B2 | 12/2010 | Se et al. |
| 7,866,818 B2 | 1/2011 | Schroeder et al. |
| 7,868,282 B2 | 1/2011 | Lee et al. |
| 7,878,652 B2 | 2/2011 | Chen et al. |
| 7,883,415 B2 | 2/2011 | Larsen et al. |
| 7,889,907 B2 | 2/2011 | Engelbart et al. |
| 7,894,877 B2 | 2/2011 | Lewin et al. |
| 7,902,825 B2 | 3/2011 | Bammer et al. |
| 7,907,987 B2 | 3/2011 | Dempsey |
| 7,908,060 B2 | 3/2011 | Basson et al. |
| 7,908,233 B2 | 3/2011 | Angell et al. |
| 7,911,207 B2 | 3/2011 | Macfarlane et al. |
| 7,912,532 B2 | 3/2011 | Schmidt et al. |
| 7,920,250 B2 | 4/2011 | Robert et al. |
| 7,920,911 B2 | 4/2011 | Hoshino et al. |
| 7,925,066 B2 | 4/2011 | Ruohonen et al. |
| 7,925,549 B2 | 4/2011 | Looney et al. |
| 7,931,370 B2 | 4/2011 | Bartomen |
| 7,944,354 B2 | 5/2011 | Kangas et al. |
| 7,944,454 B2 | 5/2011 | Zhou et al. |
| 7,945,304 B2 | 5/2011 | Feinberg |
| 7,946,921 B2 | 5/2011 | Ofek et al. |
| 7,962,197 B2 | 6/2011 | Rioux et al. |
| 7,971,999 B2 | 7/2011 | Zinser |
| 7,977,942 B2 | 7/2011 | White |
| 7,978,925 B1 | 7/2011 | Souchard |
| 7,988,288 B2 | 8/2011 | Donaldson |
| 7,990,365 B2 | 8/2011 | Marvit et al. |
| 8,005,571 B2 | 8/2011 | Sutherland et al. |
| 8,009,198 B2 | 8/2011 | Alhadef |
| 8,019,170 B2 | 9/2011 | Wang et al. |
| 8,021,231 B2 | 9/2011 | Walker et al. |
| 8,022,982 B2 | 9/2011 | Thorn |
| 8,024,026 B2 | 9/2011 | Groszmann |
| 8,031,909 B2 | 10/2011 | Se et al. |
| 8,031,933 B2 | 10/2011 | Se et al. |
| 8,036,425 B2 | 10/2011 | Hou |
| 8,041,077 B2 | 10/2011 | Bell |
| 8,041,412 B2 | 10/2011 | Glossop et al. |
| 8,048,002 B2 | 11/2011 | Ghajar |
| 8,049,867 B2 | 11/2011 | Bridges et al. |
| 8,055,020 B2 | 11/2011 | Meuter et al. |
| 8,055,049 B2 | 11/2011 | Stayman et al. |
| 8,060,185 B2 | 11/2011 | Hunter et al. |
| 8,063,929 B2 | 11/2011 | Kurtz et al. |
| 8,073,197 B2 | 12/2011 | Xu et al. |
| 8,077,914 B1 | 12/2011 | Kaplan |
| 8,085,302 B2 | 12/2011 | Zhang et al. |
| 8,086,026 B2 | 12/2011 | Schulz |
| 8,086,299 B2 | 12/2011 | Adler et al. |
| RE43,147 E | 1/2012 | Aviv |
| 8,094,193 B2 | 1/2012 | Peterson |
| 8,095,203 B2 | 1/2012 | Wright et al. |
| 8,095,209 B2 | 1/2012 | Flaherty |
| 8,098,889 B2 | 1/2012 | Zhu et al. |
| 8,113,991 B2 | 2/2012 | Kutliroff |
| 8,116,527 B2 | 2/2012 | Sabol |
| 8,121,356 B2 | 2/2012 | Friedman |
| 8,121,361 B2 | 2/2012 | Ernst et al. |
| 8,134,597 B2 | 3/2012 | Thorn |
| 8,135,201 B2 | 3/2012 | Smith et al. |
| 8,139,029 B2 | 3/2012 | Boillot |
| 8,139,896 B1 | 3/2012 | Ahiska |
| 8,144,118 B2 | 3/2012 | Hildreth |
| 8,144,148 B2 | 3/2012 | El Dokor |
| 8,150,063 B2 | 4/2012 | Chen |
| 8,150,498 B2 | 4/2012 | Gielen et al. |
| 8,160,304 B2 | 4/2012 | Rhoads |
| 8,165,844 B2 | 4/2012 | Luinge et al. |
| 8,167,802 B2 | 5/2012 | Baba et al. |
| 8,172,573 B2 | 5/2012 | Sonenfeld et al. |
| 8,175,332 B2 | 5/2012 | Herrington |
| 8,179,604 B1 | 5/2012 | Prada Gomez |
| 8,180,428 B2 | 5/2012 | Kaiser et al. |
| 8,180,432 B2 | 5/2012 | Sayeh |
| 8,187,097 B1 | 5/2012 | Zhang |
| 8,189,869 B2 | 5/2012 | Bell |
| 8,189,889 B2 | 5/2012 | Pearlstein et al. |
| 8,189,926 B2 | 5/2012 | Sharma |
| 8,190,233 B2 | 5/2012 | Dempsey |
| 8,191,359 B2 | 6/2012 | White et al. |
| 8,194,134 B2 | 6/2012 | Furukawa |
| 8,195,084 B2 | 6/2012 | Xiao |
| 8,199,983 B2 | 6/2012 | Qureshi |
| 8,206,219 B2 | 6/2012 | Shum |
| 8,207,967 B1 | 6/2012 | El Dokor |
| 8,208,758 B2 | 6/2012 | Wang |
| 8,213,693 B1 | 7/2012 | Li |
| 8,214,012 B2 | 7/2012 | Zuccolotto et al. |
| 8,214,016 B2 | 7/2012 | Lavallee et al. |
| 8,216,016 B2 | 7/2012 | Yamagishi et al. |
| 8,218,818 B2 | 7/2012 | Cobb |
| 8,218,819 B2 | 7/2012 | Cobb |
| 8,218,825 B2 | 7/2012 | Gordon |
| 8,221,399 B2 | 7/2012 | Amano |
| 8,223,147 B1 | 7/2012 | El Dokor |
| 8,224,423 B2 | 7/2012 | Faul |
| 8,226,574 B2 | 7/2012 | Whillock |
| 8,229,163 B2 | 7/2012 | Coleman |
| 8,229,166 B2 | 7/2012 | Teng |
| 8,229,184 B2 | 7/2012 | Benkley |
| 8,232,872 B2 | 7/2012 | Zeng |
| 8,235,529 B1 | 8/2012 | Raffle |
| 8,235,530 B2 | 8/2012 | Maad |
| 8,241,125 B2 | 8/2012 | Hughes |
| 8,243,136 B2 | 8/2012 | Aota |
| 8,243,269 B2 | 8/2012 | Matousek |
| 8,243,996 B2 | 8/2012 | Steinberg |
| 8,248,372 B2 | 8/2012 | Saila |
| 8,249,691 B2 | 8/2012 | Chase et al. |
| 8,253,770 B2 | 8/2012 | Kurtz |
| 8,253,774 B2 | 8/2012 | Huitema |
| 8,253,778 B2 | 8/2012 | Atsushi |
| 8,259,109 B2 | 9/2012 | El Dokor |
| 8,260,036 B2 | 9/2012 | Hamza et al. |
| 8,279,288 B2 | 10/2012 | Son |
| 8,284,157 B2 | 10/2012 | Markovic |
| 8,284,847 B2 | 10/2012 | Adermann |
| 8,287,373 B2 | 10/2012 | Marx |
| 8,289,390 B2 | 10/2012 | Aggarwal |
| 8,289,392 B2 | 10/2012 | Williams, Sr. |
| 8,290,208 B2 | 10/2012 | Kurtz |
| 8,290,229 B2 | 10/2012 | Qureshi |
| 8,295,573 B2 | 10/2012 | Bredno et al. |
| 8,301,226 B2 | 10/2012 | Csavoy et al. |
| 8,306,260 B2 | 11/2012 | Zhu |
| 8,306,267 B1 | 11/2012 | Gossweiler, III |
| 8,306,274 B2 | 11/2012 | Grycewicz |
| 8,306,663 B2 | 11/2012 | Wickham |
| 8,310,656 B2 | 11/2012 | Zalewski |
| 8,310,662 B2 | 11/2012 | Mehr |
| 8,311,611 B2 | 11/2012 | Csavoy et al. |
| 8,314,854 B2 | 11/2012 | Yoon |
| 8,315,691 B2 | 11/2012 | Sumaneeweera et al. |
| 8,316,324 B2 | 11/2012 | Boillot |
| 8,320,621 B2 | 11/2012 | McEldowney |
| 8,320,709 B2 | 11/2012 | Aratani et al. |
| 8,323,106 B2 | 12/2012 | Zalewski |
| 8,325,228 B2 | 12/2012 | Mariadoss |
| 8,330,811 B2 | 12/2012 | Maguire, Jr. |
| 8,330,812 B2 | 12/2012 | Maguire, Jr. |
| 8,331,019 B2 | 12/2012 | Cheong |
| 8,334,900 B2 | 12/2012 | Qu et al. |
| 8,339,282 B2 | 12/2012 | Noble |
| 8,351,651 B2 | 1/2013 | Lee |
| 8,368,586 B2 | 2/2013 | Mohamadi |
| 8,369,574 B2 | 2/2013 | Atu |
| 8,374,393 B2 | 2/2013 | Cobb |
| 8,374,411 B2 | 2/2013 | Ernst et al. |

(56) References Cited

U.S. PATENT DOCUMENTS

| | | |
|---|---|---|
| 8,374,674 B2 | 2/2013 | Gertner |
| 8,376,226 B2 | 2/2013 | Dennard |
| 8,376,827 B2 | 2/2013 | Cammegh |
| 8,379,927 B2 | 2/2013 | Taylor |
| 8,380,284 B2 | 2/2013 | Saranathan et al. |
| 8,386,011 B2 | 2/2013 | Wieczorek |
| 8,390,291 B2 | 3/2013 | Macfarlane et al. |
| 8,390,729 B2 | 3/2013 | Long |
| 8,395,620 B2 | 3/2013 | El Dokor |
| 8,396,654 B1 | 3/2013 | Simmons et al. |
| 8,400,398 B2 | 3/2013 | Schoen |
| 8,400,490 B2 | 3/2013 | Apostolopoulos |
| 8,405,491 B2 | 3/2013 | Fong |
| 8,405,656 B2 | 3/2013 | El Dokor |
| 8,405,717 B2 | 3/2013 | Kim |
| 8,406,845 B2 | 3/2013 | Komistek et al. |
| 8,411,931 B2 | 4/2013 | Zhou |
| 8,427,538 B2 | 4/2013 | Ahiska |
| 8,428,319 B2 | 4/2013 | Tsin et al. |
| 8,571,293 B2 | 10/2013 | Ernst et al. |
| 8,615,127 B2 | 12/2013 | Fitzpatrick |
| 8,744,154 B2 | 6/2014 | Van Den Brink |
| 8,848,977 B2 | 9/2014 | Bammer et al. |
| 8,862,420 B2 | 10/2014 | Ferran et al. |
| 8,953,847 B2 | 2/2015 | Moden |
| 8,996,094 B2 | 3/2015 | Schouenborg et al. |
| 9,076,212 B2 | 7/2015 | Ernst |
| 9,082,177 B2 | 7/2015 | Sebok |
| 9,084,629 B1 | 7/2015 | Rosa |
| 9,103,897 B2 | 8/2015 | Herbst et al. |
| 9,138,175 B2 | 9/2015 | Ernst et al. |
| 9,173,715 B2 | 11/2015 | Baumgartner |
| 9,176,932 B2 | 11/2015 | Baggen et al. |
| 9,305,365 B2 | 4/2016 | Lovberg et al. |
| 9,395,386 B2 | 7/2016 | Corder et al. |
| 9,451,926 B2 | 9/2016 | Kinahan et al. |
| 9,606,209 B2 | 3/2017 | Ernst et al. |
| 9,607,377 B2 | 3/2017 | Lovberg et al. |
| 2002/0082496 A1 | 6/2002 | Kuth |
| 2002/0091422 A1 | 7/2002 | Greenberg et al. |
| 2002/0115931 A1 | 8/2002 | Strauss et al. |
| 2002/0180436 A1 | 12/2002 | Dale et al. |
| 2002/0188194 A1 | 12/2002 | Cosman |
| 2003/0063292 A1 | 4/2003 | Mostafavi |
| 2003/0088177 A1 | 5/2003 | Totterman et al. |
| 2003/0116166 A1 | 6/2003 | Anthony |
| 2003/0130574 A1 | 7/2003 | Stoyle |
| 2004/0071324 A1 | 4/2004 | Norris et al. |
| 2004/0116804 A1 | 6/2004 | Mostafavi |
| 2004/0140804 A1 | 7/2004 | Polzin et al. |
| 2004/0171927 A1 | 9/2004 | Lowen et al. |
| 2005/0027194 A1 | 2/2005 | Adler et al. |
| 2005/0054910 A1 | 3/2005 | Tremblay et al. |
| 2005/0105772 A1 | 5/2005 | Voronka et al. |
| 2005/0107685 A1 | 5/2005 | Seeber |
| 2005/0137475 A1 | 6/2005 | Dold |
| 2005/0148854 A1 | 7/2005 | Ito et al. |
| 2005/0283068 A1 | 12/2005 | Zuccoloto et al. |
| 2006/0004281 A1 | 1/2006 | Saracen |
| 2006/0045310 A1 | 3/2006 | Tu et al. |
| 2006/0074292 A1 | 4/2006 | Thomson et al. |
| 2006/0241405 A1 | 10/2006 | Leitner et al. |
| 2007/0093709 A1 | 4/2007 | Abernathie |
| 2007/0206836 A1 | 9/2007 | Yoon |
| 2007/0239169 A1 | 10/2007 | Plaskos et al. |
| 2007/0280508 A1 | 12/2007 | Ernst et al. |
| 2008/0039713 A1 | 2/2008 | Thomson et al. |
| 2008/0181358 A1 | 7/2008 | Van Kampen et al. |
| 2008/0183074 A1 | 7/2008 | Carls et al. |
| 2008/0212835 A1 | 9/2008 | Tavor |
| 2008/0221442 A1 | 9/2008 | Tolkowsky et al. |
| 2008/0273754 A1 | 11/2008 | Hick et al. |
| 2008/0287728 A1 | 11/2008 | Mostafavi |
| 2008/0287780 A1 | 11/2008 | Chase et al. |
| 2008/0317313 A1 | 12/2008 | Goddard et al. |
| 2009/0028411 A1 | 1/2009 | Pfeuffer |
| 2009/0052760 A1 | 2/2009 | Smith et al. |
| 2009/0185663 A1 | 7/2009 | Gaines, Jr. et al. |
| 2009/0209846 A1 | 8/2009 | Bammer |
| 2009/0253985 A1 | 10/2009 | Shachar et al. |
| 2009/0304297 A1 | 12/2009 | Adabala et al. |
| 2009/0306499 A1 | 12/2009 | Van Vorhis et al. |
| 2010/0054579 A1 | 3/2010 | Okutomi |
| 2010/0057059 A1 | 3/2010 | Makino |
| 2010/0059679 A1 | 3/2010 | Albrecht |
| 2010/0069742 A1 | 3/2010 | Partain et al. |
| 2010/0091089 A1 | 4/2010 | Cromwell et al. |
| 2010/0099981 A1 | 4/2010 | Fishel |
| 2010/0125191 A1 | 5/2010 | Sahin |
| 2010/0137709 A1 | 6/2010 | Gardner et al. |
| 2010/0148774 A1 | 6/2010 | Kamata |
| 2010/0149099 A1 | 6/2010 | Elias |
| 2010/0149315 A1 | 6/2010 | Qu |
| 2010/0160775 A1 | 6/2010 | Pankratov |
| 2010/0164862 A1 | 7/2010 | Sullivan |
| 2010/0165293 A1 | 7/2010 | Tanassi et al. |
| 2010/0167246 A1 | 7/2010 | Ghajar |
| 2010/0172567 A1 | 7/2010 | Prokoski |
| 2010/0177929 A1 | 7/2010 | Kurtz |
| 2010/0178966 A1 | 7/2010 | Seydoux |
| 2010/0179390 A1 | 7/2010 | Davis |
| 2010/0179413 A1 | 7/2010 | Kadour et al. |
| 2010/0183196 A1 | 7/2010 | Fu et al. |
| 2010/0191631 A1 | 7/2010 | Weidmann |
| 2010/0194879 A1 | 8/2010 | Pasveer |
| 2010/0198067 A1 | 8/2010 | Mahfouz |
| 2010/0198101 A1 | 8/2010 | Song |
| 2010/0198112 A1 | 8/2010 | Maad |
| 2010/0199232 A1 | 8/2010 | Mistry |
| 2010/0210350 A9 | 8/2010 | Jay S. Walker |
| 2010/0214267 A1 | 8/2010 | Radivojevic |
| 2010/0231511 A1 | 9/2010 | Henty |
| 2010/0231692 A1 | 9/2010 | Perlman |
| 2010/0245536 A1 | 9/2010 | Huitema |
| 2010/0245593 A1 | 9/2010 | Kim |
| 2010/0251924 A1 | 10/2010 | Taylor |
| 2010/0253762 A1 | 10/2010 | Cheong |
| 2010/0268072 A1 | 10/2010 | Hall et al. |
| 2010/0277571 A1 | 11/2010 | Xu |
| 2010/0282902 A1 | 11/2010 | Rajasingham |
| 2010/0283833 A1 | 11/2010 | Yeh |
| 2010/0284119 A1 | 11/2010 | Coakley |
| 2010/0289899 A1 | 11/2010 | Hendron |
| 2010/0290668 A1 | 11/2010 | Friedman |
| 2010/0292841 A1 | 11/2010 | Wickham |
| 2010/0295718 A1 | 11/2010 | Mohamadi |
| 2010/0296701 A1 | 11/2010 | Hu |
| 2010/0302142 A1 | 12/2010 | French |
| 2010/0303289 A1 | 12/2010 | Polzin |
| 2010/0311512 A1 | 12/2010 | Lock |
| 2010/0321505 A1 | 12/2010 | Kokubun |
| 2010/0328055 A1 | 12/2010 | Fong |
| 2010/0328201 A1 | 12/2010 | Marbit |
| 2010/0328267 A1 | 12/2010 | Chen |
| 2010/0330912 A1 | 12/2010 | Saila |
| 2011/0001699 A1 | 1/2011 | Jacobsen |
| 2011/0006991 A1 | 1/2011 | Elias |
| 2011/0007939 A1 | 1/2011 | Teng |
| 2011/0007946 A1 | 1/2011 | Liang |
| 2011/0008759 A1 | 1/2011 | Usui |
| 2011/0015521 A1 | 1/2011 | Faul |
| 2011/0019001 A1 | 1/2011 | Rhoads |
| 2011/0025853 A1 | 2/2011 | Richardson |
| 2011/0038520 A1 | 2/2011 | Yui |
| 2011/0043631 A1 | 2/2011 | Marman |
| 2011/0043759 A1 | 2/2011 | Bushinsky |
| 2011/0050562 A1 | 3/2011 | Schoen |
| 2011/0050569 A1 | 3/2011 | Marvit |
| 2011/0050947 A1 | 3/2011 | Marman |
| 2011/0052002 A1 | 3/2011 | Cobb |
| 2011/0052003 A1 | 3/2011 | Cobb |
| 2011/0052015 A1 | 3/2011 | Saund |
| 2011/0054870 A1 | 3/2011 | Dariush |
| 2011/0057816 A1 | 3/2011 | Noble |

(56) References Cited

U.S. PATENT DOCUMENTS

| | | |
|---|---|---|
| 2011/0058020 A1 | 3/2011 | Dieckmann |
| 2011/0069207 A1 | 3/2011 | Steinberg |
| 2011/0074675 A1 | 3/2011 | Shiming |
| 2011/0081000 A1 | 4/2011 | Gertner |
| 2011/0081043 A1 | 4/2011 | Sabol |
| 2011/0085704 A1 | 4/2011 | Han |
| 2011/0092781 A1 | 4/2011 | Gertner |
| 2011/0102549 A1 | 5/2011 | Takahashi |
| 2011/0105883 A1 | 5/2011 | Lake et al. |
| 2011/0105893 A1 | 5/2011 | Akins |
| 2011/0115793 A1 | 5/2011 | Grycewicz |
| 2011/0115892 A1 | 5/2011 | Fan |
| 2011/0116683 A1 | 5/2011 | Kramer et al. |
| 2011/0117528 A1 | 5/2011 | Marciello et al. |
| 2011/0118032 A1 | 5/2011 | Zalewski |
| 2011/0133917 A1 | 6/2011 | Zeng |
| 2011/0142411 A1 | 6/2011 | Camp |
| 2011/0150271 A1 | 6/2011 | Lee |
| 2011/0157168 A1 | 6/2011 | Bennett |
| 2011/0157358 A1 | 6/2011 | Bell |
| 2011/0157370 A1 | 6/2011 | Livesey |
| 2011/0160569 A1 | 6/2011 | Cohen et al. |
| 2011/0172060 A1 | 7/2011 | Morales |
| 2011/0172521 A1 | 7/2011 | Zdeblick et al. |
| 2011/0175801 A1 | 7/2011 | Markovic |
| 2011/0175809 A1 | 7/2011 | Markovic |
| 2011/0175810 A1 | 7/2011 | Markovic |
| 2011/0176723 A1 | 7/2011 | Ali et al. |
| 2011/0180695 A1 | 7/2011 | Li |
| 2011/0181893 A1 | 7/2011 | MacFarlane |
| 2011/0182472 A1 | 7/2011 | Hansen |
| 2011/0187640 A1 | 8/2011 | Jacobsen |
| 2011/0193939 A1 | 8/2011 | Vassigh |
| 2011/0199461 A1 | 8/2011 | Horio |
| 2011/0201916 A1 | 8/2011 | Duyn et al. |
| 2011/0201939 A1 | 8/2011 | Hubschman et al. |
| 2011/0202306 A1 | 8/2011 | Eng |
| 2011/0205358 A1 | 8/2011 | Aota |
| 2011/0207089 A1 | 8/2011 | Lagettie |
| 2011/0208437 A1 | 8/2011 | Teicher |
| 2011/0216002 A1 | 9/2011 | Weising |
| 2011/0216180 A1 | 9/2011 | Pasini |
| 2011/0221770 A1 | 9/2011 | Kruglick |
| 2011/0229862 A1 | 9/2011 | Parikh |
| 2011/0230755 A1 | 9/2011 | MacFarlane et al. |
| 2011/0234807 A1 | 9/2011 | Jones |
| 2011/0234834 A1 | 9/2011 | Sugimoto |
| 2011/0235855 A1 | 9/2011 | Smith |
| 2011/0237933 A1 | 9/2011 | Cohen |
| 2011/0242134 A1 | 10/2011 | Miller |
| 2011/0244939 A1 | 10/2011 | Cammegh |
| 2011/0250929 A1 | 10/2011 | Lin |
| 2011/0251478 A1 | 10/2011 | Wieczorek |
| 2011/0255845 A1 | 10/2011 | Kikuchi |
| 2011/0257566 A1 | 10/2011 | Burdea |
| 2011/0260965 A1 | 10/2011 | Kim |
| 2011/0262002 A1 | 10/2011 | Lee |
| 2011/0267427 A1 | 11/2011 | Goh |
| 2011/0267456 A1 | 11/2011 | Adermann |
| 2011/0275957 A1 | 11/2011 | Bhandari |
| 2011/0276396 A1 | 11/2011 | Rathod |
| 2011/0279663 A1 | 11/2011 | Fan |
| 2011/0285622 A1 | 11/2011 | Marti |
| 2011/0286010 A1 | 11/2011 | Kusik et al. |
| 2011/0291925 A1 | 12/2011 | Israel |
| 2011/0293143 A1 | 12/2011 | Narayanan et al. |
| 2011/0293146 A1 | 12/2011 | Grycewicz |
| 2011/0298708 A1 | 12/2011 | Hsu |
| 2011/0298824 A1 | 12/2011 | Lee |
| 2011/0300994 A1 | 12/2011 | Verkaaik |
| 2011/0301449 A1 | 12/2011 | Maurer, Jr. |
| 2011/0301934 A1 | 12/2011 | Tardis |
| 2011/0303214 A1 | 12/2011 | Welle |
| 2011/0304541 A1 | 12/2011 | Dalal |
| 2011/0304650 A1 | 12/2011 | Canpillo |
| 2011/0304706 A1 | 12/2011 | Porter |
| 2011/0306867 A1 | 12/2011 | Gopinadhan |
| 2011/0310220 A1 | 12/2011 | McEldowney |
| 2011/0310226 A1 | 12/2011 | McEldowney |
| 2011/0316994 A1 | 12/2011 | Lemchen |
| 2011/0317877 A1 | 12/2011 | Bell |
| 2012/0002112 A1 | 1/2012 | Huang |
| 2012/0004791 A1 | 1/2012 | Buelthoff |
| 2012/0007839 A1 | 1/2012 | Tsao et al. |
| 2012/0019645 A1 | 1/2012 | Maltz |
| 2012/0020524 A1 | 1/2012 | Ishikawa |
| 2012/0021806 A1 | 1/2012 | Naltz |
| 2012/0027226 A1 | 2/2012 | Desenberg |
| 2012/0029345 A1 | 2/2012 | Mahfouz et al. |
| 2012/0032882 A1 | 2/2012 | Schlachta |
| 2012/0033083 A1 | 2/2012 | Horvinger |
| 2012/0035462 A1 | 2/2012 | Maurer, Jr. et al. |
| 2012/0039505 A1 | 2/2012 | Vastide |
| 2012/0044363 A1 | 2/2012 | Lu |
| 2012/0045091 A1 | 2/2012 | Kaganovich |
| 2012/0049453 A1 | 3/2012 | Morichau-Beauchant |
| 2012/0051588 A1 | 3/2012 | McEldowney |
| 2012/0051664 A1 | 3/2012 | Gopalakrishnan et al. |
| 2012/0052949 A1 | 3/2012 | Weitzner |
| 2012/0056982 A1 | 3/2012 | Katz |
| 2012/0057640 A1 | 3/2012 | Shi |
| 2012/0065492 A1 | 3/2012 | Gertner et al. |
| 2012/0065494 A1 | 3/2012 | Gertner et al. |
| 2012/0072041 A1 | 3/2012 | Miller |
| 2012/0075166 A1 | 3/2012 | Marti |
| 2012/0075177 A1 | 3/2012 | Jacobsen |
| 2012/0076369 A1 | 3/2012 | Abramovich |
| 2012/0081504 A1 | 4/2012 | Ng |
| 2012/0083314 A1 | 4/2012 | Ng |
| 2012/0083960 A1 | 4/2012 | Zhu |
| 2012/0086778 A1 | 4/2012 | Lee |
| 2012/0086809 A1 | 4/2012 | Lee |
| 2012/0092445 A1 | 4/2012 | McDowell |
| 2012/0092502 A1 | 4/2012 | Knasel |
| 2012/0093481 A1 | 4/2012 | McDowell |
| 2012/0098938 A1 | 4/2012 | Jin |
| 2012/0101388 A1 | 4/2012 | Tripathi |
| 2012/0105573 A1 | 5/2012 | Apostolopoulos |
| 2012/0106814 A1 | 5/2012 | Gleason et al. |
| 2012/0108909 A1 | 5/2012 | Slobounov et al. |
| 2012/0113140 A1 | 5/2012 | Hilliges |
| 2012/0113223 A1 | 5/2012 | Hilliges |
| 2012/0116202 A1 | 5/2012 | Bangera |
| 2012/0119999 A1 | 5/2012 | Harris |
| 2012/0120072 A1 | 5/2012 | Se |
| 2012/0120237 A1 | 5/2012 | Trepess |
| 2012/0120243 A1 | 5/2012 | Chien |
| 2012/0120277 A1 | 5/2012 | Tsai |
| 2012/0121124 A1 | 5/2012 | Bammer |
| 2012/0124604 A1 | 5/2012 | Small |
| 2012/0127319 A1 | 5/2012 | Rao |
| 2012/0133616 A1 | 5/2012 | Nishihara |
| 2012/0133889 A1 | 5/2012 | Bergt |
| 2012/0143029 A1 | 6/2012 | Silverstein |
| 2012/0143212 A1 | 6/2012 | Madhani |
| 2012/0154272 A1 | 6/2012 | Hildreth |
| 2012/0154511 A1 | 6/2012 | Hsu |
| 2012/0154536 A1 | 6/2012 | Stoker |
| 2012/0154579 A1 | 6/2012 | Hanpapur |
| 2012/0156661 A1 | 6/2012 | Smith |
| 2012/0158197 A1 | 6/2012 | Hinman |
| 2012/0162378 A1 | 6/2012 | El Dokor |
| 2012/0165964 A1 | 6/2012 | Flaks |
| 2012/0167143 A1 | 6/2012 | Longet |
| 2012/0169841 A1 | 7/2012 | Chemali |
| 2012/0176314 A1 | 7/2012 | Jeon |
| 2012/0184371 A1 | 7/2012 | Shum |
| 2012/0188237 A1 | 7/2012 | Han |
| 2012/0188371 A1 | 7/2012 | Chen |
| 2012/0194422 A1 | 8/2012 | El Dokor |
| 2012/0194517 A1 | 8/2012 | Ivadi |
| 2012/0194561 A1 | 8/2012 | Grossinger |
| 2012/0195466 A1 | 8/2012 | Teng |
| 2012/0196660 A1 | 8/2012 | Eo Dokor |

(56) References Cited

U.S. PATENT DOCUMENTS

| | | |
|---|---|---|
| 2012/0197135 A1 | 8/2012 | Slatkine |
| 2012/0200676 A1 | 8/2012 | Huitema |
| 2012/0201428 A1 | 8/2012 | Joshi et al. |
| 2012/0206604 A1 | 8/2012 | Jones |
| 2012/0212594 A1 | 8/2012 | Barns |
| 2012/0218407 A1 | 8/2012 | Chien |
| 2012/0218421 A1 | 8/2012 | Chien |
| 2012/0220233 A1 | 8/2012 | Teague |
| 2012/0224666 A1 | 9/2012 | Speller |
| 2012/0224743 A1 | 9/2012 | Rodriguez |
| 2012/0225718 A1 | 9/2012 | Zhang |
| 2012/0229643 A1 | 9/2012 | Chidanand |
| 2012/0229651 A1 | 9/2012 | Takizawa |
| 2012/0230561 A1 | 9/2012 | Qureshi |
| 2012/0235896 A1 | 9/2012 | Jacobsen |
| 2012/0238337 A1 | 9/2012 | French |
| 2012/0242816 A1 | 9/2012 | Cruz |
| 2012/0249741 A1 | 10/2012 | Maciocci |
| 2012/0253201 A1 | 10/2012 | Reinhold |
| 2012/0253241 A1 | 10/2012 | Ludital |
| 2012/0262540 A1 | 10/2012 | Rondinelli |
| 2012/0262558 A1 | 10/2012 | Boger |
| 2012/0262583 A1 | 10/2012 | Bernal |
| 2012/0268124 A1 | 10/2012 | Herbst et al. |
| 2012/0275649 A1 | 11/2012 | Cobb |
| 2012/0276995 A1 | 11/2012 | Lansdale |
| 2012/0277001 A1 | 11/2012 | Lansdale |
| 2012/0281093 A1 | 11/2012 | Fong |
| 2012/0281873 A1 | 11/2012 | Brown |
| 2012/0288142 A1 | 11/2012 | Gossweiler, III |
| 2012/0288143 A1 | 11/2012 | Ernst |
| 2012/0288852 A1 | 11/2012 | Willson |
| 2012/0289334 A9 | 11/2012 | Mikhailov |
| 2012/0289822 A1 | 11/2012 | Shachar et al. |
| 2012/0293412 A1 | 11/2012 | El Dokor |
| 2012/0293506 A1 | 11/2012 | Vertucci |
| 2012/0293663 A1 | 11/2012 | Liu |
| 2012/0294511 A1 | 11/2012 | Datta |
| 2012/0300961 A1 | 11/2012 | Moeller |
| 2012/0303839 A1 | 11/2012 | Jackson |
| 2012/0304126 A1 | 11/2012 | Lavigne |
| 2012/0307075 A1 | 12/2012 | Nargalit |
| 2012/0307207 A1 | 12/2012 | Abraham |
| 2012/0314066 A1 | 12/2012 | Lee |
| 2012/0315016 A1 | 12/2012 | Fung |
| 2012/0319946 A1 | 12/2012 | El Dokor |
| 2012/0319989 A1 | 12/2012 | Argiro |
| 2012/0320178 A1 | 12/2012 | Siegert et al. |
| 2012/0320219 A1 | 12/2012 | David |
| 2012/0326966 A1 | 12/2012 | Rauber |
| 2012/0326976 A1 | 12/2012 | Markovic |
| 2012/0326979 A1 | 12/2012 | Geisert |
| 2012/0327241 A1 | 12/2012 | Howe |
| 2012/0327246 A1 | 12/2012 | Senior et al. |
| 2013/0002866 A1 | 1/2013 | Hampapur |
| 2013/0002879 A1 | 1/2013 | Weber |
| 2013/0002900 A1 | 1/2013 | Gossweiler, III et al. |
| 2013/0009865 A1 | 1/2013 | Valik |
| 2013/0010071 A1 | 1/2013 | Valik |
| 2013/0013452 A1 | 1/2013 | Dennard |
| 2013/0016009 A1 | 1/2013 | Godfrey |
| 2013/0016876 A1 | 1/2013 | Wooley |
| 2013/0021434 A1 | 1/2013 | Ahiska |
| 2013/0021578 A1 | 1/2013 | Chen |
| 2013/0024819 A1 | 1/2013 | Rieffel |
| 2013/0030283 A1 | 1/2013 | Vortman et al. |
| 2013/0033640 A1 | 2/2013 | Lee |
| 2013/0033700 A1 | 2/2013 | Hallil |
| 2013/0035590 A1 | 2/2013 | Ma et al. |
| 2013/0035612 A1 | 2/2013 | Mason |
| 2013/0040720 A1 | 2/2013 | Cammegh |
| 2013/0041368 A1 | 2/2013 | Cunninghan |
| 2013/0049756 A1 | 2/2013 | Ernst et al. |
| 2013/0057702 A1 | 3/2013 | Chavan |
| 2013/0064426 A1 | 3/2013 | Watkins, Jr. |
| 2013/0064427 A1 | 3/2013 | Picard |
| 2013/0065517 A1 | 3/2013 | Svensson |
| 2013/0066448 A1 | 3/2013 | Alonso |
| 2013/0066526 A1 | 3/2013 | Mondragon |
| 2013/0069773 A1 | 3/2013 | Li |
| 2013/0070201 A1 | 3/2013 | Shahidi |
| 2013/0070257 A1 | 3/2013 | Wong |
| 2013/0072787 A1 | 3/2013 | Wallace et al. |
| 2013/0076863 A1 | 3/2013 | Rappel |
| 2013/0076944 A1 | 3/2013 | Kosaka |
| 2013/0077823 A1 | 3/2013 | Mestha |
| 2013/0079033 A1 | 3/2013 | Gupta |
| 2013/0084980 A1 | 4/2013 | Hammontree |
| 2013/0088584 A1 | 4/2013 | Malhas |
| 2013/0093866 A1 | 4/2013 | Ohlhues et al. |
| 2013/0096439 A1 | 4/2013 | Lee |
| 2013/0102879 A1 | 4/2013 | MacLaren et al. |
| 2013/0102893 A1 | 4/2013 | Vollmer |
| 2013/0108979 A1 | 5/2013 | Daon |
| 2013/0113791 A1 | 5/2013 | Isaacs et al. |
| 2013/0211421 A1 | 8/2013 | Abovitz et al. |
| 2013/0281818 A1 | 10/2013 | Vija et al. |
| 2014/0037174 A1 | 2/2014 | Ernst et al. |
| 2014/0073908 A1 | 3/2014 | Biber |
| 2014/0088410 A1 | 3/2014 | Wu |
| 2014/0148685 A1 | 5/2014 | Liu et al. |
| 2014/0159721 A1 | 6/2014 | Grodzki |
| 2014/0171784 A1 | 6/2014 | Ooi et al. |
| 2014/0205140 A1 | 7/2014 | Lovberg et al. |
| 2014/0378816 A1 | 12/2014 | Oh et al. |
| 2015/0085072 A1 | 3/2015 | Yan |
| 2015/0265220 A1 | 9/2015 | Ernst et al. |
| 2015/0297120 A1 | 10/2015 | Son et al. |
| 2015/0331078 A1 | 11/2015 | Speck et al. |
| 2015/0359464 A1 | 12/2015 | Olesen |
| 2015/0366527 A1 | 12/2015 | Yu et al. |
| 2016/0073962 A1 | 3/2016 | Yu et al. |
| 2016/0091592 A1 | 3/2016 | Beall et al. |
| 2016/0166205 A1 | 6/2016 | Ernst et al. |
| 2016/0228005 A1 | 8/2016 | Bammer et al. |
| 2016/0249984 A1* | 9/2016 | Janssen ............... A61B 6/04 |
| 2016/0256713 A1 | 9/2016 | Saunders et al. |
| 2016/0262663 A1 | 9/2016 | MacLaren et al. |
| 2016/0287080 A1 | 10/2016 | Olesen et al. |
| 2016/0310229 A1 | 10/2016 | Bammer et al. |
| 2016/0313432 A1 | 10/2016 | Feiweier et al. |
| 2017/0032538 A1 | 2/2017 | Ernst |

FOREIGN PATENT DOCUMENTS

| | | |
|---|---|---|
| DE | 102004024470 | 12/2005 |
| EP | 0904733 | 3/1991 |
| EP | 1354564 | 10/2003 |
| EP | 1524626 A2 | 4/2005 |
| EP | 2515139 | 10/2012 |
| EP | 2948056 | 12/2015 |
| EP | 2950714 | 12/2015 |
| JP | 03023838 | 5/1991 |
| WO | WO 96/17258 A2 | 6/1996 |
| WO | WO 99/38449 | 8/1999 |
| WO | WO 00/72039 A1 | 11/2000 |
| WO | WO 03/003796 A1 | 1/2003 |
| WO | WO 2004/023783 A2 | 3/2004 |
| WO | WO 2005/077293 | 8/2005 |
| WO | WO 2007/025301 | 3/2007 |
| WO | WO 2007/085241 A1 | 8/2007 |
| WO | WO 2007/136745 | 11/2007 |
| WO | WO 2009/101566 | 8/2009 |
| WO | WO 2009/129457 A1 | 10/2009 |
| WO | WO 2011/047467 A1 | 4/2011 |
| WO | WO 2011/113441 A2 | 9/2011 |
| WO | WO 2012/046202 A1 | 4/2012 |
| WO | WO 2013/032933 | 3/2013 |
| WO | WO 2014/005178 | 1/2014 |
| WO | WO 2014/116868 | 7/2014 |
| WO | WO 2014/120734 | 8/2014 |
| WO | WO 2015/042138 | 3/2015 |

(56) References Cited

FOREIGN PATENT DOCUMENTS

| WO | WO 2015/092593 | 6/2015 |
|---|---|---|
| WO | WO 2015/148391 | 10/2015 |
| WO | WO 2016/014718 | 1/2016 |

OTHER PUBLICATIONS

Aksoy et al., "Real-Time Optical Motion Correction for Diffusion Tensor Imaging, Magnetic Resonance in Medicine" (Mar. 22, 2011) 66 366-378.
Andrews et al., "Prospective Motion Correction for Magnetic Resonance Spectroscopy Using Single Camera Retro-Grate Reflector Optical Tracking, Journal of Magnetic Resonance Imaging" (Feb. 2011) 33(2): 498-504.
Angeles et al., "The Online Solution of the Hand-Eye Problem", IEEE Transactions on Robotics and Automation, 16(6): 720-731 (Dec. 2000).
Bandettini, Peter A., et al., "Processing Strategies for Time-Course Data Sets in Functional MRI of the Human Breain", Magnetic Resonance in Medicine 30: 161-173 (1993).
Barmet et al, Spatiotemporal Magnetic Field Monitoring for MR, Magnetic Resonance in Medicine (Feb. 1, 2008) 60: 187-197.
Bartels, LW, et al., "Endovascular interventional magnetic resonance imaging", Physics in Medicine and Biology 48: R37-R64 (2003).
Carranza-Herrezuelo et al, "Motion estimation of tagged cardiac magnetic resonance images using variational techniques" Elsevier, Computerized Medical Imaging and Graphics 34 (2010), pp. 514-522.
Chou, Jack C. K., et al., "Finding the Position and Orientation of a Sensor on a Robot Manipulator Using Quaternions", The International Journal of Robotics Research, 10(3): 240-254 (Jun. 1991).
Cofaru et al "Improved Newton-Raphson digital image correlation method for full-field displacement and strain calculation," Department of Materials Science and Engineering, Ghent University St-Pietersnieuwstraat, Nov. 20, 2010.
Ernst et al., "A Novel Phase and Frequency Navigator for Proton Magnetic Resonance Spectroscopy Using Water-Suppression Cycling, Magnetic Resonance in Medicine" (Jan. 2011) 65(1): 13-7.
Eviatar et al., "Real time head motion correction for functional MRI", In: Proceedings of the International Society for Magnetic Resonance in Medicine (1999) 269.
Forbes, Kristen P. N., et al., "Propeller MRI: Clinical Testing of a Novel Technique for Quantification and Compensation of Head Motion", Journal of Magnetic Resonance Imaging 14: 215-222 (2001).
Glover, Gary H., et al., "Self-Navigated Spiral fMRI: Interleaved versus Single-shot", Magnetic Resonance in Medicine 39: 361-368 (1998).
Gumus et al., "Elimination of DWI signal dropouts using blipped gradients for dynamic restoration of gradient moment", ISMRM 20th Annual Meeting & Exhibition, May 7, 2012.
Herbst et al., "Preventing Signal Dropouts in DWI Using Continous Prospective Motion Correction", Proc. Intl. Soc. Mag. Reson. Med. 19 (May, 2011) 170.
Herbst et al., "Prospective Motion Correction With Continuous Gradient Updates in Diffusion Weighted Imaging, Magnetic Resonance in Medicine" (2012) 67:326-338.
Horn, Berthold K. P., "Closed-form solution of absolute orientation using unit quaternions", Journal of the Optical Society of America, vol. 4, p. 629-642 (Apr. 1987).
International Preliminary Report on Patentability for Application No. PCT/US2007/011899, dated Jun. 8, 2008, in 13 pages.
International Search Report and Written Opinion for Application No. PCT/US2007/011899, dated Nov. 14, 2007.
International Search Report and Written Opinion for Application No. PCT/US2014/012806, dated May 15, 2014, in 15 pages.
International Preliminary Report on Patentability for Application No. PCT/US2014/013546, dated Aug. 4, 2015, in 9 pages.
International Search Report and Written Opinion for Application No. PCT/US2015/022041, dated Jun. 29, 2015, in 9 pages.
Josefsson et al. "A flexible high-precision video system for digital recording of motor acts through lightweight reflect markers", Computer Methods and Programs in Biomedicine, vol. 49:111-129 (1996).
Kiruluta et al., "Predictive Head Movement Tracking Using a Kalman Filter", IEEE Trans. On Systems, Man, and Cybernetics-Part B: Cybernetics, 27(2):326-331 (Apr. 1997).
Maclaren et al., "Combined Prospective and Retrospective Motion Correction to Relax Navigator Requirements", Magnetic Resonance in Medicine (Feb. 11, 2011) 65:1724-1732.
MacLaren et al., "Navigator Accuracy Requirements for Prospective Motion Correction", Magnetic Resonance in Medicine (Jan. 2010) 63(1): 162-70.
MacLaren, "Prospective Motion Correction in MRI Using Optical Tracking Tape", Book of Abstracts, ESMRMB (2009).
Maclaren et al., "Measurement and correction of microscopic head motion during magnetic resonance imaging of the brain", PLOS ONE, vol. 7(11):1-9 (2012).
McVeigh et al., "Real-time, Interactive MRI for Cardiovascular Interventions", Academic Radiology, 12(9): 1121-1127 (2005).
PCT Search Report from the International Searching Authority, dated Feburary 28, 2013, in 16 pages, regarding International Application No. PCT/US2012/052349.
Qin et al., "Prospective Head-Movement Correction for High-Resolution MRI Using an In-Bore Optical Tracking System", Magnetic Resonance in Medicine (Apr. 13, 2009) 62: 924-934.
Schulz et al., "First Embedded In-Bore System for Fast Optical Prospective Head Motion-Correction in MRI", Proceedings of the 28th Annual Scientific Meeting of the ESMRMB (Oct. 8, 2011) 369.
Shiu et al., "Calibration of Wrist-Mounted Robotic Sensors by Solving Homogeneous Transform Equations of the Form AX=XB", IEEE Transactions on Robotics and Automation, 5(1): 16-29 (Feb. 1989).
Tremblay et al., "Retrospective Coregistration of Functional Magnetic Resonance Imaging Data using External monitoring", Magnetic Resonance in Medicine 53:141-149 (2005).
Tsai et al., "A New Technique for Fully Autonomous and Efficient 3D Robotics Hand/Eye Calibration", IEEE Transaction on Robotics and Automation, 5(3): 345-358 (Jun. 1989).
Wang, Ching-Cheng, "Extrinsic Calibration of a Vision Sensor Mounted on a Robot", IEEE Transactions on Robotics and Automation, 8(2):161-175 (Apr. 1992).
Ward et al., "Prospective Multiaxial Motion Correction for fMRI", Magnetic Resonance in Medicine 43:459-469 (2000).
Welch at al., "Spherical Navigator Echoes for Full 3D Rigid Body Motion Measurement in MRI", Magnetic Resonance in Medicine 47:32-41 (2002).
Zaitsev, M., et al., "Prospective Real-Time Slice-by-Slice 3D Motion Correction for EPI Using an External Optical Motion Tracking System", Proc.Intl.Soc.Mag.Reson.Med.11:517(2004).
Zeitsev et al., "Magnetic resonance imaging of freely moving objects: Prospective real-time motion correction using an external optical motion tracking system", NeuroImage 31 (Jan. 29, 2006) 1038-1050.
Anishenko et al., "A Motion Correction System for Brain Tomography Based on Biologically Motivated Models." 7th IEEE International Conference on Cybernetic Intelligent Systems, dated Sep. 9, 2008, in 9 pages.
Armstrong et al., RGR-6D: Low-cost, high-accuracy measurement of 6-DOF Pose from a Single Image. Publication date unknown.
Armstrong et al., "RGR-3D: Simple, cheap detection of 6-DOF pose for tele-operation, and robot programming and calibration", In Proc. 2002 Int. Conf. on Robotics and Automation, IEEE, Washington (May 2002).
Fulton et al., "Correction for Head Movements in Positron Emission Tomography Using an Optical Motion-Tracking System", IEEE Transactions on Nuclear Science, vol. 49(1):116-123 (Feb. 2002).
Hoff et al., "Analysis of Head Pose Accuracy in Augmented Reality", IEEE Transactions on Visualization and Computer Graphics 6, No. 4 (Oct.-Dec. 2000): 319-334.

(56) References Cited

OTHER PUBLICATIONS

International Preliminary Report on Patentability for Application No. PCT/US2015/022041, dated Oct. 6, 2016, in 8 pages.
International Search Report and Written Opinion for Application No. PCT/US2015/041615, dated Oct. 29, 2015, in 13 pages.
Katsuki, et al., "Design of an Artificial Mark to Determine 3D Pose by Monocular Vision", 2003 IEEE International Conference on Robotics and Automation (Cat. No. 03CH37422), Sep. 14-19, 2003, pp. 995-1000 vol. 1.
Kiebel et al., "MRI and PET coregistration-a cross validation of statistical parametric mapping and automated image registration", Neuroimage 5(4):271-279 (1997).
Lerner, "Motion correction in fmri images", Technion-Israel Institute of Technology, Faculty of Computer Science (Feb. 2006).
Speck, et al., "Prospective real-time slice-by-slice Motion Correction for fMRI in Freely Moving Subjects", Magnetic Resonance Materials in Physics, Biology and Medicine., 19(2), 55-61, published May 9, 2006.
Yeo, et al. Motion correction in fMRI by mapping slice-to-volume with concurrent field-inhomogeneity correction:, International Conference on Medical Image Computing and Computer-Assisted Intervention, pp. 752-760 (2004).

\* cited by examiner

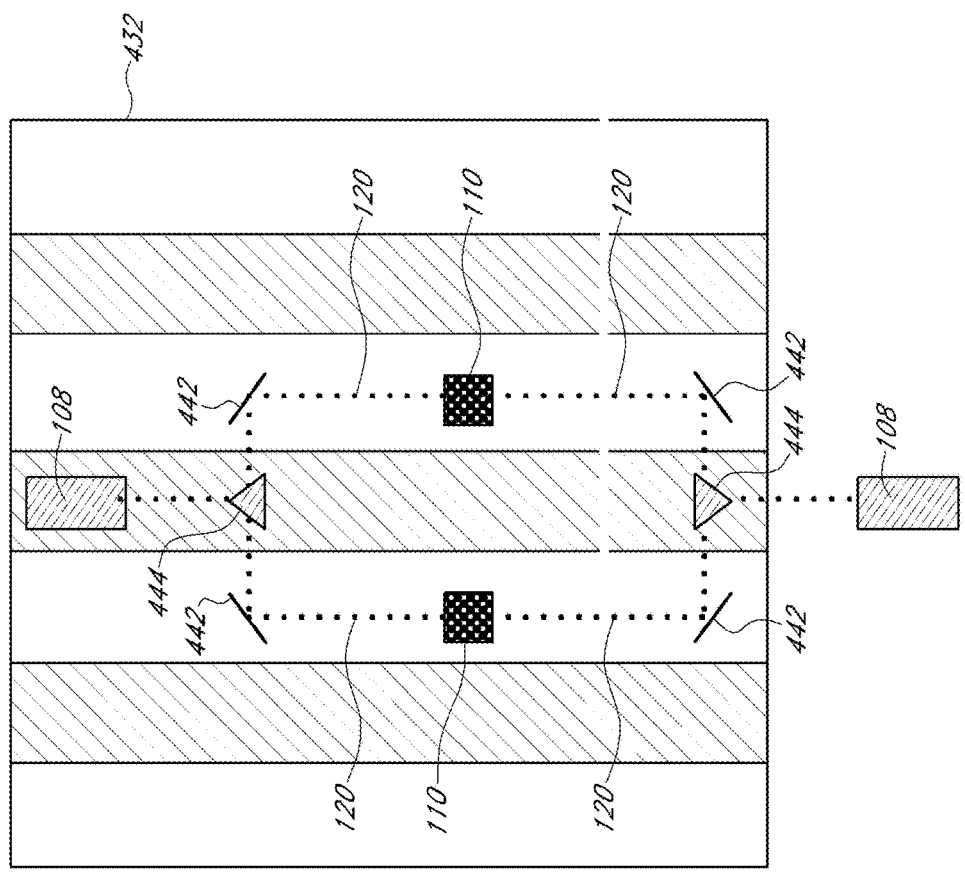

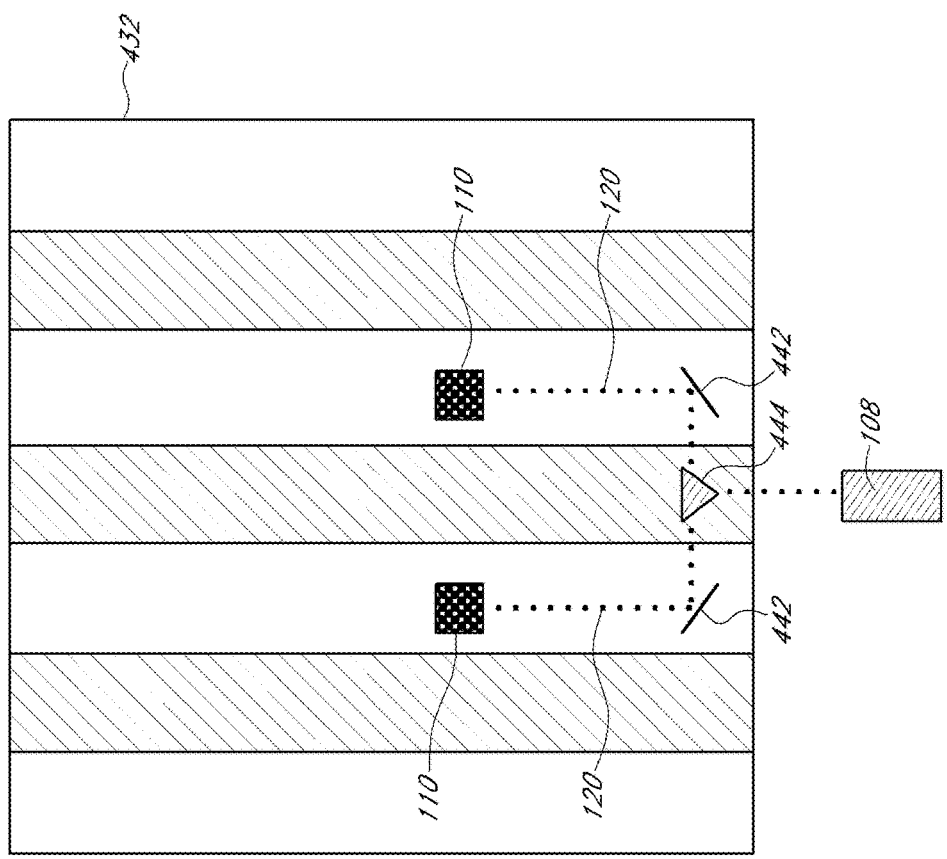

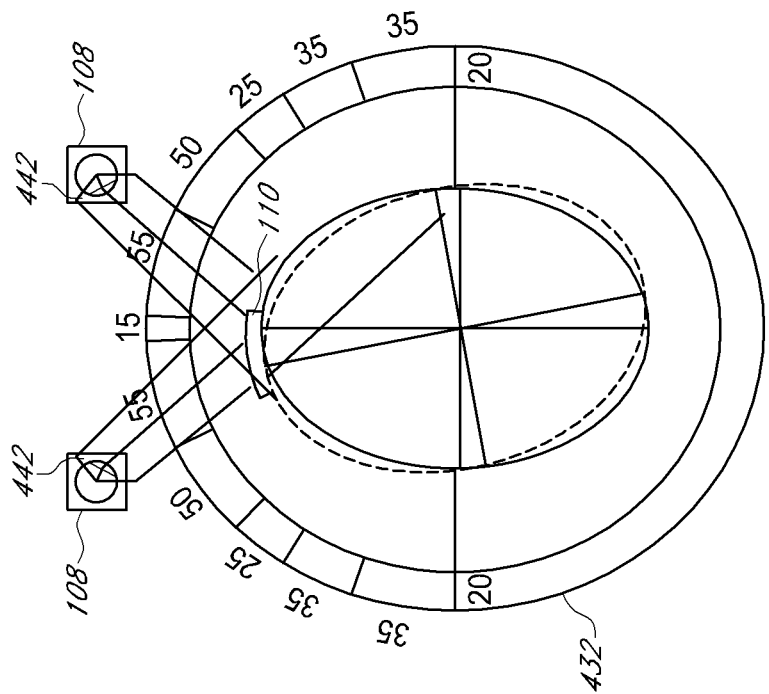
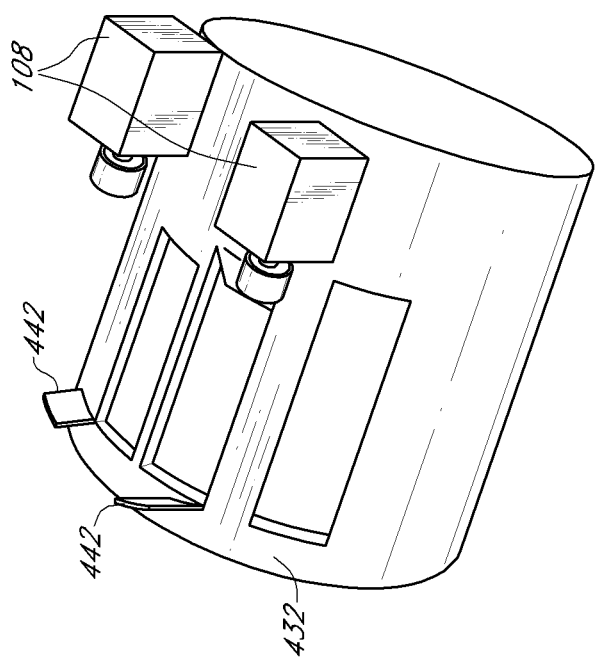
FIG. 9B
FIG. 9A

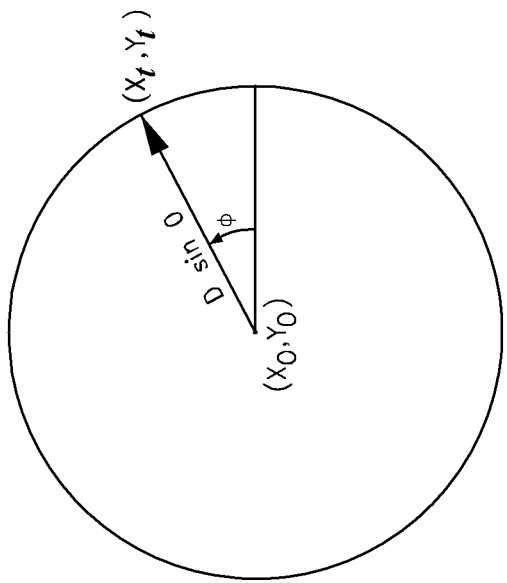

$D$ = lens focal length    $N_x = N_{x0} + \left(\dfrac{X_t - X_0}{\Delta s}\right) = N_{x0} + \left(\dfrac{D}{\Delta s}\right) \sin\theta \cos\phi$ $X_t = X_0 + D\sin\theta\cos\phi$ $Y_t = Y_0 + D\sin\theta\cos\phi$    $N_y = N_{y0} + \left(\dfrac{Y_t - Y_0}{\Delta s}\right) = N_{y0} + \left(\dfrac{D}{\Delta s}\right) \sin\theta \sin\phi$ $\Delta s$ = pixel size:  $N_{x0}$ = horiz center pixel number;  $N_{y0}$ = vert center pixel number:

FIG. 20A

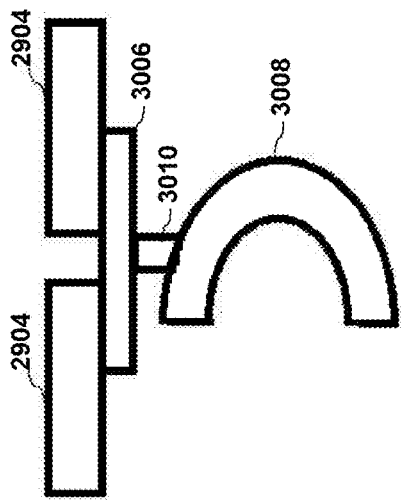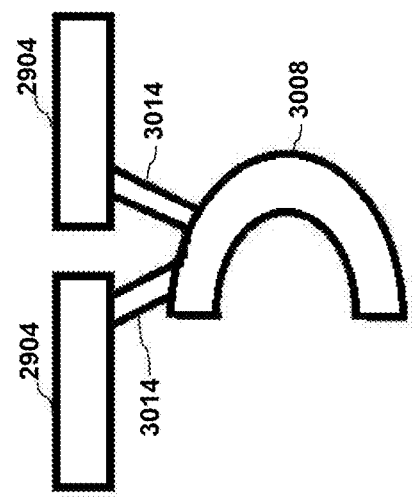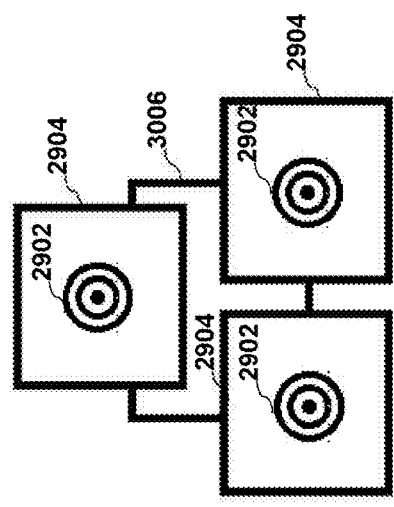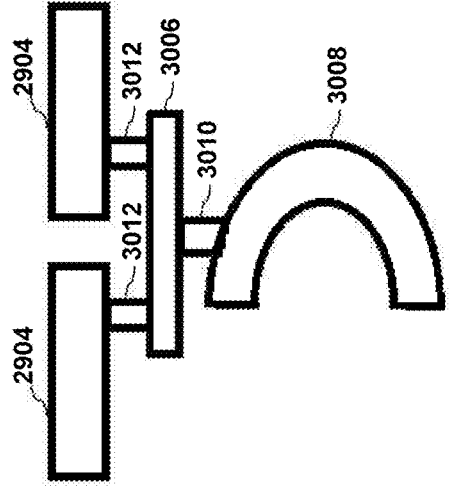

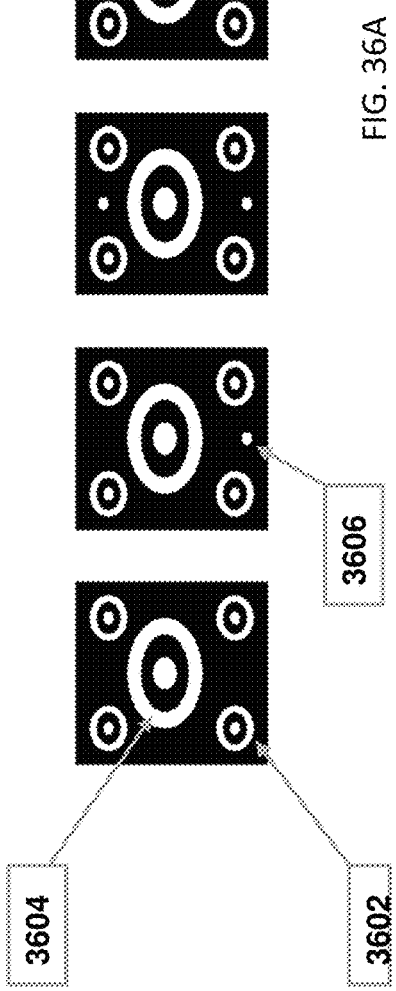
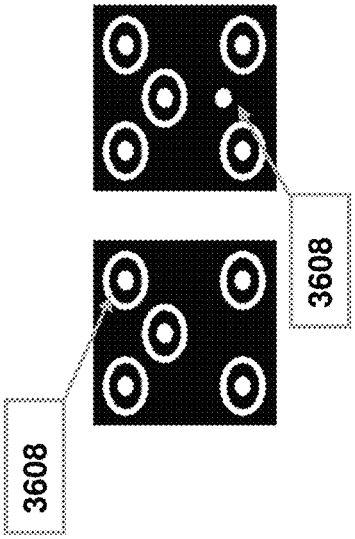
FIG. 36A
FIG. 36B

SYSTEMS, DEVICES, AND METHODS FOR TRACKING AND COMPENSATING FOR PATIENT MOTION DURING A MEDICAL IMAGING SCAN

INCORPORATION BY REFERENCE TO RELATED APPLICATIONS

The present application claims priority to U.S. Provisional Application No. 62/028,194, filed on Jul. 23, 2014, titled SYSTEMS, DEVICES, AND METHODS FOR TRACKING AND COMPENSATING FOR PATIENT MOTION DURING A MEDICAL IMAGING SCAN. The present application is related to PCT Application No. PCT/US2014/012806, filed on Jan. 23, 2014, titled SYSTEMS, DEVICES, AND METHODS FOR TRACKING AND COMPENSATING FOR PATIENT MOTION DURING A MEDICAL IMAGING SCAN, which claims priority to U.S. patent application Ser. No. 13/831,115, titled SYSTEMS, DEVICES, AND METHODS FOR TRACKING MOVING TARGETS, filed on Mar. 14, 2013, which claims the benefit of U.S. Provisional Patent Application No. 61/849,338, titled SIX DEGREES OF FREEDOM OPTICAL TRACKER, filed on Jan. 24, 2013. PCT Application No. PCT/US2014/012806 also claims priority to U.S. Provisional Patent Application No. 61/834,382, titled SYSTEMS, DEVICES, AND METHODS FOR TRACKING MOVING TARGETS, filed on Jun. 12, 2013. Each of the foregoing applications is hereby incorporated herein by reference in its entirety.

BACKGROUND

The disclosure relates generally to the field of motion tracking, and more specifically to systems, devices, and methods for tracking and compensating for patient motion during a medical imaging scan.

There are various modalities for performing medical imaging of patients. For example, magnetic resonance imaging (MRI) is a medical imaging technique used in radiology to visualize internal structures of the body in detail. An MRI scanner is a device in which the patient or a portion of the patient's body is positioned within a powerful magnet where a magnetic field is used to align the magnetization of some atomic nuclei (usually hydrogen nuclei—protons) and radio frequency magnetic fields are applied to systematically alter the alignment of this magnetization. This causes the nuclei to produce a rotating magnetic field detectable by the scanner and this information is recorded to construct an image of the scanned region of the body. These scans typically take several minutes (up to about 40 minutes in some scanners) and in prior art devices any significant movement can ruin the images and require the scan to be repeated.

U.S. Pat. No. 8,121,361, issued Feb. 21, 2012, entitled Motion Tracking System for Real Time Adaptive Imaging and Spectroscopy, describes a system that adaptively compensates for subject motion, and the disclosure therein is hereby incorporated herein by reference.

Additionally, there are various radiation therapies, proton therapies, and other therapies that can be applied to patients. For example, radiation therapy can be applied to a targeted tissue region. In some systems, radiation therapy can be dynamically applied in response to patient movements. However, in many such systems, the tracking of patient movements does not have a high degree of accuracy. Accordingly, the use of such systems can result in the application of radiation therapy to non-targeted tissue regions, thereby unintentionally harming healthy tissue while intentionally affecting diseased tissue. The foregoing is also true for proton therapies and other therapies.

SUMMARY

The disclosure herein provides systems, devices, and methods for tracking and compensating for patient motion during a medical imaging scan, such as during a magnetic resonance imaging scan.

An accurate and reliable method of determining the dynamic position and orientation of a patient's head or other body portion during MRI scanning or therapeutic procedures is a requirement in any attempt to compensate for subject motion during such procedures. Toward this end, disclosed herein are systems and methods that include practical optical head tracking capability using at least a first sensor, e.g., a first camera, and a second sensor, e.g., a second camera, such as a pair of cameras, for example ordinary CCD cameras, ordinary white light or LED illumination, and a marker or target, such as a compact, inexpensive target which mounts comfortably and rigidly to the subject's skeletal frame. The camera can be configured to detect any desired wavelength or range of wavelengths of energy, including one or more of the infrared, near-infrared, visible, or ultraviolet spectra for example. Some preferred embodiments can track head and other body motion having up to and including six degrees of freedom (sometimes referred to as 6-DOF).

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

According to some embodiments, a motion tracking system for tracking and compensating for motion of a patient during a medical imaging scan comprises: an optical marker configured to be attached to the patient, wherein the optical marker comprises a plurality of optically visible landmarks, the plurality of optically visible landmarks defining a plurality of reference points; a plurality of optical detectors, wherein each of the plurality of optical detectors is positioned to view the optical marker along a different line of sight; a marker location filter for determining locations of marker reference points, the marker location filter configured to: receive a digital image from each of the plurality of optical detectors, wherein each digital image represents a view along a different line of sight; determine, for each digital image, whether the digital image includes a view of the optical marker; and for each digital image that includes a view of the optical marker, determine positions of the plurality of reference points in the digital image; a patient orientation filter for estimating a three-dimensional pose of the patient, the patient orientation filter configured to: calculate a plurality of baseline attributes related to the plurality of reference points, the plurality of baseline attributes calculated based on the determined positions of the plurality of reference points; and estimate iteratively the three-dimensional pose of the patient, until a measure of error is within a threshold amount, the measure of error calculated based on the plurality of baseline attributes as compared to a plurality of comparison attributes, the plurality of comparison attributes calculated by assuming the object is in an estimated pose; and one or more computers configured to operate the marker location filter and patient orientation filter, wherein the one or more computers comprises a computer processor and an electronic storage medium.

In some embodiments, the patient orientation filter is configured to repeatedly estimate the three-dimensional pose of the patient at a rate of at least 100 Hz. In some embodiments, the plurality of baseline attributes comprises a set of principal quantities, the set of principal quantities comprising values associated with the relationships between the positions of reference points. In some embodiments, determining whether each digital image includes the optical marker comprises: classifying each pixel in the digital image as one of two colors; grouping one or more connected regions, wherein the connected regions are comprised of adjacent pixels with the some color; filtering out one or more connected regions based on a size threshold; computing the centroid of one or more connected regions; and grouping together one or more connected regions by their computed centroids. In some embodiments, the motion tracking system further comprises a coordinate system converter, the coordinate system converter configured to remap a coordinate system associated with the three-dimensional pose of the patient estimated by the patient orientation filter. In some embodiments, grouping together one or more connected regions comprises: identifying connected regions with centroids occurring within one pixel of each other; and calculating a centroid for each group of the one or more connected regions. In some embodiments, the motion tracking system binarizes each digital image before classifying each pixel in the digital image as white or black. In some embodiments, calculating a centroid for each group of the one or more connected regions comprises averaging the centroid for each connected region in the group of one or more connected regions. In some embodiments, the motion tracking system further comprises: a tracking filter configured to generate tracking data based on the estimated three-dimensional pose of the patient and to transmit the tracking data to a medical imaging scanner controller to enable a medical imaging scanner to dynamically adjust the medical imaging scan to compensate for patient motion. In some embodiments, the motion tracking system further comprises: the medical imaging scanner, wherein the medical imaging scanner is configured to dynamically adjust the medical imaging scan to compensate for patient motion based on the tracking data.

According to some embodiments, a motion tracking system for dynamic tracking of and compensation for motion of a patient during a magnetic resonance scan comprises: an optical marker configured to be attached to a patient being scanned; a first camera positioned to view the optical marker along a first line of sight; a second camera positioned to view the optical marker along a second line of sight; and a computer system configured to analyze images generated by the first and second cameras to determine changes in position of the optical marker, and to generate tracking data for use by a magnetic resonance scanner to dynamically adjust scans to compensate for the changes in position of the optical marker, wherein the computer system is configured to dynamically determine whether the first camera, the second camera, or both cameras are currently viewing the optical marker, and wherein the computer system is configured to dynamically adapt its image analysis to utilize images from all cameras that are currently viewing the optical marker.

In some embodiments, the motion tracking system further comprises: one or more additional cameras each positioned to view the optical marker along a different line of sight, wherein the computer system is further configured to dynamically determine which of all of the cameras are currently viewing the optical marker. In some embodiments, the motion tracking system further comprises: a third camera positioned to view the optical marker along a third line of sight; and a fourth camera positioned to view the optical marker along a fourth line of sight, wherein the computer system is further configured to dynamically determine which of all of the cameras are currently viewing the optical marker. In some embodiments, the motion tracking system further comprises: a third camera positioned to view the optical marker along a third line of sight; a fourth camera positioned to view the optical marker along a fourth line of sight; a fifth camera positioned to view the optical marker along a fifth line of sight; and a sixth camera positioned to view the optical marker along a sixth line of sight, wherein the computer system is further configured to dynamically determine which of all of the cameras are currently viewing the optical marker. In some embodiments, the motion tracking system further comprises: one or more additional optical markers configured to be attached to the patient being scanned, wherein the computer system is configured to analyze images generated by all cameras that are currently viewing at least one optical marker to determine changes in position of the optical markers, and to generate tracking data for use by the magnetic resonance scanner to dynamically adjust scans to compensate for the changes in position of the optical markers. In some embodiments, each optical marker comprises a plurality of optically visible landmarks, the plurality of optically visible landmarks defining a plurality of reference points. In some embodiments, the motion tracking system further comprises: the magnetic resonance scanner, wherein the magnetic resonance scanner is configured to dynamically adjust scans to compensate for the changes in position of the optical marker based on the tracking data.

According to some embodiments, an optical marker for use in a motion tracking system comprises: an optically visible pattern comprising a plurality of reference point locators, each reference point locator configured to define a single reference point, each reference point locator comprising alternating dark and light elliptical shapes centered on the single reference point, wherein at least one of the plurality of reference point locators is larger than at least another of the plurality of reference point locators, wherein the optically visible pattern is rotationally asymmetrical about an axis normal to a plane of the optically visible pattern.

In some embodiments, the at least one of the plurality of reference point locators that is larger than at least another of the plurality of reference point locators is centered on the optical marker in one axis of the optical marker and offset from the center of the optical marker in another axis of the optical marker. In some embodiments, the at least one of the plurality of reference point locators that is larger than at least another of the plurality of reference point locators is positioned within a boundary defined by all others of the plurality of reference point locators. In some embodiments, the optical marker further comprises: a mounting portion configured to affix the optical marker to an object being tracked. In some embodiments, the optical marker further comprises: a first substrate affixed to the mounting portion, the first substrate comprising at least one of the plurality of reference point locators; and a second substrate affixed to the mounting portion, the second substrate comprising at least one other of the plurality of reference point locators. In some embodiments, the elliptical shapes comprise circular shapes. In some embodiments, the elliptical shapes are configured to appear circular when viewed along a line of sight other than normal to the optically visible pattern. In some embodiments, each reference point is no more than 0.5 inches away from another reference point. In some embodiments, each reference point is defined by a centroid of a reference point locator. In some embodiments, the optically visible pattern further comprises one or more non-concentric dots.

According to some embodiments, a motion tracking system for dynamic tracking of and compensation for motion of a patient during a magnetic resonance scan comprises: one or more optical marker configured to be attached to a patient being scanned; one or more cameras positioned to comprise different lines of sight; and a computer system configured to analyze images generated by the one or more cameras to determine changes in position of the one or more optical markers, and to generate tracking data for use by a magnetic resonance scanner to dynamically adjust scans to compensate for changes in position of a patient based on the determined changes in position of the one or more optical markers, wherein the computer system is configured to dynamically determine which of the one or more cameras is currently viewing an optical marker, and wherein the computer system is configured to dynamically adapt its image analysis to utilize images from all cameras that are currently viewing an optical marker.

In some embodiments, each of the one or more optical markers comprises a plurality of optically visible landmarks, the plurality of optically visible landmarks defining a plurality of reference points. In some embodiments, the motion tracking system further comprises: the magnetic resonance scanner, wherein the magnetic resonance scanner is configured to dynamically adjust scans to compensate for the changes in position of the patient based on the tracking data.

In certain embodiments, a motion compensation system for tracking and compensating for patient motion during a medical imaging scan comprises: an optical marker comprising an optically visible pattern and a mounting portion, the mounting portion configured to affix the optical marker to an object being tracked, the optically visible pattern comprising a plurality of reference point locators, each locator configured to define a single reference point of a reference shape; a first optical detector positioned to digitally image the optically visible pattern along a first line of sight, the first optical detector configured to generate a first digital image of the optically visible pattern; a second optical detector positioned to digitally image the optically visible pattern along a second line of sight, the second optical detector configured to generate a second digital image of the optically visible pattern; a tracking engine configured to determine a pose of the object in six degrees of freedom by analyzing the first and second images; and a controller interface configured to generate tracking information based on the pose and to electronically transmit the tracking information to a scanner controller to enable compensation within a medical imaging scanner for object motion; wherein the tracking engine and controller interface comprise a computer processor and an electronic storage medium.

In some embodiments, the mounting portion is configured to rigidly affix the optical marker to the object being tracked. In some embodiments, the mounting portion is configured to affix the optical marker to top teeth of a patient. In some embodiments, the mounting portion is configured to be custom-fitted to the top teeth of the patient. In some embodiments, the mounting portion comprises an adhesive. In some embodiments, the optically visible pattern is located on a single unitary structure. In some embodiments, the optically visible pattern is distributed among at least two non-connected structures. In some embodiments, the optical marker is internally illuminated. In some embodiments, the plurality of reference point locators comprise alternating dark and light elliptical shapes. In some embodiments, the elliptical shapes are configured to appear circular when viewed along the first and second lines of sight when the object being tracked is in a home position. In some embodiments, the first and second lines of sight are separated by 90 degrees. In some embodiments, the elliptical shapes are configured to appear circular when viewed along a line of sight separated from a normal to the optically visible pattern by 45 degrees. In some embodiments, the first and second lines of sight are separated by 30 degrees. In some embodiments, the first and second lines of sight are separated by 60 degrees. In some embodiments, the first and second lines of sight are separated by an angle of 30 to 100 degrees. In some embodiments, the first line of sight is offset angularly by a first angle from a normal to the optically visible pattern and the second line of sight is offset angularly by a second angle from the normal to the optically visible pattern, wherein a magnitude of the first angle is the same as a magnitude of the second angle. In some embodiments, the first line of sight is offset angularly by a first angle from a normal to the optically visible pattern and the second line of sight is offset angularly by a second angle from the normal to the optically visible pattern, wherein a magnitude of the first angle is different than a magnitude of the second angle. In some embodiments, the elliptical shapes are configured to appear circular when viewed along a line of sight separated from a normal to the optically visible pattern by 15 degrees. In some embodiments, the reference shape is a triangle. In some embodiments, the reference shape is an equilateral triangle. In some embodiments, the reference shape is an equilateral triangle having a side length of 0.5 inches. In some embodiments, each reference point is no more than 0.5 inches away from another reference point. In some embodiments, each reference point is defined by a centroid of a reference point locator. In some embodiments, the reference shape is a triangle configured to appear as an equilateral triangle when viewed along the first and second lines of sight when the object being tracked is in a home position. In some embodiments, the reference shape is not optically visible. In some embodiments, the reference shape is a virtual reference shape with the reference points defining vertex points of the virtual reference shape. In some embodiments, the tracking engine is configured to take no longer than 8 milliseconds to determine the pose of the object. In some embodiments, the tracking engine is configured to take no longer than 10 milliseconds to determine the pose of the object. In some embodiments, the tracking engine is configured to repeatedly determine the pose of the object at a rate of at least 100 Hz. In some embodiments, the tracking engine is configured to repeatedly determine the pose of the object at a rate no slower than a scan rate of the medical imaging scanner. In some embodiments, the first and second optical detectors are configured to be affixed to the medical imaging scanner. In some embodiments, the first and second optical detectors are configured to be affixed to a head cage. In some embodiments, at least one of the first and second lines of sight is an indirect line of sight. In some embodiments, the indirect line of sight is redirected using a mirror. In some embodiments, the indirect line of sight is redirected using a prism. In some embodiments, the system further comprises: a light configured to illuminate the optically visible pattern. In some embodiments, the object being tracked is the head of a human patient. In some embodiments, the first and second optical detectors are configured such that the optically visible pattern is always within a field of view of the detectors when the optical marker moves within an anticipated range of motion. In some embodiments, the tracking engine is further configured to define a region of interest for each of the digital images, the region of interest comprising a portion of the digital image within which the optically visible pattern is anticipated to appear, wherein the tracking engine is configured to analyze only the region of interest in determining the pose of the object. In some embodiments, the tracking engine is configured to automatically move the region of interest based on anticipated future motion of the object being tracked. In some embodiments, analyzing the first and second images comprises: determining two-dimensional positions of the reference points in coordinate systems of the optical detectors; calculating six baseline attributes of the reference shape based on the two-dimensional positions of the reference points; estimating, iteratively, a pose of the object being tracked, until an amount of error is within a threshold amount, the amount of error being between the six baseline attributes and six comparison attributes, the six comparison attributes calculated by assuming the object is in an estimated pose. In some embodiments, the baseline and comparison attributes comprise at least one of the following: a sum of displacements of the reference shape as viewed along the first line of sight and as viewed along the second line of sight; a difference between displacements of the reference shape as viewed along the first line of sight and as viewed along the second line of sight; a difference in distance from a first reference point to a second reference point as viewed along the first line of sight and as viewed along the second line of sight; a sum of an apparent median tilt of the reference shape as viewed along the first line of sight and as viewed along the second line of sight; and a difference between an apparent median tilt of the reference shape as viewed along the first line of sight and as viewed along the second line of sight. In some embodiments, the controller interface is further configured to convert the pose of the object from a tracking coordinate system to a scanner coordinate system.

In certain embodiments, a motion compensation system for tracking and compensating for patient motion during a medical imaging scan comprises: an optical marker comprising an optically visible pattern and a mounting portion, the mounting portion configured to affix the optical marker to an object being tracked, the optically visible pattern comprising a plurality of reference point locators, each locator configured to define a single reference point of a reference shape; an optical detector positioned to digitally image the optically visible pattern along a first line of sight and along a second line of sight, the first and second lines of sight created by at least a beam splitter, the optical detector configured to generate a digital image of the optically visible pattern, the digital image comprising views of the optically visible pattern from along both the first and second lines of sight; a tracking engine configured to determine a pose of the object in six degrees of freedom by analyzing the digital image; and a controller interface configured to generate tracking information based on the pose and to electronically transmit the tracking information to a scanner controller to enable compensation within a medical imaging scanner for object motion; wherein the tracking engine and controller interface comprise a computer processor and an electronic storage medium.

In certain embodiments, a computer-implemented method of tracking motion of an object comprises: receiving, by a computer system, from a first optical detector a first digital image of an optical marker, the first digital image representing a view of the optical marker along a first line of sight; receiving, by the computer system, from a second optical detector a second digital image of the optical marker, the second digital image representing a view of the optical marker along a second line of sight, the second line of sight being different than the first line of sight, wherein the optical marker comprises a plurality of optically visible landmarks, the plurality of optically visible landmarks defining a plurality of reference points, the plurality of reference points defining a reference shape; determining, by the computer system, positions of the plurality of reference points in the first digital image; determining, by the computer system, positions of the plurality of reference points in the second digital image; calculating, using the computer system, a plurality of baseline attributes related to the reference shape, the plurality of baseline attributes calculated based on the determined positions of the plurality of reference points; and estimating iteratively, using the computer system, a three-dimensional pose of the object, until a measure of error is within an acceptable amount, the measure of error calculated based on the plurality of baseline attributes as compared to a plurality of comparison attributes, the plurality of comparison attributes calculated by assuming the object is in an estimated pose, wherein the computer system comprises a computer processor and an electronic storage medium.

In some embodiments, each of the plurality of baseline attributes is calculated based on properties of the reference shape as viewed along the first line of sight and the reference shape as viewed along the second line of sight. In some embodiments, each of the plurality of baseline attributes describes a different variation between the reference shape as viewed along the first line of sight and the reference shape as viewed along the second line of sight. In some embodiments, the plurality of baseline attributes and the plurality of comparison attributes comprise at least one of the following: a sum of displacements of the reference shape as viewed along the first line of sight and as viewed along the second line of sight; a difference between displacements of the reference shape as viewed along the first line of sight and as viewed along the second line of sight; a difference in distance from a first reference point to a second reference point as viewed along the first line of sight and as viewed along the second line of sight; a sum of an apparent median tilt of the reference shape as viewed along the first line of sight and as viewed along the second line of sight; and a difference between an apparent median tilt of the reference shape as viewed along the first line of sight and as viewed along the second line of sight. In some embodiments, the plurality of baseline attributes and the plurality of comparison attributes each comprise six attributes. In some embodiments, determining positions of the plurality of reference points in the first and second digital images comprises: determining a first coordinate set defining a first two-dimensional projection of the reference shape as viewed by the first optical detector; and determining a second coordinate set defining a second two-dimensional projection of the reference shape as viewed by the second optical detector. In some embodiments, calculating the plurality of baseline attributes comprises comparing the first projection to the second projection. In some embodiments, the method further comprises: generating, by the computer system, motion tracking data based on the estimated three-dimensional pose of the object; and transmitting electronically to a scanner controller the motion tracking data to enable a scanner to compensate for motion of the object. In some embodiments, the method takes no longer than 10 milliseconds. In some embodiments, the method takes no longer than 8 milliseconds. In some embodiments, the method further comprises repeating the method at a rate of at least 100 Hz. In some embodiments, the plurality of optically visible landmarks comprise alternative dark and light elliptical shapes. In some embodiments, the elliptical shapes are configured to appear circular when viewed along the first and second lines of sight when the object is in a home position. In some embodiments, the reference shape is a triangle. In some embodiments, the reference shape is an equilateral triangle. In some embodiments, the reference shape is a triangle configured to appear as an equilateral triangle when viewed along the first and second lines of sight when the object is in a home position. In some embodiments, the reference shape is not optically visible. In some embodiments, the reference shape is a virtual reference shape with the reference points defining vertex points of the virtual reference shape. In some embodiments, each reference point is defined by a centroid of an optically visible landmark.

Certain embodiments comprise a computer readable, non-transitory storage medium having a computer program stored thereon for causing a suitably programmed computer system to process by one or more processors computer-program code by performing a method of tracking motion of an object when the computer program is executed on the suitably programmed computer system, the method comprising: receiving, by a computer system, from a first optical detector a first digital image of an optical marker, the first digital image representing a view of the optical marker along a first line of sight; receiving, by the computer system, from a second optical detector a second digital image of the optical marker, the second digital image representing a view of the optical marker along a second line of sight, the second line of sight being different than the first line of sight, wherein the optical marker comprises a plurality of optically visible landmarks, the plurality of optically visible landmarks defining a plurality of reference points, the plurality of reference points defining a reference shape; determining, by the computer system, positions of the plurality of reference points in the first digital image; determining, by the computer system, positions of the plurality of reference points in the second digital image; calculating, using the computer system, a plurality of baseline attributes related to the reference shape, the plurality of baseline attributes calculated based on the determined positions of the plurality of reference points; and estimating iteratively, using the computer system, a three-dimensional pose of the object, until a measure of error is within an acceptable amount, the measure of error calculated based on the plurality of baseline attributes as compared to a plurality of comparison attributes, the plurality of comparison attributes calculated by assuming the object is in an estimated pose, wherein the computer system comprises a computer processor and an electronic storage medium.

In some embodiments, each of the plurality of baseline attributes is calculated based on properties of the reference shape as viewed along the first line of sight and the reference shape as viewed along the second line of sight. In some embodiments, each of the plurality of baseline attributes describes a different variation between the reference shape as viewed along the first line of sight and the reference shape as viewed along the second line of sight. In some embodiments, the plurality of baseline attributes and the plurality of comparison attributes comprise at least one of the following: a sum of displacements of the reference shape as viewed along the first line of sight and as viewed along the second line of sight; a difference between displacements of the reference shape as viewed along the first line of sight and as viewed along the second line of sight; a difference in distance from a first reference point to a second reference point as viewed along the first line of sight and as viewed along the second line of sight; a sum of an apparent median tilt of the reference shape as viewed along the first line of sight and as viewed along the second line of sight; and a difference between an apparent median tilt of the reference shape as viewed along the first line of sight and as viewed along the second line of sight. In some embodiments, the plurality of baseline attributes and the plurality of comparison attributes each comprise six attributes. In some embodiments, determining positions of the plurality of reference points in the first and second digital images comprises: determining a first coordinate set defining a first two-dimensional projection of the reference shape as viewed by the first optical detector; and determining a second coordinate set defining a second two-dimensional projection of the reference shape as viewed by the second optical detector. In some embodiments, calculating the plurality of baseline attributes comprises comparing the first projection to the second projection. In some embodiments, the method further comprises: generating, by the computer system, motion tracking data based on the estimated three-dimensional pose of the object; and transmitting electronically to a scanner controller the motion tracking data to enable a scanner to compensate for motion of the object. In some embodiments, the method takes no longer than 10 milliseconds. In some embodiments, the method takes no longer than 8 milliseconds. In some embodiments, the method further comprises repeating the method at a rate of at least 100 Hz. In some embodiments, the plurality of optically visible landmarks comprise alternative dark and light elliptical shapes. In some embodiments, the elliptical shapes are configured to appear circular when viewed along the first and second lines of sight when the object is in a home position. In some embodiments, the reference shape is a triangle. In some embodiments, the reference shape is an equilateral triangle. In some embodiments, the reference shape is a triangle configured to appear as an equilateral triangle when viewed along the first and second lines of sight when the object is in a home position. In some embodiments, the reference shape is not optically visible. In some embodiments, the reference shape is a virtual reference shape with the reference points defining vertex points of the virtual reference shape. In some embodiments, each reference point is defined by a centroid of an optically visible landmark.

In certain embodiments, a system for tracking motion of an object comprises: a marker location filter for determining locations of marker reference points, the marker location filter configured to: receive from a first optical detector a first digital image of an optical marker, the first digital image representing a view of the optical marker along a first line of sight; receive from a second optical detector a second digital image of the optical marker, the second digital image representing a view of the optical marker along a second line of sight, the second line of sight being different than the first line of sight, wherein the optical marker comprises a plurality of optically visible landmarks, the plurality of optically visible landmarks defining a plurality of reference points, the plurality of reference points defining a reference shape; determine positions of the plurality of reference points in the first digital image; and determine positions of the plurality of reference points in the second digital image;

an object orientation filter for estimating a three-dimensional pose of the object, the object orientation filter configured to: calculate a plurality of baseline attributes related to the reference shape, the plurality of baseline attributes calculated based on the determined positions of the plurality of reference points; and estimate iteratively the three-dimensional pose of the object, until a measure of error is within an acceptable amount, the measure of error calculated based on the plurality of baseline attributes as compared to a plurality of comparison attributes, the plurality of comparison attributes calculated by assuming the object is in an estimated pose; and one or more computers configured to operate the marker location filter and object orientation filter, wherein the one or more computers comprises a computer processor and an electronic storage medium.

In some embodiments, each of the plurality of baseline attributes is calculated based on properties of the reference shape as viewed along the first line of sight and the reference shape as viewed along the second line of sight. In some embodiments, each of the plurality of baseline attributes describes a different variation between the reference shape as viewed along the first line of sight and the reference shape as viewed along the second line of sight. In some embodiments, the plurality of baseline attributes and the plurality of comparison attributes comprise at least one of the following: a sum of displacements of the reference shape as viewed along the first line of sight and as viewed along the second line of sight; a difference between displacements of the reference shape as viewed along the first line of sight and as viewed along the second line of sight; a difference in distance from a first reference point to a second reference point as viewed along the first line of sight and as viewed along the second line of sight; a sum of an apparent median tilt of the reference shape as viewed along the first line of sight and as viewed along the second line of sight; and a difference between an apparent median tilt of the reference shape as viewed along the first line of sight and as viewed along the second line of sight. In some embodiments, the plurality of baseline attributes and the plurality of comparison attributes each comprise six attributes. In some embodiments, determining positions of the plurality of reference points in the first and second digital images comprises: determining a first coordinate set defining a first two-dimensional projection of the reference shape as viewed by the first optical detector; and determining a second coordinate set defining a second two-dimensional projection of the reference shape as viewed by the second optical detector. In some embodiments, calculating the plurality of baseline attributes comprises comparing the first projection to the second projection. In some embodiments, the system further comprises: a controller interface configured to: generate motion tracking data based on the estimated three-dimensional pose of the object; and transmit electronically to a scanner controller the motion tracking data to enable a scanner to compensate for motion of the object. In some embodiments, the system is configured to produce the estimated three-dimensional pose of the object in no longer than 10 milliseconds. In some embodiments, the system is configured to produce the estimated three-dimensional pose of the object in no longer than 8 milliseconds. In some embodiments, the object orientation filter is configured to repeatedly estimate the three-dimensional pose of the object at a rate of at least 100 Hz. In some embodiments, the plurality of optically visible landmarks comprise alternative dark and light elliptical shapes. In some embodiments, the elliptical shapes are configured to appear circular when viewed along the first and second lines of sight when the object is in a home position. In some embodiments, the reference shape is a triangle. In some embodiments, the reference shape is an equilateral triangle. In some embodiments, the reference shape is a triangle configured to appear as an equilateral triangle when viewed along the first and second lines of sight when the object is in a home position. In some embodiments, the reference shape is not optically visible. In some embodiments, the reference shape is a virtual reference shape with the reference points defining vertex points of the virtual reference shape. In some embodiments, each reference point is defined by a centroid of an optically visible landmark.

In certain embodiments, a computer-implemented method of tracking and compensating for motion of a patient during a medical imaging scan comprises: analyzing, by a computer system, a first digital image of an optical marker as viewed along a first line of sight, to determine a first set of two-dimensional coordinates of a plurality of reference points as viewed along the first line of sight; analyzing, by the computer system, a second digital image of the optical marker as viewed along a second line of sight, to determine a second set of two-dimensional coordinates of the plurality of reference points as viewed along the second line of sight; calculating, by the computer system, a first set of six principal quantities based on comparing attributes of the first and second sets of two-dimensional coordinates; providing, by the computer system, an estimate of an orientation of the patient in three dimensions, the estimate comprising six degrees of freedom; calculating, using the computer system, a second set of six principal quantities based on comparing attributes of theoretical reference points as viewed along the first and second lines of sight when the patient is theoretically oriented according to the estimate; determining a quantity of error between the first set of six principal quantities and the second set of six principal quantities; repeatedly modifying the estimate, calculating the second set of six principal quantities, and determining the quantity of error if the quantity of error is not within an acceptable threshold and until the quantity of error is within the acceptable threshold; generating, by the computer system, motion tracking data based on the estimate of the orientation of the patient; and transmitting electronically the motion tracking data to a scanner controller to enable compensating a medical imaging scanner for motion of the patient during the medical imaging scan, wherein the computer system comprises a computer processor and an electronic storage medium.

In some embodiments, the first set of six principal quantities is calculated based on properties of a reference shape formed by the plurality of reference points as viewed along the first line of sight and as viewed along the second line of sight. In some embodiments, each of the principal quantities of the first and second sets of six principal quantities describes a different variation between a reference shape formed by the plurality of reference points as viewed along the first line of sight and as viewed along the second line of sight. In some embodiments, the principal quantities of the first and second sets of six principal quantities comprise at least one of the following: a sum of displacements of a reference shape formed by the plurality of reference points as viewed along the first line of sight and as viewed along the second line of sight; a difference between displacements of a reference shape formed by the plurality of reference points as viewed along the first line of sight and as viewed along the second line of sight; a difference in distance from a first reference point to a second reference point as viewed along the first line of sight and as viewed along the second line of sight; a sum of an apparent median tilt of a reference shape formed by the plurality of reference points as viewed along the first line of sight and as viewed along the second line of sight; and a difference between an apparent median tilt of a reference shape formed by the plurality of reference points as viewed along the first line of sight and as viewed along the second line of sight. In some embodiments, the method takes no longer than 10 milliseconds. In some embodiments, the method takes no longer than 8 milliseconds. In some embodiments, the method further comprises repeating the method at a rate of at least 100 Hz. In some embodiments, a reference shape formed by the plurality of reference points is a triangle. In some embodiments, a reference shape formed by the plurality of reference points is an equilateral triangle. In some embodiments, a reference shape formed by the plurality of reference points is a triangle configured to appear as an equilateral triangle when viewed along the first and second lines of sight when the patient is in a home orientation. In some embodiments, a reference shape formed by the plurality of reference points is not optically visible. In some embodiments, a reference shape formed by the plurality of reference points is a virtual reference shape with the plurality of reference points defining vertex points of the virtual reference shape. In some embodiments, each reference point is defined by a centroid of an optically visible landmark.

Certain embodiments comprise a computer readable, non-transitory storage medium having a computer program stored thereon for causing a suitably programmed computer system to process by one or more processors computer-program code by performing a method of tracking and compensating for motion of a patient during a medical imaging scan when the computer program is executed on the suitably programmed computer system, the method comprising: analyzing, by a computer system, a first digital image of an optical marker as viewed along a first line of sight, to determine a first set of two-dimensional coordinates of a plurality of reference points as viewed along the first line of sight; analyzing, by the computer system, a second digital image of the optical marker as viewed along a second line of sight, to determine a second set of two-dimensional coordinates of the plurality of reference points as viewed along the second line of sight; calculating, by the computer system, a first set of six principal quantities based on comparing attributes of the first and second sets of two-dimensional coordinates; providing, by the computer system, an estimate of an orientation of the patient in three dimensions, the estimate comprising six degrees of freedom; calculating, using the computer system, a second set of six principal quantities based on comparing attributes of theoretical reference points as viewed along the first and second lines of sight when the patient is theoretically oriented according to the estimate; determining a quantity of error between the first set of six principal quantities and the second set of six principal quantities; repeatedly modifying the estimate, calculating the second set of six principal quantities, and determining the quantity of error if the quantity of error is not within an acceptable threshold and until the quantity of error is within the acceptable threshold; generating, by the computer system, motion tracking data based on the estimate of the orientation of the patient; and transmitting electronically the motion tracking data to a scanner controller to enable compensating a medical imaging scanner for motion of the patient during the medical imaging scan, wherein the computer system comprises a computer processor and an electronic storage medium.

In some embodiments, the first set of six principal quantities is calculated based on properties of a reference shape formed by the plurality of reference points as viewed along the first line of sight and as viewed along the second line of sight. In some embodiments, each of the principal quantities of the first and second sets of six principal quantities describes a different variation between a reference shape formed by the plurality of reference points as viewed along the first line of sight and as viewed along the second line of sight. In some embodiments, the principal quantities of the first and second sets of six principal quantities comprise at least one of the following: a sum of displacements of a reference shape formed by the plurality of reference points as viewed along the first line of sight and as viewed along the second line of sight; a difference between displacements of a reference shape formed by the plurality of reference points as viewed along the first line of sight and as viewed along the second line of sight; a difference in distance from a first reference point to a second reference point as viewed along the first line of sight and as viewed along the second line of sight; a sum of an apparent median tilt of a reference shape formed by the plurality of reference points as viewed along the first line of sight and as viewed along the second line of sight; and a difference between an apparent median tilt of a reference shape formed by the plurality of reference points as viewed along the first line of sight and as viewed along the second line of sight. In some embodiments, the method takes no longer than 10 milliseconds. In some embodiments, the method takes no longer than 8 milliseconds. In some embodiments, the method further comprises repeating the method at a rate of at least 100 Hz. In some embodiments, a reference shape formed by the plurality of reference points is a triangle. In some embodiments, a reference shape formed by the plurality of reference points is an equilateral triangle. In some embodiments, a reference shape formed by the plurality of reference points is a triangle configured to appear as an equilateral triangle when viewed along the first and second lines of sight when the patient is in a home orientation. In some embodiments, a reference shape formed by the plurality of reference points is not optically visible. In some embodiments, a reference shape formed by the plurality of reference points is a virtual reference shape with the plurality of reference points defining vertex points of the virtual reference shape. In some embodiments, each reference point is defined by a centroid of an optically visible landmark.

In certain embodiments, a motion tracking system for tracking and compensating for motion of a patient during a medical imaging scan comprises: a marker location filter configured to: analyze a first digital image of an optical marker as viewed along a first line of sight to determine a first set of two-dimensional coordinates of a plurality of reference points as viewed along the first line of sight; and analyze a second digital image of the optical marker as viewed along a second line of sight to determine a second set of two-dimensional coordinates of the plurality of reference points as viewed along the second line of sight; an object orientation filter configured to: calculate a first set of six principal quantities based on comparing attributes of the first and second sets of two-dimensional coordinates; provide an estimate of an orientation of the patient in three dimensions, the estimate comprising six degrees of freedom; calculate a second set of six principal quantities based on comparing attributes of theoretical reference points as viewed along the first and second lines of sight when the patient is theoretically oriented according to the estimate; determine a quantity of error between the first set of six principal quantities and the second set of six principal quantities; and repeatedly modify the estimate, calculate the second set of six principal quantities, and determine the quantity of error if the quantity of error is not within an acceptable threshold and until the quantity of error is within the acceptable threshold; a controller interface configured to: generate motion tracking data based on the estimate of the orientation of the patient; and transmit electronically the motion tracking data to a scanner controller to enable compensating a medical imaging scanner for motion of the patient during the medical imaging scan; and one or more computers configured to operate the marker location filter, object orientation filter, and controller interface, wherein the one or more computers comprises a computer processor and an electronic storage medium.

In some embodiments, the first set of six principal quantities is calculated based on properties of a reference shape formed by the plurality of reference points as viewed along the first line of sight and as viewed along the second line of sight. In some embodiments, each of the principal quantities of the first and second sets of six principal quantities describes a different variation between a reference shape formed by the plurality of reference points as viewed along the first line of sight and as viewed along the second line of sight. In some embodiments, the principal quantities of the first and second sets of six principal quantities comprise at least one of the following: a sum of displacements of a reference shape formed by the plurality of reference points as viewed along the first line of sight and as viewed along the second line of sight; a difference between displacements of a reference shape formed by the plurality of reference points as viewed along the first line of sight and as viewed along the second line of sight; a difference in distance from a first reference point to a second reference point as viewed along the first line of sight and as viewed along the second line of sight; a sum of an apparent median tilt of a reference shape formed by the plurality of reference points as viewed along the first line of sight and as viewed along the second line of sight; and a difference between an apparent median tilt of a reference shape formed by the plurality of reference points as viewed along the first line of sight and as viewed along the second line of sight. In some embodiments, the system is configured to produce the estimate of the orientation of the patient in no longer than 10 milliseconds. In some embodiments, the system is configured to produce the estimate of the orientation of the patient in no longer than 8 milliseconds. In some embodiments, the system is configured to repeatedly produce estimates of the orientation of the patient at a rate of at least 100 Hz. In some embodiments, a reference shape formed by the plurality of reference points is a triangle. In some embodiments, a reference shape formed by the plurality of reference points is an equilateral triangle. In some embodiments, a reference shape formed by the plurality of reference points is a triangle configured to appear as an equilateral triangle when viewed along the first and second lines of sight when the patient is in a home orientation. In some embodiments, a reference shape formed by the plurality of reference points is not optically visible. In some embodiments, a reference shape formed by the plurality of reference points is a virtual reference shape with the plurality of reference points defining vertex points of the virtual reference shape. In some embodiments, each reference point is defined by a centroid of an optically visible landmark.

In certain embodiments, an optical marker for use in a motion tracking system comprises: an optically visible pattern comprising a plurality of reference point locators, each reference point locator configured to define a single reference point of a reference shape, each reference point locator comprising alternating dark and light elliptical shapes centered on the single reference point; and a mounting portion configured to affix the optical marker to an object being tracked.

In some embodiments, the elliptical shapes are configured to appear circular when viewed along a line of sight other than normal to the optically visible pattern. In some embodiments, the reference shape is a triangle. In some embodiments, the reference shape is an equilateral triangle. In some embodiments, the reference shape is an equilateral triangle having a side length of 0.5 inches. In some embodiments, each reference point is no more than 0.5 inches away from another reference point. In some embodiments, each reference point is defined by a centroid of a reference point locator. In some embodiments, the reference shape is a triangle configured to appear as an equilateral triangle when viewed along a line of sight other than normal to the optically visible pattern. In some embodiments, the reference shape is not optically visible. In some embodiments, the reference shape is a virtual reference shape with the reference points defining vertex points of the virtual reference shape. In some embodiments, the marker further comprises an internal light source to illuminate the optically visible pattern. In some embodiments, the mounting portion is configured to rigidly affix the optical marker to the object being tracked. In some embodiments, the mounting portion is configured to affix the optical marker to top teeth of a patient. In some embodiments, the mounting portion is configured to be custom-fitted to the top teeth of the patient. In some embodiments, the mounting portion comprises an adhesive. In some embodiments, the optical marker is configured to be utilized as a marker for a motion compensation system for compensating for motion during a medical imaging scan. In some embodiments, the optical marker is configured to be utilized as a marker for a motion compensation system for compensating for motion during a radiation therapy process.

In certain embodiments, a system for tracking a moving target having up to six degrees of freedom and rapidly determining positions of the moving target comprises: an optical target fixed to the moving target, the optical target defining a target point; at least two cameras positioned so as to view the optical target from different directions with each of the at least two cameras being adapted to record two-dimensional images of the optical target; and a computer processor programmed to determine a target position in six degrees of freedom utilizing an algorithm configured to: identify the target point on the optical target and x, y and z displacement of the target point based on optical images collected by the at least two cameras; utilize an iteration procedure whereby an approximate first-order solution is proposed and tested against the identified target point to determine residual errors which are then divided by local derivatives with respect to each component of rotation and translation, to determine an iterative correction; repeat the iteration procedure until residual error becomes smaller than a desired accuracy; and utilize the results of the repeated iteration procedure to determine the target position at a rate of at least 100 times per second.

In some embodiments, the moving target is a human head. In some embodiments, the system is configured to interface as a component of an MRI device. In some embodiments, the iteration procedure is a variant of the Newton-Raphson method. In some embodiments, movements are measured relative to a pivot point in a patient's neck. In some embodiments, measurements are updated at a rate of at least 100 solutions per second with a latency of less than 10 milliseconds. In some embodiments, measurements are updated at a rate of at least 200 solutions per second with a latency of less than 10 milliseconds. In some embodiments, the system is adapted to report to MRI systems a position of a patient's head with accuracies better than 0.1 mm in distances and 0.1 degree in angles. In some embodiments, the optical target comprises at least three concentric sub-targets. In some embodiments, the concentric sub-targets comprise dark concentric sub targets on a high contrast diffusely reflective background. In some embodiments, the concentric sub-targets comprise high contrast diffusely reflective concentric sub-targets on a dark background. In some embodiments, the concentric sub-targets comprise dark concentric sub-targets on a high contrast retro-reflective background. In some embodiments, the concentric sub-targets comprise high contrast retro-reflective concentric sub-targets on a dark background. In some embodiments, the optical target is fixed to at least one of a patient's upper teeth. In some embodiments, the three concentric sub-targets are each concentric ellipses. In some embodiments, the computer processor is programmed to calculate centroids of each sub-target by dividing (a) a sum of a product of pixel intensity and pixel position by (b) a sum of pixel intensity in a sub-pixel array. In some embodiments, the pixel array is about 48×48 pixels.

In some embodiments, the iteration procedure comprises: locating positions of three target centroids on each of the two cameras and calculating six principal quantities: $\Sigma_{HD}$ $\Delta_{HD}$ $\Sigma_{VD}$ $\Delta_{BL}$ $\Sigma_{MT}$ $\Delta_{MT}$; making an initial guess of (0, 0, 0, 0, 0, 0) for the subject displacements and rotations ($\phi$, $\theta$, $\psi$, $\Delta x$, $\Delta y$, $\Delta z$) leading to those centroid positions; entering the guess values for ($\phi$, $\theta$, $\psi$, $\Delta x$, $\Delta y$, $\Delta z$) into a translation matrix and calculating a corresponding translated 3-D target position ($x_\perp i, y_\perp i, z_\perp i$) for each of the three target centroids; calculating a position (horizontal and vertical pixel number) of a projection of each of the three target centroids located on each camera system and calculating six principal quantities using this data from the two cameras: $\Sigma_{HD}$ $\Delta_{HD}$ $\Sigma_{VD}$ $\Delta_{BL}$ $\Sigma_{MT}$ $\Delta_{MT}$; comparing these six calculated principal quantities with measured values from locating the positions of the three target centroids; listing the differences as a matrix of errors in the guessed/calculated quantities relative to the measured quantities: ($\sigma_{\Sigma_{HD}}$, $\sigma_{\Delta_{HD}}$, $\sigma_{\Sigma_{VD}}$, $\sigma_{\Delta_{BL}}$, $\sigma_{\Sigma_{MT}}$, $\sigma_{\Delta_{MT}}$); determining local partial derivatives of: $\Sigma_{HD}$ $\Delta_{HD}$ $\Sigma_{VD}$ $\Delta_{BL}$ $\Sigma_{MT}$ $\Delta_{MT}$ by repeating the iteration procedure six times with small added displacements in each degree of freedom, one at a time; determining a coarse correction matrix by dividing the error matrix by the derivative matrix, to improve the initial guess and reduce the residual error; creating a better displacement matrix:

$$[\phi+\Delta\phi, \theta+\Delta\theta, \psi+\Delta\psi, \Delta x+\Delta(\Delta x), \Delta y+\Delta(\Delta y), \Delta z+\Delta(\Delta z)];$$

repeating a portion of the iteration procedure for a second and final iteration, starting with the coarse-corrected displacement matrix as the guess value; after each successive camera frame increment, repeating the iteration procedure, but using the result of the second and final iteration for the guess value.

In certain embodiments, a computer-implemented method for tracking a moving target having up to six degrees of freedom and rapidly determining positions of the target comprises: attaching an optical target to the moving target; positioning at least two cameras positioned so as to view the optical target from different directions with each of the at least two cameras being adapted to record two dimensional images of the optical target defining a target point; programming a computer processor to determine a target position in six degrees of freedom utilizing an algorithm adapted to: identify the target point on the optical target and the x, y and z displacement of the target point based on optical images collected by the at least two cameras; utilize an iteration procedure whereby an approximate first-order solution is proposed and tested against the identified target point to determine residual errors which are then divided by local derivatives with respect to each component of rotation and translation, to determine an iterative correction; repeat the iteration procedure until residual error becomes smaller than a desired accuracy, and utilize the results of the repeated iteration procedure to determine the target position at a rate of at least 100 times per second.

In some embodiments, the target is a human head. In some embodiments, tracking results are utilized as an input to an MRI device so as to adjust its magnetic fields to compensate for movements of the human head. In some embodiments, the iteration procedure is a variant of the Newton-Raphson method. In some embodiments, movements are measured relative to a pivot point in a patient's neck. In some embodiments, measurements are updated at a rate of at least 100 solutions per second with a latency of less than 10 milliseconds. In some embodiments, measurements are updated at a rate of at least 200 solutions per second with a latency of less than 10 milliseconds. In some embodiments, the system is adapted to report to MRI systems the position of the head with accuracies better than 0.1 mm in distances and 0.1 degree in angles. In some embodiments, the optical target comprises at least three concentric sub-targets. In some embodiments, the concentric sub-targets comprise dark concentric sub targets on a high contrast diffusely reflective background. In some embodiments, the concentric sub-targets comprise high contrast diffusely reflective concentric sub-targets on a dark background. In some embodiments, the concentric sub-targets comprise dark concentric sub-targets on a high contrast retro-reflective background. In some embodiments, the concentric sub-targets comprise high contrast retro-reflective concentric sub-targets on a dark background. In some embodiments, the three concentric sub-targets are each concentric ellipses. In some embodiments, the computer processor is programmed to calculate centroids of each sub-target by dividing (a) a sum of a product of pixel intensity and pixel position by (b) a sum of pixel intensity in a sub-pixel array. In some embodiments, the pixel array is about 48×48 pixels.

In some embodiments, the iteration procedure comprises: locating positions of three target centroids on each of the two cameras and calculating six principal quantities: $\Sigma_{HD}$ $\Delta_{HD}$ $\Sigma_{VD}$ $\Delta_{BL}$ $\Sigma_{MT}$ $\Delta_{MT}$; making an initial guess of (0, 0, 0, 0, 0, 0) for the subject displacements and rotations ($\phi$, $\theta$, $\psi$, $\Delta x$, $\Delta y$, $\Delta z$) leading to those centroid positions; entering the guess values for ($\phi$, $\theta$, $\psi$, $\Delta x$, $\Delta y$, $\Delta z$) into a translation matrix and calculating a corresponding translated 3-D target position ($x_\perp i, y_\perp i, z_\perp i$) for each of the three target centroids; calculating a position (horizontal and vertical pixel number) of a projection of each of the three target centroids located on each camera system and calculating six principal quantities using this data from the two cameras: $\Sigma_{HD}$ $\Delta_{HD}$ $\Sigma_{VD}$ $\Delta_{BL}$ $\Sigma_{MT}$ $\Delta_{MT}$; comparing these six calculated principal quantities with measured values from locating the positions of the three target centroids; listing the differences as a matrix of errors in the guessed/calculated quantities relative to the measured quantities: ($\sigma_{\Sigma_{HD}}$, $\sigma_{\Delta_{HD}}$, $\sigma_{\Sigma_{VD}}$, $\sigma_{\Delta_{BL}}$, $\sigma_{\Sigma_{MT}}$, $\sigma_{\Delta_{MT}}$); determining local partial derivatives of: $\Sigma_{HD}$ $\Delta_{HD}$ $\Sigma_{VD}$ $\Delta_{BL}$ $\Sigma_{MT}$ $\Delta_{MT}$ by repeating the iteration procedure six times with small added displacements in each degree of freedom, one at a time; determining a coarse correction matrix by dividing the error matrix by the derivative matrix, to improve the initial guess and reduce the residual error; creating a better displacement matrix:

[ϕ+Δϕ,θ+Δθ,ψ+Δψ,Δx+Δ(Δx),Δy+Δ(Δy),Δz+Δ(Δz)];

repeating a portion of the iteration procedure for a second and final iteration, starting with the coarse-corrected displacement matrix as the guess value; after each successive camera frame increment, repeating the iteration procedure, but using the result of the second and final iteration for the guess value.

In an embodiment, a system is configured for tracking a moving target having up to six degrees of freedom and rapidly determining positions of the target, said system includes an easy to locate precision optical target fixed to the target. The system can also include at least two cameras positioned so as to view the optical camera from different directions with each of the at least two cameras being adapted to record two dimensional images of the precision optical target defining a precise target point. In an embodiment, a computer processor is programmed to determine the target movement in Cartesian coordinates of x, y and z and pitch, roll and yaw utilizing an algorithm adapted to identify a set of precise target points on the precision optical target and the x, y and z displacement and the pitch, roll and yaw rotation of the precise target points based on optical images collected by the at least two cameras. The system can utilize an iteration procedure whereby an approximate first-order solution is proposed and tested against the identified precise target point projections on the cameras to determine residual errors which are then divided by the local derivatives with respect to each component of rotation and translation, to determine an iterative correction. The system can be configured to repeat the above actions until residual error becomes smaller than desired accuracy. Using this process the system can be configured to determine the position of the target at rates of at least 100 times per second with translations accuracies of about or no more than about 0.1 mm and angle accuracies of about or no more than about 0.1 degrees. With repetition rates in the range of 100 times per second, the full 6-DOF movement determination can be performed for each repetition. In these embodiments the results of each movement determination is used for the initial first order solution during the next iteration.

The six degrees of freedom movements are over orthogonal directions x, y, and z and roll, pitch and yaw angles. Direction x is along the spinal axis. Direction y perpendicular to x is along the shoulder to shoulder direction and direction z is perpendicular to both x and y and in the floor-to-ceiling direction assuming the patient is lying on his back parallel to the floor. The roll angle is about the x-axis; the angle made by a shaking head "No". The pitch angle is about the y-axis; the angle made by shaking head "Yes" and the Yaw angle is about the z-axis, the angle made by leaning head toward a shoulder.

In an embodiment, the desired accuracy is about 0.1 mm for each of the directions and about 0.1 degrees for each of the angles. Movements are measured relative to a pivot point in the patient's neck. In an embodiment the pivot point is located at the base of the patient's neck where the head swivels for nod turn and lean motions. The offset of the precision optical target from this pivot point position is Δy=0, Δx=−4.5", Δz=5.5". The precision of these offsets is not critical since all motions of interest are relative motions. The six measurements are x, y, and z distances and roll, pitch and yaw angles. In some embodiments, the measurements are up-dated at a rate of about 100 solutions per second with a latency of about 10 milliseconds. The system can be configured to report to MRI systems the exact position or the approximate position of the head with accuracies of about or better than about 0.1 mm in distances and about 0.1 degree in angles.

One possible coordinate system for reporting 6-DOF motions to the MRI field compensation system is a Cartesian system aligned with the symmetry axis of the head coil. The head coil coordinate system is coincident with body coordinates in the nominal ("square") head position. Target displacements and rotations can be reported to the coil field compensation system using this system of coordinates.

BRIEF DESCRIPTION OF THE DRAWINGS

The foregoing and other features, aspects, and advantages of the present inventions are described in detail below with reference to the drawings of various embodiments, which are intended to illustrate and not to limit the inventions. The drawings comprise the following figures in which:

FIG. 4M is another embodiment of a schematic diagram illustrating a motion compensation system.

FIG. 4N is another embodiment of a schematic diagram illustrating a motion compensation system.

FIGS. 9A and 9B show how a patient's head and two cameras are located in an MRI device, according to some embodiments of the invention.

FIGS. 20A and 20B display features of an iteration technique utilized to precisely monitor head movement utilizing the camera images of the precision optical target, according to some embodiments of the invention.

FIGS. 30A-30F illustrate various embodiments of optical marker sub targets on individual substrates.

FIGS. 36A and 36B illustrate embodiments of sets of uniquely identifiable markers.

DETAILED DESCRIPTION

Figure 1A:
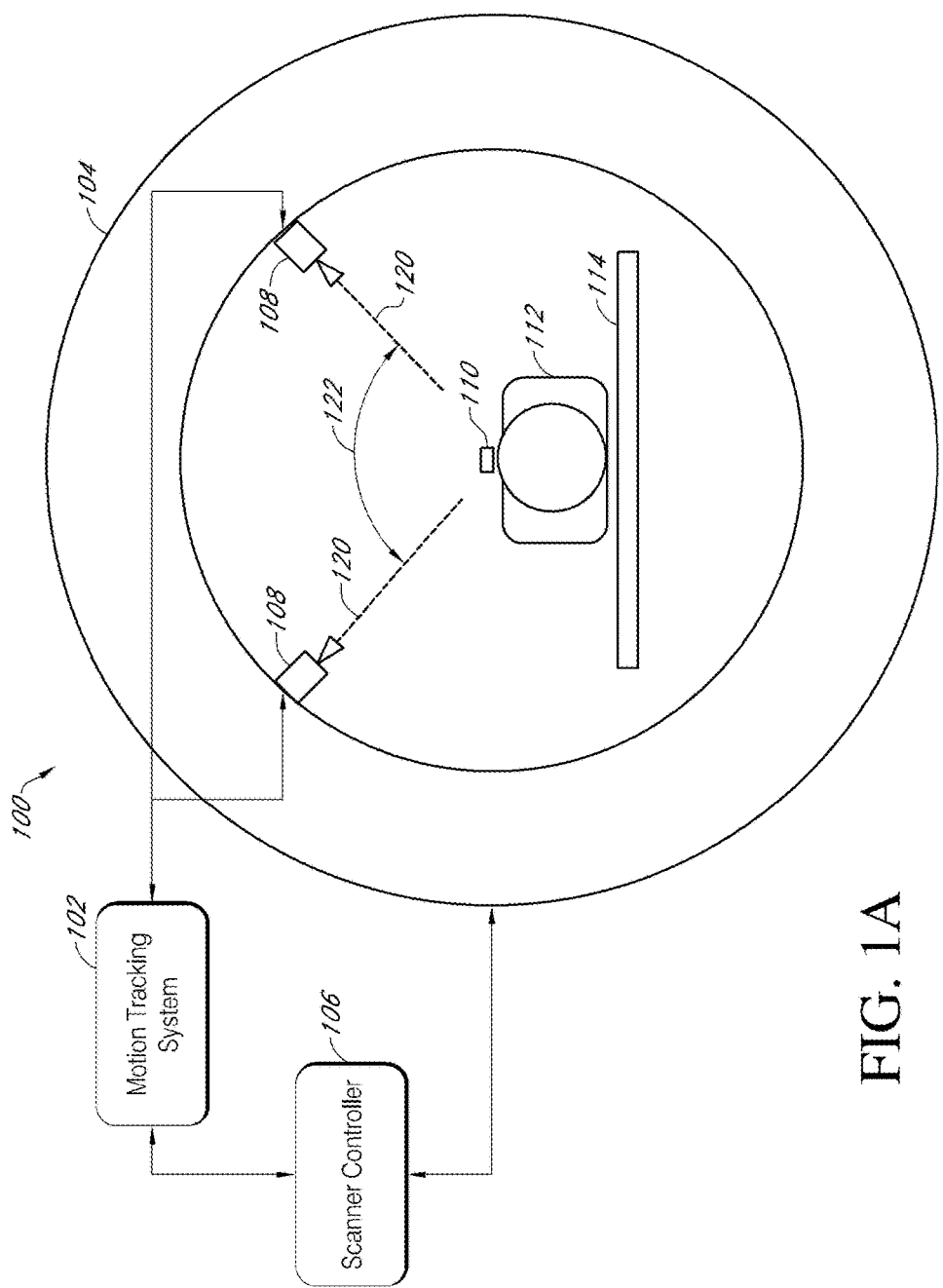
FIG. 1A is an embodiment of a schematic diagram illustrating a front view of a medical imaging scanner as a part of a motion compensation system.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

With the use of diagnostic technologies and therapeutic technologies, it can be advantageous to track for patient movement with a high degree of accuracy. Such high accuracy tracking can improve the imaging quality obtained and produced by diagnostic equipment, such as imaging technologies. Further, the use of high accuracy patient movement tracking technology can improve the application of patient therapies, such as radiation treatment, proton treatment, and the like. By accounting for patient movement with a high degree of accuracy, therapeutic technologies can apply therapies only to the targeted tissue and avoid healthy surrounding tissue.

The embodiments disclosed herein relate to a patient motion tracking system that can track patient movement with translation accuracies of about 0.1 mm and angle accuracies of about 0.1 degrees. As disclosed herein, the system can be configured to utilize a non-stereo approach to determining the 6 degrees of freedom movement of the patient. In an embodiment, the system can comprise two cameras that are positioned orthogonal and perpendicular on a single plane. In an embodiment, the two cameras need not be in a single plane, but are positioned such that the two cameras are not viewing the target from generally the same direction. The system can be configured to compare the appearance of the target on one camera with the other camera while not accounting for which pixel number they fall on in either camera. By comparing the appearance of the target between the two cameras, the system can be configured to extract the 6 degrees of freedom movement on a very small target.

In an embodiment, the system can be configured to extract the movement data based on analyzing the images of the target from the two cameras in order to generate a predicted value for at least one of the variables in the 6 degrees of freedom. For example, the system can be configured to analyze the image of the target and predict a value for the pitch. The system can then be configured to compare the predicted value to the value of the particular variable with that which is shown in the actual image of the target. The system can be configured to repeat this process using an iterative approach to continuously improve the predicted value of one of the variables in the 6 degrees of freedom. The system can be configured to perform this iterative process for each variable in the 6 degrees of freedom.

The foregoing methodology for tracking patient movement can be applied in the diagnostic context as well as in the therapeutic context. For example, as disclosed herein, the system can be configured to track patient movement in order to feed such movement data to an MRI scanner such that the MRI scanner can adjust the focus and position of the scanner in order to produce a clear MRI image of the patient. Further, the system can be configured to connect to therapeutic technologies. For example, the system can be configured to track patient movement in order to direct a therapeutic radiation beam at a diseased tissue region while avoiding surrounding healthy tissue.

There are various technologies for therapeutic radiation and other therapeutics. For example, it can be advantageous in radiation therapy, proton therapy, or other therapies to dynamically apply the radiation to a targeted area in order to account for patient movement. Patient movement can include respiration, twitches or any other voluntary or involuntary movements of the patient. By dynamically and automatically tracking patient movement, radiation therapy, proton therapy, and any other kind of therapy can be applied in a more targeted way, thereby allowing surrounding healthy tissue to be avoided and/or unharmed. The systems disclosed herein can be adapted and configured to track patient translations with accuracies of about 0.1 mm and angle accuracies of about 0.1 degrees in order to better apply radiation therapy, proton therapy, or any other therapy to the targeted tissue or area of the body.

In an embodiment, a system can be configured to utilize optical tracking based on the methods disclosed herein in order to track patient movement and/or or another device, for example, electronics packages that are configured to identify fiducial markers implanted inside a patient. In an embodiment, the system can be configured to utilize the electronics package in order to identify the location of the fiducial markers within the patient. By identifying the location of the fiducial markers, the system needs to identify the location of the electronics package in order to determine the location of the fiducial markers with respect to a scanner and/or a therapeutic equipment device.

The patient tracking movement system, disclosed herein, can be utilized to track periodic involuntary movement of the patient, such as breathing. By tracking the periodic patient movement with a high degree of accuracy, the system can be configured to apply a radiation therapy, a proton therapy, or the like during strategic moments when the target tissue is in a certain position while the patient's involuntary movements continue. Additionally, the system can be configured to track not only normal breathing movement of the patient, but also the system can be configured to track irregular movement of the patient caused by patient activity or based on diseased tissue of the patient. For example, when a patient is running, the ribs of the patient have a larger egression that the system can track in order to continuously identify a target tissue area. In another example, the patient may be suffering from COPD or other breathing disorder or diagrammatic issues. For example, the patient could be suffering from theurofusion, which is water outside the lung that prevents the patient from breathing or a tumor is irritating a lung region thereby preventing normal breathing. The system can be configured to track such irregular patient movements due to such conditions.

In order to apply a therapy, such as radiation therapy, the radiation beam generator must determine the location of the electronics package relative to the beam generator in order to properly direct the radiation therapy to the targeted tissue. Accordingly, it is necessary to track the position of the electronics package relative to the radiation beam generator or other therapeutic equipment. It can be advantageous to track the position of the electronics package with a high degree of accuracy in order to better target the desired tissue. In systems where the electronics package is configured to track the location of fiducial markers implanted within the patient, such systems have two possible sources of error. One source of error can be derived from tracking the position of the fiducial markers using the electronics package and the second source of error can be derived from tracking the position of the electronics package relative to the therapeutic equipment generator. Accordingly, it can be advantageous to identify the position of the electronics package with a high degree of accuracy in order to avoid compounding the sources of error.

Motion Compensation Systems

Figure 1B:
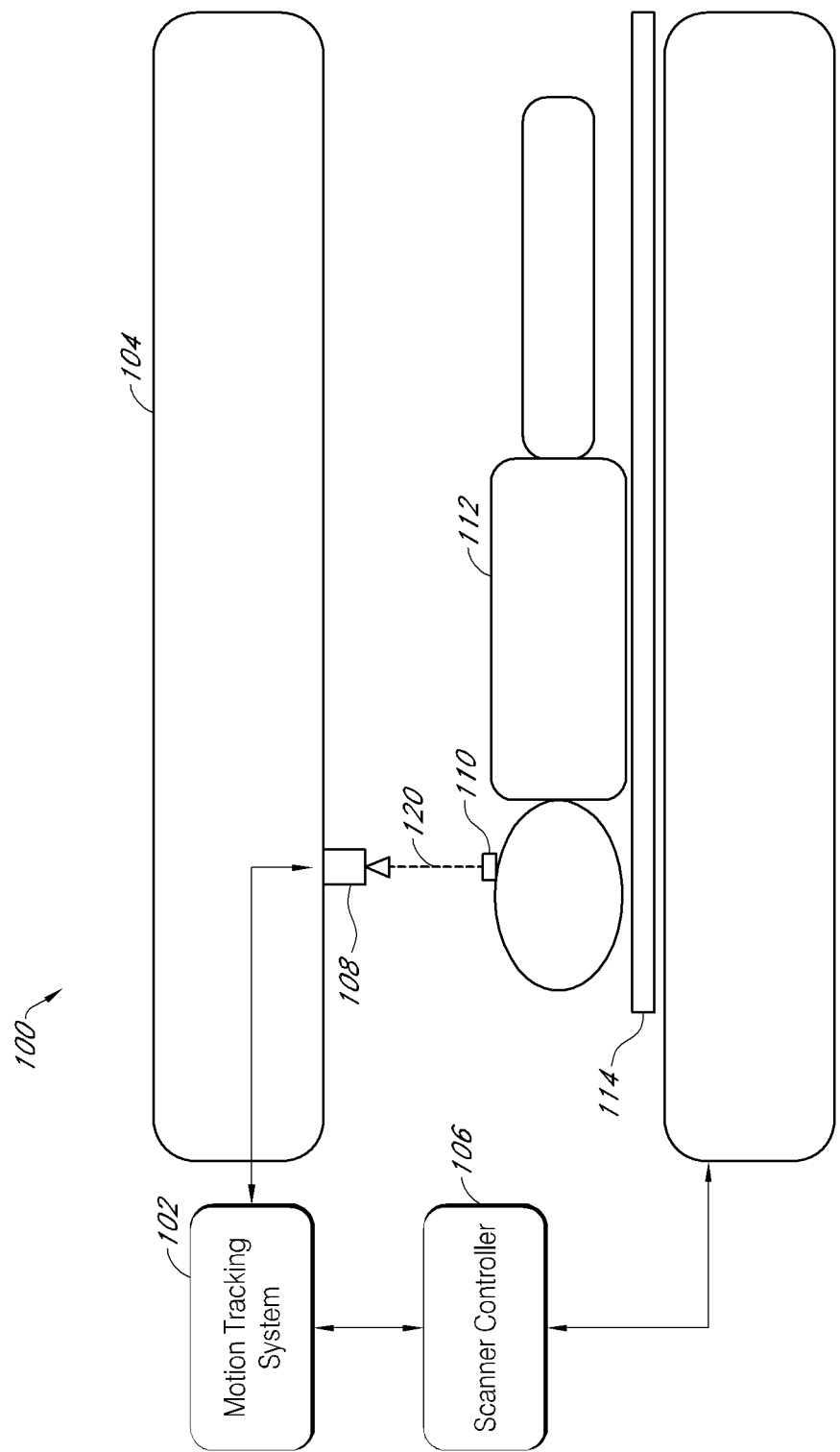
FIG. 1B is a schematic diagram illustrating a side view of the medical imaging scanner as a part of the motion compensation system of FIG. 1A.

FIG. 1A is an embodiment of a schematic diagram illustrating a front view of a medical imaging scanner 104 as part of a motion compensation system 100. FIG. 1B is a schematic diagram illustrating a side view of the medical imaging scanner 104 as a part of the motion compensation system 100 of FIG. 1A. The motion compensation system 100 can be used to, for example, track the motion of a patient undergoing a medical imaging procedure to enable a medical imaging scanner to adjust or otherwise compensate for that motion, to reduce or eliminate motion artifacts in the resulting medical images. The motion compensation system 100 illustrated in FIGS. 1A and 1B comprises a motion tracking system 102, a scanner 104, a scanner controller 106, two detectors 108, and an optical marker or target 110. In this embodiment, the optical marker 110 is shown attached to a patient 112 positioned on a table 114 of the medical imaging scanner 104. The scanner 104 can be, for example, a magnetic resonance imaging scanner. The optical marker 110 can be configured as further described below, for example as described in reference to FIG. 2A.

In this embodiment, the optical marker 110 is configured to be viewable by each of the two detectors 108. The detectors 108 can be, for example, digital cameras capable of acquiring images of the optical marker 110 and transmitting those images to the motion tracking system 102. In this embodiment, each of the detectors 108 is configured to view the optical marker 110 from along a different line of sight. This can be helpful, for example, to enable the motion tracking system 102 to analyze two dimensional images of the optical marker 110 from different vantage points to help in locating the optical marker 110 to estimate patient motion or pose. In this embodiment, the detectors 108 each are configured to view the optical marker 110 along a line of sight 120 separated from each other by an angle 122. In this embodiment, the angle 122 is approximately 90 degrees. Other angles may be used, such as 30 degrees, 45 degrees, 60 degrees, 70 degrees, etc. In some embodiments, 90 degrees is an optimal angle to enable maximum differentiation of in plane and out of plane motion of the optical marker 110, as further described below with reference to FIGS. 8A and 8B. For example, if the optical marker 110 moves in a direction that is directly along the line of sight of one detector, that detector may have a harder time distinguishing motion of the optical marker 110 than the other detector. On the other hand, the other detector may relatively easily detect the motion of the optical marker 110, as the motion is perpendicular to that detector's line of sight.

In some embodiments, the angle 122 may be referred to as a scissor angle. In the embodiment illustrated in FIG. 1A, the scissor angle is the angle at which the detectors 108 are directly viewing the marker 110. However, in other embodiments, the scissor angle may be a virtual angle, as the lines of sight from the detectors to the marker may be redirected by mirrors and/or other means, such as beam splitters, prisms, fiber optics, and/or the like. In that case, the scissor angle is the apparent angle at which the detectors are viewing the marker. For example, as further described below with reference to FIGS. 4E and 4F, the detectors 108 of the motion compensation system 440 are positioned with lines of sight collinear to each other near the detectors. However, mirrors are utilized to redirect the lines of sight such that a virtual scissor angle of approximately 90 degrees is accomplished near the marker.

Mirrors or other devices used to redirect a line of sight have both advantages and disadvantages. For example, disadvantages of mirrors include that they could potentially vibrate, potentially introducing error into the object orientation determination process. As another example, the further away a mirror is from a detector, generally the larger the mirror needs to be to enable an equivalent range of vision. Accordingly, it can be advantageous to position a mirror relatively close to a detector to enable the mirror to be relatively small. One advantage of using mirrors or other sight line redirection methods is that a virtual scissor angle can be configured to be closer to an optimal scissor angle of 90°, even when a particular medical imaging scanner configuration may not allow for detectors that are positioned to directly view a marker using a 90° scissor angle. Further, some mirrors are not conductive, which can be advantageous in magnetic resonance imaging, because nonconductive mirrors will not introduce artifacts into MRI images. A digital camera, on the other hand, may include conductive components and/or a wire leading to the detector may include conductive components. When a digital camera and/or its wire are within the medical imaging envelope, they may introduce artifacts into MRI images.

The embodiment of a motion compensation system 100 illustrated in FIGS. 1A-1B is not shown to scale, but is rather show at a scale that helps facilitate illustration of the system. Other figures, such as is shown in FIGS. 4A-4K, are also not shown to scale. Additionally, most embodiments illustrated in these figures and described in this specification comprise a motion compensation system operating in real time or substantially in real time to correct a scanner for motion of a patient or object. However, in other embodiments, a motion compensation system can be configured to operate by processing images using post-processing after they have been created by a scanner to remove any motion artifacts.

In the embodiment of a motion compensation system 100 illustrated in FIGS. 1A and 1B, the detectors 108 are positioned at an angle of approximately 90 degrees along a transverse axis of the scanner 104, but are positioned at an angle of approximately 0 degrees along a longitudinal axis of the scanner 104, as shown in FIG. 1B. In this embodiment, the detectors 108 are configured to be positioned directly above a nominal home position of the optical marker 110, as shown in FIG. 1B. However, the detectors may be setup in various other configurations, as further described below.

Figure 2B:
FIG. 2B is a perspective view of the optical marker of FIG. 2A in use with a patient.
Figure 2C:
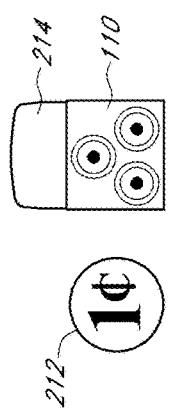
FIG. 2C is a front view of the optical marker of FIG. 2A, the optical marker shown next to a U.S. penny for scale.
Figure 2A:
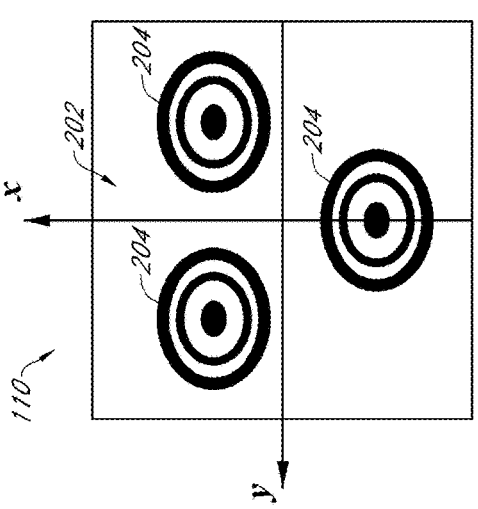
FIG. 2A is a front view of an embodiment of an optical marker.

FIGS. 2A-2C illustrate one embodiment of an optical marker 110 used with a motion compensation system. FIG. 2A is a front view of the optical marker 110. FIG. 2B is a perspective view of the optical marker 110 of FIG. 2A in use with a patient 112. FIG. 2C is a front view of the optical marker of FIG. 2A, the optical marker shown next to a U.S. penny 212 for scale.

The optical marker 110 comprises a pattern 202 that defines a reference shape. In this embodiment, the pattern 202 defines a reference shape of an equilateral triangle having sides of approximately 0.5 inches. At each vertex of the equilateral triangle reference shape is a reference point locater 204. In this embodiment, each reference point locater 204 comprises a series of alternating black and white (or dark and light) elliptical shapes, with a centroid of the reference point locater 204 being positioned at the vertex of the equilateral triangle reference shape. In various embodiments, different reference shapes can be used and reference point locators can take various forms, as long as the reference point locators are able to be detected and analyzed by a motion tracking system to determine important points, inflection points, critical points, or vertex points of a reference shape.

In this embodiment, the reference point locators 204 are elliptical in shape and positioned such that they are configured to be visible as a circular pattern from a 45 degree viewing angle. This can be advantageous, because, when used in a system such as the example illustrated in FIGS. 1A and 1B, where the detectors 108 are viewing the optical marker 110 along a 45 degree sight line, any images of the optical marker 110 at the nominal home location will illustrate the reference point locators 204 as circles. Then, if the marker is moved, that motion will result in a non-circular elliptical pattern showing up on the images of the optical marker. Further description of the optical marker configuration is given below.

FIG. 2B illustrates that the optical marker 110 can, in some embodiments, be configured to mount to a patient's top teeth. This can be advantageous to retain or affix the optical marker 110 in a rigid or substantially rigid location with respect to the patient's skull. As described below, various methods and devices may be used to attach an optical marker to a patient or other object of interest.

Figure 3A:
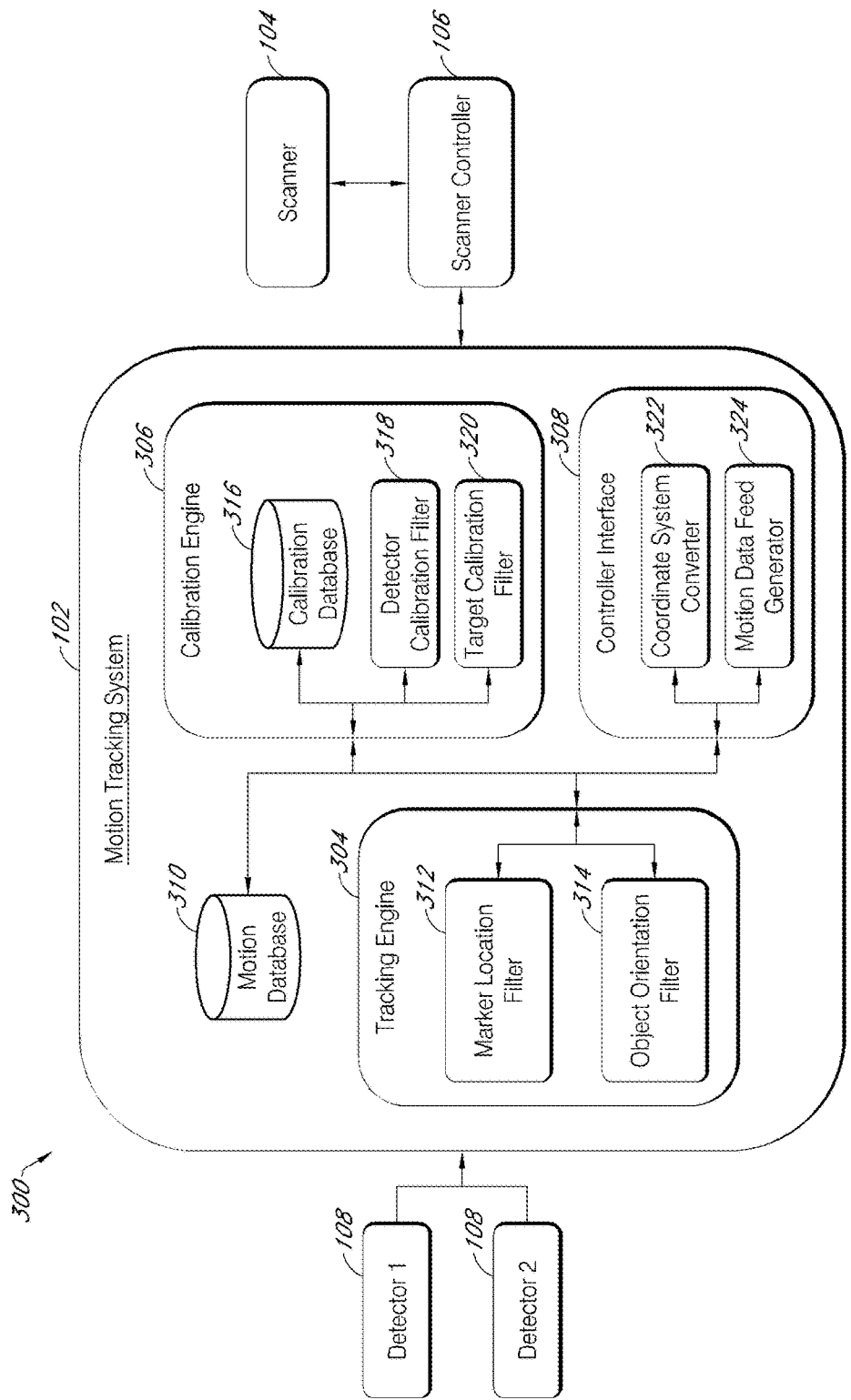
FIG. 3A is a block diagram depicting an embodiment of a motion compensation system.

FIG. 3A is a block diagram depicting an embodiment of a motion compensation system 300. The motion compensation system 300 can be similar to, for example, the motion compensation system 100 illustrated in FIGS. 1A and 1B. The motion compensation system 300 comprises two detectors 108, a motion tracking system 102, a scanner 104, and a scanner controller 106. The scanner 104 is a medical imaging scanner, such as an MRI machine. The scanner controller 106 can be configured to operate and control the scanner 104, such as by adjusting the scanner 104 in real time or substantially real time to correct for motion of the object or patient being scanned. The scanner controller 106 can adjust for motion based on motion tracking data or information received from the motion tracking system 102.

The detectors 108 can comprise, for example, digital cameras. Although in this embodiment there are two detectors 108, various other embodiments may utilize more or fewer detectors based on the application. For example, an embodiment of a motion compensation system may comprise more detectors to increase accuracy of motion tracking and/or to add redundancy to a motion compensation system. For example, a motion compensation system may comprise four detectors, with motion tracking being performed only using two of the detectors at any one time. This may be advantageous, for example, when obstructions may hide an optical marker from view of one or more detectors depending on the position of the object being tracked.

Although in this embodiment and various other embodiments described herein the detectors are optical digital cameras, various other motion compensation systems may utilize detectors other than optical cameras. For example, a detector may be an infrared camera configured to view a target or marker viewable by an infrared camera. In other embodiments, the detectors may comprise laser detectors, sonar detectors, radar detectors, and various other types of detectors capable of locating a marker and/or creating a two dimensional digital image or representation of a marker.

The motion tracking system 102 comprises a tracking engine 304, a calibration engine 306, a controller interface 308, and a motion database 310. The motion database 310 can be configured to store motion tracking information, such as object pose estimates created by the tracking engine 304. In some embodiments, the motion database 310 can be configured to be persistent storage to store the motion information for later retrieval and usage after the completion of an imaging scan. In some embodiments, the motion database 310 comprises a short term memory or buffer or cache to store object pose estimates just temporarily until they are included in motion data and sent to the scanner controller 106 by the controller interface 308.

The calibration engine 306 can be configured to calibrate the motion compensation system. The calibration engine 306 comprises a calibration database 316, a detector calibration filter 318, and a target calibration filter 320. In some embodiments, the calibration engine 306 can be configured to calibrate the system at initial startup or initial system assembly, with calibration not being needed for later operation of the motion compensation system 300. In other embodiments, the calibration engine 306 is utilized for at least some calibration procedures during some or all motion tracking procedures. The detector calibration filter 318 can be configured to calibrate the detectors 108 to the motion compensation system. In some embodiments, the detector calibration filter 318 can be configured to calibrate the detectors by enabling a manufacturer or assembler of the motion compensation system to input information specific to each detector 108, such as focal length, resolution, etc. In some embodiments, the detector calibration filter 318 can be configured to automatically determine some or all of the parameters needed to calibrate a detector 108. The parameters determined in calibration of the detectors can be stored in the calibration database 316 for later use by the tracking engine 304.

The target calibration filter 320 can be configured to calibrate the system to one or more specific targets or markers. For example, the target calibration filter 320 can be configured to, upon initial startup of a motion tracking routine, analyze images received from the detectors 108 to determine a region of interest in the images where it is most likely that the optical marker exists. This information can be stored in the calibration database 316. This initial calibration upon startup of a motion tracking routine can, for example, help to speed up a tracking routine.

The tracking engine 304 comprises a marker location filter 312 and an objection orientation filter 314. The tracking engine 304 can be configured to track the location of one or more optical markers during an imaging scan and to determine an estimate of the pose of the object or patient being scanned. In some embodiments, the marker location filter 312 can be configured to analyze images from the detectors 108 to determine locations of reference points of an optical marker in the 2D images from the detectors. The marker location filter 312 can be configured to analyze these images to determine both the locations of these points and the orientation of the reference shape or shapes formed by the reference points. The object orientation filter 314 can be configured to utilize the marker location information from the marker location filter 312 to convert that information into an estimated object pose. The object orientation filter 314 can be configured to then pass the estimated object pose information off to the motion database 310 and/or the controller interface 308 for use by the scanner controller 106.

The tracking engine 304 can utilize various processes or algorithms in determining the location of marker reference points and converting this information into estimated object poses. Some examples of these processes or algorithms are described in more detail below. However, various other processes or algorithms can be used with the techniques disclosed herein.

The controller interface 308 can be configured to convert object pose information into a coordinate system of the imaging scanner and to pass this information to the scanner controller 106. The controller interface 308 comprises a coordinate system converter 322 and a motion data feed generator 324. The coordinate system converter 322 can be configured to take the estimated object pose information from the tracking engine 304 and/or the motion database 310 and convert that object pose information from the motion tracking system's coordinate system into the scanner's coordinate system. The motion data feed generator 324 can be configured to take the converted object pose information and transmit it to the scanner controller 106. In some embodiments, the motion data feed generator 324 is configured to transmit object pose information to the scanner controller 106 immediately as the object pose information becomes available. In other embodiments, the motion data feed generator 324 can be configured to sync the timing of the motion tracking system 102 with the scanner controller 106. For example, the motion tracking system 102 may be configured to acquire images and estimate object poses at a rate of approximately 100 hertz. The scanner controller 106 and scanner 104 may, on the other hand, be configured to take scans at a different rate. The motion data feed generator 324 can therefore be configured to match the motion tracking system's output speed to the scanner and/or scanner controller speed. In some embodiments, this may involve caching converted object pose information until it is necessary to send that information to the scanner controller 106. In some embodiments, the motion data feed generator 324 is configured to obtain multiple object poses and to combine these, such as by averaging, before sending them to the scanner controller 106. In other embodiments, the motion data feed generator 324 is configured to transmit only the latest object pose estimate to the scanner controller 106. In some embodiments, the motion data feed generator 324 is configured to retransmit the last object pose estimate sent to the scanner controller 106 if the motion tracking system 102 has not generated a new object pose estimate since the last time the motion data feed generator 324 sent an object pose estimate to the scanner controller 106.

As described above, although the motion compensation system 300 illustrated in FIG. 3A is disclosed in a system configured to adjust a scanner in real time or substantially in real time to adjust for patient motion, other embodiments may utilize a motion compensation system to adjust acquired images after the scanning process to remove motion artifacts. In some embodiments, the scanner can be configured to adjust for motion in real time and to post process images to remove any remaining motion artifacts based on the tracked motion.

Although the motion compensation system 300 illustrated in FIG. 3A illustrates the motion tracking system 102 as being a separate system from the scanner controller 106, in some embodiments, the motion tracking system 102 can be integrated into the scanner controller 106. For example, a medical imaging scanner can be produced with an integrated scanner controller comprising features to both control the scanner and to track object or patient motion during scan.

Figure 3B:
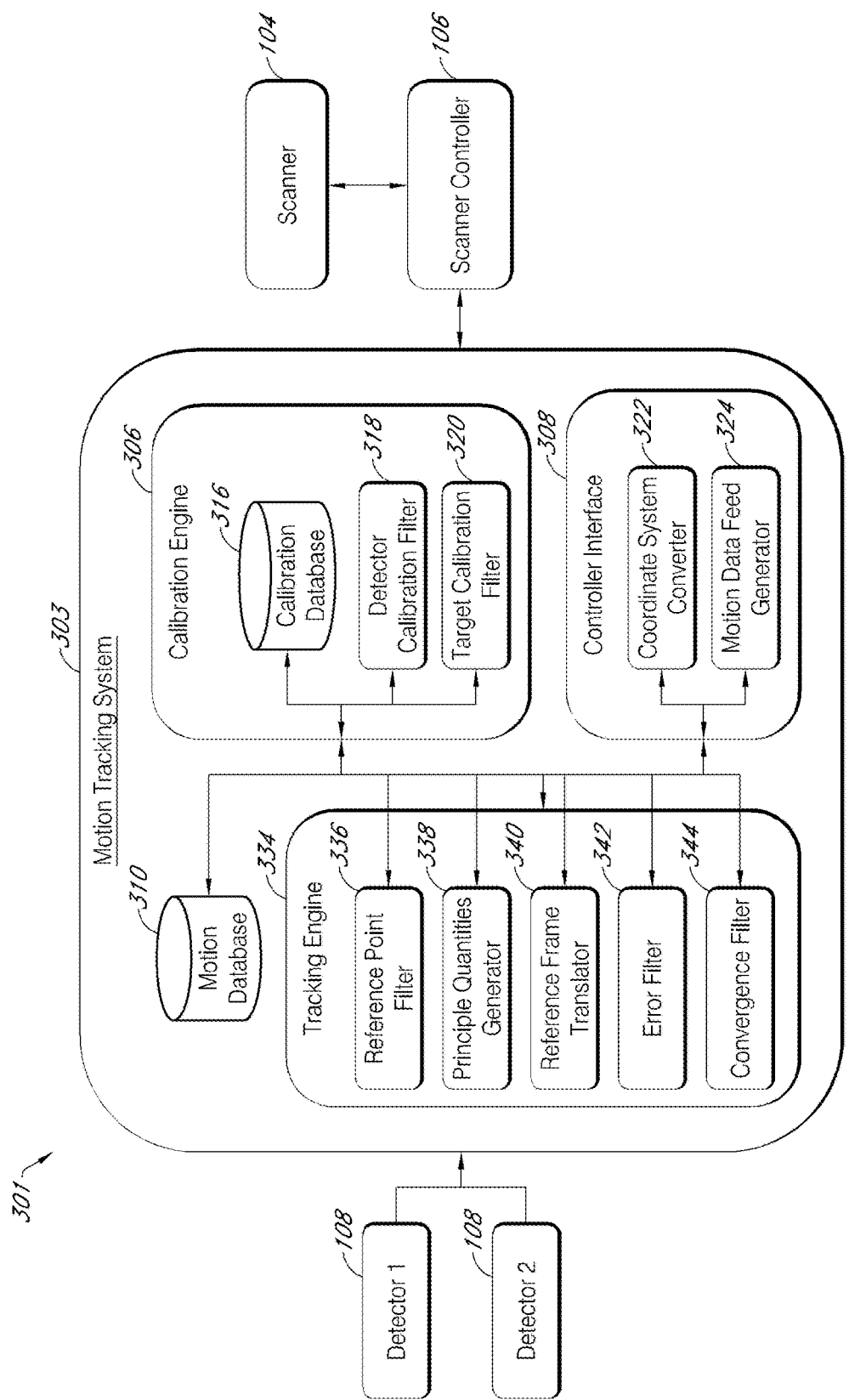
FIG. 3B is a block diagram depicting another embodiment of a motion compensation system.

FIG. 3B is a block diagram depicting another embodiment of a motion compensation system 301. The motion compensation system 301 illustrated in FIG. 3B is similar to the motion compensation system 300 illustrated in FIG. 3A. The motion compensation system 301, however, utilizes a different tracking engine 334 than the tracking engine 304 illustrated in FIG. 3A. The tracking engine 334 comprises a reference point filter 336, a principal quantities generator 338, a reference frame translator 340, an error filter 342, and a convergence filter 344. The components of the tracking engine 334 can be configured to operate to track the motion of an object or patient using, for example, the process flow described below with reference to FIG. 7C.

The reference point filter 336 can be configured to, among other things, analyze two dimensional images of an optical marker to determine the locations of the reference points of that marker. The principal quantities generator 338 can be configured to analyze the reference shape formed by the reference points, as viewed by two or more detectors, to determine a number of principal quantities, such as six, that can be used to help describe or define the 3D position and orientation of the optical marker.

The reference frame translator 340 can be configured to convert between the two dimensional reference frame of each detector and the three dimensional frame of the motion tracking system. The error filter 342 can be configured to analyze differences in principal quantities based on the visualized reference points and based on estimates of an object pose to determine an amount of error between the two. The convergence filter 344 can be configured to perform iterative processes to reduce an amount of error in an object pose estimate until an object pose estimate has an acceptable amount of error. The tracking engine 334 can be configured to communicate with the motion database 310, calibration engine 306, and controller interface 308 similarly to as described above with respect to the motion compensation system 300 of FIG. 3A.

Other Embodiments of Motion Compensation Systems

Figure 4A:
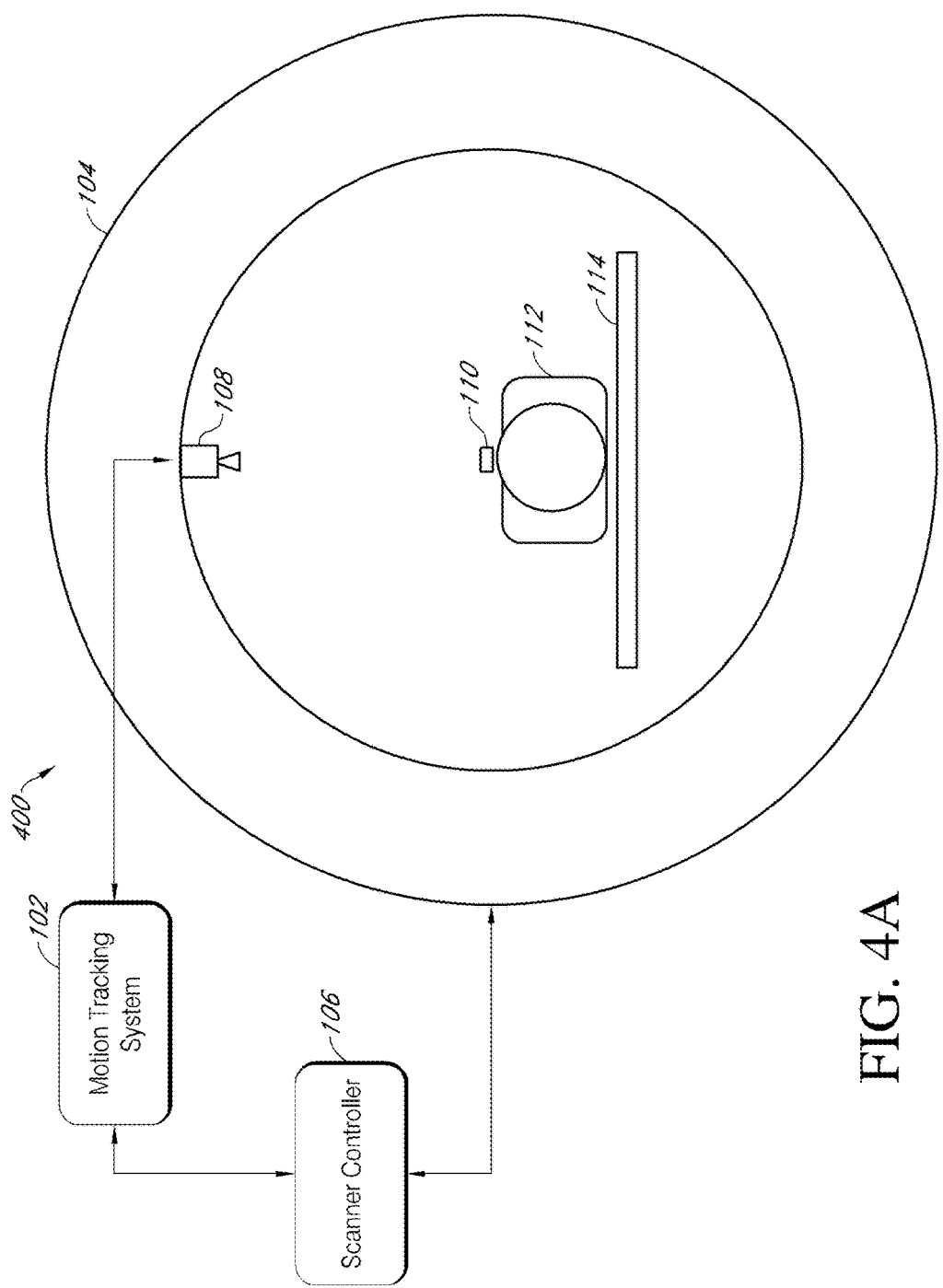
FIG. 4A is another embodiment of a schematic diagram illustrating a front view of a medical imaging scanner as part of a motion compensation system.
Figure 4B:
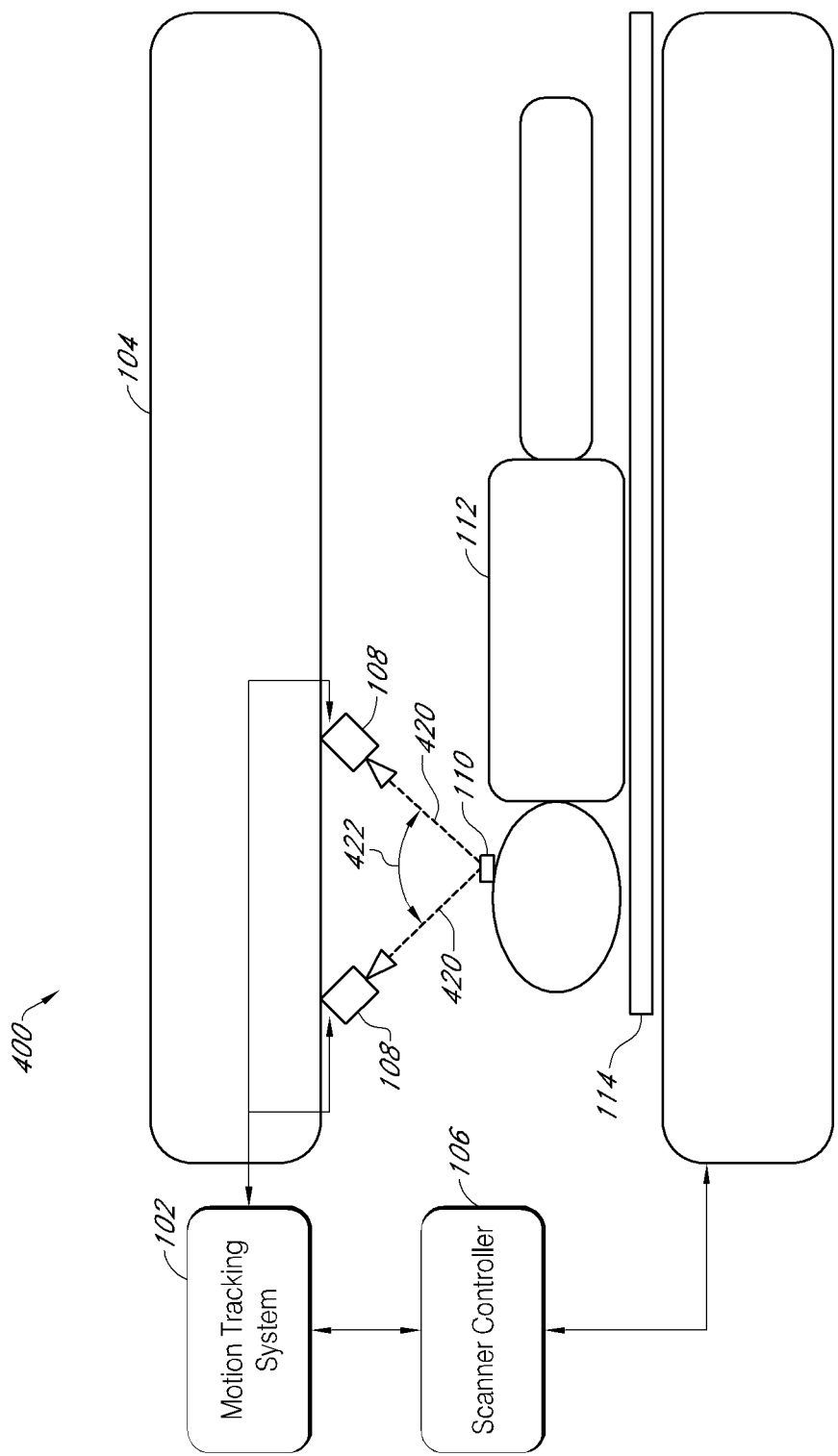
FIG. 4B is a schematic diagram illustrating a side view of the medical imaging scanner as a part of the motion compensation system of FIG. 4A.

FIG. 4A is another embodiment of a schematic diagram illustrating a front view of a medical imagine scanner 104 as part of a motion compensation system 400. FIG. 4B is a schematic diagram illustrating a side view of the medical imaging scanner 104 as part of the motion compensation system 400. The motion compensation system 400 is similar to the motion compensation system 100 illustrated in FIGS. 1A and 1B. However, the motion compensation system 100, as described above, comprises two detectors 108 positioned at a 90 degree angle to each other along a transverse axis of the scanner 104. In the motion compensation system 400, the detectors 108 are positioned at a 90 degree angle 422 to each other along the longitudinal axis of the scanner 104. The detectors 108 of the motion compensation system 400 are still configured to view the optical marker 110 along two different lines of sight 420. The motion compensation system 400 illustrates that the detectors 108 can be positioned in various ways, as long as each detector 108 views the optical marker 110 along a different line of sight. The angle 422, as described above with respect to the angle 122, can vary and be larger or smaller. In some embodiments, the angle 422 can be between 100 degrees and 70 degrees. In other embodiments, the angle 422 can be 30 degrees. For example, FIG. 4K illustrates a motion compensation system 490 similar to the motion compensation system 400, except that the angle 422 is 30 degrees. In other embodiments, the angle can be various other angles, as long as the two lines of sight 420 are different. Further, in some embodiments, as described above, a motion compensation system may comprise more than two detectors, such as four, six, eight, and the like, to add redundancy to the motion compensation system. For example, an MRI head cage may obstruct a view of a marker when the patient is in a particular position. However, if there are redundant detectors, there is an increased chance that robust motion tracking will continue despite one or more detectors' lines of sight being obstructed. In some embodiments, the detectors may be positioned as is illustrated in FIG. 4K, but at different angles 122. For example, a first set of two detectors 108 may be positioned at an angle 122 of 30 degrees, and a second set of redundant detectors 108 (for a total of four detectors) may be positioned at a different angle, such as, for example, 40, 50, 60, 70, 80, or 90 degrees.

Figure 4C:
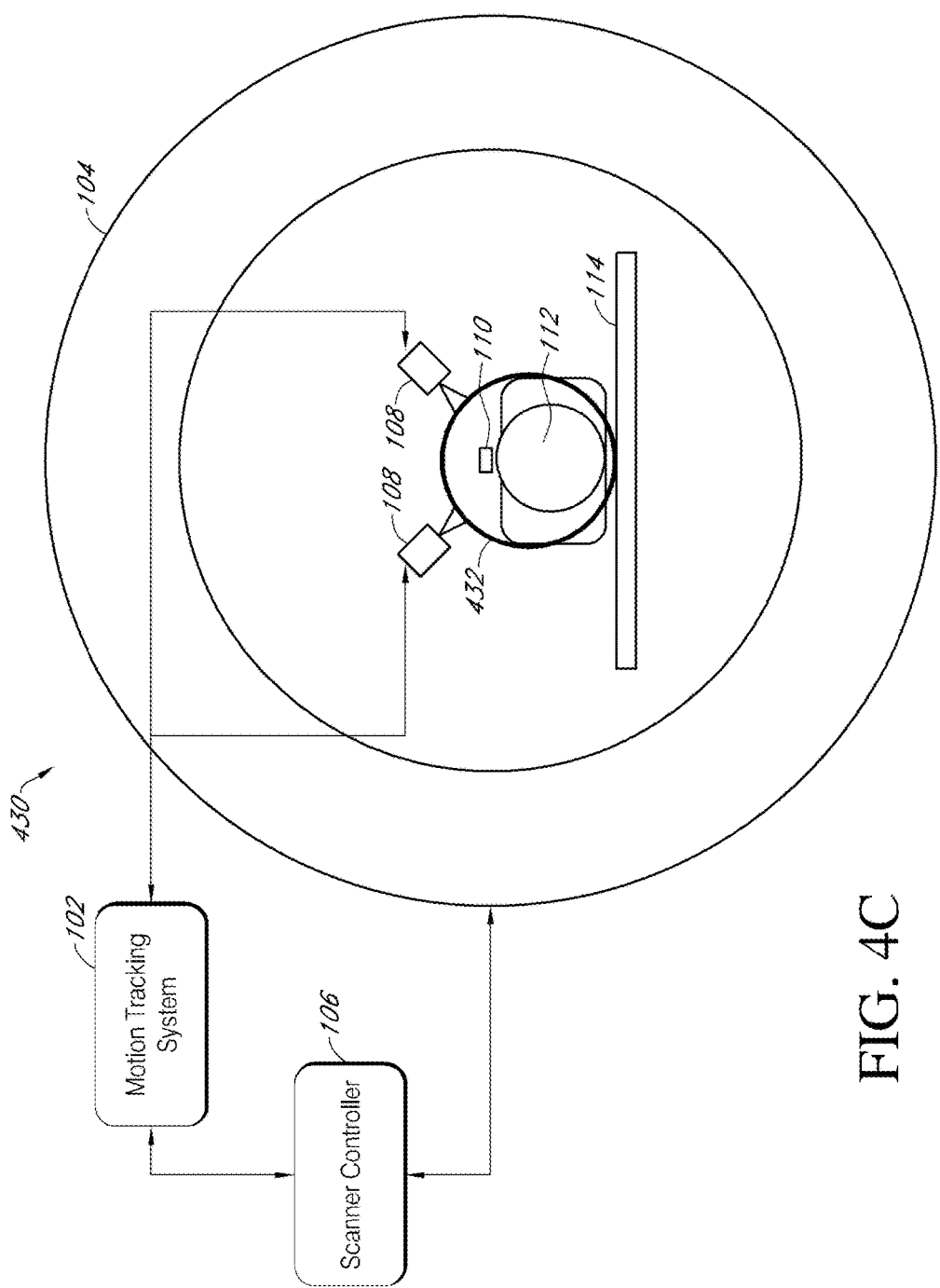
FIG. 4C is another embodiment of a schematic diagram illustrating a front view of a medical imaging scanner as part of a motion compensation system.
Figure 4D:
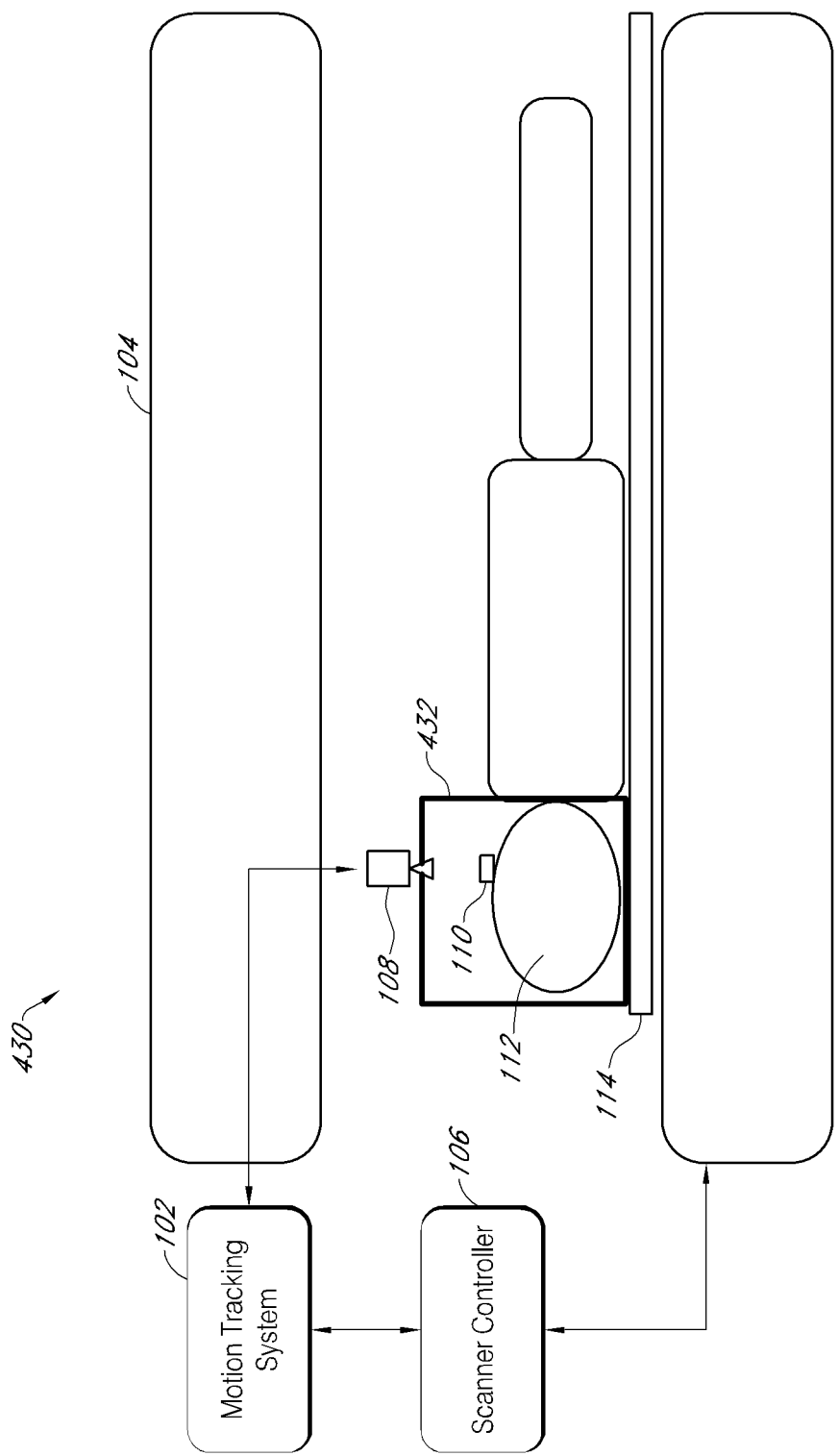
FIG. 4D is a schematic diagram illustrating a side view of the medical imaging scanner as a part of the motion compensation system of FIG. 4C.

FIG. 4C is another embodiment of a schematic diagram illustrating a front view of a medical imaging scanner 104 as part of a motion compensation system 430. FIG. 4D is a schematic diagram illustrating a side view of the medical imaging scanner 104 as a part of the motion compensation system 430. The motion compensation system 430 is similar to the motion compensation system 100 illustrated in FIGS. 1A and 1B. However, the motion compensation system 430 further comprises a head cage or head coil 432 configured to be positioned around a patient's head. In certain medical imaging tasks, such as certain MRI head scans, a head cage 432 can be utilized and positioned around the patient's head. The head cage can make it more difficult for a detector 108 to image the optical marker 110 if the detectors 108 were mounted to the bore of the scanner body 104. Accordingly, the motion compensation system 430 comprises two detectors 108 mounted to the head cage instead of the scanner body. The detectors 108 and motion tracking system 102 are configured to operate similarly to as described above. The term head cage as utilized herein may be used to describe a device configured to help position the head of a patient during an MRI scan. The term head cage may also refer to a head coil device configured to wrap around a patient's head to perform MRI scanning functions.

Figure 4E:
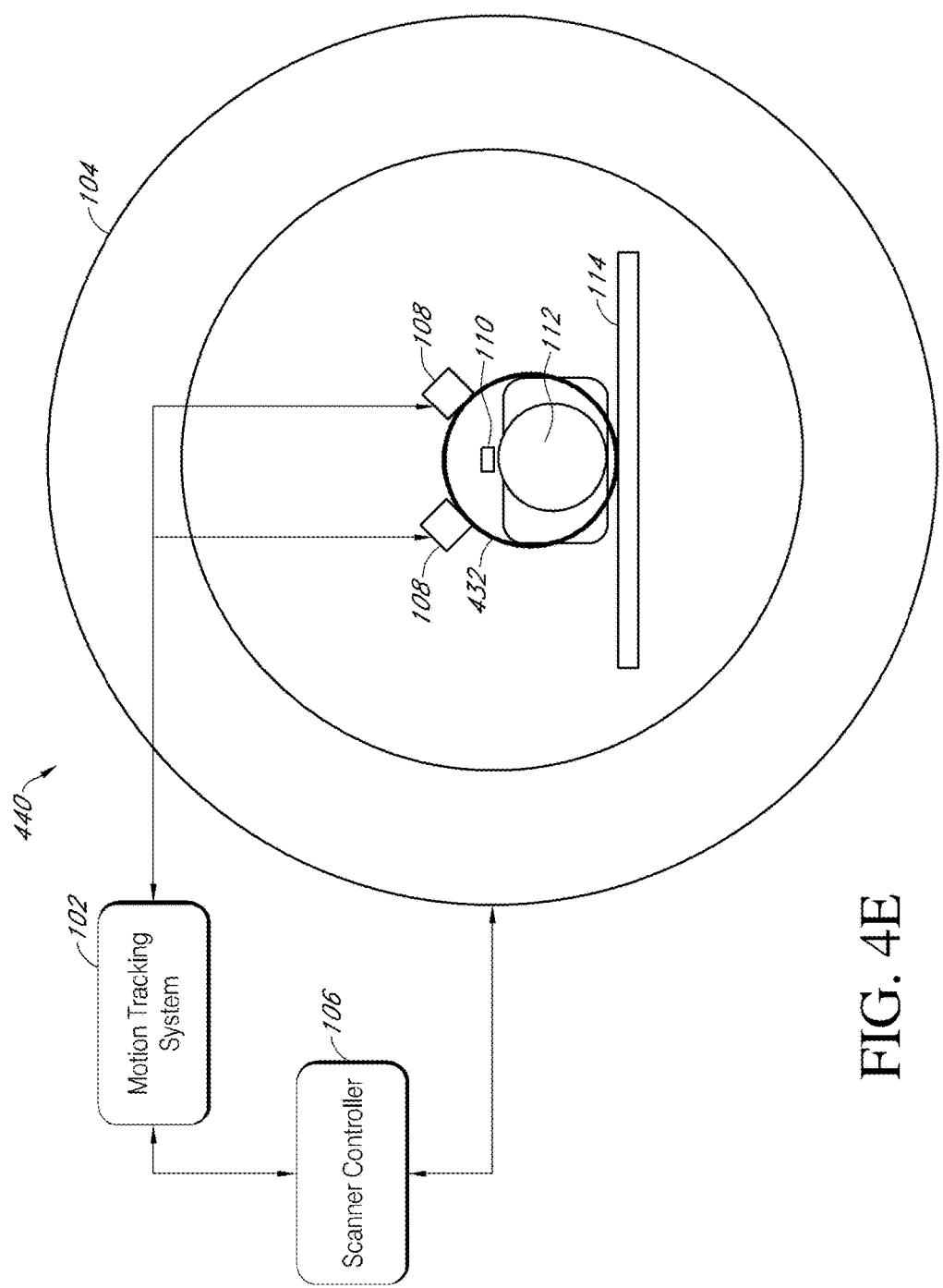
FIG. 4E is another embodiment of a schematic diagram illustrating a front view of a medical imaging scanner as part of a motion compensation system.
Figure 4F:
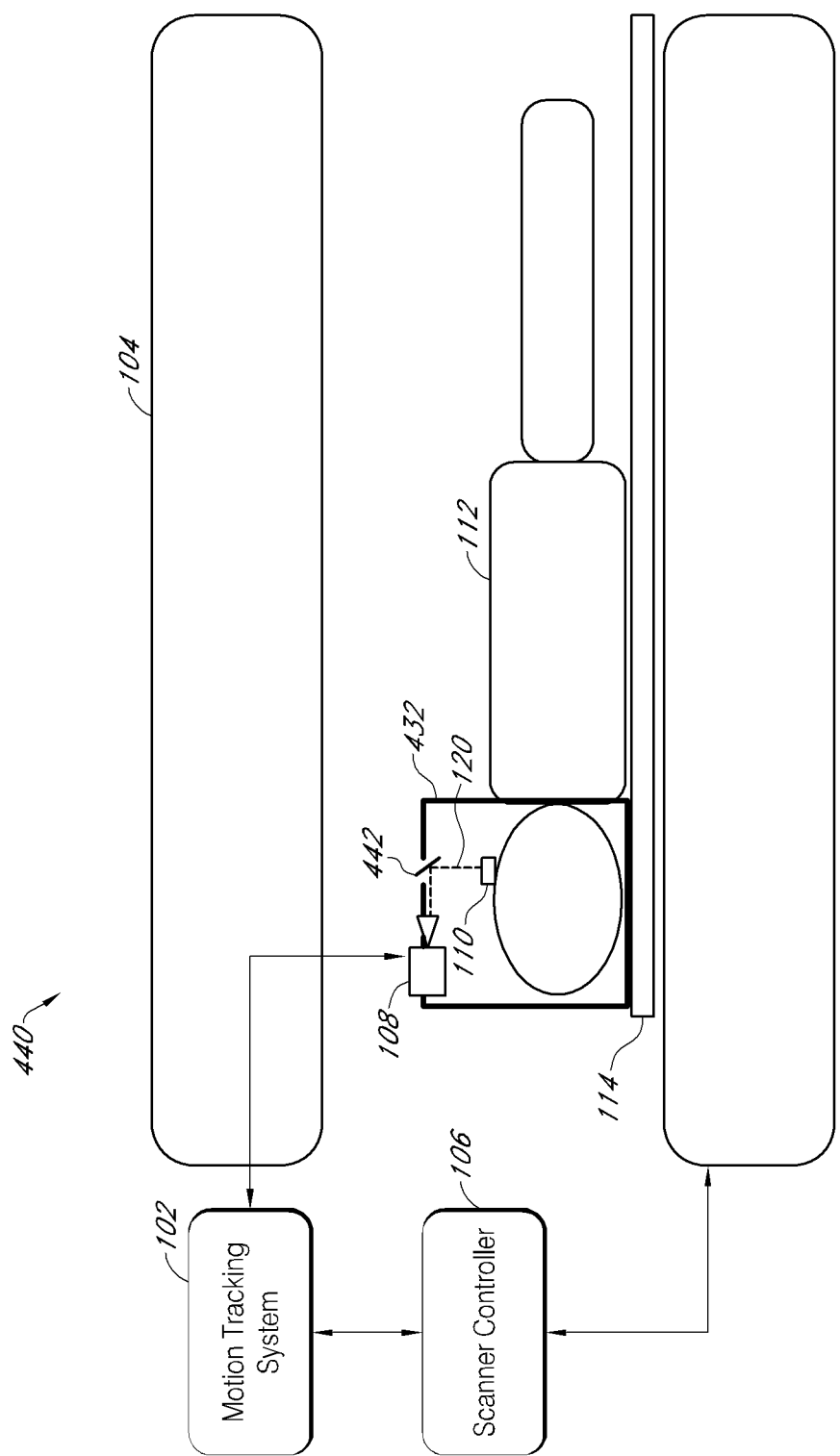
FIG. 4F is a schematic diagram illustrating a side view of the medical imaging scanner as a part of the motion compensation system of FIG. 4E.

FIG. 4E is another embodiment of a schematic diagram illustrating a front view of a medical imaging scanner 104 as part of a motion compensation system 440. FIG. 4F is a schematic diagram illustrating a side view of the medical imaging scanner 104 as a part of the motion compensation system 440. The motion compensation system 440 is similar to the motion compensation system 430 illustrated in FIGS. 4C and 4D. However, in some cases, there can be limited space within the bore of a scanner 104. In those cases, it can be difficult to position detectors 108 to have a direct line of sight between their lens and the optical marker 110. Accordingly, the motion compensation system 440 comprises two detectors 108 positioned flat against the head cage 432 with a line of sight 120 being through a mirror 442 to the optical marker 110. The mirrors 442 enable an indirect line of sight to make the system more compact but to still enable viewing of the optical marker 110 from along two different lines of sight 120. Although this embodiment illustrates the use of mirrors with detectors mounted to a head cage, various other embodiments may use mirrors and/or detectors attached to the scanner body, the head cage, or any other location, as long as the detectors can view the optical marker through the mirrors. In some embodiments, multiple mirrors are used to redirect the line of sight 120 multiple times. For example, a detector 108 may be positioned outside of the scanner and have its line of sight pass through one or more mirrors positioned within the scanner to image the optical marker.

Although the motion compensation system 440 comprises mirrors to redirect the lines of sight, other methods of redirecting a line of sight may be used, alone or in combination with mirrors. For example, fiber optics or prisms may be used to redirect a line of sight and create a virtual scissor angle.

Figure 4G:
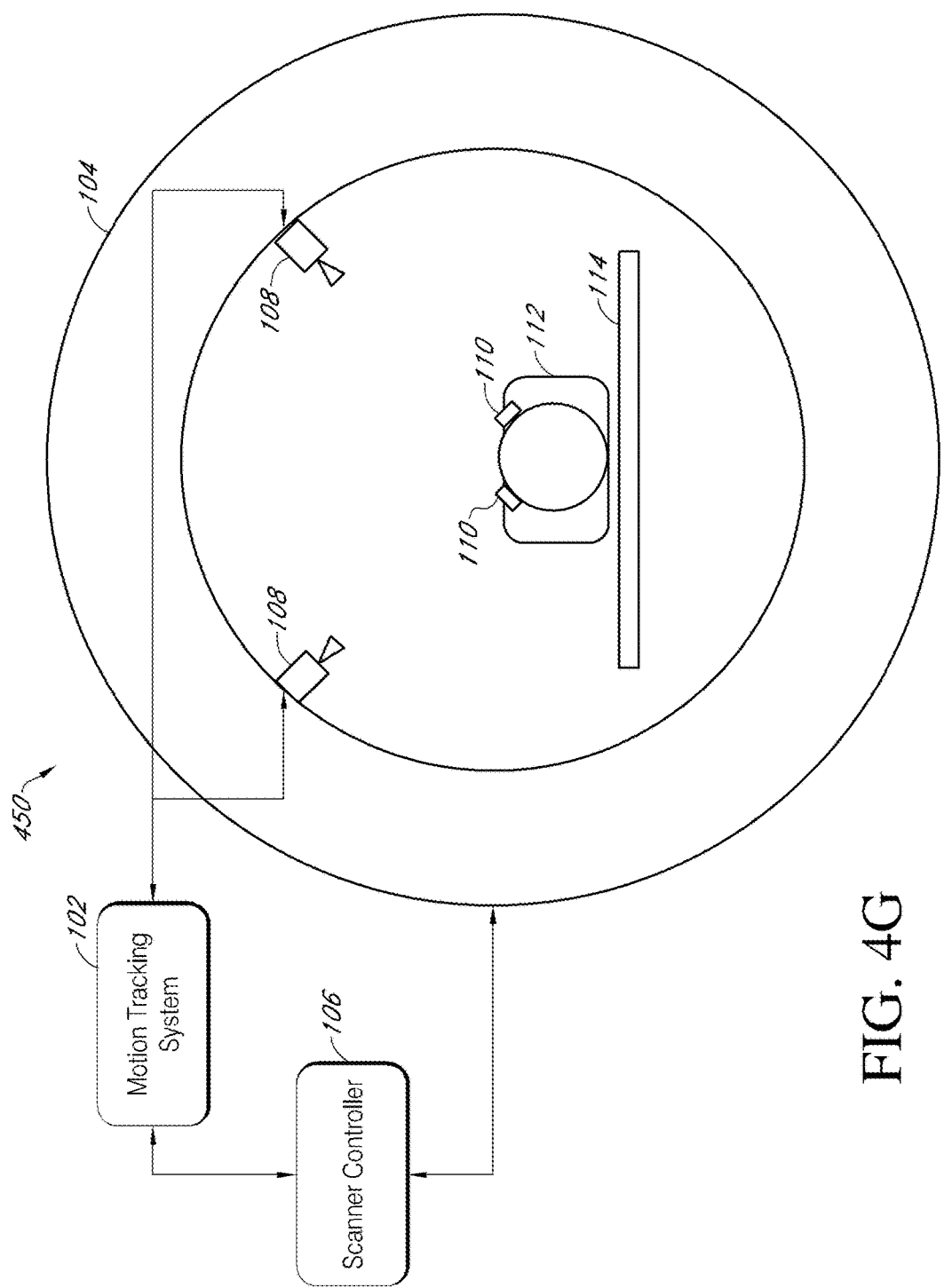
FIG. 4G is another embodiment of a schematic diagram illustrating a front view of a medical imaging scanner as part of a motion compensation system.

FIG. 4G is another embodiment of a schematic diagram illustrating a front view of a medical imaging scanner 104 as part of a motion compensation system 450. The motion compensation system 450 is similar to the motion compensation system 100 illustrated in FIGS. 1A and 1B. However, the motion compensation system 450 comprises two optical markers 110. In this embodiment, each of the two optical markers 110 is positioned to be directly in the line of sight of one of the detectors 108. However, in other embodiments, multiple optical markers 110 may be utilized and positioned in other ways. For example, multiple optical markers may be positioned at various rigid or substantially rigid portions of the object being imaged. For example, as further described below, one optical marker 110 may be positioned on a patient's top teeth, while one or more other markers may be positioned on a patient's forehead.

Optical markers may also be positioned at locations that are not rigid or substantially rigid. For example, an optical marker may be attached to a patient's skin. In some embodiments, such as when the marker is attached to a patient's skin, due to skin movement or skin elasticity, the marker may at times move in relation to the object being scanned, which can introduce inaccuracies into a medical imaging scan. Accordingly, in some embodiments, a motion compensation system can be configured to differentiate between movements of the object being scanned, such as a patient's head, and skin movement, which may not correlate to actual movement of the object being scanned. In some embodiments, the system can be configured to compare the positioning of two or more markers relative to themselves in order to differentiate between head movement and skin movement.

Utilizing multiple optical markers 110 can have various benefits. For example, multiple markers may be used for redundancy, in case one or more markers is not currently visible to one or more detectors based on the current object's pose. Another advantage is that multiple optical markers can be analyzed simultaneously by the motion tracking system 102 to obtain multiple object pose estimates. Those multiple object pose estimates can then be combined to generate a single more accurate estimate. For example, the multiple estimates can be averaged to come up with an average estimate. In another example, there may be a measure of margin of error for each estimate and the estimates may be combined using a weighted average based on the margin of error. In other embodiments, only the most accurate estimate is used and other estimates are dropped.

Figure 4H:
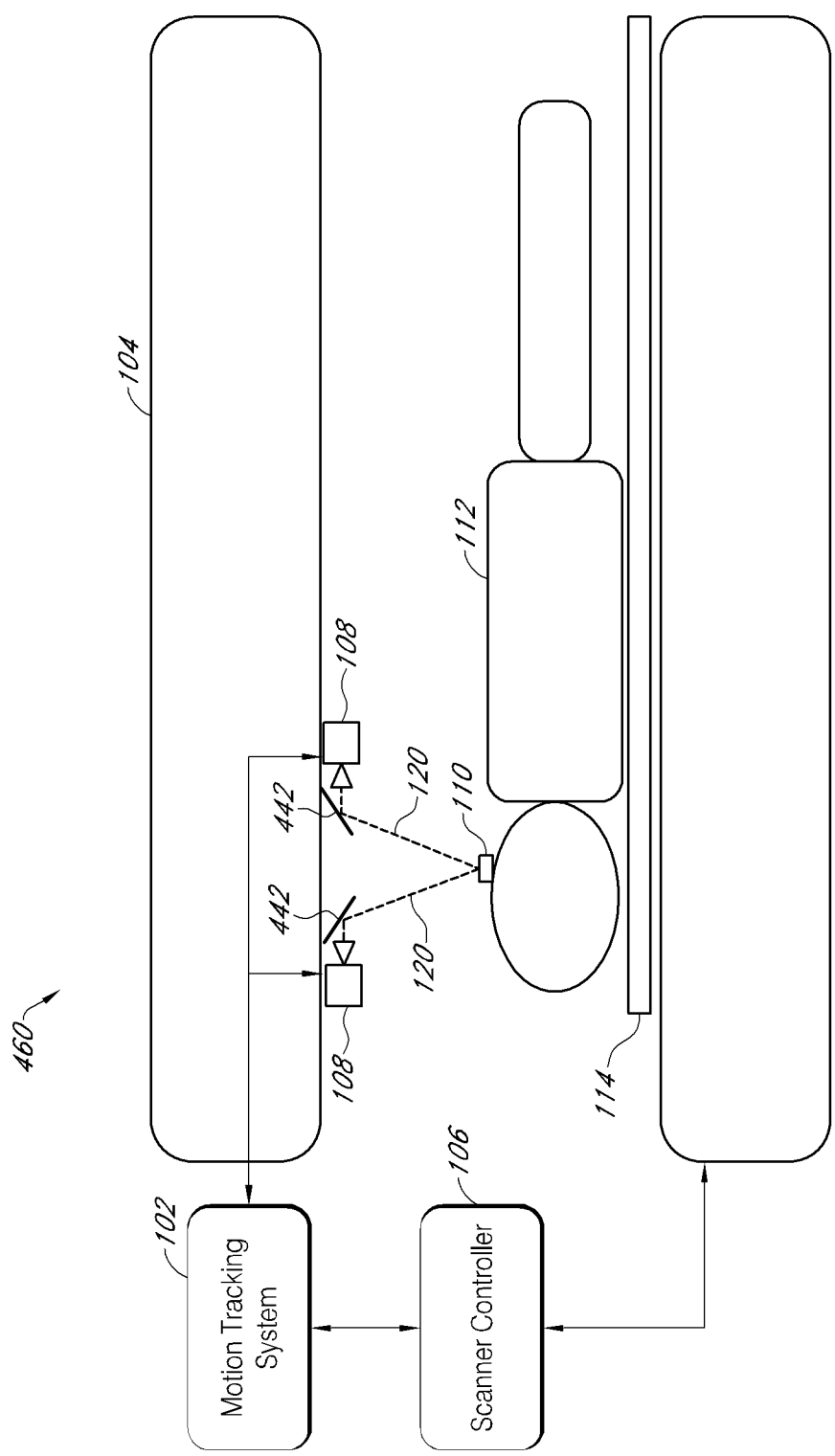
FIG. 4H is another embodiment of a schematic diagram illustrating a side view of a medical imaging scanner as part of a motion compensation system.
Figure 4I:
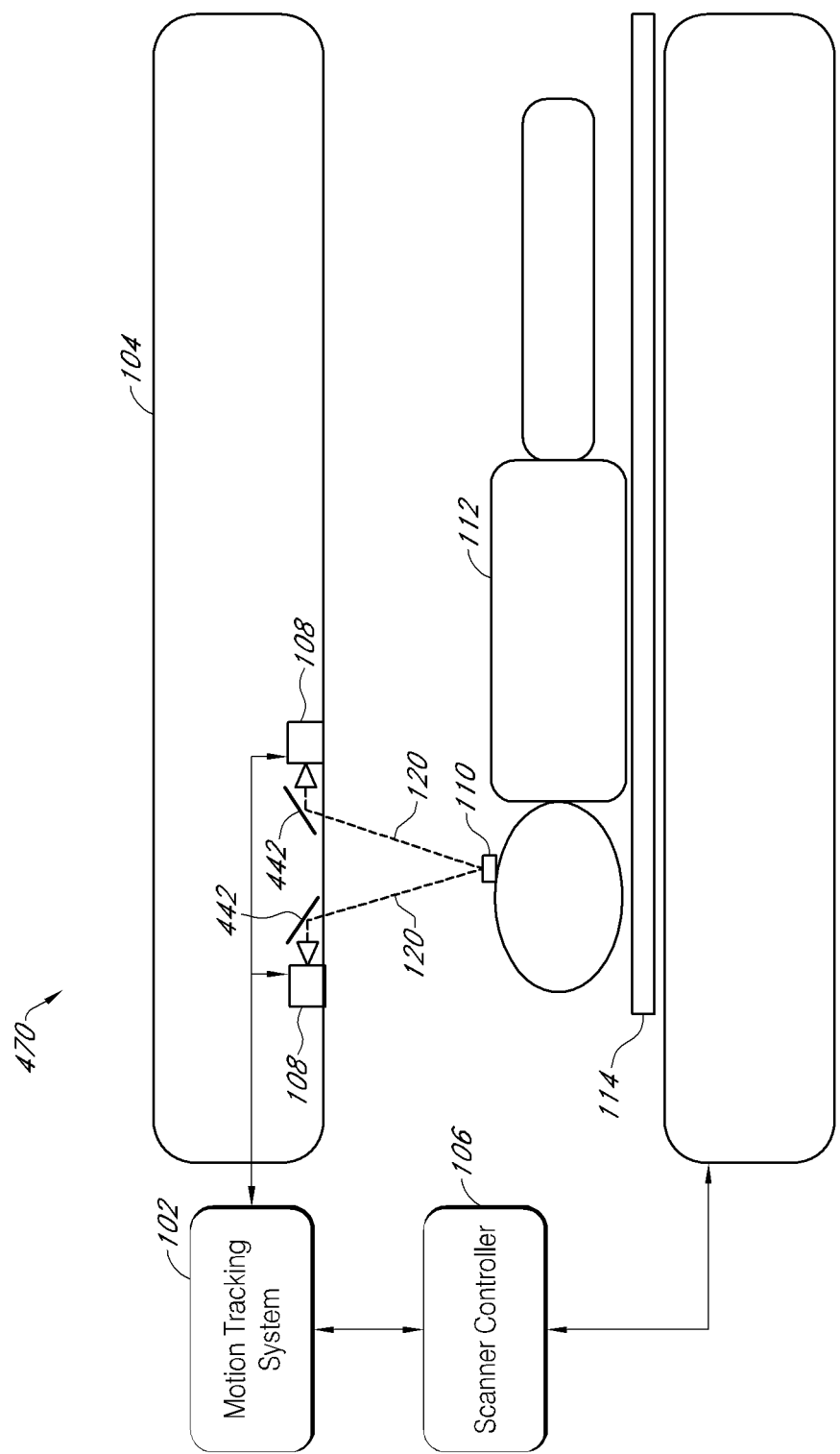
FIG. 4I is another embodiment of a schematic diagram illustrating a side view of a medical imaging scanner as part of a motion compensation system.
Figure 4J:
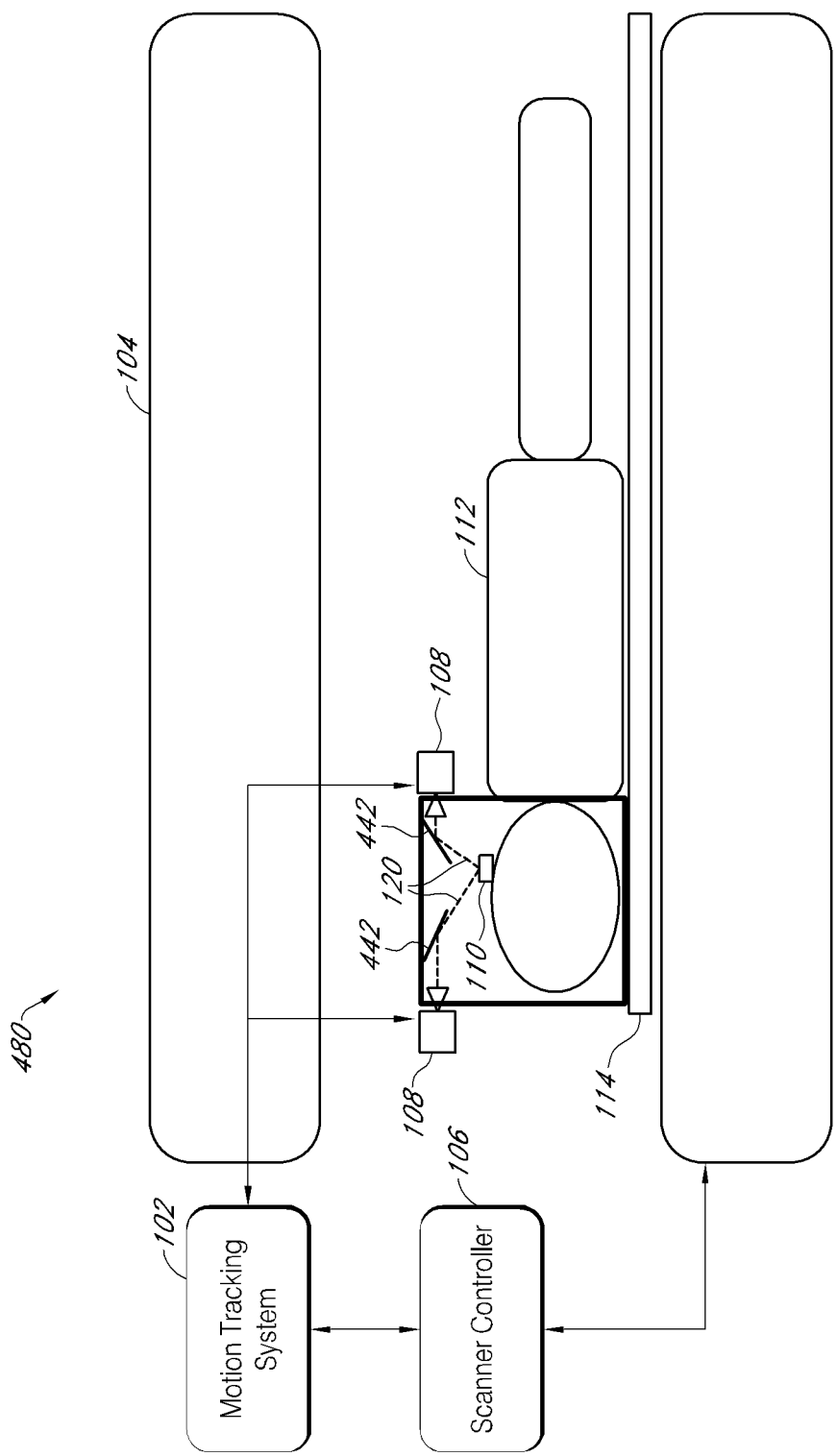
FIG. 4J is another embodiment of a schematic diagram illustrating a side view of a medical imaging scanner as part of a motion compensation system.
Figure 4K:
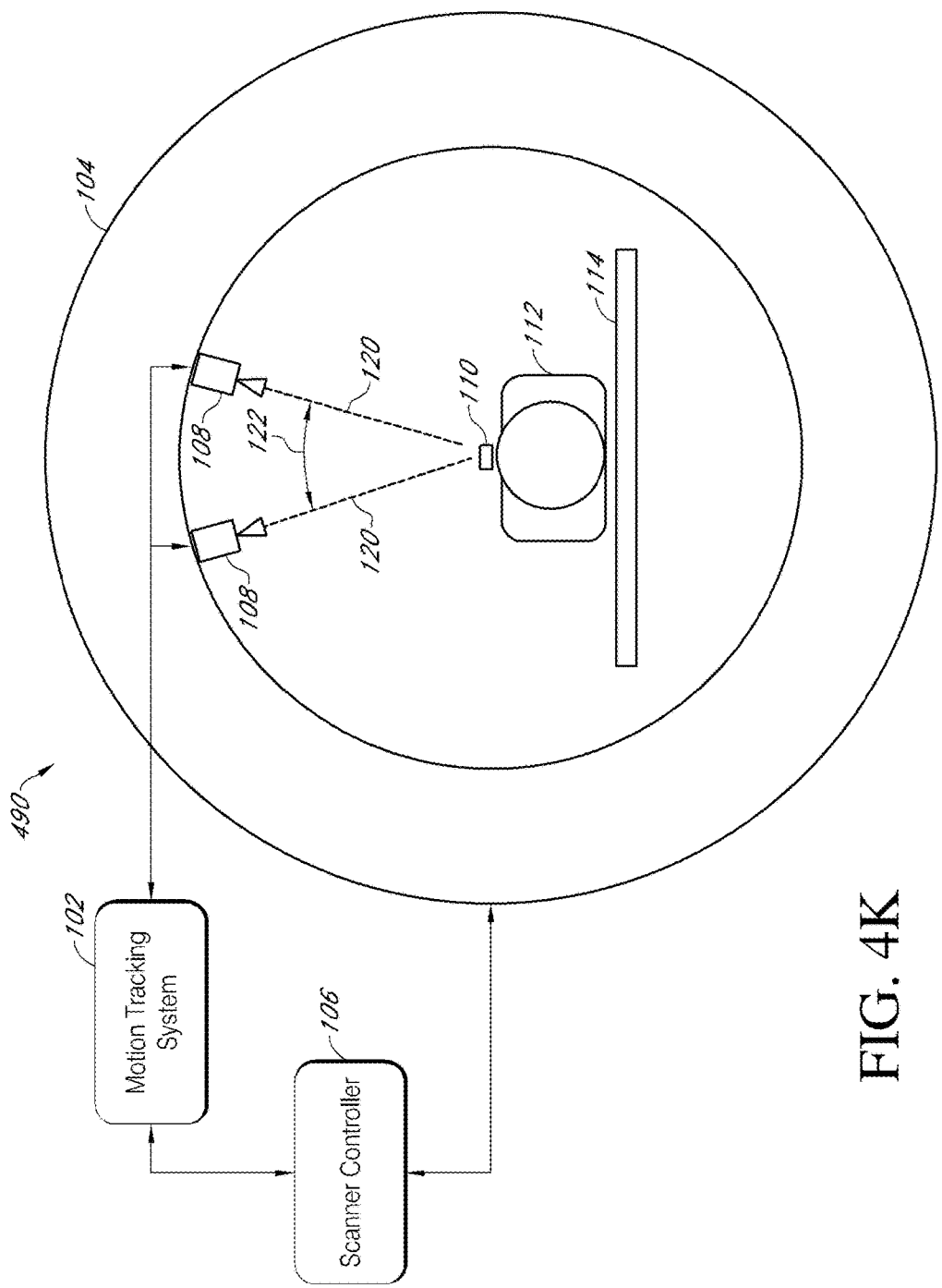
FIG. 4K is another embodiment of a schematic diagram illustrating a front view of a medical imaging scanner as part of a motion compensation system.

FIGS. 4H-4J illustrate additional embodiments of motion compensation systems configured to use indirect lines of sight. Given that many medical imaging systems have limited space within the bore of the device, it can be advantageous to position detectors to be generally flat against a bore of the device or flush within the bore of the device. The embodiment of a motion tracking system 460 shown in FIG. 4H illustrates a system wherein two optical detectors 108 are positioned flat against a bore of the medical imaging scanner 104. In this embodiment, the detectors 108 are positioned facing each other along a longitudinal axis of the bore. Two mirrors 442 are positioned relatively close to the detectors to redirect their lines of sight 120 toward the optical marker 110. In this embodiment, the scissor angle is significantly smaller than 90 degrees. However, in other embodiments, the detectors and/or mirrors may be positioned differently to increase or decrease the scissor angle.

The motion compensation system 470 illustrated in FIG. 4I is similar to the motion compensation system 460 illustrated in FIG. 4H. However, the motion compensation system 470 comprises two detectors 108 and two mirrors 442 mounted within the medical imaging scanner 104 such that they do not protrude into the bore of the scanner 104. The scanner 104 body can comprise openings to enable the lines of sight 120 to pass from the marker 110 to the detectors 108. In some embodiments, detectors may be positioned on a surface of the scanner bore, partially within the body of the scanner, fully within the body of the scanner, and/or the like. One determining factor of whether detectors can be mounted within a scanner body and/or whether any of the detector must protrude beyond the scanner body is the size of the detectors and the space available within the scanner body. More space available within the scanner body and/or smaller detectors may enable more or all of the detectors to be positioned within the scanner body.

FIG. 4J illustrates a motion compensation system 480. The motion compensation system 480 is similar to the motion compensation system 460 illustrated in FIG. 4H. However, the motion compensation system 480 comprises a head cage 432, and the detectors 108 and mirrors 442 are mounted opposite each other on opposite ends of the head cage 432, rather than being mounted to the bore of the scanner. In various embodiments, the detectors 108 may be mounted in various positions, not necessarily facing each other. For example, both detectors 108 may be positioned on the same side of the head cage 432. As can be seen in FIG. 4J, each of the two detectors 108 is configured to view the optical marker 110 along a line of sight 120 viewing the optical marker 110 along a different angle relative to the marker. The line of sight 120 on the left-hand side is at a shallower angle than the line of sight 120 on the right-hand side. In other embodiments, the positioning of the detectors, the optical marker, and/or the mirrors may be adjusted to adjust the angles of each of the lines of sight relative to the marker and/or to adjust the scissor angle.

Figure 4L:
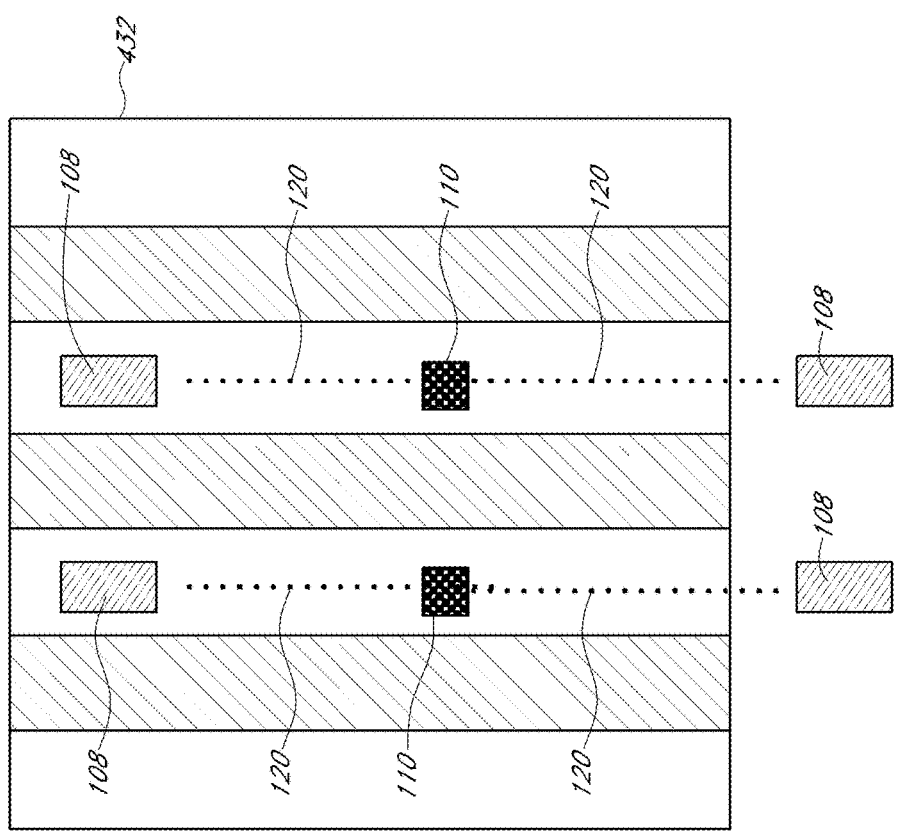
FIG. 4L is another embodiment of a schematic diagram illustrating a motion compensation system.

FIGS. 4L-4N illustrate additional embodiments of schematic diagrams of motion compensation systems. Each of the motion compensation systems illustrated in FIGS. 4L-4N comprise one or more detectors 108, multiple lines of sight 120, one or more optical markers 110, and a head cage or head coil 432. Some embodiments also comprise one or more mirrors 442 and one or more beam splitters 444. In some embodiments, the beam splitters 444 comprise prisms. Although each of the motion compensation systems illustrated in FIGS. 4L-4N include two optical markers 110, the concepts disclosed herein may be applied to a system using any number of optical markers. In some embodiments, the motion compensation system uses two optical markers to add redundancy to the system. For example, one optical marker may at some times have lines of sight to it blocked by, for example, a portion of the head coil 432. The optical markers can be positioned such that when one optical marker's line of sight is obstructed, the other optical marker is still able to be imaged by one or more detectors 108. Although the optical markers 110 illustrated in FIGS. 4L-4N comprise a checkerboard pattern, the optical markers 110 may also or alternatively comprise a pattern similar to the pattern illustrated in the optical marker 110 shown in FIG. 2A.

The embodiment illustrated in FIG. 4L comprises four detectors 108 imaging two optical markers 110. Each of the optical markers 110 is simultaneously imaged by two of the optical detectors 108 along two different lines of sight 120. The embodiment illustrated in FIG. 4M is similar to the embodiment illustrated in FIG. 4L, except the number of detectors is reduced by two. In this embodiment, each of the two detectors 108 is configured to simultaneously image both of the optical markers 110. The system is configured to accomplish this by splitting a sight line from a detector through a beam splitter 444 and also redirecting the resulting multiple sight lines through mirrors 442. A resulting digital image from the optical detector 108 may comprise digital representations of both optical markers 110 (or potentially only one optical marker if, for example, one of the lines of sight is blocked). The motion compensation system can be configured to analyze the representations of each of the optical markers separately, even if the representations are included in the same digital image.

The embodiment illustrated in FIG. 4N is similar to the embodiment illustrated in FIG. 4M, except only one optical detector 108 is utilized. The sight line of the optical detector 108 is split at beam splitter 444 into two lines of sight 120, with each line of sight being directed toward one of the two optical markers 110. As with the configuration illustrated in FIG. 4M, a digital image resulting from the detector 108 may comprise representations of both optical markers 110 (or potentially only one optical marker if, for example, one of the lines of sight is blocked).

Mounting of Optical Markers

Figure 5B:
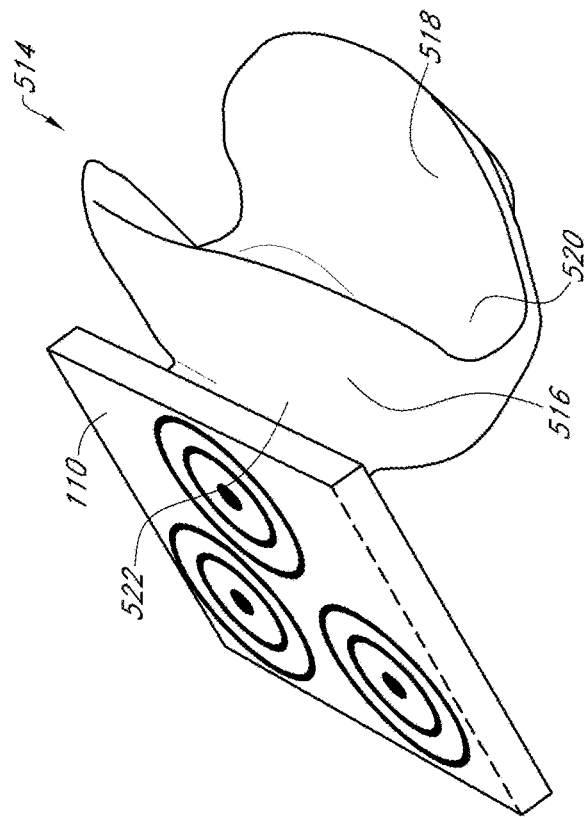
FIG. 5B is a side perspective view of the optical marker of FIG. 5A.
Figure 5A:
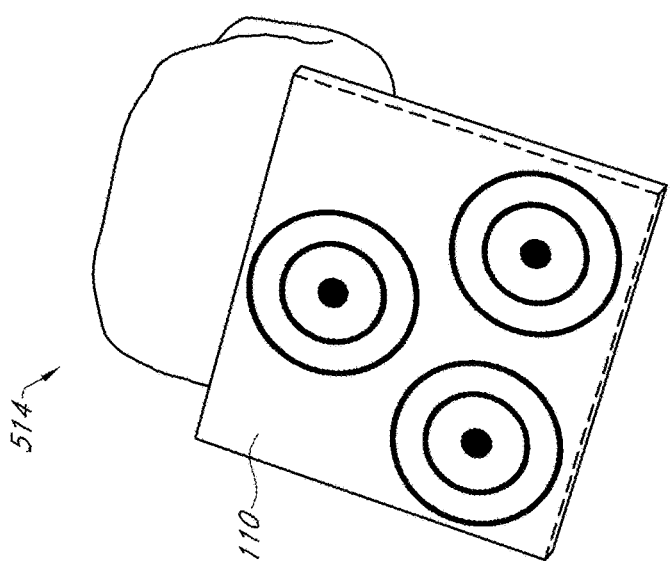
FIG. 5A is a front perspective view of an embodiment of an optical marker connected to a mounting portion.

Optical markers can be mounted to an object being tracked in various ways. FIGS. 5A-5E illustrate various options for mounting an optical marker to an object. FIG. 5A is a front perspective view of an embodiment of an optical marker connected to a mounting portion 514. FIG. 5B is a side perspective view of the optical marker 110 of FIG. 5A mounted to the mounting portion 514. The optical marker 110 illustrated in FIGS. 5A and 5B is similar to the optical marker 110 illustrated in FIGS. 2A-2C. This embodiment is configured to attach to a patient's top teeth. The mounting portion 514 comprises a front portion 516, a back portion 518, and a trough 520 between the front portion 516 and back portion 518. The front portion 516 is configured to pass in front of a person's top teeth, while the back portion 518 is configured to pass behind a user's top front teeth. The trough 520 is configured to conform or substantially conform to the user's teeth.

In some embodiments, the mounting portion 514 is configured to be shaped to a specific user to enhance the fit and/or rigidity of the optical marker 110. For example, the mounting portion 514 can be configured to be softened and placed onto the user's teeth and then hardened. In one embodiment, the mounting portion 514 comprises a polymer that softens when heated and hardens when cooled. In that example, the mounting portion 514 may, for example, be heated in warm water and then placed in the user's mouth to set. In another embodiment, the mounting portion 514 comprises an ultraviolet curable polymer. For example, the mounting portion 514 can be placed on a user's teeth in a soft condition and then cured to a hardened condition using an ultraviolet light. In other embodiments, the mounting portion 514 can be configured to have an adhesive or moldable polymer material placed into the trough 520 to conform to or adhere to a user's teeth.

The mounting portion 514 can be connected to the optical marker 110 using the connection portion 522. In some embodiments, the optical marker 110 and mounting portion 514 are an integral inseparable unit. In other embodiments, the connection portion 522 enables the optical marker 110 to be detached and reattached to the mounting portion 514. This may be advantageous, for example, to enable the mounting portion 514 to be shaped to a user's teeth without the optical marker 110 mounted to it. In some embodiments, the connection portion 522 is relatively small and enables the optical marker 110 to be relatively close to the mounting portion 514. In other embodiments, the connecting portion 522 is longer and enables the optical marker 110 to be positioned further away from the object being tracked. In some embodiments, the connection portion 522 is configured to position the optical marker 110 such that it will not be covered by a patient's lips when the mounting portion 514 is positioned over the user's teeth. In some embodiments, the mounting portion 514 comprises an additional flap configured to be positioned over a user's lip to keep their lip from blocking the optical marker 110.

In some embodiments, an optical marker can be internally lighted. For example, an optical marker can include one or more LED lights or the like inside the optical marker to uniformly or substantially uniformly light the optical marker or individual reference points. Illumination of an optical marker can be advantageous to enable a detector to more clearly image the optical marker and to make it easier for a motion tracking system to distinguish the reference points on the optical marker and/or to distinguish centroids of the reference points. In some embodiments, the detectors and/or another part of a motion compensation system includes lights configured to illuminate the optical marker. In some embodiments, such as when infrared detectors are used, the lighting can be infrared lights. In some embodiments, an optical marker can be configured to glow in the dark to enable enhanced illumination without using auxiliary lighting. In some embodiments, an optical marker can be configured to be charged with light by being placed in front of a light source for a period of time, after which the optical marker will glow for a period of time.

Figure 5D:
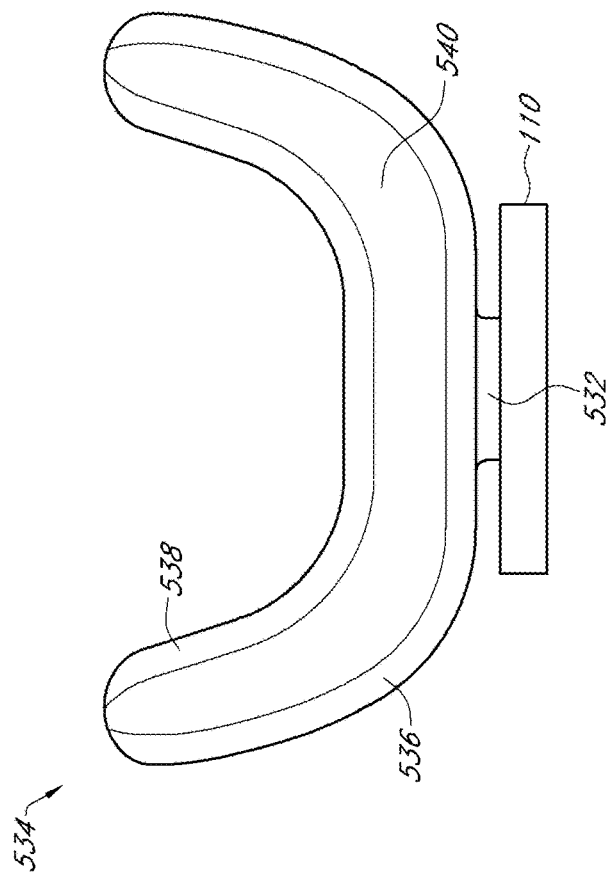
FIG. 5D is a top view of another embodiment of an optical marker connected to a mounting portion.
Figure 5C:
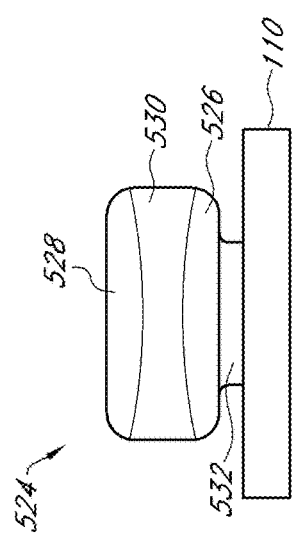
FIG. 5C is a top view of another embodiment of an optical marker connected to a mounting portion.

FIG. 5C is a top view of another embodiment of an optical marker 110 connected to a mounting portion 524. FIG. 5D is a top view of yet another embodiment of an optical marker 110 connected to a mounting portion 534. The mounting portion 524 illustrated in FIG. 5C is a relatively narrow mounting portion comprising a front portion 526, back portion 528, and a trough 530 therebetween. The mounting portion 534 illustrated in FIG. 5D is, however, a relatively wide mounting portion. The mounting portion 534 comprises a front portion 536, a back portion 538, and a trough 540 therebetween. The embodiments illustrated in FIGS. 5C and 5D illustrate that mounting portions can take various shapes. For example, the mounting portion 524 is similar in size to the mounting portion illustrated in FIGS. 5A and 5B. This mounting portion may engage only a couple teeth of the patient. On the other hand, the mounting portion 534 illustrated in FIG. 5D comprises a more U-shaped mounting portion configured to engage several teeth of the patient. The mounting portion 534 may be in some embodiments similar in design to a mouthguard typically used by athletes. The mounting portions 524 and 534 are both connected to an optical marker 110 using a connection portion 532.

Figure 5E:
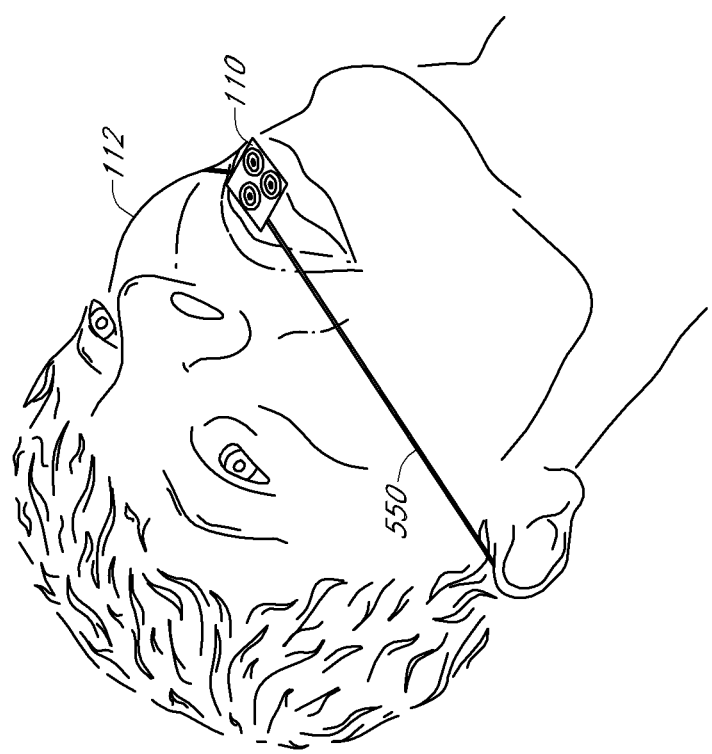
FIG. 5E is a perspective view of an embodiment of an optical marker connected to a patient.

FIG. 5E is a perspective view of an embodiment of an optical marker 110 connected to a patient 112. In this embodiment, the optical marker 110 is attached to a strap 550 configured to go around the patient's head to help retain the optical marker 110 in position. In some embodiments, the optical marker 110 also is attached to a mounting portion, such as the mounting portions described above configured to attach to a patient's teeth. Various embodiments of mounting an optical marker to a patient have been described. However, various other methods may be used such as, but not limited to, adhesives, tape, tattoos, paint, and/or the like.

Figure 6A:
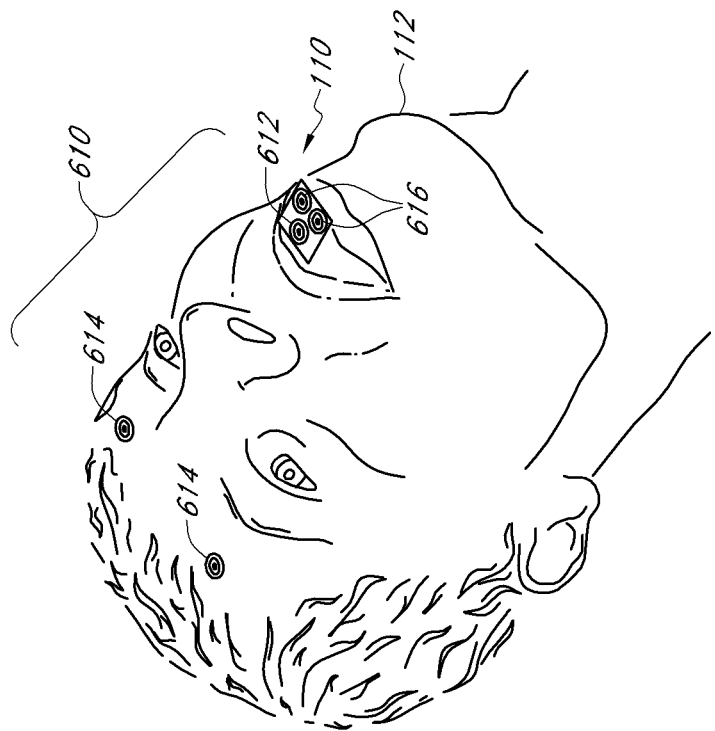
FIG. 6A is a perspective view of an embodiment of an optical marker using distributed reference points.

FIG. 6A is a perspective view of an embodiment of an optical marker 610 using distributed reference points 614 and 612. Like the optical marker 110 illustrated in FIG. 2B, the optical marker 610 comprises three reference points 612 and 614 comprising elliptical shapes and forming a triangular reference shape when viewed together. However, the optical marker 610 is a distributed optical marker, in that the reference points are not part of the same physical object. In this embodiment, the reference point 612 is on a substrate attached to the patient's top teeth, similar to as described above. However, the other two reference points 614 are stickers attached to the patient's forehead above his or her eyes. One advantage of the configuration illustrated in FIG. 6A is that detectors that have a lower resolution, and are therefore cheaper, may be used. Another advantage is that smaller movements of the patient 112 may be able to be more accurately detected in images of the optical marker 610. A disadvantage of the configuration shown in FIG. 6A is, however, that the three reference points are not rigid with respect to each other. For example, if the patient 112 moves his or her skin over the forehead, the reference points 614 may move with respect to the reference point 612 attached to his or her teeth. In some embodiments, the motion tracking system can be configured to analyze relative motion of the reference points to determine whether the motion is due to local skin motion or deformations or actual patient movement.

The concept of utilizing distributed reference points may take various forms. For example, each reference point may be positioned on a block, substrate, or other backing, with the backing being affixed or attached to the patient or object being tracked. For example, the reference point 612 illustrated in FIG. 6A is shown attached to a substantially rigid backing. The reference points 614 are illustrated as individual points not having a backing and being directly affixed to the patient's forehead. However, in some embodiments, the reference points 614 may also be attached to a backing, block, or other backing to help in attaching the reference point to the object and/or to reduce any flexing of the reference point and/or to keep the reference point shape flat. In some embodiments, an optical marker and/or an individual reference point can be configured to attach to an object being tracked using a variety of means. For example, double-sided surgical tape can be utilized to attach a marker to an object. Other adhesives may also be used. Other mechanical affixing means may also be used, such as other types of tape, clamps, straps, fasteners, and/or the like.

Although the embodiments illustrated in FIG. 6A illustrate reference points located at a patient's top teeth and forehead, reference points and/or markers may be positioned at various locations. For example, a reference point or marker may be positioned at a patient's nose, cheeks, chin, temples, ears, and various other locations as long as the reference point or marker will be visible to a detector during at least a portion of the object's range of motion, either through a direct or indirect line of sight. Further, although the reference points illustrated in FIG. 6A are spaced relatively far apart from each other, in some embodiments, the reference points may be spaced relatively close together, although still not attached to the same backing or mounting material. For example, the reference points may be located and spaced a similar distance apart as shown in the optical marker 110 illustrated in FIG. 2B, even if the three reference points are each attached to a different backing material or mounting portion. In another embodiment, the three reference points can be spaced in a similar fashion to the optical marker 110 illustrated in FIG. 2B, except the reference points are each a separate object adhered to the patient and not connected to each other.

In some embodiments of a motion compensation system, obstructions may exist that could potentially block a line of sight to an optical marker. For example, a head cage or head coil, such as is shown in FIG. 9A may have bars or other portions that may obstruct a line of sight to a marker. Accordingly, in some embodiments, a marker or reference point can be positioned on an object at a location that eliminates or reduces any blockage of a line of sight to the marker. In some embodiments, mirrors or other devices configured to redirect a line of sight may be used to enable a detector to image a marker through a hole or opening in an obstruction such as a head cage or head coil.

Figure 6B:
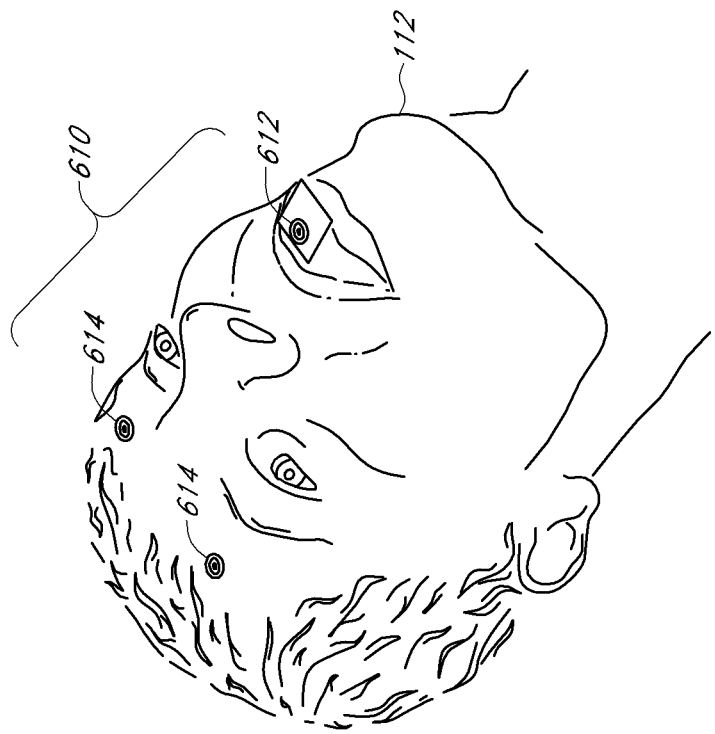
FIG. 6B is a perspective view of an embodiment of an optical marker using distributed reference points and an embodiment of an optical marker using integrated reference points.

FIG. 6B is a perspective view of an embodiment of an optical marker 610 using distributed reference points 614 and 612, and an embodiment of an optical marker 110 using integrated reference points 612 and 616. The embodiment illustrated in FIG. 6B is similar to the embodiment illustrated in FIG. 6A, but utilizing two different-sized optical markers. The configuration in FIG. 6B utilizes the distributed optical marker 610 illustrated in FIG. 6A and the non-distributed optical marker 110 illustrated in FIG. 2B. Such a configuration can be advantageous to, for example, obtain the benefits of a larger marker 610 while counteracting some of the issues with a distributed marker by using the non-distributed marker 110.

In some embodiments, a motion tracking system can be configured to track the larger marker 610 and/or the smaller marker 110 based on the motion the detectors are capturing. For example, if a system is concerned with local motion or twitching of the patient's forehead skin that may introduce inaccuracies into the system, the system may be configured to stop tracking utilizing the larger optical marker 610 when motion in a direction consistent with a localized motion of a marker 614 is detected. For example, if a marker 614 is imaged moving in a longitudinal direction, such as up and down with respect to the patient's head, this may be indicative of local skin motion and may introduce inaccuracies if tracking the optical marker 610 is used. However, if motion of the reference point 614 in a side-to-side direction is detected, especially if both reference points 614 are moving in the same direction, this is less likely indicative of local skin motion and is more likely that the patient is turning his or her head. Accordingly, tracking based on the larger optical marker 610 may be more accurate during that motion than tracking the smaller optical marker 110. In one embodiment, a motion tracking system can be configured to track motion utilizing a larger distributed marker when motions not indicative of localized skin motion are detected, but to track using a smaller non-distributed marker when motions indicative of localized skin motion are detected.

Figure 6C:
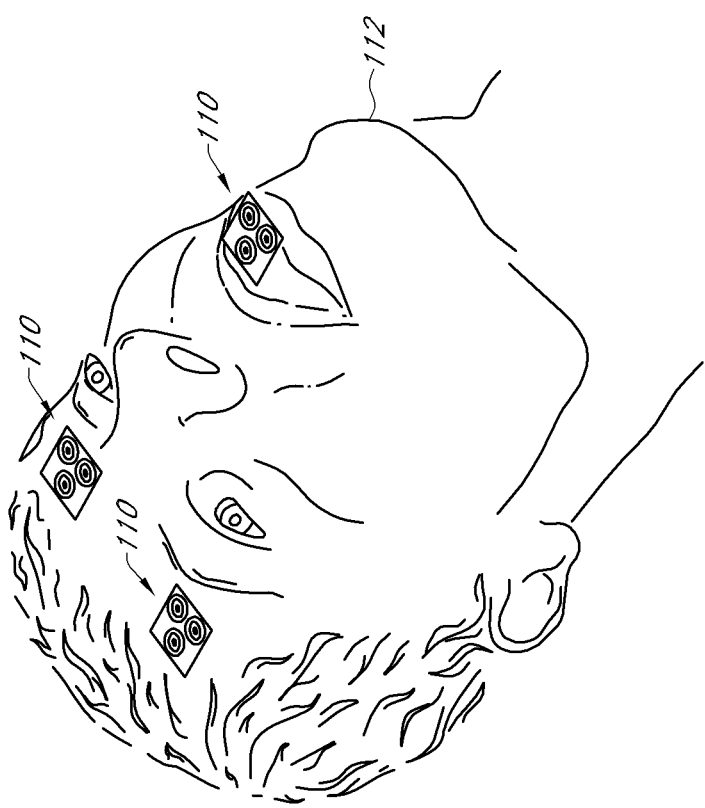
FIG. 6C is a perspective view of an embodiment of multiple optical markers attached to an object being tracked.

FIG. 6C is a perspective view of an embodiment of multiple optical markers 110 attached to an object being tracked, in this case the patient 112. This embodiment illustrates that multiple complete optical markers 110 can be affixed to the same object. Although, in this embodiment, the optical markers are attached at the patient's top teeth and forehead, optical markers may be attached in addition to or in lieu of these locations at, for example, the cheeks, the temples, ears, chin, nose, below the eyes, and/or the like. Utilizing multiple optical markers may be advantageous to increase accuracy and/or redundancy.

Motion Compensation System Processes

Figure 7A:
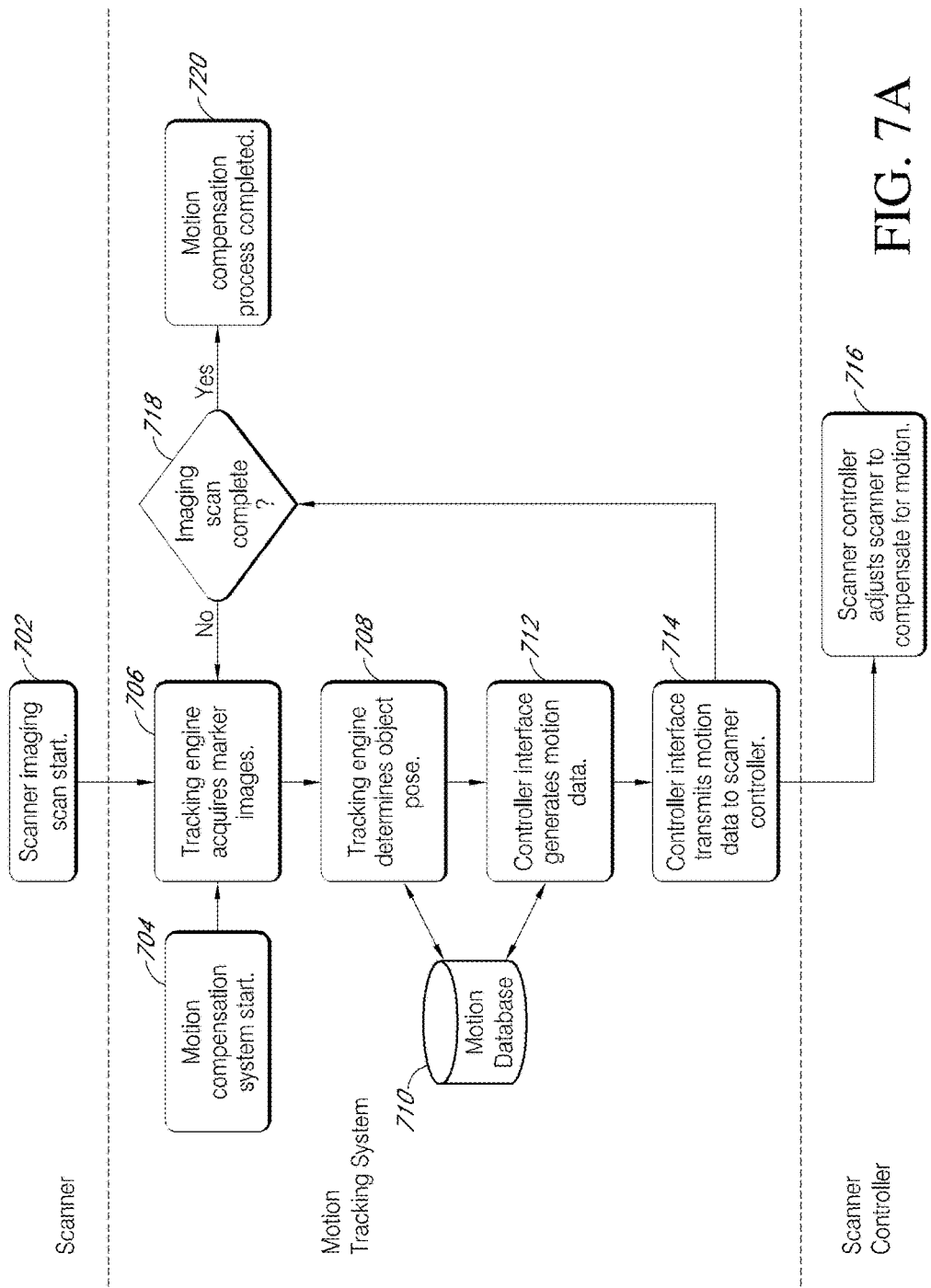
FIG. 7A depicts an embodiment of a process flow diagram illustrating an example of a motion compensation process.

FIG. 7A depicts an embodiment of a process flow diagram illustrating an example of a motion compensation process. For example, the process flow illustrated in FIG. 7A can be implemented by, for example, the motion compensation systems 300 or 301 illustrated in FIGS. 3A and 3B. At block 702, the scanner starts an imaging scan. At block 704, the motion compensation system starts its process. At block 706, a tracking engine acquires marker images. For example, the tracking engine 304 illustrated in FIG. 3A can be configured to acquire one image frame each from detector 1 and detector 2. At block 708, the tracking engine determines an object pose. For example, the marker location filter 312 can be configured to determine two dimensional locations of marker reference points, and the object orientation filter 314 can be configured to estimate a three dimensional pose of the object being tracked using the two dimensional locations of the marker reference points. The tracking engine may store this information in the motion database shown at block 710. The motion database shown at block 710 may be, for example, the motion database 310 illustrated in FIG. 3A.

At block 712, a controller interface generates motion data. For example, the controller interface 308 illustrated in FIG. 3A can be configured to convert the object pose information into the scanner coordinate system and generate data for enabling the scanner controller to adjust for the motion. At block 714, the controller interface transmits the motion data to a scanner controller. At block 716, the scanner controller operates to adjust the scanner to compensate for the motion. At block 718, the process varies depending on whether the imaging scan is complete. If the imaging scan is not complete, the process flow proceeds back to block 706 and proceeds as described above. If the scan is complete, the process flow proceeds to block 720, and the motion compensation process is completed.

Figure 7B:
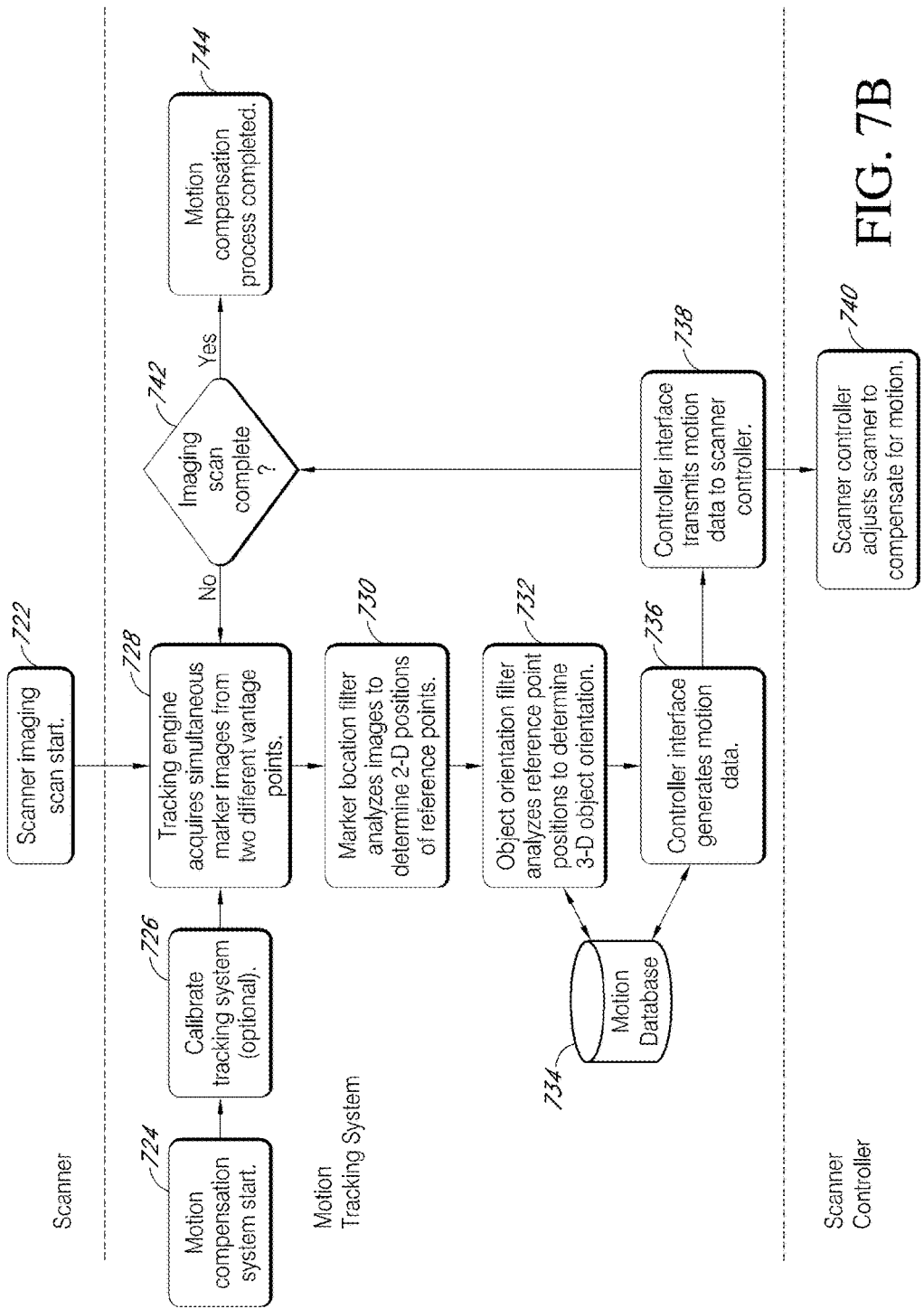
FIG. 7B depicts another embodiment of a process flow diagram illustrating an example of a motion compensation process.

FIG. 7B depicts another embodiment of a process flow diagram illustrating an example of a motion compensation process. At block 722, a scanner starts the imaging process. At block 724, a motion compensation system starts its process. For example, this process may be implemented by the motion compensation system 300 illustrated in FIG. 3A. At block 726, the motion tracking system is optionally calibrated. For example, the target calibration filter 320 can be configured to determine a general location of the optical marker in each detector's field of view.

At block 728, a tracking engine acquires simultaneous marker images from two different vantage points. For example, the tracking engine 304 illustrated in FIG. 3A can be configured to obtain simultaneous or substantially simultaneous images from the first and second detectors 108. At block 730, a marker location filter analyzes the images to determine two dimensional positions of reference points of an optical marker. For example, the marker location filter 312 can be configured to analyze the images acquired in block 728. The marker location filter can be configured to analyze these images to determine where the reference points of the optical marker appear in each image.

At block 732, an object orientation filter analyzes the reference point positions to determine a three dimensional object orientation or pose. For example, the object orientation filter 314 can be configured to analyze the information created at block 730 to estimate a three dimensional object pose in 6 degrees of freedom and, in some embodiments, to perform an iterative process to obtain a better estimate. The objection orientation filter can be configured to store this 3D object orientation or pose information in the motion database illustrated at block 734. At block 736, the controller interface can be configured to generate motion data. For example, the controller interface 308 illustrated in FIG. 3A can be configured to acquire the object pose or orientation information from the motion database or the object orientation filter and convert this information to be readable by a scanner controller. At block 738, the controller interface transmits the motion data to the scanner controller. At block 740, the scanner controller adjusts the scanner to compensate for the motion.

At block 742, the process flow varies depending on whether the imaging scan is complete. If the imaging scan is not complete, the process flow proceeds back to bock 728 and proceeds as described above. If the imaging scan is complete, the process flow proceeds to block 744 and the motion compensation process is completed.

Figure 7C:
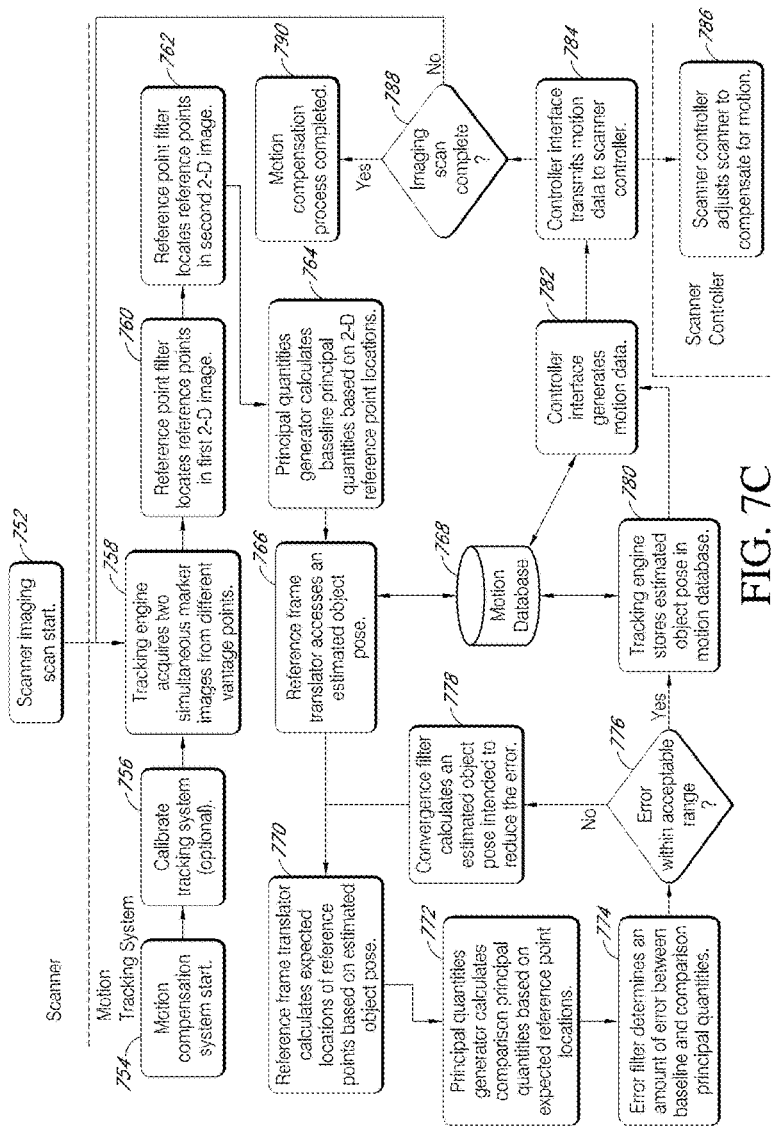
FIG. 7C depicts another embodiment of a process flow diagram illustrating an example of a motion compensation process.

FIG. 7C depicts another embodiment of a process flow diagram illustrating an example of a motion compensation process. The process flow illustrated in FIG. 7C can be performed by, for example, the motion compensation system 301 illustrated in FIG. 3B. At block 752, a scanner imaging scan is started. At block 754, the motion compensation system starts its process. At block 756, the motion compensation system optionally calibrates the tracking system. At block 758, a tracking engine acquires two simultaneous marker images from different vantage points. For example, the tracking engine 334 can be configured to acquire simultaneous or substantially simultaneous image frames from the first and second detectors 108.

At block 760, a reference point filter locates reference points and the first two dimensional image. For example, the reference point filter 336 can be configured to analyze the first two dimensional image to locate the alternating ellipses or circles of the optical marker illustrated in FIG. 2A and to determine a centroid of each of those sets of alternating ellipses. The centroid will be the reference point. At block 762, the reference point filter locates the reference points in the second dimensional image. Accordingly, after blocks 760 and 762, if the optical marker illustrated in FIG. 2A is being used, six different coordinates for six different reference points will be or will have been determined. The six different reference points comprise the three reference points of the optical marker as seen by the first detector and the same three reference points as seen by the second detector.

At block 764, a principal quantities generator calculates baseline principal quantities or attributes based on the two dimensional reference point locations. For example, the principal quantities generator 338 illustrated in FIG. 3B can be configured to analyze the locations of the reference points as determined in blocks 760 and 762 to determine six principal quantities describing various attributes of the reference shape formed by the reference points and/or describing differences or similarities between the reference shape as viewed along a first and second line of sight. These baseline principal quantities can be utilized at another point in this process to be compared to principal quantities based on an estimate of an object pose to determine an amount of error. Further discussion on the principal quantities and specific examples of principal quantities can be found below.

At block 766, a reference frame translator accesses an estimated object pose. For example, the reference frame translator 340 illustrated in FIG. 3B can be configured to access a motion database shown at block 768 to retrieve an estimated object pose. In some embodiments, the estimated object pose is arbitrary, such as (0, 0, 0, 0, 0, 0) in a 6 degree of freedom orientation. In other embodiments, the estimated object pose retrieved at block 766 is the immediately prior estimated object pose from the last time this process was performed.

At block 770, a reference frame translator calculates expected locations of reference points based on the estimated object pose. For example, the reference frame translator 340 illustrated in FIG. 3B can be configured to convert the three dimensional estimated object pose from block 766 into expected three dimensional and two dimensional locations of the reference points as if the object were in that estimated pose. At block 772, the principal quantities generator calculates comparison principal quantities based on the expected reference point locations. The principal quantities generator can be configured to calculate these principal quantities similarly to how it calculated the baseline principal quantities at block 764; but at block 772 the principal quantities are based on the expected reference points as a result of the estimated object pose.

At block 774, an error filter determines an amount of error between the baseline and comparison principal quantities. For example, the error filter 342 illustrated in FIG. 3B can be configured to compare the baseline and comparison principal quantities and determine a quantitative error estimate. At block 776, the process flow varies depending on whether the error determined at block 774 is within an acceptable range. If the error is not within an acceptable range, the process flow proceeds to block 778. At block 778, a convergence filter calculates an estimated object pose intended to reduce the error. For example, the convergence filter 344 can be configured to analyze the estimated object pose from block 766 and determine how to alter that estimated pose to reduce the error. The process flow then proceeds back to block 770 and proceeds as described above using the new estimated object pose.

Returning to block 776, if the error is within an acceptable range, the process flow proceeds to block 780. At block 780, the tracking engine stores the estimated object pose in the motion database. At block 782, a controller interface generates motion data. For example, the controller interface 308 illustrated in FIG. 32B can be configured to convert a coordinate system of the object pose into the scanner coordinate system and to package this information for transmission to the scanner controller. At block 784, the controller interface transmits the motion data to the scanner controller. At block 786, the scanner controller adjusts the scanner to compensate for the motion.

At block 788, the process flow varies depending on whether the imagine scan is complete. If the imaging scan is complete, the process flow proceeds to block 790 and the motion compensation process is completed. If the imaging scan is not complete at block 788, the process flow proceeds back to block 758 and proceeds as described above.

Although various embodiments described herein describe images from multiple detectors being acquired simultaneously or substantially simultaneously, in some embodiments, the images must merely be acquired within a certain time of each other. For example, in some embodiments, the images must just be acquired within a timeframe that is equal to or less than the frequency of the motion tracking system providing motion updates to the scanner controller. Another example of a process flow diagram illustrating an example of a motion compensation process is shown in FIG. 20C.

In some embodiments, the processes illustrated in FIG. 7C and as described elsewhere in this disclosure requires a computer system and/or computer hardware to implement. For example, to enable real-time motion tracking during a medical imaging scan, in some embodiments, a motion compensation system must operate at a speed of at least 100 Hz, for example, performing an object orientation estimate at a rate of at least 100 times per second. Such a process is impossible for a human to perform in his or her mind. Even if a human were able to implement the processes described herein, a human would not be able to implement them at the speeds necessary for some embodiments. However, even if speed were not a requirement, a human would likely not be able to perform at least some of the components of processes described herein in his or her head due to the large number of variables and relatively complex equations involved. Further, the human eye likely cannot distinguish small movements of an optical marker within the resolution necessary to implement some of the processes disclosed herein. Accordingly, computer systems and/or computer hardware is required to implement some embodiments of the processes and systems and methods described herein.

Figure 7D:
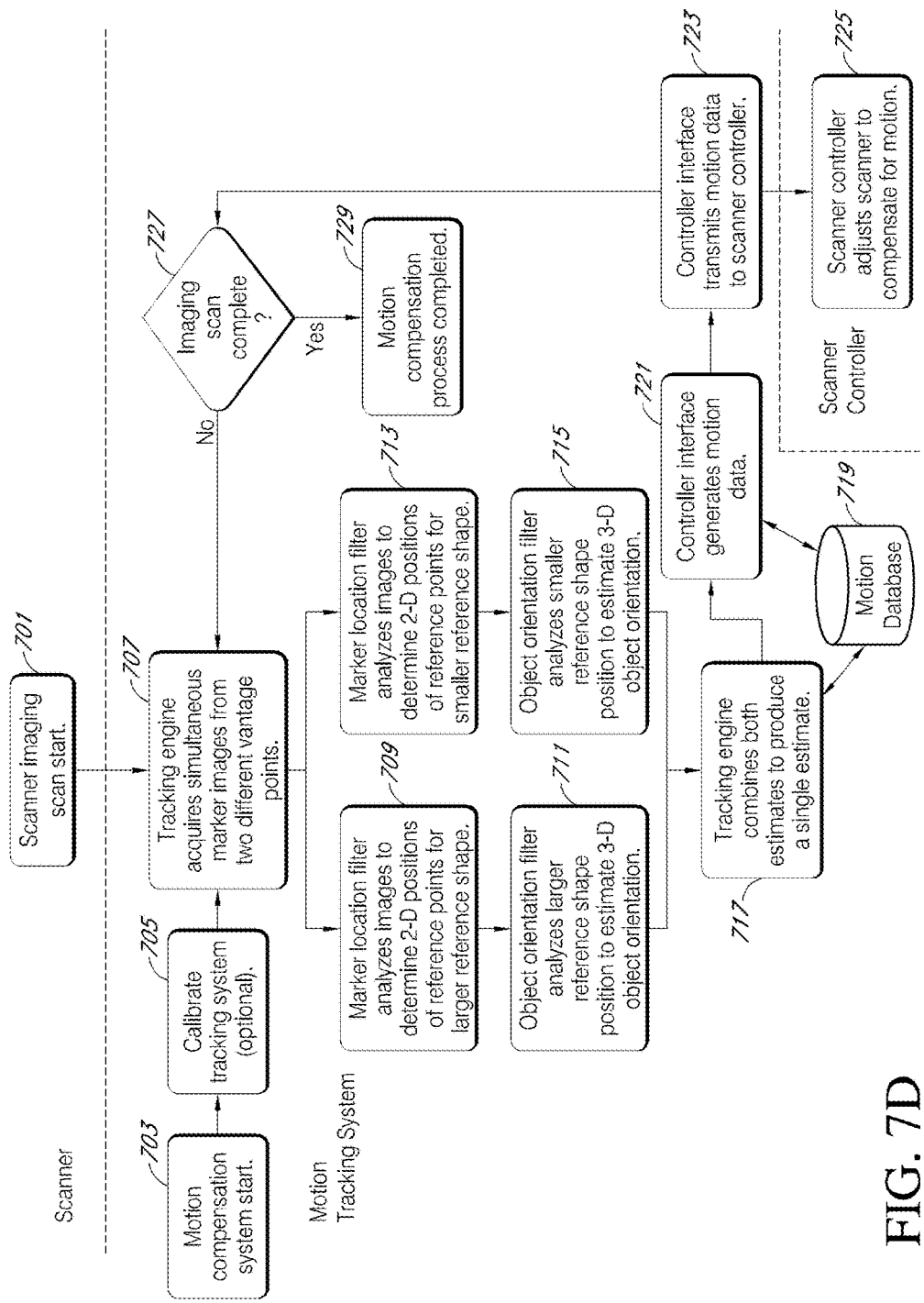
FIG. 7D depicts another embodiment of a process flow diagram illustrating an example of a motion compensation process.

FIG. 7D depicts another embodiment of a process flow diagram illustrating an example of a motion compensation process. The process flow illustrated in FIG. 7D illustrates one example of a process of using multiple optical markers. In this embodiment, a motion tracking system is tracking one larger optical marker and one smaller optical marker, such as is shown in FIG. 6B. However, the concepts described herein may be used in various other embodiments of multiple marker systems. At block 701, a scanner imaging scan is started. At block 703, a motion compensation system starts its motion compensation process. At block 705, the motion tracking system is optionally calibrated. At block 707, a tracking engine acquires simultaneous marker images from two different vantage points.

At block 709, a marker location filter analyzes images to determine two dimensional positions of reference points for the larger reference shape. For example, a marker location filter can be configured to determine the reference point locations of the reference points 614 and 612 illustrated in FIG. 6B. At block 711, an objection orientation filter analyzes the larger reference shape position to estimate a 3D object orientation or pose.

At block 713, the marker location filter analyzes the images from the detectors to determine 2D positions of reference points for the smaller reference shape. For example, the marker location filter can be configured to determine the positions of the reference points 612 and 616 illustrated in FIG. 6B. The locations of these reference points define the position of the reference shape defined by those reference points. At block 715, the object orientation filter analyzes the smaller reference shape position to estimate the 3D object orientation or pose.

At block 717, the tracking engine combines both object orientation or pose estimates from blocks 711 and 715 to produce a single estimate. For example, the tracking engine may average the estimates. In another example, the tracking engine may use one estimate or the other depending on which is most likely to be the more accurate estimate at this point in time. The tracking engine can be configured to communicate with the motion database illustrated at block 719 to store the estimate. At block 721, a controller interface generates motion data. For example, the controller interface can be configured to convert the object orientation or pose estimate into a scanner's coordinate system. At block 723, the controller interface transmits the motion data to a scanner controller. At block 725, the scanner controller adjusts the scanner to compensate for the motion. At block 727, the process flow varies depending on whether the imaging scan is complete. If the imaging scan is not complete, the process flow proceeds back to block 707 and proceeds as described above. If the imaging scan is complete at block 727, the process flow proceeds to block 729 and the motion compensation process is completed.

Optical Target Fixed to an Anatomical Location, e.g., the Head

A challenge in optical head tracking is locating a head feature which moves rigidly with the body's skeletal frame. The skin is elastic and allows significant motion (relative to the displacement desired accuracy; for instance while blinking, twitching or wrinkling the nose or forehead. To overcome this challenge, in an embodiment, the system is configured to employ two or more optical tracking targets for placement on the patient. For example, two or more optical tracking targets can be coupled (for example, painted or affixed to the face of the patient) to the skin of the patient. By employing two or more optical tracking targets, the system can be configured to compensate for the elastic nature of the skin in order to determine the motion of the patient. For example, the system can be configured to track motion of the two or more optical tracking targets and average the detected motion in order to determine the approximate motion of the patient. Alternatively, in an embodiment, the system can be configured to analyze the detected motion from the two or more optical tracking targets and compare the detected motion from each to a predicted motion value. The system can be configured to select the detected motion value that is closest to the predicted motion value and ignore the rest of the detected values. Alternatively, the system can be configured to ignore the detected values that are substantially different from the predicted motion value. The system can be configured to average the detected motion values that have not been ignored. In an embodiment, the system can be configured to apply or combine one or more of the foregoing techniques.

To overcome the challenge of the elastic nature of skin, in an embodiment, an optical tracking target can be coupled to the upper teeth of the patient. One accessible feature which is rigid to the skull is the upper teeth. Unlike the teeth on the lower jawbone, the upper teeth are rigidly affixed to the skull of the patient. In an embodiment, a compact and reliable optical tracking target can be attached to one or more of the upper teeth with a clip-on or other coupling device. Such attachment devices can be configured to be extremely comfortable. In an embodiment, a printed precision optical target is attached to the top front teeth of a patient.

An optical target can be configured to be easy to locate with a high degree of accuracy regardless of orientation in a sensor field of view. A circle or series of concentric circles or ellipses can be potentially advantageous in this regard. Furthermore, to accommodate the fastest composite 2D data processing methods, a number (at least 3) of centroid positions can be discernible at every instant in time. The target can be, in some embodiments, composed of three sets of concentric circles or ellipses located at the vertices of an equilateral triangle. Compactness is desired for practical reasons, but the minimum size and spacing of the targets is dictated to large extent by characteristics of the sensors and the available non-occluded optical lines of sight through the MRI field compensation coil. A tradeoff arises, for instance, between the minimum size of the target and the cost of the imaging cameras used to sense the head motion—the smaller the edge dimension of the target triangle, the more pixels required in the camera sensor, and the faster the readout and processing electronics required.

As a reasonable compromise, in some embodiments an equilateral triangle side length of 0.5 inches can be adopted. The printed target pattern includes a solid central elliptical dot of 1/16" minor diameter at each triangle vertex, and each dot is surrounded by a first concentric ellipse of 3/16" minor diameter and 1/32" line width, and a second concentric ellipse of 5/16" minor diameter and 1/32" line width (ellipses scaled to look circular from camera nominal 45° look angle). In this embodiment, the entire target measures about 1 inch wide by about 0.93 inches high. Other dimensions are possible.

A camera viewing this target is able to determine the centroid of each ellipse on the target pattern using a simple brightness moment calculation, independent of orientation of the target. The target itself subtends only a small portion of the camera field of view, but is recognizable by its high contrast and lack of gray scale. In embodiments the computer processor is programmed to track each of the three sub-targets by enclosing each of the three sub-targets within a sub-pixel array of 48×48 pixels and to calculate centroids of each sub-target by dividing (a) the sum of the product of pixel darkness and pixel position by (b) the sum of the pixel darkness of all of the pixels in the 48×48 sub-pixel array. The processor is also programmed to move each of the 48×48 pixel arrays so that its target is always located fully within the sub-pixel array. With sufficient camera spatial and brightness resolution and target illumination and contrast, centroid positional accuracy of about 0.1 pixels in row and/or column or less is achievable using this target.

FIG. 2A is an enlarged view of the optical target and two of the three Cartesian axes. FIG. 2C shows a full-scale target (compared to a U.S. penny) affixed to NTI coupling device for placement on the upper teeth of the patient. (Lower right) Subject with optical target and night guard clipped onto front teeth.

Latency

Latency in the measurement of head motion using optical tracking techniques is comprised of the camera sensor integration and readout time, the target centroid determination time and the 6-DOF decomposition time. In order to reliably track head motions as fast as 2 cm/second and head rotations as fast as 10 degrees per second, a camera frame rate of about 100 Hz is desired, with electronic shuttering to freeze motion at rates up to 10 times this speed for sharp resolution of the optical target without blurring. A significant field of view is required to accommodate large motions, so fast camera readout without expensive mechanical tracking capabilities will require either a low pixel density or a camera with a larger focal plane but the ability to window a smaller region of interest for readout. Centroid and 6-DOF decomposition algorithms running in composite 2D, rather than full 3D space, and utilizing rapidly converging solution methods can be capable of returning solutions to the compensating head coil electronics at 100 solutions per second, with about 10 ms of latency. In some embodiments, the system can be configured to operate with a latency that enables it to update the scanner in between each image acquisition Cameras For a subject wearing or coupled with the optical head tracking target, the target size and subject rotation angles and translation position determine the physical location of the three target centroids precisely in three dimensions. With precise knowledge of these angles and the optical sensor (camera and lens) parameters—pixel pitch, lens focal length and radial distortion, camera location and orientation relative to nominal target position—the location of the target centroid projections on the focal plane sensor can be predicted to any level of accuracy even prior to measurement.

In principle, the inverse problem should be equally simple as long as the 3D position of the target centroids can be ascertained optically. Using two cameras, a stereo view of the centroid projections can be used to determine the 3D location in space of each target centroid, and the 6-DOF displacement vector can then be determined through a simple matrix inversion. In practice, however, this approach leads to expensive and complicated requirements on camera pixel density, pixel count, camera alignment and camera calibration.

An alternate unfolding approach dispenses with stereo ranging but uses separate 2D projections from two cameras without attempting to correlate absolute target positions on the two cameras. This approach eliminates the strict requirements on camera alignment and magnification matching characteristic of the stereo vision approach, and also relaxes the pixel density and count requirements needed to obtain the required positional accuracy (about 0.1 mm in translation and about 0.1 degrees in rotation) by about a factor of 20, resulting in significant savings in cost and processing speed. Although various embodiments described herein may not utilize stereo ranging, imaging, or vision, some embodiments may utilize concepts of stereo ranging, imaging, or vision, either alone or in combination with other object orientation determination techniques described herein.

Even for this 2D measurement approach some basic steps can be taken to calibrate camera parameters once the cameras are integrated with the head coil; these can be performed at the manufacturing facility. These include measuring the projected pixel location of a single reference point on both cameras, as well as the camera magnification factors for pixel displacement per degree of rotation in pitch, yaw and roll, and per mm of translation along x, y and z. However, as stated before, it is not necessary that the cameras be exactly aligned in space (e.g. perfectly normal) or that their magnifications (lens focal length and distance to reference point) be identical, as is easily verified by simulation.

Stereo Versus Composite 2D Vision Requirements

Figure 8B:
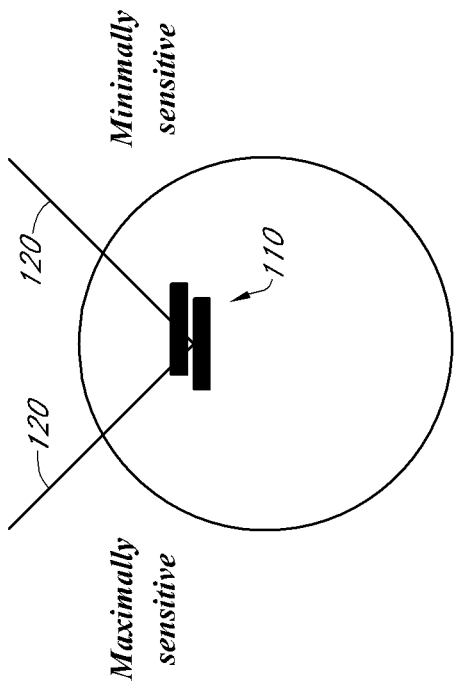
FIGS. 8A and 8B show how two cameras together provide sensitivity needed to track motion, according to some embodiments of the invention.
Figure 8A:
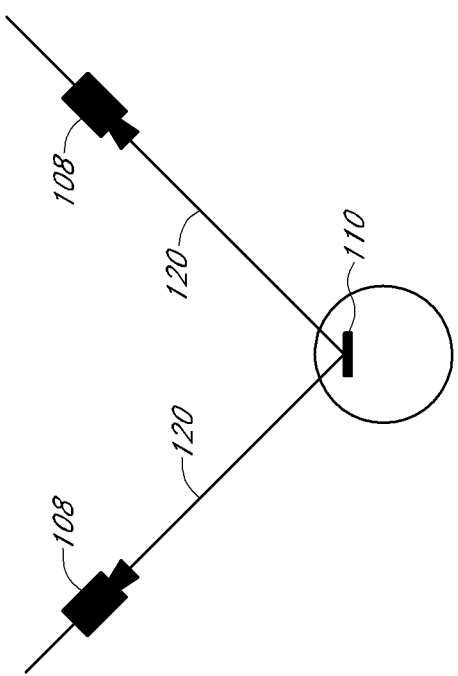

With a single camera viewing the target from 45 degrees off of vertical in the target plane, the camera sees very little centroid displacement when the target moves in the direction of the camera (e.g. upward vertical translation equal to horizontal translation in the camera direction, with no rotation). Assuming a 7 micron pixel pitch, a 25 mm lens, and a working distance of 14 inches, target displacement in the camera direction may be at least 0.6 mm before the target can be detected as a 0.1-pixel increase in target centroid separation. However, as shown in FIGS. 8A and 8B a second camera placed orthogonally, e.g. at −45 degrees relative to vertical in the same plane, is maximally sensitive to this same motion, seeing a full pixel displacement of each centroid for a diagonal translation of only 0.1 mm. The second camera eliminates the "blind spot" that a single camera has to motion along its optical axis. While certain embodiments described systems in which cameras are positioned orthogonally, cameras can also be placed at relative angles other than orthogonal with respect to vertical in the same plane, depending on the desired clinical result.

Camera Depth of Field

To accommodate head roll of +/−15 degrees plus the 0.85-inch target width at a working distance of 14 inches, the lens can be configured to provide sharp focus for distances between 13" and 15.5". At f/22, assuming a circle of confusion slightly smaller than a camera pixel (7 microns), a 25 mm focal-length lens provides this necessary depth of field a nominal 14-inch focus. At this working distance, the optical path can be folded with a turning mirror (FIG. 3) or otherwise configured to fit within the 70 cm diameter bore of the main MRI coil. A non-ferrous camera can be utilized in the MRI environment. In an embodiment, it can be cost effective to repackage a commercial camera for use in the strong magnetic field.

In some embodiments, one possible camera that can be utilized or modified for use with systems and methods as disclosed herein, is produced by Allied Vision Technologies and designated the Prosilica GE-680 Monochrome CCD Camera. This camera features a Kodak KAI-0340 ⅓" 640× 480 VGA focal plane sensor with 7.4 μm square pixels and a fast Gigabit Ethernet output delivering up to 205 frames per second at 12-bit pixel depth. An inexpensive possible lens for use is an Edmund Optics TechSpec 25 mm high-resolution fixed focal length lens.

For this camera and lens, at 14 inches from the target at 45° incidence, the ⁵⁄₁₆" diameter target circles project to ellipses on the camera, with the minor diameter of the largest ellipses at about 28 pixels and the major diameter at about 40 pixels. With sufficient S/N ratio (target illumination) and lens MTF (sharpness), this pattern should allow accurate centroiding to about 0.1 pixels in row and/or column or less. The entire projected target subtends about 128 H×168 V pixels, and allowing for head roll of +/−11.5 degrees, a camera with 640 horizontal pixels (pixel columns) can accommodate the entire field of interest without mechanical tracking provisions.

FIGS. 9A and 9B show a modified head coil with cameras mounted longitudinally and turning mirrors to accommodate a longer working distance than is possible with a straight optical path in the constrained space of the main MRI coil bore. In embodiment, the system is configured with two or more cameras with a direct view of the optical tracking targets without the use of mirrors.

Six Degree-of-Freedom Measurement and Reporting Algorithm

In some embodiments, the MRI Head Tracker takes real-time input from two 2D imaging sensors and analyzes these data to determine and report motions in six degrees of freedom with minimal latency. This task can be performed by detecting and measuring the three centroid positions on the target and utilizing those positions with a reporting algorithm to determine the position of the patient's head.

Six-Degree-of-Freedom Coordinate System

Figure 10B:
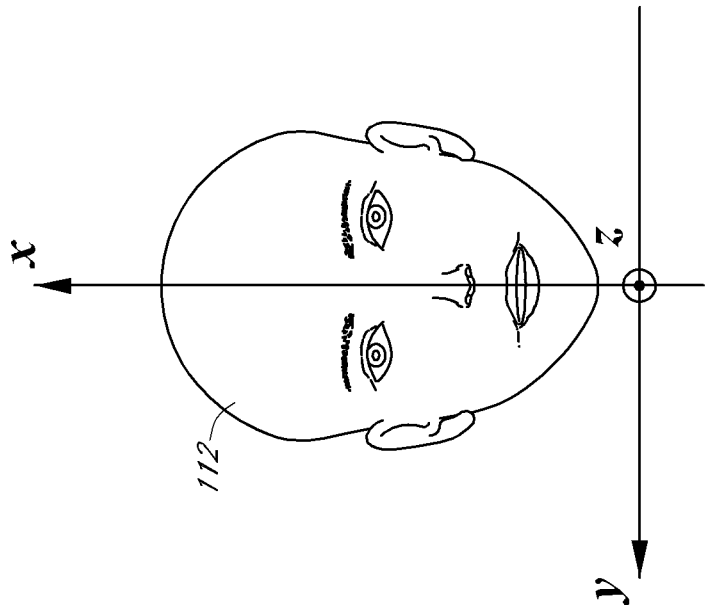
FIGS. 10A and 10B show how Cartesian coordinates are used relative to a patient's head for the purpose of tracking motions, according to some embodiments of the invention.
Figure 10A:
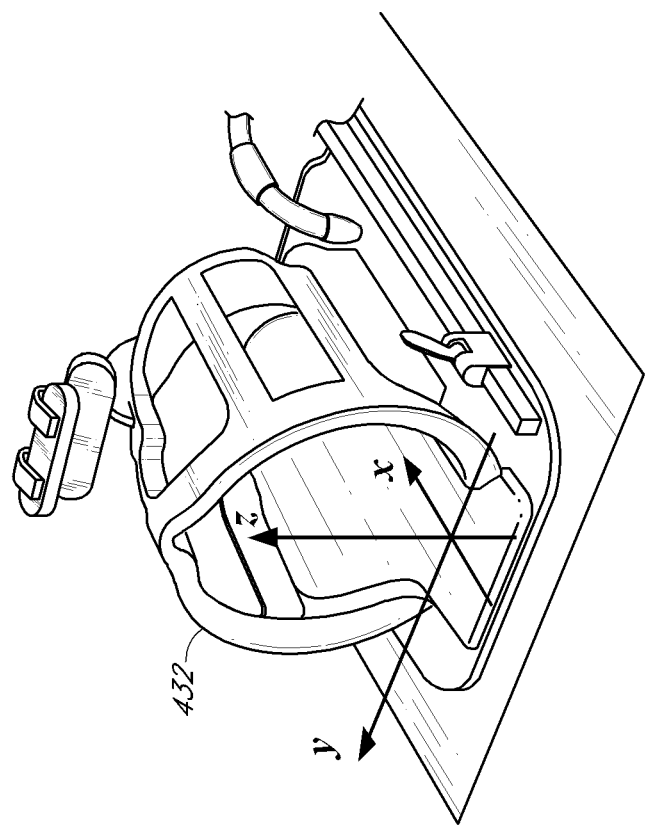

In an embodiment, the system is configured to use a coordinate system for reporting 6-DOF motions to the MRI field compensation system that is a Cartesian system aligned with the symmetry axis of the head coil as shown in FIGS. 10A and 10B. Head coil coordinate system shown in FIG. 10A is coincident with body coordinates in the nominal ("square") head position as shown in FIG. 10B. The z direction is into and out of the plane of the drawing. Target displacements and rotations are reported to the coil field compensation system using this system of coordinates.

Coordinate definitions are adopted by the same conventions used in defining aircraft motion, except that the rotation directions are taken to be right-handed (positive for counter-clockwise rotation about the basis direction vectors):

x is the longitudinal (chin-to-crown) direction, with values increasing toward the top of the head y is the transverse (left-to-right) direction, with increasing values toward the patient's right ear z is the up-down direction, with increasing values toward the ceiling $$\psi = \tan^{-1}\left(\frac{\Delta y}{\Delta x}\right)$$

is the yaw angle or right-handed rotation about the z-axis (head lean toward shoulder while facing forward, zero at normal "square" position, positive values for patient leaning toward patient's right shoulder)

$$\theta = \tan^{-1}\left(\frac{\Delta x}{\Delta z}\right)$$

is the pitch angle or right-handed rotation about the y-axis (nodding "yes," zero at normal "square" position, positive values for patient looking "upward")

$$\varphi = \tan^{-1}\left(\frac{-\Delta y}{\Delta z}\right)$$

is the roll angle or right-handed rotation about the x-axis (shaking the head "no," zero at normal "square" position, positive values for patient looking toward patient's left side).

The origin of coordinates and angle zero references are arbitrary, as only relative motions are reported, however two convenient reference origin positions exist: 1) at the center of the target in its normal ("square") head position, and 2) at the base of the neck at the point where the head swivels for nod, turn and lean motions. The latter is adopted here (as shown in FIG. 2), simply for ease in orthogonalizing the set of principal observation parameters with common motion directions in the 6-DOF decomposition algorithm.

Target Displacement Equations

The full 6-DOF translation is composed of a 3-D displacement as well as a 3-axis rotation. To first order we assume that the skull moves as a rigid body about a single rotation point somewhere in the neck. From this point the translation becomes separable from the rotation, so this is chosen as the coordinate origin. The rotations are separated into roll, pitch and yaw as described above, and the translated position through rotation follows the Euler rotation matrix formulation as follows (using right-handed angle conventions). The x, y, and z displacement coordinates then follow the independent translations:

$$\begin{pmatrix} x' \\ y' \\ z' \end{pmatrix} = \begin{pmatrix} 1 & 0 & 0 \\ 0 & \cos\varphi & -\sin\varphi \\ 0 & \sin\varphi & \cos\varphi \end{pmatrix} \begin{pmatrix} \cos\theta & 0 & \sin\theta \\ 0 & 1 & 0 \\ -\sin\theta & 0 & \cos\theta \end{pmatrix} \begin{pmatrix} \cos\psi & -\sin\psi & 0 \\ \sin\psi & \cos\psi & 0 \\ 0 & 0 & 1 \end{pmatrix} \begin{pmatrix} x \\ y \\ z \end{pmatrix} + \begin{pmatrix} \Delta x \\ \Delta y \\ \Delta z \end{pmatrix}.$$

Decomposing the six independent translations from the absolute and relative displacements of the measured target centroids is the subject of this effort. The 2D inverse problem is somewhat more difficult than the 3D problem, in that after the target centroid projections in focal plane row and column are determined, significant degeneracies remain in the unfolding matrices for each camera. Combining the data from both cameras removes these degeneracies through a series of interrelated, nonlinear equations. The fastest procedure for solving this inverse problem is obtained by the Newton-Raphson method or a variant thereof, whereby an approximate first-order solution is proposed and tested against the known (measured) centroid locations on the two camera focal planes. The residual error is divided by the local derivatives with respect to each component of rotation and translation, to determine an iterative correction. The first-order solution is chosen by considering the features of the projected target pattern which are most strongly affected by a single rotation angle or displacement, and linearizing the inversion problem along these feature axes.

A 6-DOF motion simulation and decomposition algorithm was developed and tested to allow simulation of arbitrary motions and then verify the ability of a pair of orthogonal cameras to decompose centroid measurements at the 0.1-pixel level into distinct x, y, z, roll, pitch and yaw components at the requisite level of accuracy.

Six-Degree-of-Freedom Motion Determination Algorithm

General subject motion is a superposition of translation along x, y, and z as well as rotation about the x, y and z axes (designated roll, pitch and yaw respectively). Displacements along each of these degrees of freedom are not sensitive to coordinate system origin; however it is convenient (as explained above) for modeling purposes to place an origin near the region of the spine about which the head rotates and swivels, and a secondary reference point at the center of the optical tracking target in the nominal ("correct") head position and orientation. This secondary reference is typically offset from the spinal origin by ~10 cm in x and ~10 cm in z.

Figure 11:
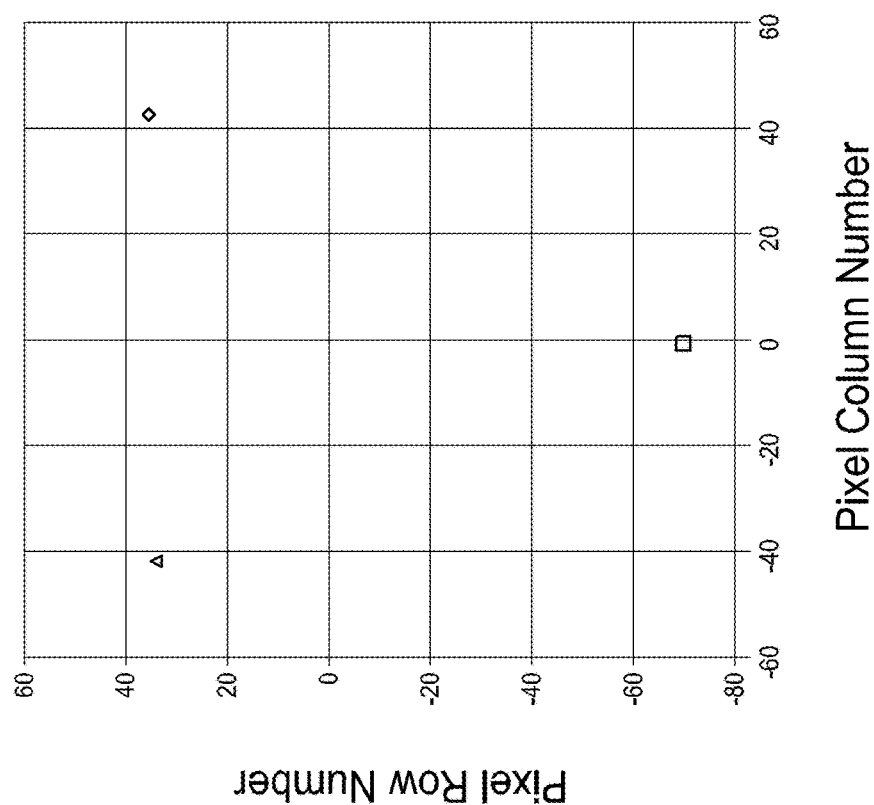
FIG. 11 shows how three points of the precision optical target are imaged on the focal plane of each of the two cameras, according to some embodiments of the invention.

The target shown in FIG. 1, as viewed from a single camera, appears as three sets of concentric ellipses with centroids projected onto three different positions (column, row) on the camera focal plane. The camera is centered along the (x=constant) plane of the target and aligned such that the central pixel row images this plane, at an angle of 45 degrees with respect to both the y and z axes and with the nominal target center projected to the central pixel column. Using a camera with 7.4 micron pixels and a 25 mm lens, positioned at a distance of 14.1 inches from the nominal target center, centroids from the vertices of an equilateral triangle target with sides of length 0.5 inches are projected onto the camera focal plane as shown in FIG. 11. This figure shows projected positions of target centroids for a target with sets of concentric circles arranged about the vertices of an equilateral triangle of side length 0.5 inches, using a camera focal length 25 mm, pixel pitch 7.4 microns and view angle 45 degrees (camera to right and above paper), aligned with the camera centerline. The 45-degree view angle results in the foreshortening of the equilateral triangle from left to right across the focal plane.

Yaw

Figure 12:
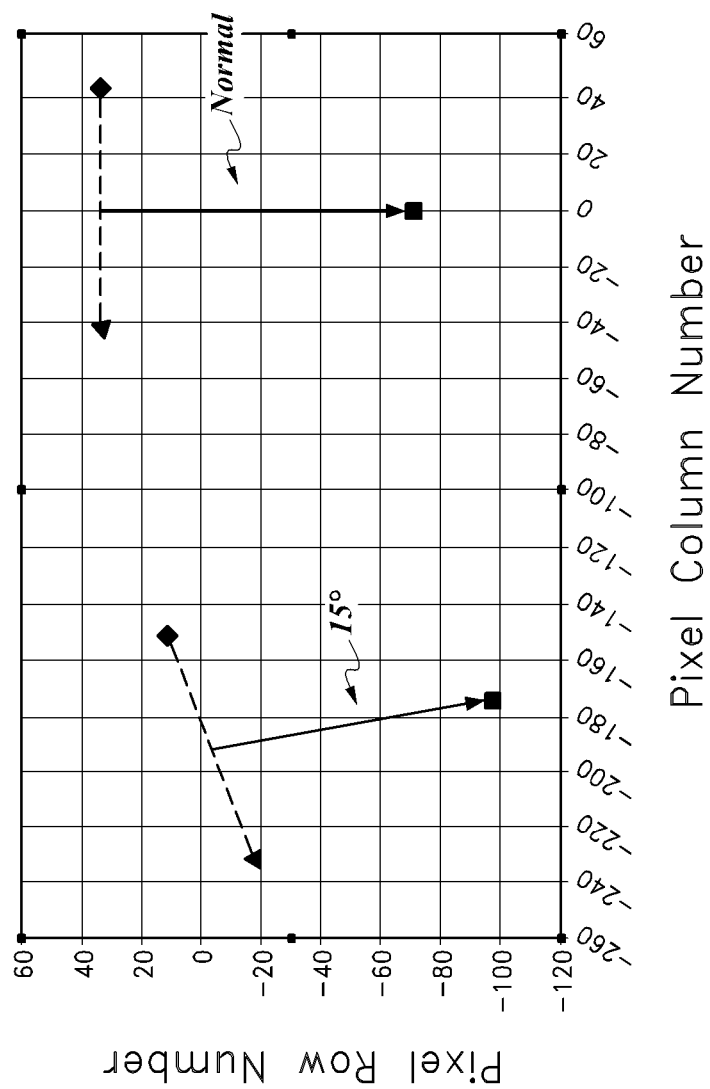
FIG. 12 shows the results on one camera image of a 15 degree yaw movement (about the z-axis), according to some embodiments of the invention.

Rotation about the z-axis is designated as yaw; a positive or "right handed" rotation about this axis (head leaning to subject's right shoulder) results in a counterclockwise rotation of the target. Because this rotation usually occurs about a point lower in the neck, it is typically accompanied by a translation to the subject's right side (camera left), as seen in FIG. 12. Projected positions of target centroids for same conditions as FIG. 11, but before and after inducing a yaw of 15 degrees.

The median of the centered target triangle (as shown at the right in FIG. 12) is aligned approximately with a single column of camera pixels, but is rotated out of this alignment (as shown at the left side of FIG. 12) by yaw. For the camera, lens, target distance and target size described above, a yaw of only 0.1 degrees results in a relative displacement of 0.13 pixel columns between the two ends of the median. Assuming that the centroid algorithm is able to determine position of the triangle vertices to 0.1 pixels in row and column, the yaw angle determination is measurable down to and accurate to about 0.1 degrees.

Pitch

Rotation about the y-axis is designated as pitch; a positive or "right-handed" rotation about this axis (head tipped back) results in motion of the target upward off the gantry (+z) and toward the top of the head (+x). For a single camera this projection is not easily distinguishable from a simultaneous target displacement in x and y (see FIG. 7), but for two cameras at opposite sides of the head the apparent y-displacement is in the opposite direction, removing this degeneracy. A second degeneracy with pitch rotation remains, for simultaneous target translation in +x and +z—this is discussed in more detail later—but the tilt of the target plane during a pitch rotation yields a small difference in the amount of translation of the base of the target triangle relative to its apex, thus resulting in a slight apparent rotation of the target triangle as shown in FIG. 7, which is not a characteristic of simple translation. This becomes in some embodiments the defining characteristic of pitch motion.

Figure 13B:
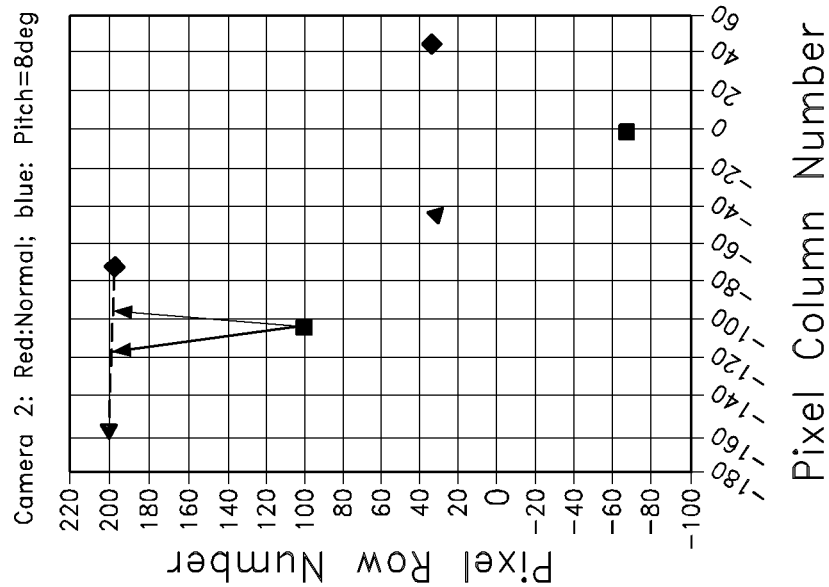
FIGS. 13A and 13B shows how two cameras are able to monitor precisely a pitch movement (about the y-axis), according to some embodiments of the invention.
Figure 13A:
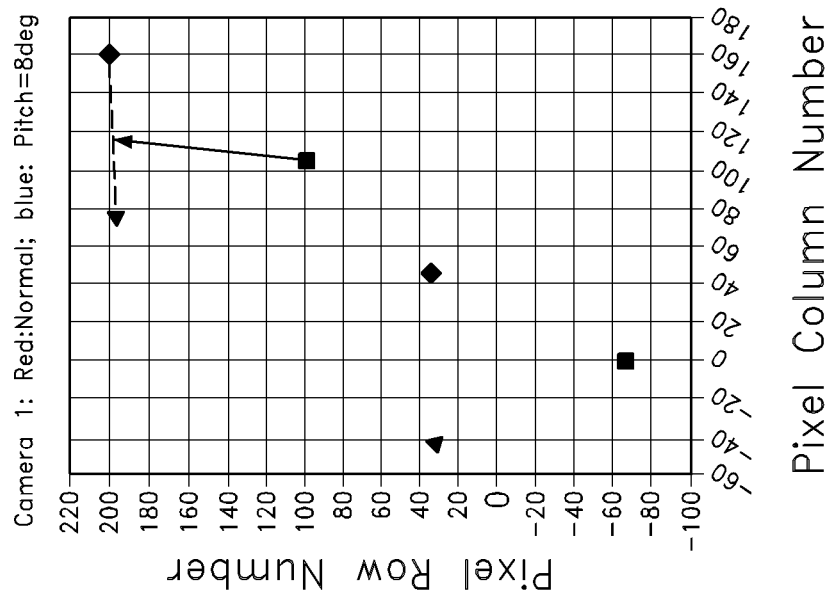

FIGS. 13A and 13B show the projected positions of target centroids for same conditions as FIG. 11, but before and after a target pitch of 8 degrees. Left is view from a camera at the left side and above the paper, right is view from a camera at the right side and above the paper. In each case motion away from the gantry (+z) makes the target appear more distant from the observer.

Roll

Rotation about the x-axis is designated as roll; a positive or "right-handed" rotation about this axis (head pointing toward subject's left side) results in a motion of the target toward the subject's left (−y). For a single camera this motion is not easily distinguishable from a displacement in y (see FIG. 8), but for two cameras the difference in position and in apparent foreshortening of the triangle is much more pronounced for rotation than for translation. This is because the roll moves the target plane closer to normal incidence with one camera sightline and further from normal incidence with the other camera sightline, at a rate which is much larger than that for a simple translation (or yaw). There is a significant degeneracy between roll and simultaneous +y and +z translation which is only resolved comparing the lengths of the triangle base as seen between the two cameras. A large difference in the base lengths is a characteristic of roll motions and not a characteristic of y+z translation, hence this is the distinguishing characteristic for roll.

Figure 14B:
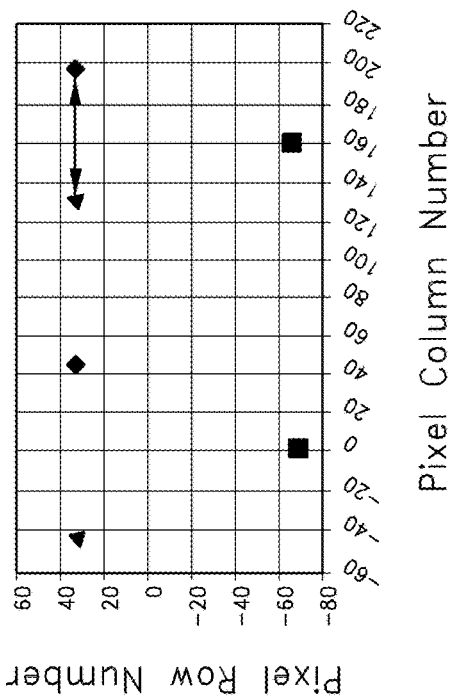
FIGS. 14A and 14B show how a roll movement (about the x-axis) is monitored, according to some embodiments of the invention.
Figure 14A:
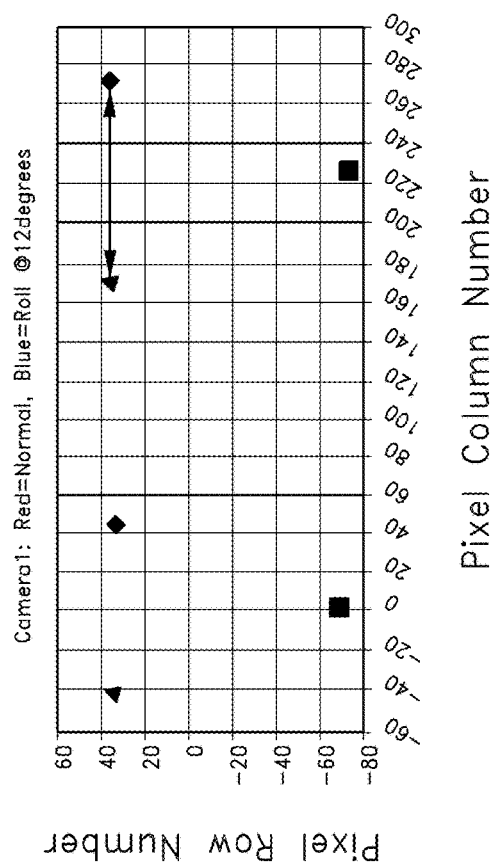

As shown in FIGS. 14A and 14B the projected positions of target centroids for same conditions as for FIG. 11, but before and after target roll of 12 degrees. Left is view from a camera at the left side and above the paper, right is view from a camera at the right side and above the paper. The camera at the left side sees much wider triangle because target plane is closer to normal to this camera sightline. The camera at the left also sees much larger displacement of triangle center.

X-Axis Translation

Figure 15:
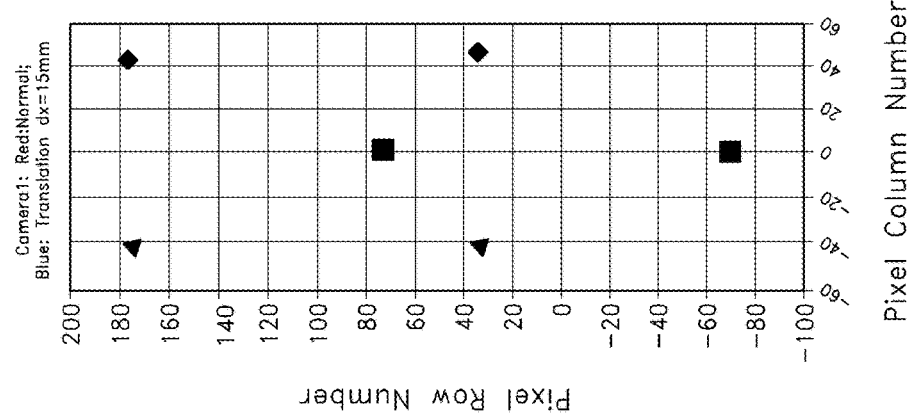
FIG. 15 shows how x-axis translation (positive toward the top of the patient's head) is monitored on one camera, according to some embodiments of the invention.

Translation along the x-axis (positive toward top of head) results in a motion of the target along the vertical direction of the camera focal plane (see FIG. 15). Unlike for pitch rotation (which also involves a translation in z), the target does not move significantly between pixel columns, and rotation of the target triangle is minimal. This up-down camera translation without accompanying rotation is the distinguishing characteristic of x-axis translation. FIG. 15 shows the projected positions of target centroids for same conditions as for FIG. 11, but before and after target translation of 12 mm in x.

Y-Axis Translation

Figure 16A:
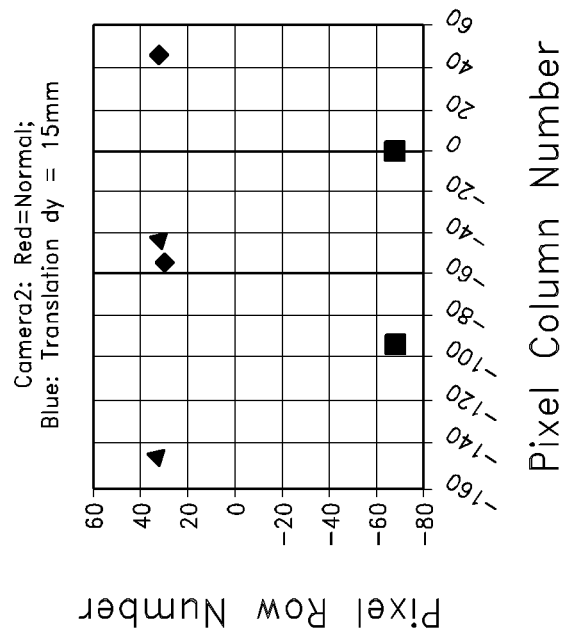
FIGS. 16A and 16B shows the effect of y-axis translation (positive to the patient's right side) as monitored on the two cameras, according to some embodiments of the invention.
Figure 16B:
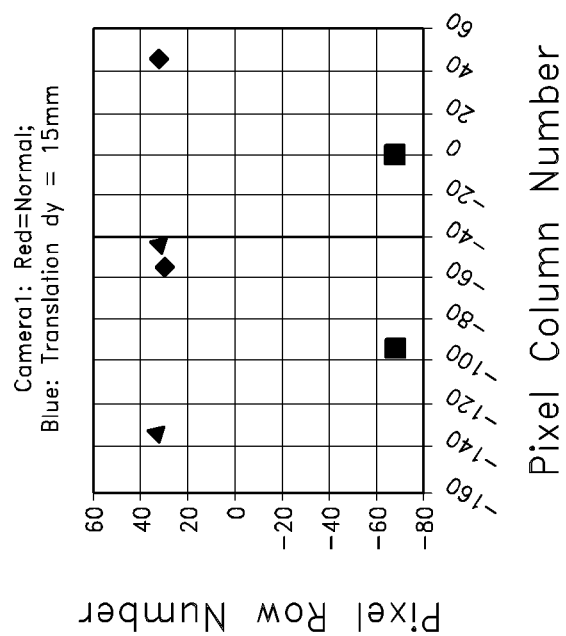

Translation along the y-axis (positive toward subject's right side) results in a motion of the target along the horizontal axis of the camera focal plane (see FIGS. 16A and 16B). Unlike for roll (which also involves a differential rotation of the target plane as seen by the left and right side cameras), the target's projected size, displacement and rotation varies only slightly between left and right camera views for y-axis translation; this is the distinguishing characteristic for y-displacement. FIGS. 16A and 16B show projected positions of target centroids for same conditions as FIG. 11, but before and after target translation of 15 mm along y-axis. Left is view from a camera at the left side and above the paper, right is view from a camera at the right side and above the paper. Unlike roll, target displacements and sizes are similar for two cameras viewing y-axis translation.

Z-Axis Translation

Figure 17B:
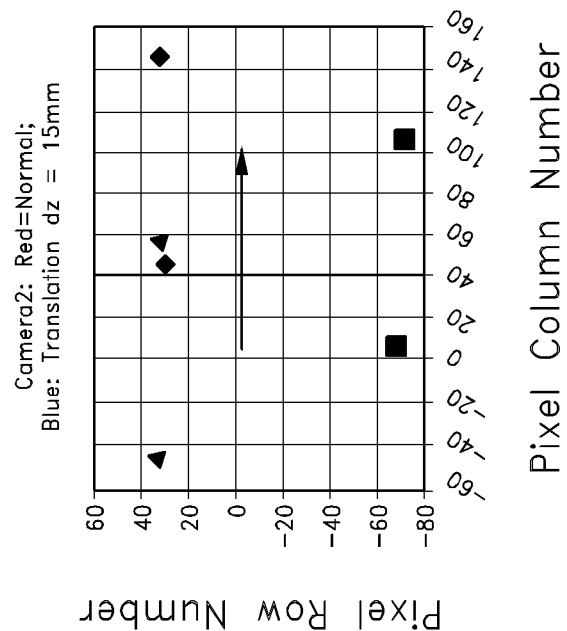
FIGS. 17A and 17B show the effect of z-axis translation (toward the ceiling), according to some embodiments of the invention.
Figure 17A:
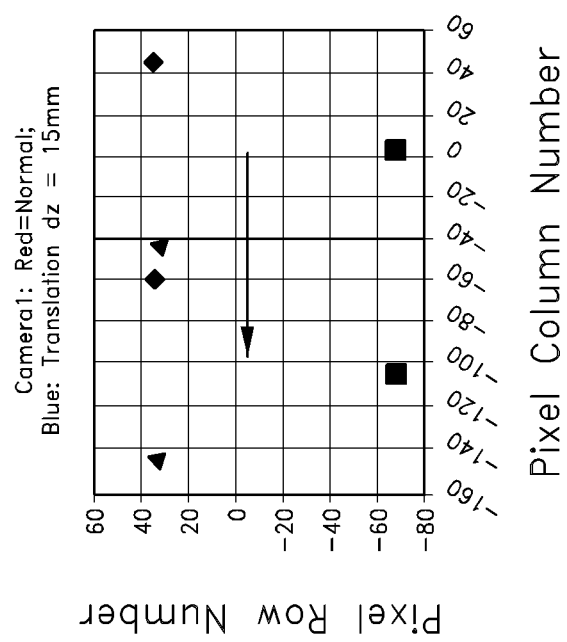

Translation along the z-axis (positive toward the ceiling) results in apparent motion of the target along the horizontal axis of the camera focal plane. Unlike for y translation, however, the direction of the horizontal displacement is opposite between the left-side and right-side cameras (see FIGS. 17A and 17B). This is the distinguishing characteristic for z-axis translation. FIGS. 17A and 17B show projected positions of target centroids for same conditions as for FIG. 11, but before and after target translation of 15 mm along the z-axis. Left is view from a camera at the left side and above the paper, right is view from a camera at the right side and above the paper. Unlike translation along y, apparent target displacement is in opposite direction in two camera views.

Non-Degenerate Target Motion Parameters

Pitch Versus (X+Z) Translation Degeneracy

Figure 18B:
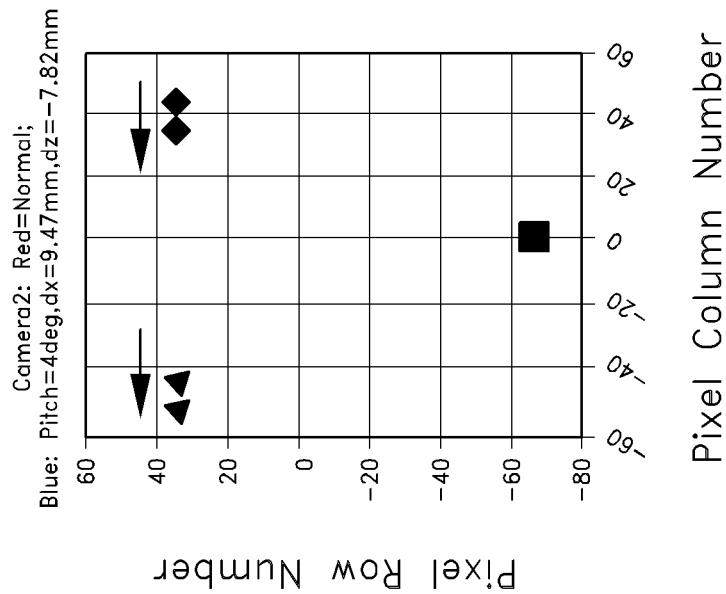
FIGS. 18A and 18B show the effect of simultaneous pitch and x-axis and z-axis translation, according to some embodiments of the invention.
Figure 18A:
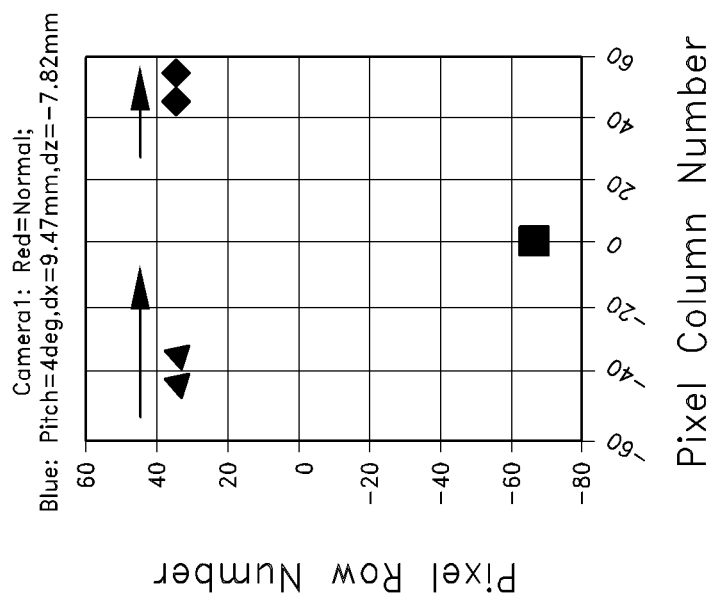

Pitch is nearly degenerate with simultaneous x and z translation, except for a small tilt in the triangle vertical which results from the tilt of the target plane about the y axis. This tilt creates an apparent clockwise rotation of the triangle from the left-side view and an apparent counterclockwise rotation from the right side view, as shown in FIGS. 18A and 18B. These drawings show projected positions of target centroids for same conditions as FIG. 11, but before and after target pitch of 4 degrees and translations in x and z of −9.5 mm and +7.8 mm respectively. FIG. 18A is view from a camera at the left side and above the paper, FIG. 18B is view from a camera at the right side and above the paper. The camera at left sees triangle rotated clockwise, with upper vertices rotated away from the camera because of an increase in z relative to the lower vertex. The camera at the right sees triangle rotated counterclockwise for the same reason. For a pitch motion of 0.1 degrees accompanied by translations in x and z of −0.244 mm and 0.187 mm respectively, the triangle apex centroid does not move in either camera view. However, in this case, the left-side camera sees the triangle base displaced by 0.13 pixels to the right while the right-side camera sees the triangle base displaced by 0.13 pixels to the left. Assuming the centroiding routine can locate the vertices of the target triangle to an accuracy of 0.1 pixels, a pitch as small as 0.1 degrees is distinguishable from a simple translation by comparison of the vertical tilts.

Roll Versus (Y+Z) Translation Degeneracy

Figure 19B:
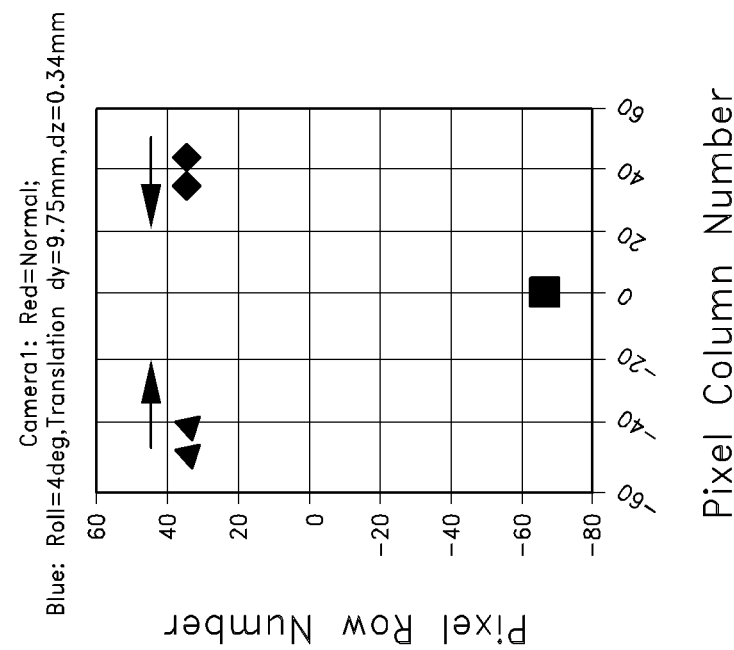
FIGS. 19A and 19B show the effect of simultaneous roll and y-axis and z-axis translation, according to some embodiments of the invention.
Figure 19A:
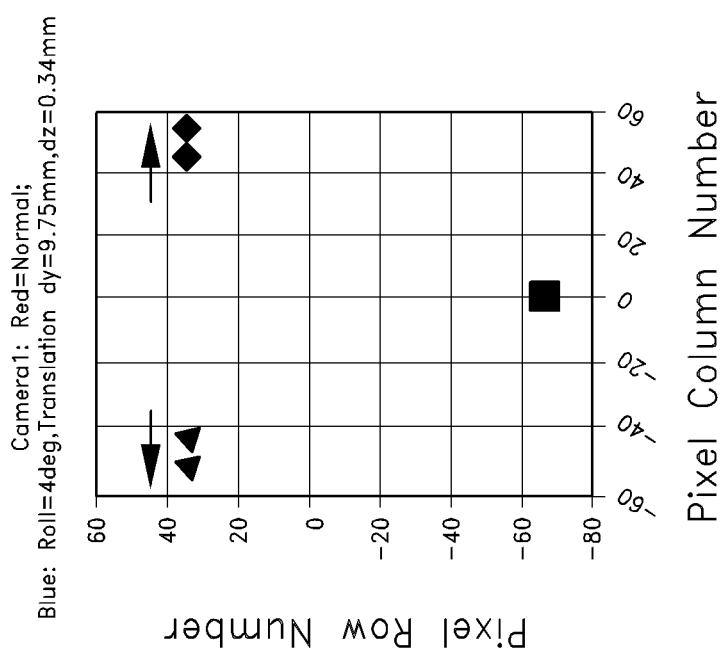

Roll is nearly degenerate with simultaneous y and z translation, except for larger camera-to-camera differences in apparent target size encountered with roll, resulting from tilt of the target's plane about the x-axis. A significant difference in the apparent length of the target triangle base is a reliable distinguishing characteristic of roll motion rather than simple translation. FIGS. 19A and 19B show projected positions of target centroids for the same conditions as in FIG. 11, but before and after target roll of 4 degrees and translations in y and z of 9.75 mm and 0.34 mm respectively. FIG. 19A is view from a camera at the left side and above the paper, FIG. 19B is view from a camera at the right side and above the paper. Camera at left sees triangle base shrink due to rotation about the x-axis away from camera normal, while camera at right sees triangle base grow due to rotation toward camera normal.

For a roll of 0.1 degrees and translations in y and z of −0.244 mm and 0.0002 mm respectively, the lower centroid is unchanged in both camera views. In this case, the left-side camera sees the target triangle base shrink by 0.15 pixels while the right-side camera sees the triangle base grow by 0.15 pixels. Assuming the centroiding routine can locate the target centroids to an accuracy of 0.1 pixels, shifts of 0.14 pixels should be discernible, so a pitch as small as 0.1 degrees is distinguishable from a simple translation by comparison of the length of the target triangle base.

Six-Degree-of-Freedom Motion Determination Algorithm Architecture

Complementary Projections Versus Stereo Imaging

The target size, rotation angles and translation vector determine the relative displacement of the three target centroids precisely in three dimensions. Precise knowledge of camera and lens parameters (e.g., pixel pitch, lens focal length and radial distortion, camera location and orientation relative to nominal target position), are then sufficient to predict the location of the target centroid projections to better than 0.1 pixels in row and column for each camera. In principle, the inverse problem should be equally simple; the stereo view of the centroid projections determine the 3D location in space of each target centroid, and the 6-DOF displacement vector can then be determined through a simple matrix inversion. In practice, however, this approach leads to expensive and complicated requirements on camera pixel density, pixel count, camera alignment and camera calibration. An alternate unfolding approach dispenses with stereo ranging and uses the two camera projections separately without strict requirements on precise matching of camera alignment and magnification, to determine the 6-DOF displacement vector to within 0.1 degrees in each rotation angle and 0.1 mm along each translation axis. This approach relaxes the pixel density and count requirements by about a factor of 20 relative to the stereo approach, resulting in significant savings in cost and processing speed.

Even for this 2D approach some basic measurements can be made to calibrate camera parameters once the cameras are integrated with the head coil; these can be easily performed at the manufacturing facility. These measurements include the projected pixel location of a single reference point on both cameras, as well as the camera magnification factors for pixel displacement per degree of rotation in pitch, yaw and roll, and per mm of translation along x, y and z. However, as stated before, it is not necessary that the cameras be exactly aligned in space (e.g. perfectly normal) or that their magnifications (lens focal length and distance to reference point) be identical, as has been easily verified by simulation.

Inversion Equations

The 2D inversion problem is somewhat more difficult than the 3D problem, in that after the target centroid projections in focal plane row and column are determined, significant degeneracies remain in the unfolding matrices for each camera. Combining the data from both cameras removes these degeneracies through a series of interrelated, nonlinear equations. The fastest procedure for solving this inverse problem is obtained by a variant of the Newton-Raphson method, whereby an approximate first-order solution is proposed and tested against the known (measured) centroid locations on the two camera focal planes. The residual error is divided by the local derivatives with respect to each component of rotation and translation, to determine an iterative correction. The first-order solution is chosen by considering the features of the projected target pattern which are most strongly affected by a single rotation angle or displacement, and linearizing the inversion problem along these feature axes.

6-DOF Extraction Algorithm

Below is described one embodiment of a method for extracting the 6 degree of freedom displacement matrix from the observed target location on two focal plane cameras. Other embodiments may be used consistent with the disclosure herein. Further, although the embodiment below refers to steps, in some embodiments not all steps are included, additional steps are included, and/or the steps are not always performed in a set order.

Step 1: Characterizing the Target Images

The optical target consists of elliptical targets shown in FIG. 2A that are drawn so as to appear as circular patterns when imaged at 45 degrees by the two cameras shown in FIG. 8A. The center of each of the three circular patterns define one of the three vertices of an equilateral triangle at the focal plane of each of the two cameras. A centroid calculation routine determines the positions of the centroids at each of the three vertices, on each of two independent cameras. These centroids are displayed on a computer monitor displaying the 640×480 pixels of each of the two cameras. FIG. 11 shows the three vertices being displayed on one of the cameras. These vertex positions are $(X_{i,j}, Y_{i,j})$ designated for vertex index i from 1 to 3, and camera index j from 1 to 2, resulting in twelve measured coordinates. From the twelve measured coordinates, and initialized values of these coordinates, six principal quantities are computed to characterize the two camera views of the equilateral triangle target:

a) $\Sigma_{HD}$—the sum of the horizontal displacements (in pixels) of the target center on camera 1 and camera 2; the formula used is $$\sum_{i=1}^{3}\sum_{j=1}^{2}(X_{i,j}-X_{0i,j}),$$

where is $X_{0i,j}$ the initial (zero displacement) horizontal camera coordinate of each centroid projection.

b) $\Delta_{HD}$—the difference between the horizontal displacements (in pixels) of the target center for camera 1 and camera 2; the formula used is $$\sum_{i=1}^{3}(X_{i,1}-X_{0i,1})-(X_{i,2}-X_{0i,2}).$$

c) $\Sigma_{VD}$—the sum of the vertical displacements (in pixels) of the target center for camera 1 and camera 2; the formula used is $$\sum_{i=1}^{3}\sum_{j=1}^{2}(Y_{i,j}-Y_{0i,j}),$$

where $Y_{0i,j}$ is the initial (zero displacement) vertical camera coordinate of each centroid projection.

d) $\Delta_{BL}$—the difference in the apparent base length of the target triangle (in pixels) for camera 1 and camera 2; the formula used is $$\left\{\sqrt{(X_{3,1}-X_{1,1})^2+(Y_{3,1}-Y_{1,1})^2}-\sqrt{(X_{3,2}-X_{1,1})^2+(Y_{3,2}-Y_{1,2})^2}\right\}.$$

e) $\Sigma_{MT}$—the sum of the apparent median tilt of the target triangle (offset in horizontal pixels between center-of-base and apex) for camera 1 and camera 2; the formula used is $$\sum_{j=1}^{2}\left\{\left(X_{2,j}-\frac{X_{3,j}+X_{1,j}}{2}\right)-\left(X_{02,j}-\frac{X_{03,j}+X_{01,j}}{2}\right)\right\}.$$

f) $\Delta_{MT}$—the difference between the apparent median tilt of the target triangle (in pixels) for camera 1 and camera 2; the formula used is $$\left\{\left(X_{2,1}-\frac{X_{3,1}+X_{1,1}}{2}\right)-\left(X_{02,1}-\frac{X_{03,1}+X_{01,1}}{2}\right)\right\}-$$
$$\left\{\left(X_{2,2}-\frac{X_{3,2}+X_{1,2}}{2}\right)-\left(X_{02,2}-\frac{X_{03,2}+X_{01,2}}{2}\right)\right\}$$

Step 2: Characterizing Global Variation in Principal Quantities with 6-DOF Motions Partial derivatives relative to subject displacements and rotations ($\phi$, $\theta$, $\psi$, $\Delta x$, $\Delta y$, $\Delta z$), of the principal quantities described above, about the initial (non-displaced) position, are computed numerically. Here:

Roll $\phi$ is right-handed rotation about the x-axis
Pitch $\theta$ is right-handed rotation about the y-axis
Yaw $\psi$ is right-handed rotation about the z-axis
$\Delta x$ is toe-to-head direction
$\Delta y$ is left-to-right direction
$\Delta z$ is down-to-up direction Starting from an initial target position in 3-D world space, defined as ($\phi$, $\theta$, $\psi$, $\Delta x$, $\Delta y$, $\Delta z$)=(0, 0, 0, 0, 0, 0), the initial target vertex world coordinates ($x_{0i}, y_{0i}, z_{0i}$) are determined for vertex index i=1 to 3, based on the geometric size and shape of the target triangle and definition of a convenient coordinate origin.

Local partial derivatives of each of the principal quantities, with respect to each of the 6 degrees of freedom (roll, pitch, yaw, dx, dy, dz), are performed numerically by evaluating changes in these quantities for small increments in each degree of freedom. Changes in the target vertex positions for specified motions along the six degrees of freedom are computed using the Euler rotation matrices and translation vector:

$$\begin{pmatrix} x_i \\ y_i \\ z_i \end{pmatrix} = \begin{pmatrix} 1 & 0 & 0 \\ 0 & \cos\varphi & -\sin\varphi \\ 0 & \sin\varphi & \cos\varphi \end{pmatrix} \quad [1]$$

$$\begin{pmatrix} \cos\theta & 0 & \sin\theta \\ 0 & 1 & 0 \\ -\sin\theta & 0 & \cos\theta \end{pmatrix} \begin{pmatrix} \cos\psi & -\sin\psi & 0 \\ \sin\psi & \cos\psi & 0 \\ 0 & 0 & 1 \end{pmatrix} \begin{pmatrix} x_{oi} \\ y_{oi} \\ z_{oi} \end{pmatrix} + \begin{pmatrix} \Delta x \\ \Delta y \\ \Delta z \end{pmatrix}$$

Subsequently, the camera projections of these new target vertex positions are determined using a geometric projection calculation. Given accurate knowledge of camera positions, pixel size and lens focal length, the horizontal and vertical pixel numbers on each camera focal plane (camera index j equal to 1 or 2) that these new 3-D positions in space should project onto is as follows:

$$X_{i,j} = X_{0,j} + \left(\frac{f.l.}{s_{pix}}\right) \sin\alpha_{i,j} \cos\beta_{i,j}, \quad [2]$$

$$Y_{i,j} = Y_{0,j} + \left(\frac{f.l.}{s_{pix}}\right) \sin\alpha_{i,j} \sin\beta_{i,j}$$

Here and $X_{i,j}$ are $Y_{i,j}$ the horizontal and vertical pixel numbers for translated target vertex i projected onto the camera j sensor, $X_{0,j}$ and $Y_{0,j}$ are the horizontal and vertical number of the pixel column and row intersected by the optical axis of that camera (typically at or very near the camera center), f.l. and $s_{pix}$ are the lens focal length and camera pixel pitch, and the angles $\alpha_{i,j}$ and $\beta_{i,j}$ are the polar and azimuth angles locating target vertex i, relative to the camera j focal axis. These angles are calculated from the vertex world coordinates as follows:

$$\alpha_{i,j} = \sin^{-1}\left(\frac{\sqrt{(x_{\perp,j}-x_i)^2+(y_{\perp,j}-y_i)^2+(z_{\perp,j}-z_i)^2}}{\sqrt{(x_{cj}-x_i)^2+(y_{cj}-y_i)^2+(z_{cj}-z_i)^2}}\right), \quad [3]$$

$$\beta_{i,j} = \pm\cos^{-1}\left(\frac{(x_{\perp,j}-x_i)(y_{cj}-y_0)-(y_{\perp,j}-y_i)(x_{cj}-x_0)}{\sqrt{(x_{\perp,j}-x_i)^2+(y_{\perp,j}-y_i)^2+(z_{\perp,j}-z_i)^2}\sqrt{(x_{cj}-x_0)^2+(y_{cj}-y_0)^2}}\right), \quad [4]$$

where the point $(x_{\perp,j}, y_{\perp,j}, z_{\perp,j})$ is the point of intersection between the camera optical axis and the plane perpendicular to the optical axis which includes the translated target vertex $(x_\perp i, y_\perp i, z_\perp i)$:

$$x_{\perp,j} = x_0 + \kappa(x_{cj}-x_0); y_{\perp,j} = y_0 + \kappa(y_{cj}-y_0); z_{\perp,j} = z_0 + \kappa(z_{cj}-z_0), \quad [5]$$

with $(x_\perp cj, y_\perp cj, z_\perp cj)$ defining the 3-D position of camera j, $(x_\perp 0, y_\perp 0, z_\perp 0)$ defining the nominal boresight position of both cameras at the un-displaced target center and the constant $\kappa$ based on geometric projection and given by:

$$\kappa = \left\{\frac{(x_{cj}-x_0)(x_i-x_0)+(y_{cj}-y_0)(y_i-y_0)+(z_{cj}-z_0)(z_i-z_0)}{(x_{cj}-x_0)^2+(y_{cj}-y_0)^2+(z_{cj}-z_0)^2}\right\}. \quad [6]$$

In equation [4], the inverse cosine function is taken to range from 0 to $\pi$, and the appropriate sign for $\beta_{i,j}$ is given by:

$$\text{sign}[\beta_{i,j}] = \text{sign}[(z_{cj}-z_i)\{(x_{cj}-x_0)(x_{\perp,j}-x_i)+(y_{cj}-y_0)(y_{\perp,j}-y_i)\}-(z_{\perp,j}-z_i)\{(x_{cj}-x_0)^2+(y_{cj}-y_0)^2\}]$$

During this determination of the camera projection of the 3-D target vertices, a compensation function may be applied for large values of the polar angle $\alpha_{i,j}$ to account for barrel distortion in the lens, based on prior lens calibration measurements. The geometric value for $\alpha_{i,j}$ is first computed based on equation [3] and then adjusted for lens distortion by way of a pre-determined look-up table or measured fit function, and this new compensated value for $\alpha_{i,j}$ is then used in the calculation of $X_{i,j}$ and $Y_{i,j}$ through equation [2].

To numerically evaluate the partial derivatives of the principal quantities about the initialized target position, the un-displaced 3-D target vertex coordinates $(x_{0i}, y_{0i}, z_{0i})$ are first projected to camera coordinates using equations [2] through [6] above, and initial values are computed for each of the principal quantities described in Step 1 (most should be zero or near-zero at the starting position). Then small increments of roll, pitch, yaw, x-, y- and z-axis displacements are introduced one at a time; for each increment the new world coordinates and the new camera projections of the target vertices are computed and the principal quantities are re-calculated. The change in each principal quantity is divided by the small angular or displacement increment to determine the partial derivative.

For instance, to determine the partial derivatives with respect to roll, the displacement vector $(\varphi, \theta, \psi, \Delta x, \Delta y, \Delta z) = (\delta\varphi, 0, 0, 0, 0, 0)$ is introduced to the general displacement equation [1] to determine the translated target vertex positions $(x_i, y_i, z_i)$. The conversion to camera coordinates is then performed using equations [2] through [6], and the principal quantities are calculated as outlined in Step 1. The difference between each principal quantity and the corresponding value of that quantity for the un-displaced calculation is divided by the small increment in roll, to give the partial derivative of each quantity with respect to roll. To determine partial derivatives with respect to pitch, the displacement vector $(\varphi, \theta, \psi, \Delta x, \Delta y, \Delta z) = (0, \delta\theta, 0, 0, 0, 0)$ is used to initiate the calculations, and so on for all six degrees of freedom.

Each of these six repetitions produces one column of the global partial derivative matrix:

$$\begin{pmatrix} \frac{\partial \Sigma_{HD}}{\partial \varphi} & \frac{\partial \Sigma_{HD}}{\partial \theta} & \frac{\partial \Sigma_{HD}}{\partial \psi} & \frac{\partial \Sigma_{HD}}{\partial x} & \frac{\partial \Sigma_{HD}}{\partial y} & \frac{\partial \Sigma_{HD}}{\partial z} \\ \frac{\partial \Delta_{HD}}{\partial \varphi} & \frac{\partial \Delta_{HD}}{\partial \theta} & \frac{\partial \Delta_{HD}}{\partial \psi} & \frac{\partial \Delta_{HD}}{\partial x} & \frac{\partial \Delta_{HD}}{\partial y} & \frac{\partial \Delta_{HD}}{\partial z} \\ \frac{\partial \Sigma_{VD}}{\partial \varphi} & \frac{\partial \Sigma_{VD}}{\partial \theta} & \frac{\partial \Sigma_{VD}}{\partial \psi} & \frac{\partial \Sigma_{VD}}{\partial x} & \frac{\partial \Sigma_{VD}}{\partial y} & \frac{\partial \Sigma_{VD}}{\partial z} \\ \frac{\partial \Delta_{BL}}{\partial \varphi} & \frac{\partial \Delta_{BL}}{\partial \theta} & \frac{\partial \Delta_{BL}}{\partial \psi} & \frac{\partial \Delta_{BL}}{\partial x} & \frac{\partial \Delta_{BL}}{\partial y} & \frac{\partial \Delta_{BL}}{\partial z} \\ \frac{\partial \Sigma_{MT}}{\partial \varphi} & \frac{\partial \Sigma_{MT}}{\partial \theta} & \frac{\partial \Sigma_{MT}}{\partial \psi} & \frac{\partial \Sigma_{MT}}{\partial x} & \frac{\partial \Sigma_{MT}}{\partial y} & \frac{\partial \Sigma_{MT}}{\partial z} \\ \frac{\partial \Delta_{MT}}{\partial \varphi} & \frac{\partial \Delta_{MT}}{\partial \theta} & \frac{\partial \Delta_{MT}}{\partial \psi} & \frac{\partial \Delta_{MT}}{\partial x} & \frac{\partial \Delta_{MT}}{\partial y} & \frac{\partial \Delta_{MT}}{\partial z} \end{pmatrix}_{(0,0,0,0,0,0)}$$

Step 3: Determining First-Order Displacement Vector

A first-order approximation to the displacement matrix is determined by multiplying the matrix of measured principal quantities, as determined in Step 1, by the inverse of the partial derivative matrix computed in Step 2:

$$\begin{pmatrix} \varphi_0 \\ \theta_0 \\ \psi_0 \\ (\Delta x)_0 \\ (\Delta y)_0 \\ (\Delta z)_0 \end{pmatrix} = \begin{pmatrix} \frac{\partial \Sigma_{HD}}{\partial \varphi} & \frac{\partial \Sigma_{HD}}{\partial \theta} & \frac{\partial \Sigma_{HD}}{\partial \psi} & \frac{\partial \Sigma_{HD}}{\partial x} & \frac{\partial \Sigma_{HD}}{\partial y} & \frac{\partial \Sigma_{HD}}{\partial y} \\ \frac{\partial \Delta_{HD}}{\partial \varphi} & \frac{\partial \Delta_{HD}}{\partial \theta} & \frac{\partial \Delta_{HD}}{\partial \psi} & \frac{\partial \Delta_{HD}}{\partial x} & \frac{\partial \Delta_{HD}}{\partial y} & \frac{\partial \Delta_{HD}}{\partial z} \\ \frac{\partial \Sigma_{VD}}{\partial \varphi} & \frac{\partial \Sigma_{VD}}{\partial \theta} & \frac{\partial \Sigma_{VD}}{\partial \psi} & \frac{\partial \Sigma_{VD}}{\partial x} & \frac{\partial \Sigma_{VD}}{\partial y} & \frac{\partial \Sigma_{VD}}{\partial z} \\ \frac{\partial \Delta_{BL}}{\partial \varphi} & \frac{\partial \Delta_{BL}}{\partial \theta} & \frac{\partial \Delta_{BL}}{\partial \psi} & \frac{\partial \Delta_{BL}}{\partial x} & \frac{\partial \Delta_{BL}}{\partial y} & \frac{\partial \Delta_{BL}}{\partial z} \\ \frac{\partial \Sigma_{MT}}{\partial \varphi} & \frac{\partial \Sigma_{MT}}{\partial \theta} & \frac{\partial \Sigma_{MT}}{\partial \psi} & \frac{\partial \Sigma_{MT}}{\partial x} & \frac{\partial \Sigma_{MT}}{\partial y} & \frac{\partial \Sigma_{MT}}{\partial z} \\ \frac{\partial \Delta_{MT}}{\partial \varphi} & \frac{\partial \Delta_{MT}}{\partial \theta} & \frac{\partial \Delta_{MT}}{\partial \psi} & \frac{\partial \Delta_{MT}}{\partial x} & \frac{\partial \Delta_{MT}}{\partial y} & \frac{\partial \Delta_{MT}}{\partial z} \end{pmatrix}^{-1} \begin{pmatrix} \Sigma_{HD} \\ \Delta_{HD} \\ \Sigma_{VD} \\ \Delta_{BL} \\ \Sigma_{MT} \\ \Delta_{MT} \end{pmatrix}$$

Step 4: Characterizing Local Variation in Principal Quantities with 6-DOF Motions First order values for $(\varphi, \theta, \psi, \Delta x, \Delta y, \Delta z)$ determined in Step 3 are entered into the translation equation [1] to determine the corresponding translated 3-D target position $(x_\perp i, y_\perp i, z_\perp i)$ for each of the three target vertices. These world coordinates are projected to camera coordinates $(X_{i,j}, Y_{i,j})$ using equations [2] through [6], and the principal quantities are re-calculated. These six quantities are compared against the measured values of these quantities determined in Step 1, to create a residual error matrix:

$$(\sigma_{\Sigma_{HD}}, \sigma_{\Delta_{HD}}, \sigma_{\Sigma_{VD}}, \sigma_{\Delta_{BL}}, \sigma_{\Sigma_{MT}}, \sigma_{\Delta_{MT}}).$$

Local partial derivatives of the principal quantities are calculated by introducing small increments in roll, pitch, yaw, x-, y- and z-axis displacements one at a time as before, but this time the increments are relative to the first-order displacement vector. For each increment, the new world coordinates and the new camera projections of the target vertices are re-computed and the principal quantities are re-calculated. The change in each principal quantity is divided by the small angular or displacement increment to determine a local partial derivative. For instance, to calculate partial derivatives with respect to roll, the first-order displacement vector $\{\varphi_0, \theta_0, \psi_0, (\Delta x)_0, (\Delta y)_0, (\Delta z)_0\}$ is replaced by $\{\varphi_0 + \delta\varphi, \theta_0, \psi_0, (\Delta x)_0, (\Delta y)_0, (\Delta z)_0\}$ and resulting changes to each of the principal quantities is divided by $\delta\varphi$ to determine the local derivative with respect to roll. This is repeated for each of the six degrees of freedom.

Each of these six repetitions produces one column of the new local partial derivative matrix:

$$\begin{pmatrix} \frac{\partial \Sigma_{HD}}{\partial \varphi} & \frac{\partial \Sigma_{HD}}{\partial \theta} & \frac{\partial \Sigma_{HD}}{\partial \psi} & \frac{\partial \Sigma_{HD}}{\partial x} & \frac{\partial \Sigma_{HD}}{\partial y} & \frac{\partial \Sigma_{HD}}{\partial z} \\ \frac{\partial \Delta_{HD}}{\partial \varphi} & \frac{\partial \Delta_{HD}}{\partial \theta} & \frac{\partial \Delta_{HD}}{\partial \psi} & \frac{\partial \Delta_{HD}}{\partial x} & \frac{\partial \Delta_{HD}}{\partial y} & \frac{\partial \Delta_{HD}}{\partial z} \\ \frac{\partial \Sigma_{VD}}{\partial \varphi} & \frac{\partial \Sigma_{VD}}{\partial \theta} & \frac{\partial \Sigma_{VD}}{\partial \psi} & \frac{\partial \Sigma_{VD}}{\partial x} & \frac{\partial \Sigma_{VD}}{\partial y} & \frac{\partial \Sigma_{VD}}{\partial z} \\ \frac{\partial \Delta_{BL}}{\partial \varphi} & \frac{\partial \Delta_{BL}}{\partial \theta} & \frac{\partial \Delta_{BL}}{\partial \psi} & \frac{\partial \Delta_{BL}}{\partial x} & \frac{\partial \Delta_{BL}}{\partial y} & \frac{\partial \Delta_{BL}}{\partial z} \\ \frac{\partial \Sigma_{MT}}{\partial \varphi} & \frac{\partial \Sigma_{MT}}{\partial \theta} & \frac{\partial \Sigma_{MT}}{\partial \psi} & \frac{\partial \Sigma_{MT}}{\partial x} & \frac{\partial \Sigma_{MT}}{\partial y} & \frac{\partial \Sigma_{MT}}{\partial z} \\ \frac{\partial \Delta_{MT}}{\partial \varphi} & \frac{\partial \Delta_{MT}}{\partial \theta} & \frac{\partial \Delta_{MT}}{\partial \psi} & \frac{\partial \Delta_{MT}}{\partial x} & \frac{\partial \Delta_{MT}}{\partial y} & \frac{\partial \Delta_{MT}}{\partial z} \end{pmatrix}_{\{\varphi_0, \theta_0, \psi_0, (\Delta x)_0, (\Delta y)_0, (\Delta z)_0\}}$$

Step 5: Determining Coarse Correction to First-Order Displacement Vector

A coarse correction is computed to improve the first-order displacement vector and reduce residual error, by multiplying the residual error matrix determined in Step 4 by the inverse of the local partial derivative matrix, also determined in Step 4:

$$\begin{pmatrix} \Delta\varphi \\ \Delta\theta \\ \Delta\psi \\ \Delta(\Delta x) \\ \Delta(\Delta y) \\ \Delta(\Delta z) \end{pmatrix} =$$

$$\begin{pmatrix} \frac{\partial \Sigma_{HD}}{\partial \varphi} & \frac{\partial \Sigma_{HD}}{\partial \theta} & \frac{\partial \Sigma_{HD}}{\partial \psi} & \frac{\partial \Sigma_{HD}}{\partial x} & \frac{\partial \Sigma_{HD}}{\partial y} & \frac{\partial \Sigma_{HD}}{\partial y} \\ \frac{\partial \Delta_{HD}}{\partial \varphi} & \frac{\partial \Delta_{HD}}{\partial \theta} & \frac{\partial \Delta_{HD}}{\partial \psi} & \frac{\partial \Delta_{HD}}{\partial x} & \frac{\partial \Delta_{HD}}{\partial y} & \frac{\partial \Delta_{HD}}{\partial z} \\ \frac{\partial \Sigma_{VD}}{\partial \varphi} & \frac{\partial \Sigma_{VD}}{\partial \theta} & \frac{\partial \Sigma_{VD}}{\partial \psi} & \frac{\partial \Sigma_{VD}}{\partial x} & \frac{\partial \Sigma_{VD}}{\partial y} & \frac{\partial \Sigma_{VD}}{\partial z} \\ \frac{\partial \Delta_{BL}}{\partial \varphi} & \frac{\partial \Delta_{BL}}{\partial \theta} & \frac{\partial \Delta_{BL}}{\partial \psi} & \frac{\partial \Delta_{BL}}{\partial x} & \frac{\partial \Delta_{BL}}{\partial y} & \frac{\partial \Delta_{BL}}{\partial z} \\ \frac{\partial \Sigma_{MT}}{\partial \varphi} & \frac{\partial \Sigma_{MT}}{\partial \theta} & \frac{\partial \Sigma_{MT}}{\partial \psi} & \frac{\partial \Sigma_{MT}}{\partial x} & \frac{\partial \Sigma_{MT}}{\partial y} & \frac{\partial \Sigma_{MT}}{\partial z} \\ \frac{\partial \Delta_{MT}}{\partial \varphi} & \frac{\partial \Delta_{MT}}{\partial \theta} & \frac{\partial \Delta_{MT}}{\partial \psi} & \frac{\partial \Delta_{MT}}{\partial x} & \frac{\partial \Delta_{MT}}{\partial y} & \frac{\partial \Delta_{MT}}{\partial z} \end{pmatrix}^{-1} \begin{pmatrix} \sigma_{\Sigma_{HD}} \\ \sigma_{\Delta_{HD}} \\ \sigma_{\Sigma_{VD}} \\ \sigma_{\Delta_{BL}} \\ \sigma_{\Sigma_{MT}} \\ \sigma_{\Delta_{MT}} \end{pmatrix}.$$

The first-order displacement vector is incremented by the coarse correction matrix to create a better approximation to the displacement vector:

$\{\varphi_0 + \Delta\varphi, \theta_0 + \Delta\theta, \psi_0 + \Delta\psi, (\Delta x)_0 + \Delta(\Delta x), (\Delta y)_0 + \Delta(\Delta y), (\Delta z)_0 + \Delta(\Delta z)\}.$ Step 6: Performing Fine Correction to Determine Final 6DOF Displacement Vector Steps 4 and 5 are repeated, starting with the coarse-corrected displacement vector, to determine a final fine correction to the displacement vector. After this iteration, the resultant fine correction increments are added to the coarse-corrected vector to create the final 6-DOF displacement vector. Empirical results from a general simulation indicate that this fine correction is sufficient in all cases to reduce residual errors to well below the stated 0.1-degree, 0.1-mm tolerances.

Algorithm Numerical Simulation to Verify Absolute Convergence

As cameras, targets and rotation stages are being procured and assembled, the 6 DOF decomposition algorithm can be coded and tested for a test set of rotations. It is clear that the routine will converge for small translations and rotations, but it can be potentially advantageous to determine whether there are limitations on its convergence for extreme displacements in all six degrees of freedom. To this end, we imagine an extreme target displacement, calculate the 3D position of the displaced target, calculate the centroid positions that will be seen on each of the two cameras, and run the decomposition algorithm to determine speed of convergence.

In some embodiments, to demonstrate absolute convergence of the iterative 6DOF unfolding algorithm, the simulation is started with a test set of very large rotations and displacements, as listed in Table 1 below.

TABLE 1

Example of a set of extreme angular rotations and linear translations of an imaginary patient for purposes of testing algorithm convergence.

| | |
|---|---|
| Head Yaw (Lean) Psi (deg toward patient's right shoulder) | 8.0000 |
| Head Pitch (Nod) Theta (deg relative to level; pos is toward top of head) | 15.0000 |
| Head Roll (Shake) Phi (deg relative to square; pos toward patient's left side) | 12.0000 |
| Head shift dx (mm toward top of head) | −9.0000 |
| Head shift dy (mm to patient's right) | 3.0000 |
| Head shift dz (mm away from table) | 7.0000 |

The simulation begins by determining the locations of the displaced centroids that will be seen by each camera, allowing for some degree of mispointing and misalignment of each camera. The original (nominal) target location is rotated and displaced by the Euler rotation formalism presented in Section 2.5.2.2, to determine the three displaced target centroid locations in three-dimensional space. Next these "world coordinates" are translated to 2-D "camera coordinates" for each of the two cameras independently, as described in the same Section.

Assuming the target is imaged into these camera coordinates, but that the operator has no prior knowledge of the displacement matrix giving rise to this target position, we use the algorithm as described in Section 2.5.2 from end to end to recreate the displacement matrix. By the end of Step 3 (Section 2.5.2.3), the algorithm returns an initial estimate of the 6DOF displacement vector, as shown in Table 2 below.

TABLE 2

First estimate of 6DOF displacement based on method described in Section 2.5.2.

| | |
|---|---|
| First Approximation Yaw (degrees) | 4.4313 |
| First Approximation Pitch (degrees) | −19.4474 |
| First Approximation Roll (degrees) | 8.8784 |
| First Approximation X displacement (mm) | −6.4257 |
| First Approximation Y displacement (mm) | −2.5639 |
| First Approximation Z displacement (mm) | −5.9428 |

As expected, residual errors at this stage are atypically large, due to the extreme magnitudes of the translations and rotations chosen for this simulation along and about each axis; this situation creates a good test for absolute convergence of the Newton Raphson algorithm methodology. Assuming this estimate to be correct, the algorithm in Step 4 (Section 2.5.2.4) again calculates the displaced position of the target, the resulting centroid positions seen by each camera, and the principal quantities (vertical tip sum and difference, base length difference, vertical displacement sum, and horizontal displacement sum and difference) which would result, for comparison with the actual observed values. The residual errors, in pixels, and the local derivatives of each of the principal values for small changes (pixels per 0.1 degrees) in yaw, pitch, and roll, and for small changes (pixels per 0.1 mm) in dx, dy and dz are calculated as described in Section 2.5.2.4, and tabulated as shown in Table 3 below.

TABLE 3

Residual Error (in pixels) and local derivatives with respect to Yaw, Pitch, Roll (pixels per 0.1 deg), x-displacement, y-displacement, and z-displacement (pixels per 0.1 mm), of the principal quantities Vertical Tip Sum, Vertical Tip Difference, Base Length Difference, Vertical Displacement Sum, Horizontal Displacement Sum, and Horizontal Displacement Difference.

| | $\partial/\partial Y$ | $\partial/\partial P$ | $\partial/\partial R$ | $\partial/\partial x$ | $\partial/\partial y$ | $\partial/\partial z$ | Residual Error |
|---|---|---|---|---|---|---|---|
| VT1 + VT2 | 0.2575 | 0.0383 | −0.099 | 0.0021 | 0.0045 | 0.0021 | −3.6538 |
| VT1 − VT2 | 0.0657 | −0.2756 | −0.0131 | 0.0005 | 0.0018 | 0.0274 | 6.8709 |
| BL1 − BL2 | −0.5223 | 0.0277 | 0.4988 | 0.0109 | −0.0702 | 0.0105 | −2.9918 |
| VDT + VD2 | −0.3118 | 5.8134 | 0.0350 | 1.8813 | 0.0112 | −0.2223 | −168.5591 |
| HD1 + HD2 | −2.5875 | −0.1680 | 3.3651 | 0.0117 | −1.3090 | −0.0124 | 58.1859 |
| HD1 − HD2 | 0.5823 | 1.4452 | 0.7697 | −0.0140 | 0.1114 | −1.4280 | 20.793 |

The matrix of derivatives at the left of Table 3 is inverted and multiplied by the residual error vector at the right, to yield first-order corrections to the initial estimate of the displacement vector, as described in Section 2.5.2.5, and as shown at the left of Table 4 below. These are added to the initial estimates, to produce the more refined estimate of the 6 DOF displacement vector, shown at the right of Table 4.

TABLE 4

(left) First-Order Corrections to Initial Estimates of Yaw, Pitch, Roll, dx, dy and dz, obtained by inverting the matrix of derivatives at left of Table 3 above and multiplying this inverse matrix by the residual error vector at right of Table 3. These corrections are added to initial 6DOF motion estimates to produce improved estimates at right above.

| | | | |
|---|---|---|---|
| Yaw Adjustment (deg) | 3.8632 | First Newton Iteration Yaw (deg) | 8.2945 |
| Pitch Adjustment (deg) | 4.5672 | First Newton Iteration Pitch (deg) | −14.8803 |

TABLE 4-continued (left) First-Order Corrections to Initial Estimates of Yaw, Pitch, Roll, dx, dy and dz, obtained by inverting the matrix of derivatives at left of Table 3 above and multiplying this inverse matrix by the residual error vector at right of Table 3. These corrections are added to initial 6DOF motion estimates to produce improved estimates at right above.

| | | | |
|---|---|---|---|
| Roll Adjustment (deg) | 3.5642 | First Newton Iteration Roll (deg) | 12.4426 |
| dx Adjustment (mm) | −3.0846 | First Newton Iteration Delta X (mm) | −9.5103 |
| dy Adjustment (mm) | 6.5969 | First Newton Iteration Delta Y (mm) | 4.0329 |
| dz Adjustment (mm) | 12.9426 | First Newton Iteration Delta Z (mm) | 6.9998 |

This process is repeated for a second and final time as described in Section 2.5.2.6, assuming again that the (now refined) 6 DOF displacement vector is accurate, and calculating first the 3D target centroid positions and then the locations of the target centroids as projected onto each of the two camera focal planes. Again the six principal quantities are computed and compared with the actual observations to produce a vector of residual errors. Again the local derivatives are computed, this time at the location of the first-order displacement vector. The results are tabulated as shown in Table 5 below.

TABLE 5

First-Order Residual Error (in pixels) and new local derivatives with respect to Yaw, Pitch, Roll (pixels per 0.1 deg), x-displacement, y-displacement, and z-displacement (pixels per 0.1 mm), of the principal quantities Vertical Tip Sum, Vertical Tip Difference, Base Length Difference, Vertical Displacement Sum, Horizontal Displacement Sum, and Horizontal Displacement Difference.

| | ∂/∂Y | ∂/∂P | ∂/∂R | ∂/∂x | ∂/∂y | ∂/∂z | Residual Error |
|---|---|---|---|---|---|---|---|
| VT1 + VT2 | 0.2498 | 0.0545 | 0.0785 | 0.0020 | 0.0028 | 0.0007 | 0.1715 |
| VT1 − VT2 | 0.0682 | 0.2935 | 0.0223 | 0.0012 | 0.0034 | 0.0212 | 0.0827 |
| BL1 − BL2 | −0.3146 | 0.0536 | 0.4966 | 0.0372 | 0.0723 | 0.0094 | 0.5096 |
| VD1 + VD2 | −0.5927 | 5.7797 | 0.0405 | 1.9353 | 0.0084 | 0.1911 | −4.3941 |
| HD1 + HD2 | −2.5162 | 0.3237 | 3.7395 | 0.0074 | 1.3067 | 0.0135 | 4.8578 |
| HD1 − HD2 | −0.6876 | 1.779 | 0.7547 | 0.0177 | −0.0884 | −1.4784 | 2.5723 |

The matrix of derivatives at the left of Table 5 is inverted and multiplied by the residual error vector at the right, to yield final corrections to the first-order estimate of the displacement vector, as shown at the left of Table 6 below. These corrections are added to the first-order estimates, to produce the final second-order estimate of the 6 DOF displacement vector, shown at the right of Table 6.

TABLE 6

(left) Second-Order Corrections to First-Order Estimates of Yaw, Pitch, Roll, dx, dy and dz, obtained by inverting the matrix of derivatives at left of Table 5 above and multiplying this inverse matrix by the residual error vector at right Table 5. These corrections are added to first-order correction obtained by the same method, to produce final values for each of the 6 DOF motions used in the simulation.

| | | | |
|---|---|---|---|
| Yaw Adjustment (deg) | −0.2947 | Final Yaw (deg) | 7.9999 |
| Pitch Adjustment (deg) | 0.2440 | Final Pitch (deg) | 15.0003 |
| Roll Adjustment (deg) | 0.4408 | Final Roll (deg) | 11.9978 |
| dx Adjustment (mm) | 0.5114 | Final Delta X (mm) | −8.9989 |
| dy Adjustment (mm) | 1.0377 | Final Delta Y (mm) | 2.9952 |
| dz Adjustment (mm) | 0.0058 | Final Delta Z (mm) | 6.994 |

Even for the extreme rotations and displacements used in this model, the algorithm is shown to converge to within 0.003 degrees and 0.006 mm in only two iterations. Given the number of floating-point operations needed to perform the initial estimate and two successive iterations of the Newton method, the algorithm can produce a solution on a typical laptop computer in less than 5 milliseconds.

Quaternion Representation

The head coil ICD specifies the rotation vector in terms of the quaternion, for which (still using right-handed Euler angle rotation conventions):

$$q = \begin{bmatrix} q_r \\ q_x \\ q_y \\ q_z \end{bmatrix} = \begin{bmatrix} \cos(\varphi/2)\cos(\theta/2)\cos(\psi/2) - \sin(\varphi/2)\sin(\theta/2)\sin(\psi/2) \\ -\sin(\varphi/2)\cos(\theta/2)\cos(\psi/2) - \cos(\varphi/2)\sin(\theta/2)\sin(\psi/2) \\ -\cos(\varphi/2)\sin(\theta/2)\cos(\psi/2) + \sin(\varphi/2)\cos(\theta/2)\sin(\psi/2) \\ -\cos(\varphi/2)\cos(\theta/2)\sin(\psi/2) - \sin(\varphi/2)\sin(\theta/2)\cos(\psi/2) \end{bmatrix}$$

The translation vector is unchanged from the form calculated here.

Centroid Determination Algorithm

The centroid location on the focal plane is given by:

$$x_0 = \frac{\sum_{ij} x_{ij} I_{ij}}{\sum_{ij} I_{ij}}, \quad y_0 = \frac{\sum_{ij} y_{ij} I_{ij}}{\sum_{ij} I_{ij}}.$$

Figure 20B:
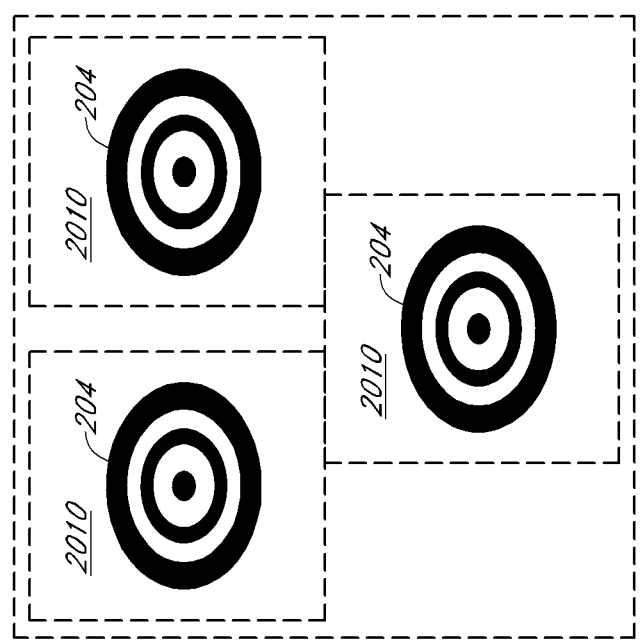
Figure 20C:
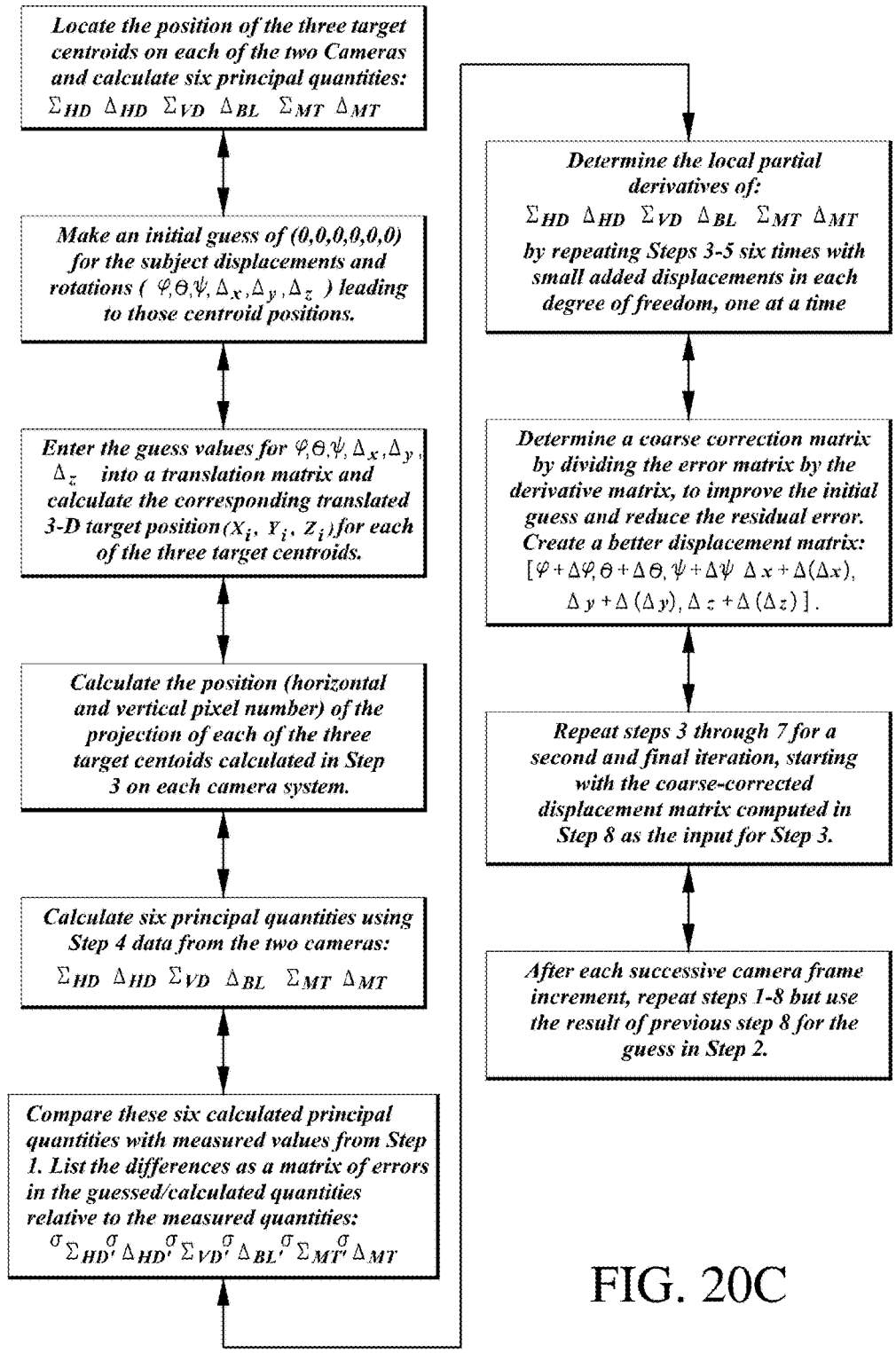
FIG. 20C is a flow diagram of an iterative process for tracking movement.

This calculation is performed for three subregions 2010 on the target as shown in FIG. 20B (the dashed lines do not appear on the real target), inverting the image such that large count numbers correspond to black (near 4095, for the 12-bit monochrome camera readout) and small count numbers for white (near 0). With a minimal amount of sophistication, the routine can detect the pattern of circles and approximately locate these subregions 2010 automatically. In some embodiments, the routine can be initialized with a key click to identify the approximate position of each centroid at startup. Subsequently, the three regions of interest for each new frame will be centered at the centroid locations from the previous frame, plus and minus 48 pixel rows and plus and minus 48 pixel columns. Regions of interest around each of the three target circles which can be integrated to determine target centroids.

Centroid Determination

In some embodiments, a test target can be printed and mounted in the view field of a monochrome camera at an angle of approximately 45 degrees. At this angle the elliptical target projected to an approximately round target on the camera focal plane. In some embodiments the camera can be focused at a full-scale printed target oriented at 45 degrees at a distance of 14.1 inches. Camera field of view is roughly the size of the rectangle in the center of the camera calibration target mounted next to the target.

The calculated target centroid is displayed as a red dot at the center of a LabView image, and displayed as a floating point (x,y) pair to the right of the image. At illumination levels above about 20% of full scale, the measured centroid location does not fluctuate above the 0.1-pixel level in row or column; for lower intensity levels, statistical fluctuations exceed this threshold. It is noted, however, that for the black-on-white printed target, uniformity of illumination can be potentially important—if the target is illuminated significantly more strongly from the left or right side, for instance, the moment calculation could add bias in the horizontal direction and would shift the centroid outside of the specified error threshold. This effect could in some cases put an undesirable cost constraint on the illumination approach, so an intensity thresholding algorithm is first implemented, by which the target histogram is clipped near the lower extrema for the bright and dark region intensities, eliminating the undesirable effect. In some embodiments, a Camera Control screen view can allow control of camera frame rate and readout resolution, showing manually-selected region of interest. Full camera field of view is approximately represented by a black region on the screen. The centroid can be displayed as a red dot at the center of the circular target, and camera x-y coordinates are displayed as floating point numbers to 2-decimal precision to the right of the display.

EXAMPLE 1

Camera Calibration

As with any camera lens, the lens used for the head tracker could have some level of distortion as a function of distance from imaging axis. Azimuthal distortion should be negligible, but radial distortion can be measured after lens installation and fit to a polynomial curve to allow rapid compensation of centroid positions near the edges of the camera field of view. The 6DOF unfolding algorithm can be constructed to accommodate typical levels of radial distortion as a second-order compensation during the application of the Newton Raphson iteration method.

Figure 22B:
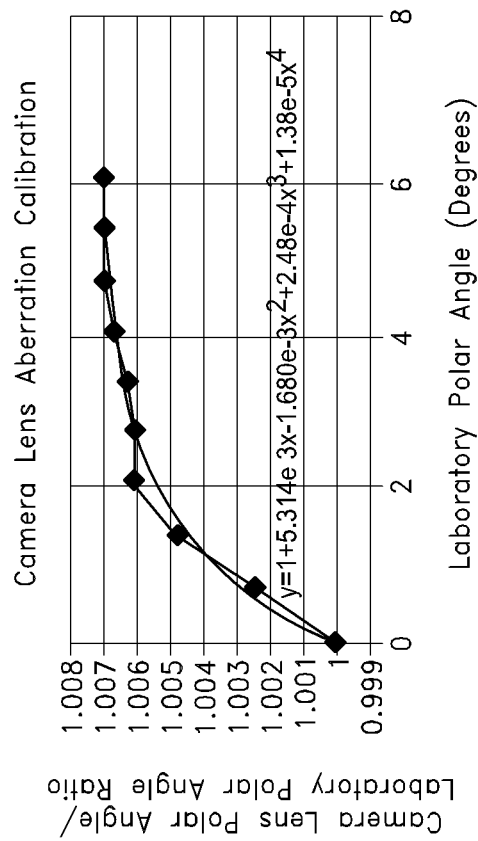
FIGS. 22A and 22B show techniques for camera calibration, according to some embodiments of the invention.
Figure 22A:
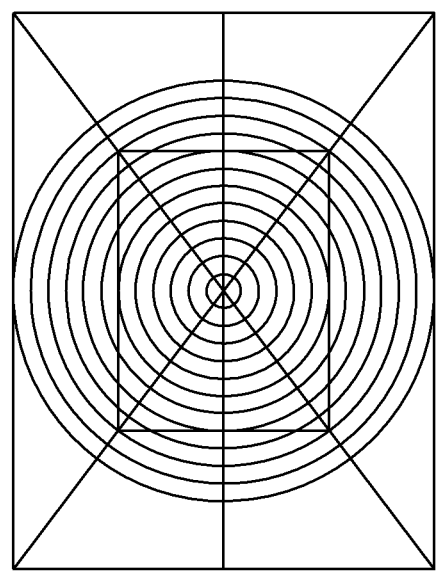

Radial distortion can be determined using a printed reference target with concentric circles of diameter ⅓", ⅔", 1", and so on up to a maximum diameter of 4 inches, as shown in FIGS. 22A and 22B. The approximate FOV of the camera and 25 mm lens at a working distance of 14.08 inches is 2"×2.67", as indicated by the inner rectangle printed on the target. The camera is mounted 14.24 inches from the target such that the inner rectangle is visible at the edges of the camera FOV, and the target is centered in this field. A single image frame is captured and the intersections of the circles and radial lines are identified and precisely located through local centroid calculations on the image. The polar angles of the world coordinate system are compared against the polar angles recorded on the camera to determine the radial distortion. FIG. 22A is the Camera Calibration Target and FIG. 22B is the off-axis radial distortion of the 25 mm fixed-focal length camera lens, measured by comparing the diameters of circles recorded on the camera focal plane.

In one embodiment, the measured radial distortion measured for the TechSpec High Resolution Fixed Focus 25 mm lens follows camera polar angle $\theta_C = (1 + 0.0053144\theta - 0.0016804\theta^2 + 0.0002483\theta^3 - 0.0000138\theta^4)\theta$, with laboratory polar angle $\theta$ in degrees. At the extreme corner of the viewing field, where $\theta \sim 6.75°$, camera aberration results in a radial growth in camera angle of about 0.7% relative to true angle, or about 2.8 pixels in radius.

Full 6-DOF Tracking

The full 6-DOF tracking algorithm was coded in LabView with the Graphical User Interface (GUI). The upper left side of the GUI screen gives centroid information for target circles in the current frame, and the lower left side gives the same information for the prior frame. For each, one nested target circle from the set of three is displayed in negative (white on black) along with a histogram of its pixel brightness within a 48-by-48 pixel box centered on the centroid location of the previous frame. This histogram is split into two sections to display (at left) the peak from background pixels at one end of the brightness scale, and (at right) the peak from the pixels of the target itself, at the other end of the brightness scale. A long continuum of pixels in between represents pixels at dark-light boundaries in the target frame. From analysis of the two histograms, the target field is clipped at the lower-brightness shoulder on the bright side, and the upper brightness shoulder on the dark side, to create a binary target field that is not sensitive to variations in illumination across the target. Although displayed in real time for only one target circle, all three target circles are processed in this way.

Next to the target histograms, the x-y camera centroid locations are displayed to two-decimal precision for each of the three nested circle targets; again at the upper half of the screen for the current data and at the lower half of the screen for the prior frame.

The right side of the screen displays the processed 6-DOF data, after analysis using the approach described in Section 2.5. An analog meter-style display shows the acquisition and processing time per frame, which is limited at its low end to the camera frame integration and readout time of about 8 milliseconds. Using a single iteration of the Newton-Raphson routine described in Section 2.5, the algorithm runs during the integration period for the successive frame, so the processing time is approximately 8 milliseconds, corresponding to a 120 Hz camera readout rate. The 6-DOF data can be displayed in either analog or digital format, but the digital format can be read to precision of 0.01 mm and 0.01 degree for comparison with the 0.1 mm, 0.1 degree accuracy requirements.

Laboratory Mechanical Layout for Head Tracking Simulation

The laboratory setup was designed to mimic head rotation and displacement using a six-degree-of-freedom optical rotation mount. This mount included three ganged translation stages along the x-, y-, and z-axes of the optical table, and three ganged rotation stages corresponding to yaw, roll and pitch respectively. The two monochrome cameras and turning mirrors were mounted in the appropriate geometry for use with an existing 12-channel head coil. The two monochrome cameras are in foreground, mounted at ±45° relative to horizontal to accommodate rotation by the turning mirrors. The turning mirrors are mounted 10 inches behind cameras (slightly obscured by the cameras in the picture). The target is partially visible in the reflection of each mirror. The 6-DOF rotation stage is at center in foreground, with the y-axis stage at bottom, x-axis stage next, and z-axis stage above that, followed by the yaw rotation stage, the roll stage, and finally the pitch stage with target at the top (the pitch rotation handle is obscured by the stage). A near-IR illumination LED is at the center in background; light from this stage is within the camera spectral range, but hardly visible to the human eye.

X-Axis Translation

The second translation stage from the bottom in the 6-DOF displacement assembly controls x-axis displacement (aligned with the patient's spine). The x-axis translation stage control knob is turned four full rotations (corresponding to −2.54 mm), and the absolute position change is calculated from the resulting motion of the centroid camera coordinates. Results are: the displacement determined by the unfolding algorithm is −2.56 mm in x, less than 0.1 mm in y and z, and less than 0.1° in roll, pitch and yaw. The target displacement by dx=−2.54 mm, with zoom on lower right display section of GUI showed calculated dx=−2.56 mm, dy=0.08 mm, dz=0.02 mm, $d\phi$=0.05°, $d\theta$=−0.03°, and $d\psi$=−0.01°.

Y-Axis Translation

The bottom translation stage in the 6-DOF displacement assembly controls y-axis displacement (patient's left-to-right). The y-axis translation stage control knob is turned four full rotations (corresponding to −2.54 mm), and the absolute position change is calculated from the resulting motion of the centroid camera coordinates. This resulted in a target displacement by dy=−2.54 mm, with zoom on lower right display section of GUI showing dx=0.00 mm, dy=−2.47 mm, dz=−0.01 mm, $d\phi$=0.64°, $d\theta$=−0.04°, and $d\psi$=−0.03°.

Z-Axis Translation

The top translation stage in the 6-DOF displacement assembly controls z-axis displacement (patient's down to up, with the patient lying on his back). The z-axis translation stage control knob is turned four full rotations (corresponding to −2.54 cm), and the absolute position change is calculated from the resulting motion of the centroid camera coordinates. The displacement determined by the unfolding algorithm was −2.54 mm in z, less than 0.1 mm in x and y, and less than 0.1° in roll, pitch and yaw. The results were a target displacement by dz=−2.54 mm, with zoom on lower right display section of GUI showing dx=0.01 mm, dy=−0.01 mm, dz=−2.59 mm, $d\phi$=−0.02°, $d\theta$=−0.06° and $d\psi$=0.01°.

Yaw Rotation

The bottom rotation stage in the 6-DOF displacement assembly controls yaw rotation (patient's left shoulder—to—right shoulder lean direction). The yaw rotation stage control knob is turned by +4° degrees (heading 315° to heading 311° on stage, corresponds to movement toward right shoulder), and the absolute position change is calculated from the resulting motion of the centroid camera coordinates. The displacement determined by the unfolding algorithm is less than 0.1 mm in dx, dy and dz, 0.1° in roll and less than 0.1° in pitch, and 3.94° in yaw. The results were a target rotation by $d\psi$=+4.00°, with zoom on lower right display section of GUI showing dx=0.07 mm, dy=−0.05 mm, dz=0.02 mm, $d\phi$=0.10°, $d\theta$=−0.01°, and $d\psi$=3.94°.

Roll Rotation

The middle rotation stage in the 6-DOF displacement assembly controls roll rotation (patient's right shoulde—to—left shoulder "head shaking" direction). The roll goniometer control knob is turned by +5° degrees, and the absolute position change is calculated from the resulting motion of the centroid camera coordinates. The displacement determined by the unfolding algorithm is less than 0.1 mm in dx, and dz, 1.78 mm in dy, 4.97° in roll and less than 0.1° in pitch and yaw. Displacement in y is expected due to the fact that the center of rotation for the Thorlabs GNL18 goniometer stage is 44.5 mm above the mount surface, while the target is only 22 mm above the stage. For the resulting −20.5 mm lever arm, the y-displacement due to a 5° roll rotation is −(−20.5 mm)*sin(5°)=+1.79 mm, in good agreement with the measured data.

The results were a target rotation by $d\phi$=+5.00°, with zoom on lower right display section of GUI showing dx=0.07 mm, dy=1.78 mm, dz=−0.01 mm, $d\phi$=4.97°, $d\theta$=−0.03°, and $d\psi$=0.08°.

Pitch Rotation

The top rotation stage in the 6-DOF displacement assembly controls pitch rotation (patient's "nodding" direction). The pitch goniometer control knob is turned by +5° degrees, and the absolute position change is calculated from the resulting motion of the centroid camera coordinates. The calculated pitch is 4.95°, with less than 0.1° in yaw. The center of rotation for the Thorlabs GNL10 goniometer stage is 25.4 mm above the mount surface, while the target is only 6.4 mm above the stage. For the resulting −19 mm lever arm, the x-displacement due to a 5° rotation is −19 mm*sin(5°)=−1.66 mm, the y-displacement is 0.00 mm, and the z-displacement is −19 mm* [1−cos(5°)]=0.07 mm. These displacements are all within 0.1 mm of measured data.

The results were a target pitch rotation by $d\theta$=+5.00°, with zoom on lower right display section of GUI showing dx=−1.63 mm, dy=0.09 mm, dz=0.17 mm, $d\phi$=0.21°, $d\theta$=4.95°, and $d\psi$=−0.07°.

Laboratory Testing of an Embodiment

Figure 27A:
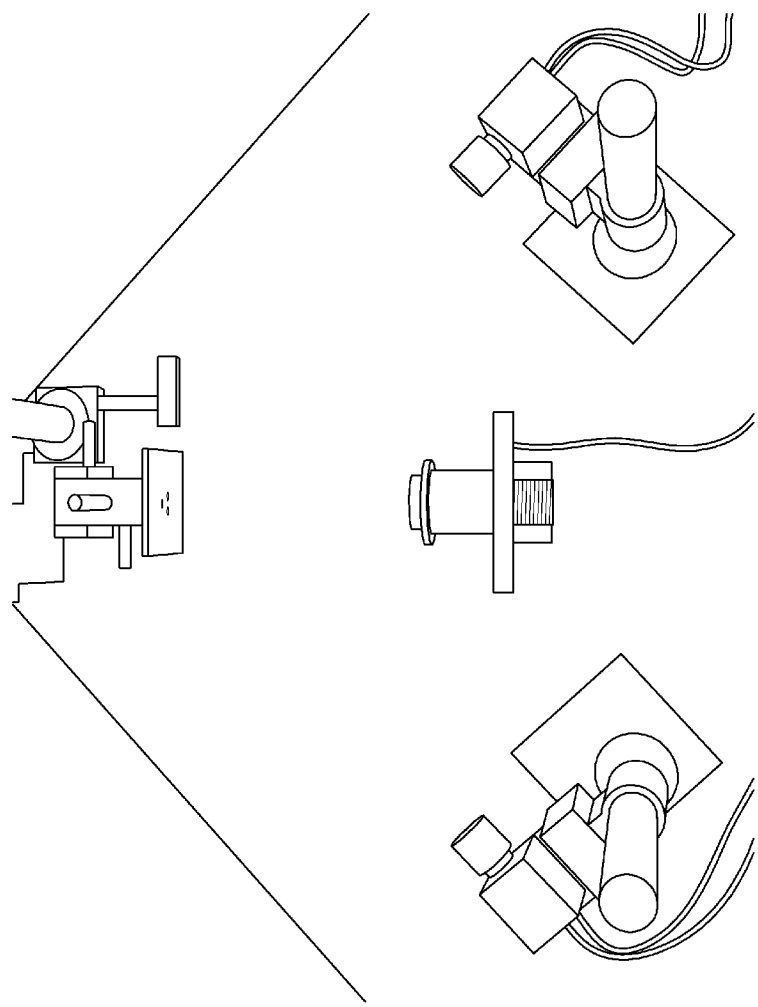
FIGS. 27A-27G illustrate a laboratory configuration testing an embodiment of the concepts described herein.
Figure 27B:
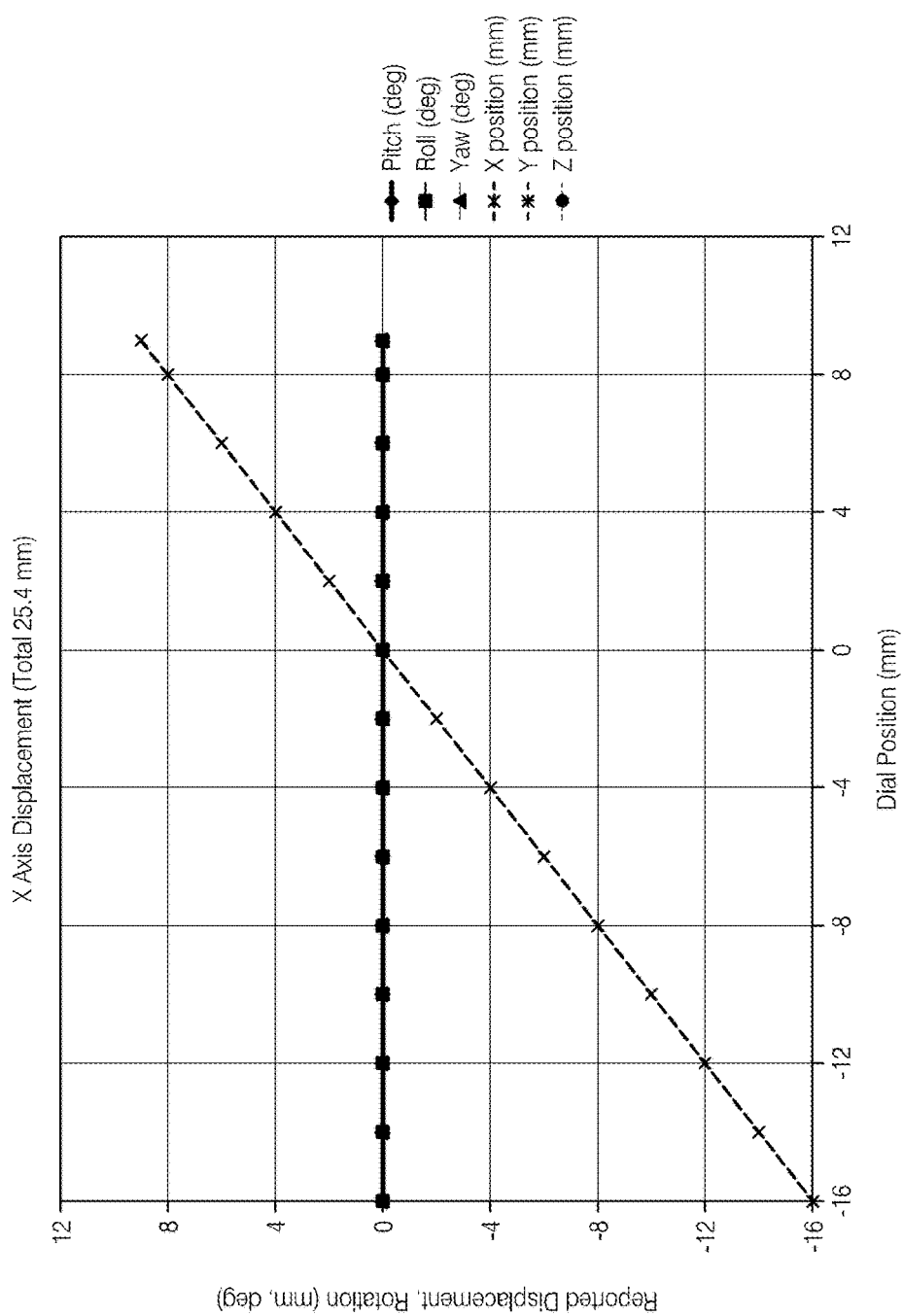
Figure 27C:
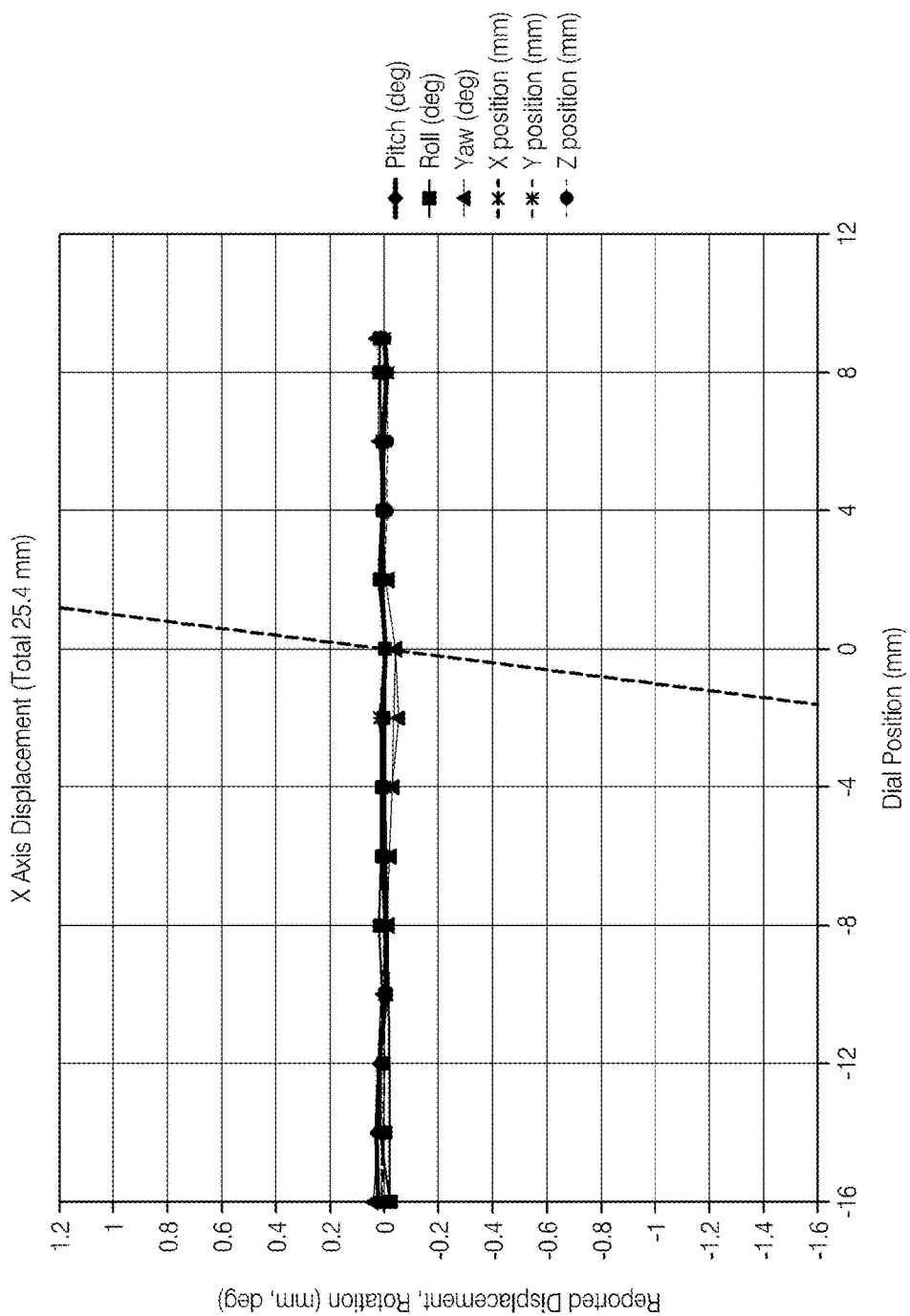
Figure 27D:
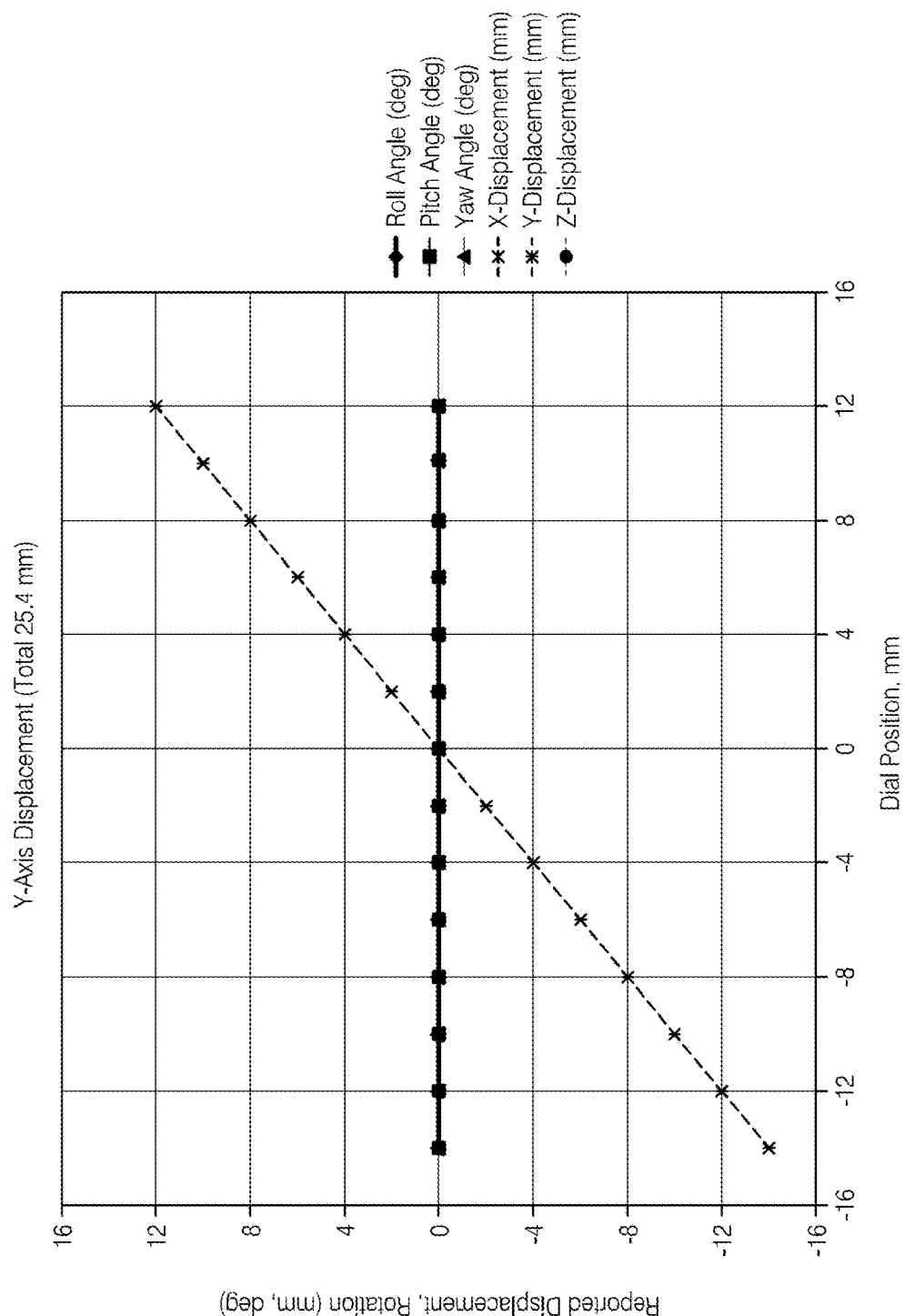
Figure 27E:
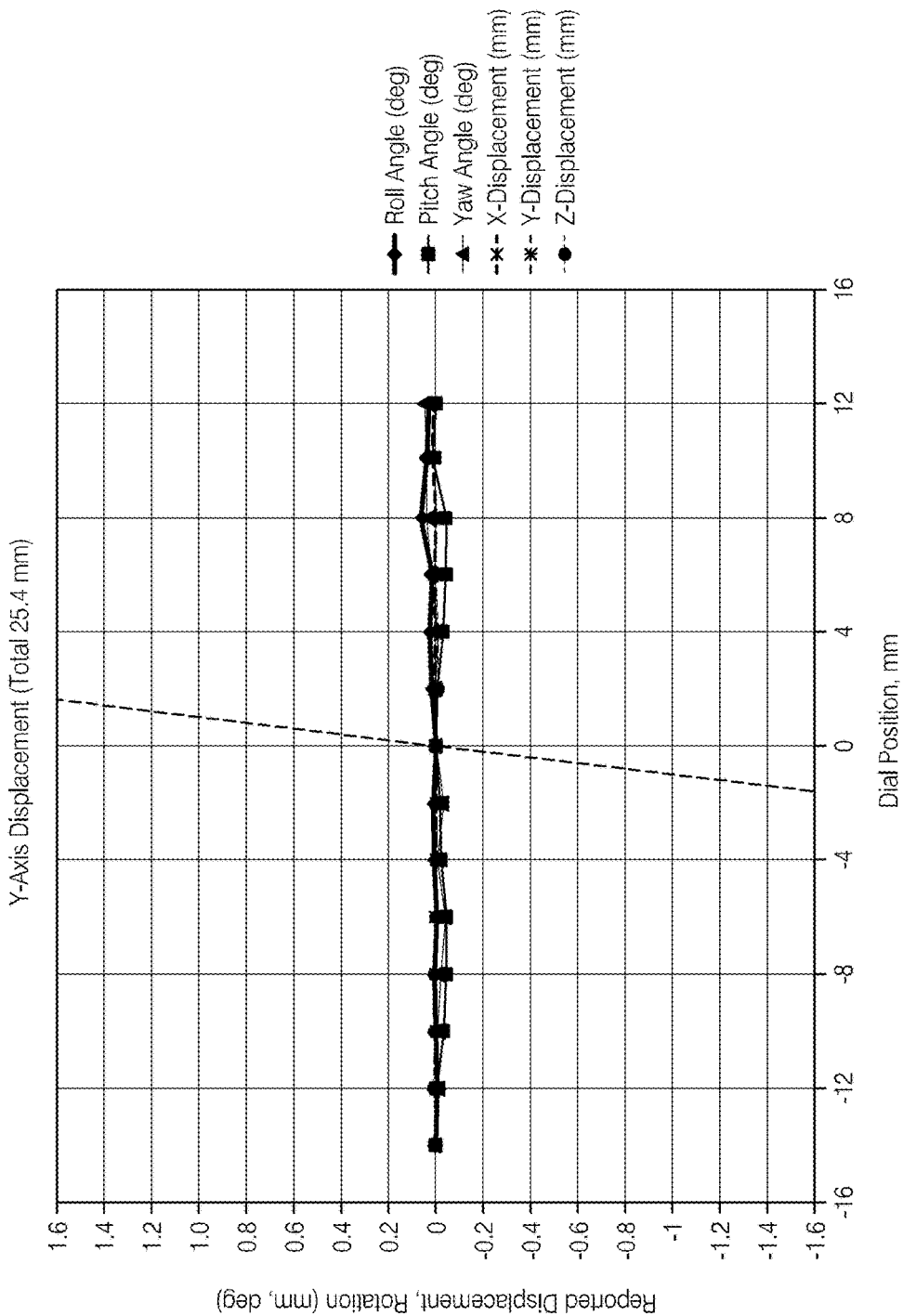
Figure 27F:
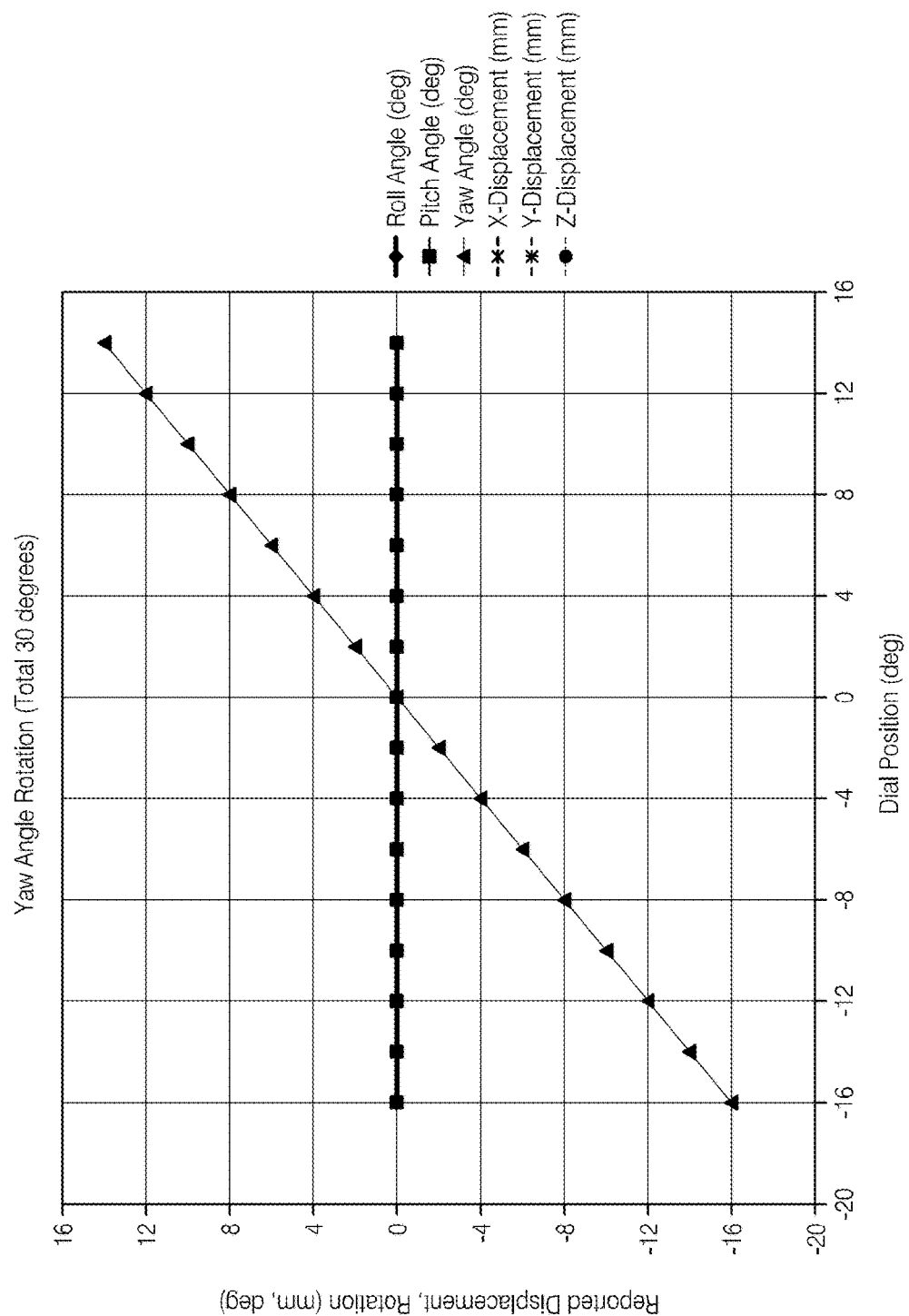
Figure 27G:
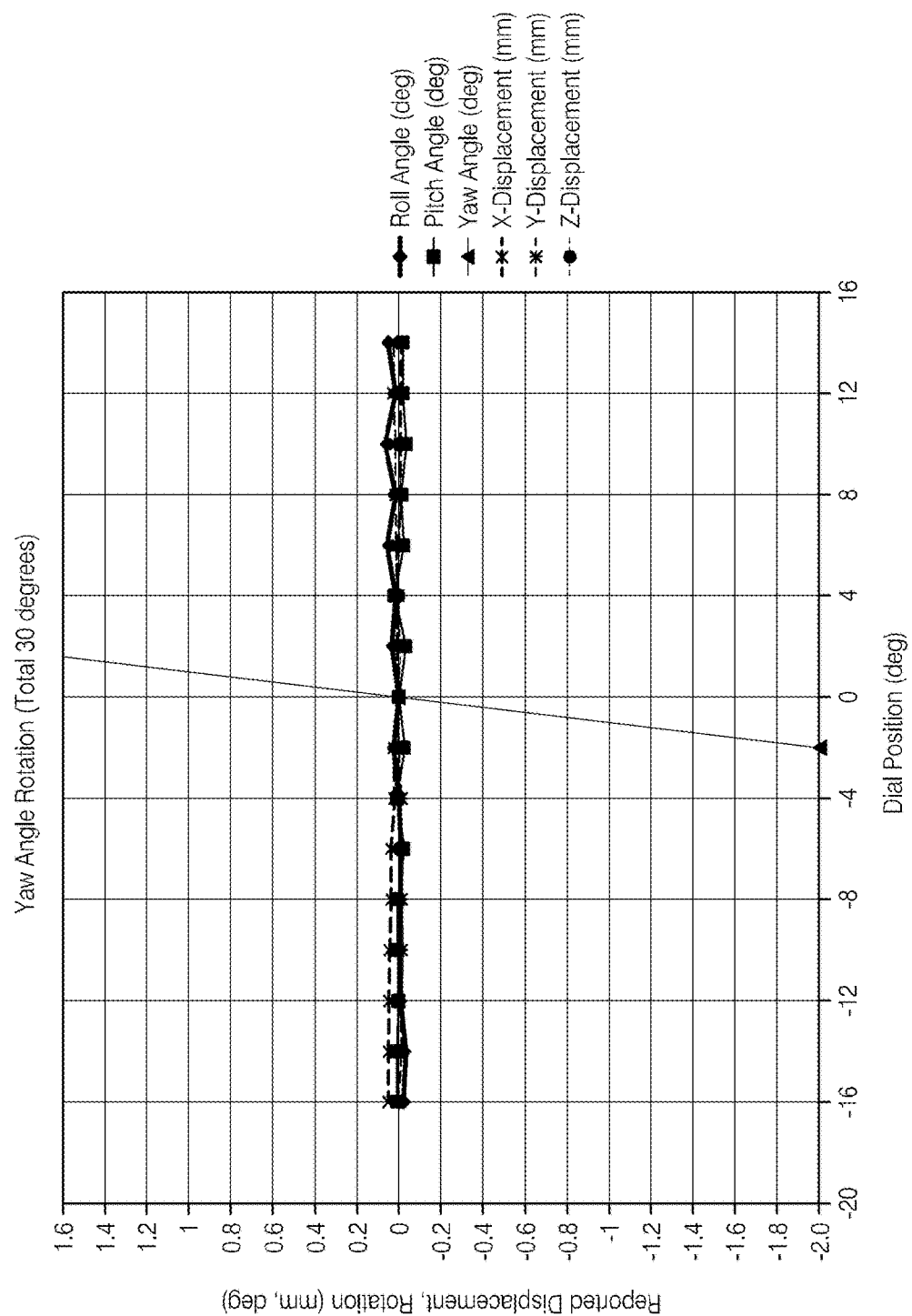

FIGS. 27A-27G illustrate a laboratory configuration testing an embodiment of the concepts described herein. FIG. 27A shows a top view of a laboratory configuration comprising two optical detectors imaging an optical marker utilizing an approximately 90 degree scissor angle. FIGS. 27B-27G illustrate charts of motion tracking information as calculated by an embodiment of a motion tracking system as a result of moving the optical marker to represent motion of an object being tracked.

Additional Marker Embodiments

Figure 28:
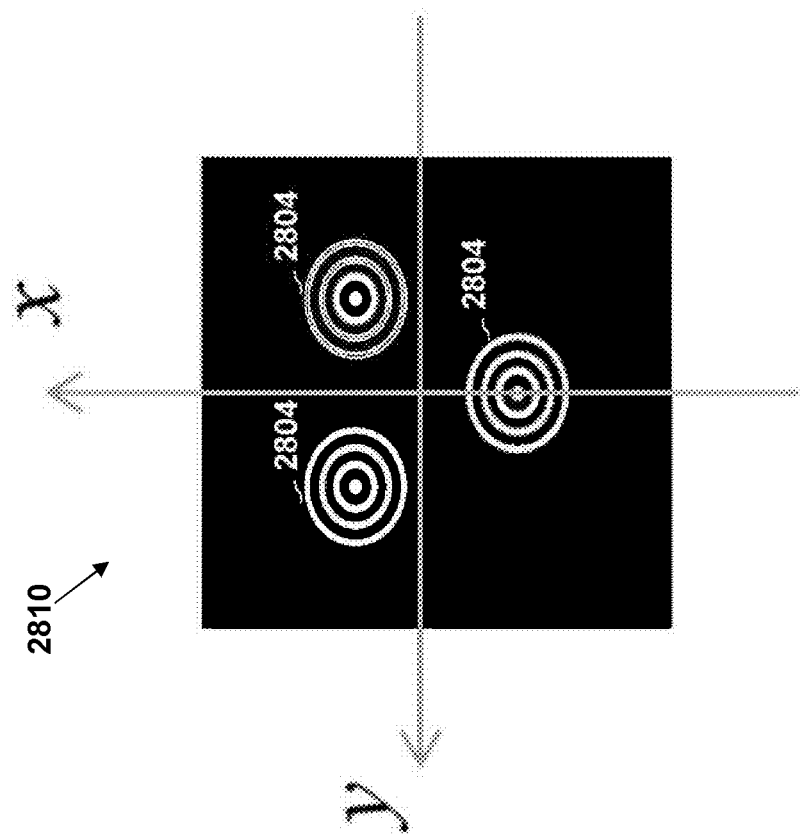
FIG. 28 is an embodiment of an optical marker.

Various embodiments of optical trackers can be used with motion tracking systems disclosed herein. For example, the marker 110 illustrated in FIG. 2A comprises a white or light colored background having three sub targets of a black or dark color. However, in some embodiments, it may be advantageous to reverse this color scheme, for example, to use white concentric sub targets on a black background. Such a marker can in some embodiments improve image processing and/or result in faster image processing. As an example, in some embodiments, an image processing routine monitoring the marker 110 illustrated in FIG. 2A includes a process of inverting a digital image of the marker so that the processed digital image appears to be of a marker with a black background and white sub targets. To make the process more efficient, however, the image inversion process can be eliminated when the marker itself already comprises a dark background with light colored sub targets. The motion tracking process can accordingly exploit this contrast and a known geometry of the sub targets to rapidly locate centroids of the sub targets with minimal processing. FIG. 28 illustrates an embodiment of a marker 2810 comprising a black background and three white sub targets 2804. Each of the sub targets 2804 comprises a plurality of concentric white ellipses, similar to as described above.

In some embodiments of markers, sub-targets comprise dark concentric sub targets on a high contrast diffusely reflective background. In some embodiments, the sub-targets comprise high contrast diffusely reflective concentric sub-targets on a dark background. In some embodiments, the concentric sub-targets comprise dark concentric sub-targets on a high contrast retro-reflective background. In some embodiments, the concentric sub-targets comprise high contrast retro-reflective concentric sub-targets on a dark background. Retro reflective material or surfaces are configured to reflect light back to a source with minimal scattering. Retro-reflective materials can provide benefits to a motion tracking system to, for example, in combination with the concentric sub targets, enable even faster and efficient processing. For example, a background or sub target with retro-reflective properties can provide additional information to the motion tracking system when the motion tracking system is analyzing an image of the target.

Various embodiments as disclosed herein have been disclosed with reference to a plurality of sub targets, in some embodiments three sub targets, on a single substrate that is connected to the patient being monitored. Further, in some embodiments, such as the embodiments illustrated in FIGS. 6A and 6B, sub targets can be distributed, rather than located on a single substrate. As further examples, FIGS. 29A, 29B, and 30A through 30E illustrate additional embodiments of markers or targets wherein individual sub targets are separated out onto their own individual substrates. For example, FIG. 29A illustrates a perspective view of three sub targets 2902 each on their own substrate 2904 attached to a patient 112. In this embodiment, two of the substrates 2904 are attached to the patient's forehead, and one of the substrates 2904 is attached at the patient's mouth.

Figure 29B:
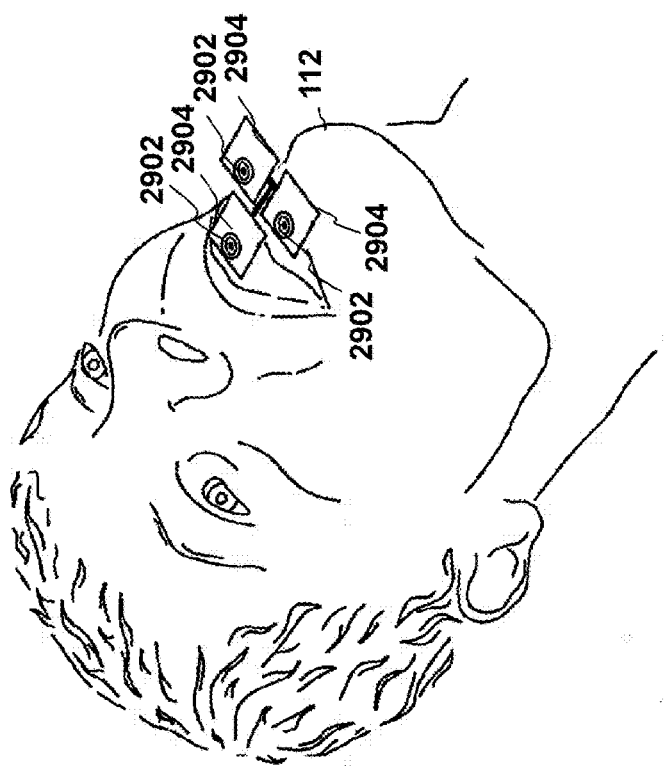
FIGS. 29A-29B illustrate embodiments of optical markers comprising sub targets on distributed substrates.
Figure 29A:
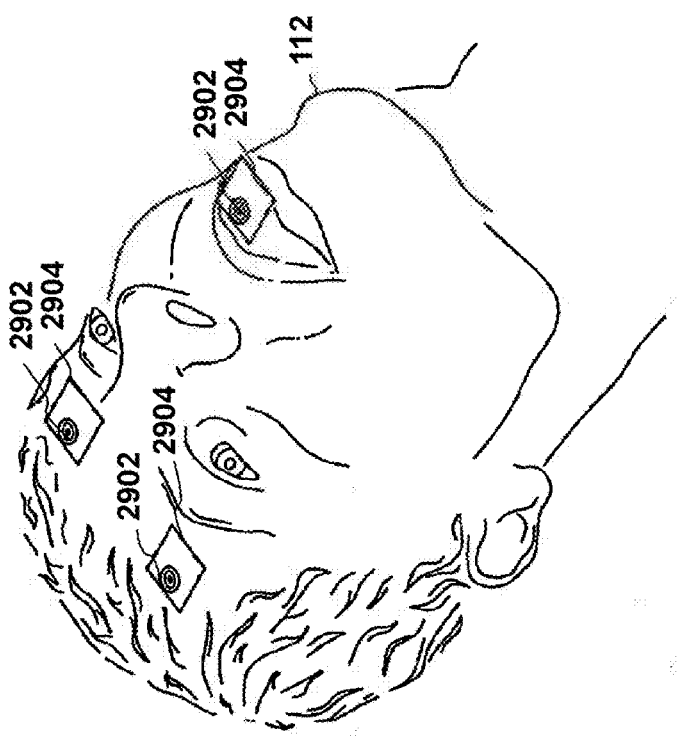

FIG. 29B illustrates another embodiment of a marker utilizing distributed sub targets 2902 and substrates 2904. In this case, however, the three substrates 2904 are connected together and all attached to the patient's mouth. The substrates 2004 may be connected together in various ways, with some examples shown in FIGS. 30A through 30F.

FIG. 30A illustrates a front view of an embodiment of a distributed marker comprising three sub targets 2902 each on their own substrate 2904. The substrates 2904 are in turn connected to a backing 3006. Accordingly, although each sub target 2902 is on its own substrate 2904, the relative position of the three sub targets 2902 in relation to each other remains the same.

Figure 30F:
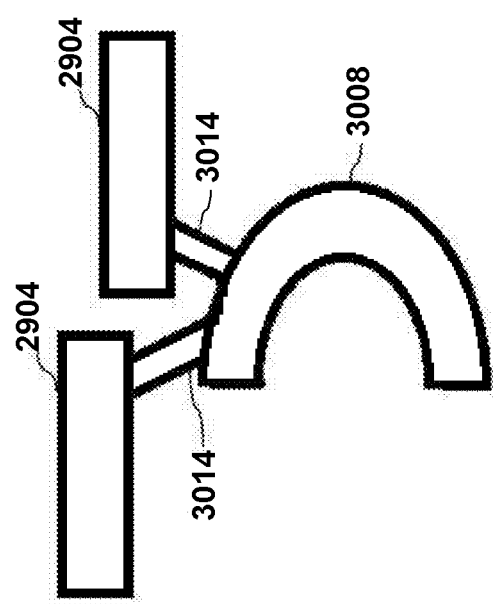

FIGS. 30B through 30F illustrate a variety of embodiments of side views of a distributed marker utilizing a separate substrate 2904 for each sub target 2902. The embodiment illustrated in FIG. 30B is a side view of the embodiment illustrated in FIG. 30A. In this embodiment, a mouthpiece 3008, similar in design to the mouthpieces illustrated in FIGS. 5A-5D, is attached to the backing 3006 through a post 3010. Although in this embodiment the backing is attached to the mouthpiece 3008 using a post 3010, the backing 3006 may in some embodiments be directly attached to the mouthpiece 3008 or attached to the mouthpiece using means other than a post. Further, although in these embodiments the markers are illustrated attached to a mouthpiece 3008 adapted to connect to a human mouth, various embodiments of optical markers disclosed herein may be adapted to attached to other portions of an object being tracked. For example, a marker may be configured to attached to the bridge of a human nose, a chin, a forehead, one or more ears, hair, and/or the like. In some embodiments, a marker attachment mechanism comprises a clamp sized to engage a bridge of a nose. In some embodiments, a marker is configured to attach to an eyeglasses-like structure that engages both the bridge of a person's nose and the person's ears.

FIG. 30C depicts an alternative embodiment of a side view of a marker comprising multiple substrates 2904. The embodiment illustrated in FIG. 30C is similar to the embodiment illustrated in FIG. 30B. However, in the embodiment illustrated in FIG. 30C, the substrates 2904 are each connected to the backing 3006 using their own post 3012.

FIG. 30D depicts an embodiment of a distributed marker wherein each of the substrates 2904 is directly attached to the mouthpiece 3008 using its own post 3014. Accordingly, there is no backing 3006 connecting the substrates 2904 together. It should be noted that, although various embodiments disclosed herein are described with reference to a mouthpiece to attach the markers to a human mouth, markers may be attached in various other ways to a patient being monitored, as further described above.

Figure 30E:
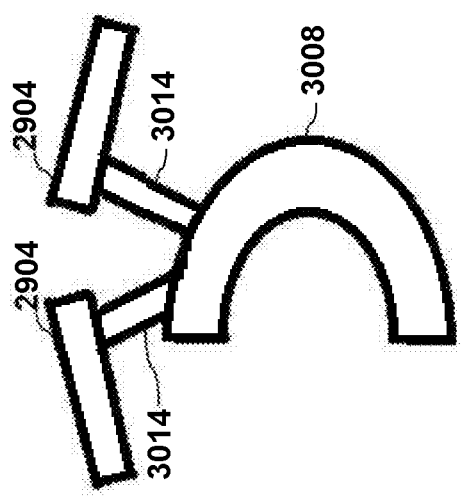

FIG. 30E depicts a marker with distributed substrates 2904 that is similar in design to the marker depicted in FIG. 30D. However, the markers illustrated in FIGS. 30E and 30F illustrate that in some embodiments the substrates 2904 and/or the sub targets 2902 do not necessarily have to be in the same plane and/or oriented at the same angle. In FIG. 30E, the substrates 2904 are oriented at different angles. In FIG. 30F, the substrates 2904 are oriented at the same angle, but are not in the same plane. Such configurations may be advantageous in some embodiments, such as to enable viewing of markers and/or sub targets at greater ranges of motion. Further, markers or sub targets may be in different planes to help conform a marker envelope shape to an area available. For example, when an MRI head cage is around a patient, there may be little room in front of the patient's mouth. Accordingly, the substrates 2904 may need to be adjusted to fit within the head cage. In some embodiments, when a substrate 2904 is not in a same plane as another substrate 2904, the printing of the sub targets 2902 may be adjusted so that to a camera the sub targets 2902 still appear as if they are in the same plane.

In various embodiments wherein sub targets 2902 are each positioned on their own substrate 2904, the substrates 2904 can be permanently attached to a backing 3006, removably attached to a backing 2006, or setup in various other ways to be permanently attached together or removably attached. For example, a substrate 2904 may be connected to a backing 3006 using glue, other adhesive, hook and loop fasteners, screws, tape, and/or the like.

Additional Process Flow Embodiments

Figure 31:
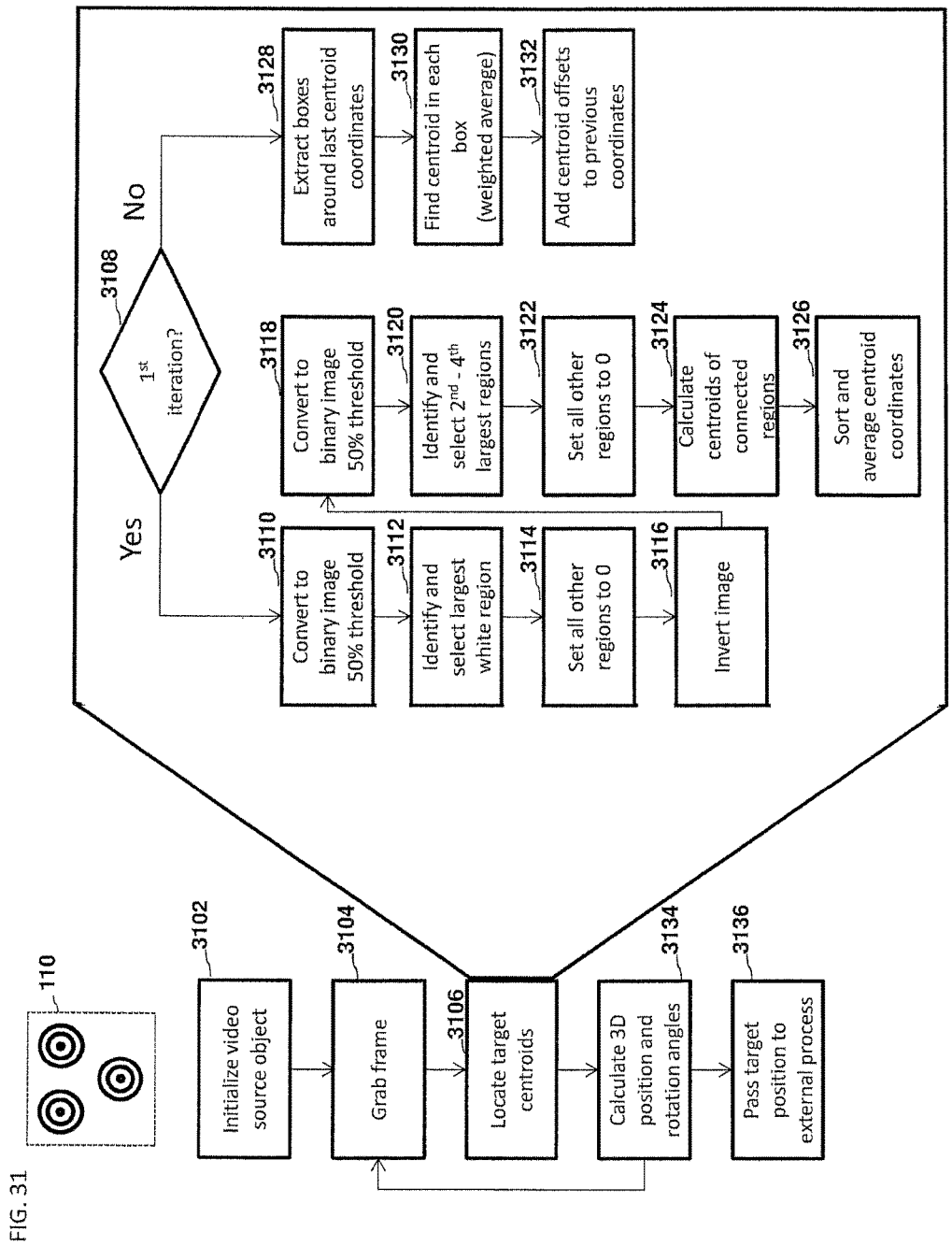
FIG. 31 is an embodiment of a process flow diagram illustrating an example of a motion tracking process.

FIG. 31 depicts an embodiment of a process flow diagram showing an example of a motion compensation process. In this process flow, the process is analyzing movements of a marker 110 utilizing a white background with black sub targets. However, a process such as the process flow shown in FIG. 31 may be modified to process a marker utilizing a dark background with light sub targets. An example of such a process may be seen below in FIG. 32.

The process flow begins at block 3102. At block 3102, the system initializes a video source object. At block 3104, the system grabs a frame from the video source, such as a camera. At block 3106, the system analyzes the frame to locate target centroids, such as centroids of the sub targets of a marker. The target centroid locating sub process is shown with reference to blocks 3108 through 3132. At block 3108, the process flow varies depending on whether this is the first iteration of locating the target or whether it is a subsequent iteration. If it is the first iteration, the process flow proceeds to block 3110. At block 3110, the frame is converted to a binary image with a 50% threshold (e.g., any pixels with a value lower than 50% of maximum are set to zero and any pixels with a value greater than 50% of maximum are set to one). At block 3112, the system identifies in the binary image the largest white region and selects that region. At block 3114, the system sets all other regions in the binary image to zero. At block 3116, the system inverts the image.

At block 3118, the system again converts to a binary image with a 50% threshold. At block 3120, the system identifies the second, third, and fourth largest regions. At block 3122, the system sets all other regions to zero. At block 3124, the system calculates centroids of the connected regions. At block 3126, the system sorts and averages centroid coordinates. The centroid coordinates are then passed on to the operation at block 3134.

Returning to block 3108, if the process being performed at block 3106 is being performed subsequent to the first iteration, the process flow proceeds from block 3108 to block 3128. At block 3128, the system extracts boxes around the last known centroid coordinates. At block 3130, the system performs a weighted average to find a centroid in each box. At block 3132, the system adds a centroid offset to each of the previous coordinates to produce the final centroid coordinates. These coordinates are then passed on to the process at block 3134.

At block 3134, the system calculates the 3-D position and rotation angles of the optical target. In some embodiments, the 3-D position and rotation angles are also converted from the optical detector coordinate system to, for example, an MRI machine coordinate system. At block 3136, the target position and rotation angles are passed onto an external process to enable motion compensation.

Figure 32:
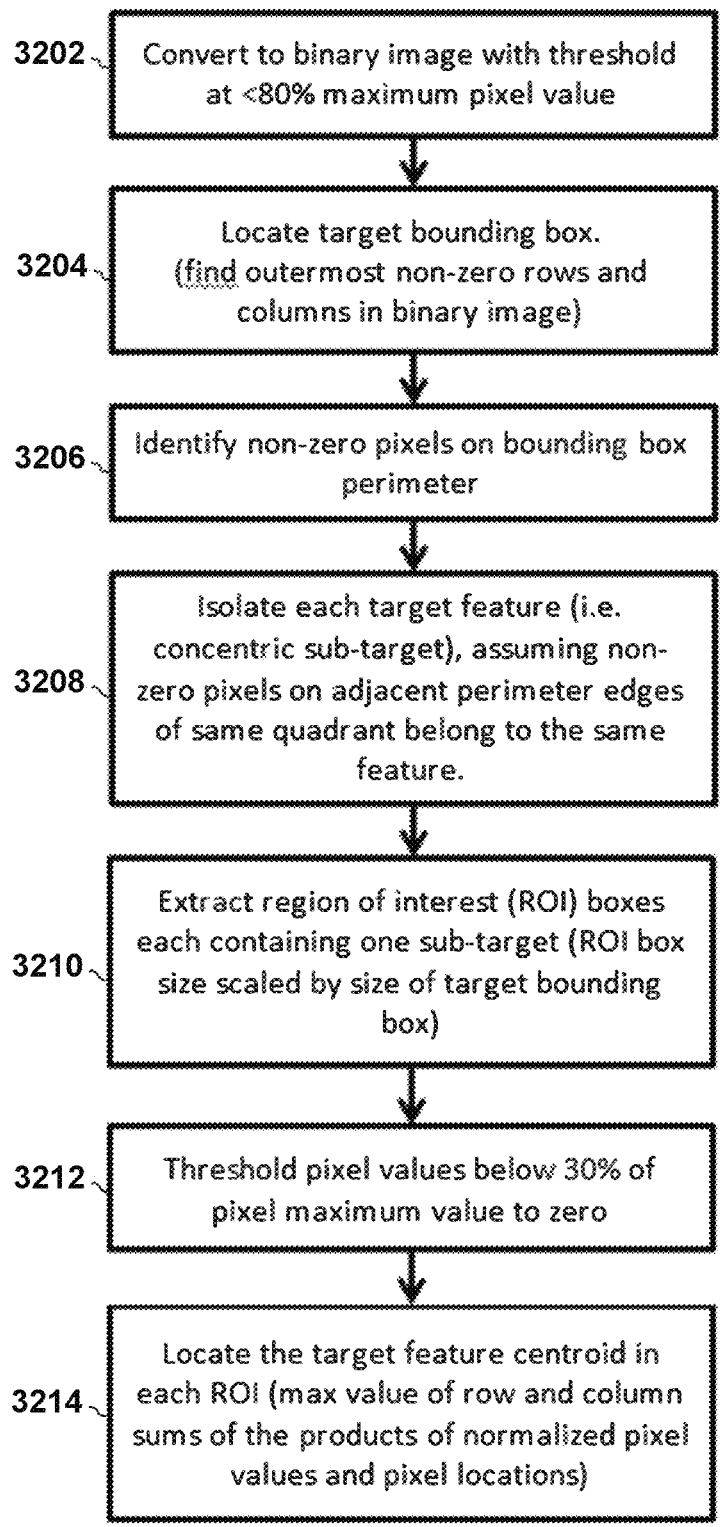
FIG. 32 is an embodiment of a process flow diagram illustrating an example of a marker centroid determination process.
Figure 33:
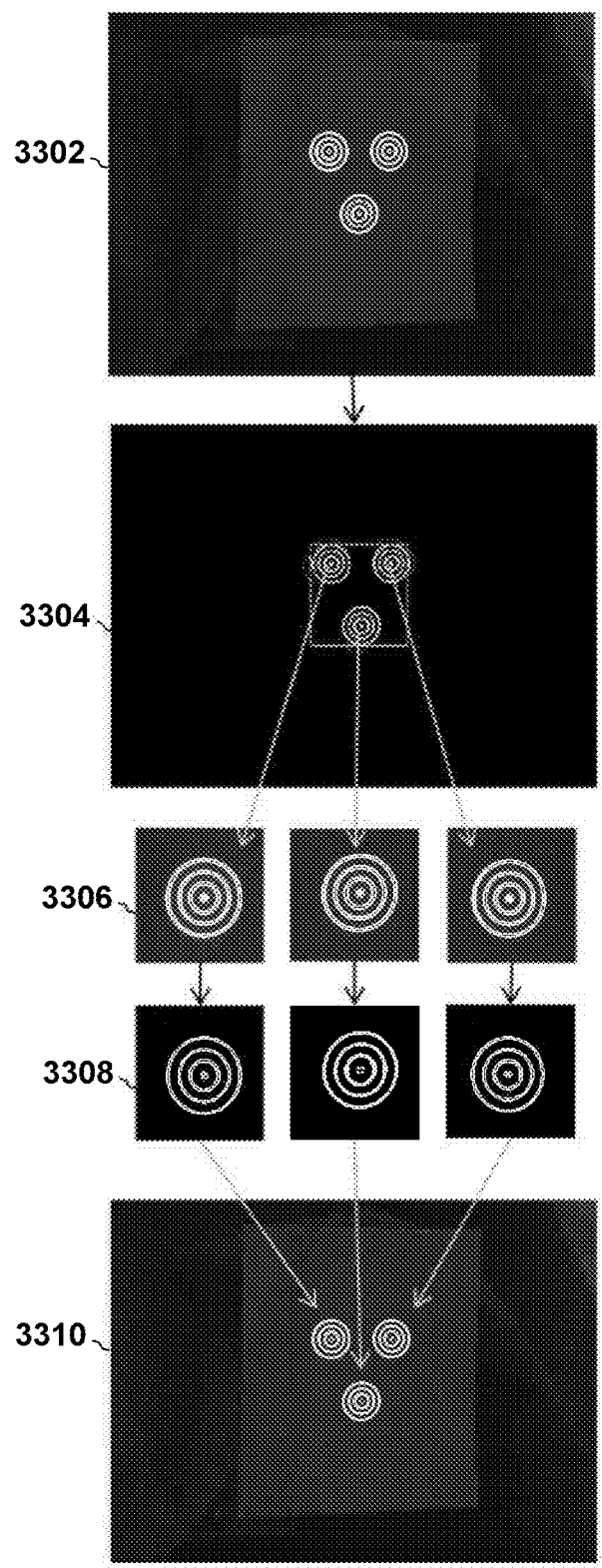
FIG. 33 is an embodiment of a process flow diagram illustrating example images as a part of the process flow illustrated in FIG. 32.

FIG. 32 illustrates another embodiment of a process flow diagram illustrating an example of a centroid location process. For example, the process flow illustrated in FIG. 32 may be utilized to replace the sub-process illustrated in block 3106 of FIG. 31 when the target being utilized is a target with a dark background and light sub targets. Accordingly, the process flow illustrated in FIG. 32 may enable a motion tracking system to perform faster and more efficiently than when using a target with a light background and dark sub targets. FIG. 33 illustrates a variety of images depicting stages of the process flow illustrated in FIG. 32. Accordingly, some of the images in FIG. 33 will be referred to in describing the process flow of FIG. 32.

The process flow illustrated in FIG. 32 begins with a raw image of a target from a camera. For example, block 3302 of FIG. 33 depicts an example raw image from a camera of a target having a dark background and light sub targets. At block 3202, the system converts the raw target image to a binary image with a threshold at less than 80% of the maximum pixel value. An example of a converted binary image can be seen in block 3304 of FIG. 33. At block 3204, the system locates a target bounding box. For example, in an embodiment, the systemic can be configured to find the outermost nonzero rows and columns in the binary image. As can be seen in block 3304 of FIG. 33, the target bounding box has been added.

At block 3206, the system is configured to identify nonzero pixels on the bounding box perimeter. By identifying nonzero picture of pixels on the bounding box perimeter, the system can estimate where each of the sub targets is. As can be seen in block 3304 of FIG. 33, the nonzero pixels on the bounding box perimeter have been identified and circled. For example, the points where the top left sub target touches the bounding box have been circled in red. The points where the top right sub target touches the bounding box have been circling green. Finally, the point where the bottom sub target touches the bounding box perimeter has been circled in blue. At block 3208, the system isolates each sub target feature, for example, each concentric sub target, by assuming that nonzero pixels on adjacent perimeter edges of a same quadrant belong to the same target feature.

At block 3210, the system is configured to extract region of interest (ROI) boxes each containing one sub target. In some embodiments, the region of interest box is size scaled by the size of the target bounding box. As can be seen in block 3306 of FIG. 33, three region of interest boxes have been extracted from the binary image at block 3304.

At block 3212, the system is configured to set pixel values below 30% of the pixel maximum value to zero. For example, as seen in block 3308 of FIG. 33, the concentric circles have been further isolated by setting pixel values below 30% of pixel maximum 20. At block 3214, the system is configured to locate the centroid of each sub target in each region of interest. For example, in some embodiments, the system can be configured to take a maximum value of row and column sums of the products of normalized pixel values and pixel locations.

Block 3310 of FIG. 33 illustrates the sub target centroids calculated at block 3214 overlaid on the original image from 3302. As can be seen, the system has efficiently determined the correct centroids of the sub targets. These centroids can then be passed on to other portions of the motion tracking process to enable tracking of a patient and compensating for that patients motion.

In some embodiments, a motion tracking system can be configured to run only one iteration of the centroid determination process illustrated in FIG. 32 for each image frame being processed. By using only one iteration, the system is efficient and quick in determining a patient's position. In some embodiments, however, the process flow illustrated in FIG. 32 or a similar process flow may comprise two or more iterations, such as 2, 3, 4, 5, 10, 15, 20, 30, 40, 50, or more iterations.

Additional Marker Embodiments

Various embodiments of optical trackers or markers used with motion tracking systems have been described in the present disclosure. For example, some embodiments, such as the marker 110 illustrated in FIG. 2A, have comprised a white or light colored background having three subtargets of a black or dark color, wherein the three subtargets are three sets of concentric circles or ellipses located at the vertices of an equilateral triangle. In other embodiments, the color scheme was reversed such as in FIG. 28, so that the marker comprised a black background with three white subtargets, wherein each subtarget was a plurality of concentric white ellipses. The subtargets in this embodiment were also arranged so that the centroids of the subtargets were equidistant from one another, such that they could be imagined as residing on the vertices of an equilateral triangle.

However, in some embodiments, it may be advantageous to use a marker that has no rotational ambiguity in order to allow for unique identification in the location and orientation of the subtargets in the marker. A marker with three identically-sized subtargets, with their centroids arranged as the vertices of an equilateral triangle, may be limited by rotational degeneracy. Such a marker may not have a unique pattern or arrangement for every in-plane rotation angle (e.g., rotations about an axis oriented normal to the plane of FIG. 2A, perpendicular to axes x and y of FIG. 2A). For example, rotating such a marker in-plane by 60 degrees would result in the same centroid pattern as the marker before it was rotated, which may, in some embodiments, make it difficult to determine if there was even a rotation. In some embodiments, such as when the subtargets comprise concentric circles, an in-plane rotation of 60 degrees may result in both a same perceived centroid angular position and a same visual image of the marker. In some embodiments, such as when the subtargets comprise ellipses or other nonuniform shapes, an in-plane rotation of 60 degrees may result in a different visual image of the marker, even though the centroid angular position may be perceived as the same as before the rotation. Some embodiments of tracking systems disclosed herein may be configured to compensate for the potential rotational ambiguity of such a target, such as by analyzing other differences in the visual image, and/or continuous or semi-continuous tracking of the marker during its in-plane rotation to gain additional context for analysis. It can be desirable, however, to utilize a marker that does not have such rotational ambiguity, which may allow faster and/or more efficient tracking. Thus, in some embodiments, the design of the marker may deviate from having three identically-sized, triangularly-arranged subtargets (or other designs having in-plane rotational ambiguities) in order to avoid rotational degeneracy. There are many numerous, different patterns or designs having a rotational asymmetry that would prevent rotational degeneracy.

Figure 34:
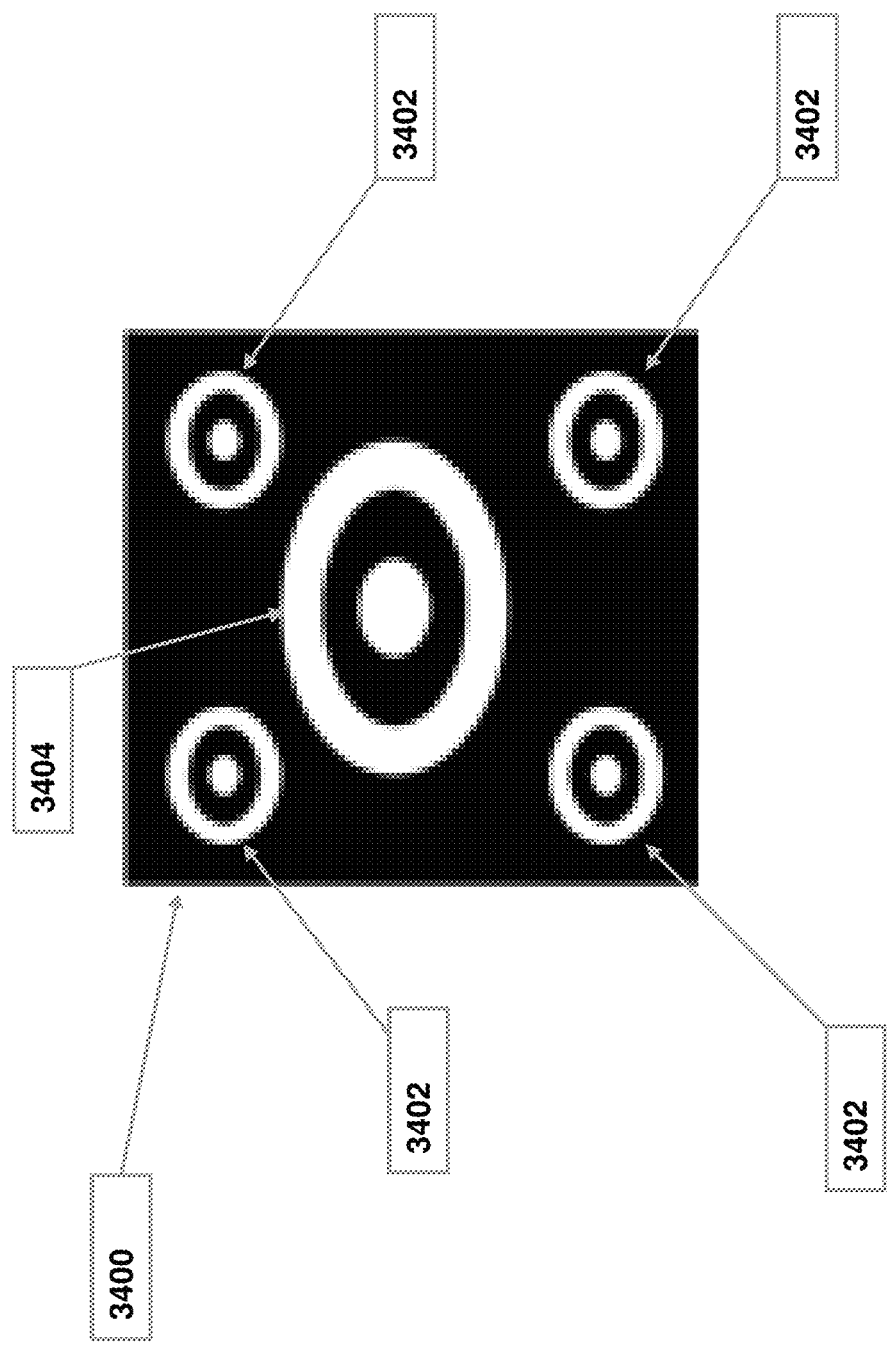
FIG. 34 illustrates an example of a marker or optical tracker that avoids rotational degeneracy, according to one embodiment.

FIG. 34 illustrates an example of a marker or optical tracker 3400 that avoids rotational degeneracy, according to one embodiment. Furthermore, the marker 3400 in FIG. 34 may allow the system to locate the marker with a high degree of accuracy regardless of the orientation of the marker in a sensor's field of view, and it may also allow the system to more quickly identify the various subtargets of the marker. Marker 3400 is shown to have five reference point locators, or subtargets, that comprise concentric pairs that are elliptical in shape and white colored against a dark background. When these reference point locators are viewed from a 45 degree viewing angle by a detector, an image of these reference point locators may illustrate the reference point locators as circles. Marker 3400 may have four small concentric pairs 3402, which are reference point locators located in the corners of marker 3400. Marker 3400 may also have a large concentric pair 3404, which is a reference point locator positioned near the center of the marker (e.g., subtarget 3404's centroid positioned within a bounding box defined by the four centroids of the outer smaller subtargets 3402) that is larger in size than each of the small concentric pairs 3402. The large concentric pair 3404 may be offset in one direction of the marker, which allows the relative positions of the five concentric pairs to uniquely identify the in-plane rotation of the marker. In this embodiment, the larger subtarget 3404 is moved upward with respect to a vertically central portion or axis of the marker 3400 and/or a bounding box defined by the smaller subtargets 3402. In other embodiments, various other techniques may be used to make the marker not rotationally ambiguous. For example, the larger central subtarget 3404 may be moved away from a center point of the marker 3400 or bounding box defined by the subtargets 3402 in a different direction. As another example, one or more of the outer subtargets 3402 may be moved to a different location.

As mentioned above, in some embodiments, rotational asymmetry is achieved in the marker through an offset of one concentric target from the center of the marker along the vertical axis. This rotational asymmetry may enable tracking of the marker through 360-degree in-plane rotation with no degeneracy (e.g., no ambiguity as to the current in-plane rotation orientation throughout a full 360 degrees). In some embodiments, the shapes of the subtargets of the marker are elongated in the horizontal dimension to increase the horizontal cross section of the marker as it rotates away from a given camera. In some embodiments, the markers may comprise three or more separate subtargets arranged in a rotationally asymmetric pattern, with each subtarget comprising at least two concentric shapes. Additional shapes may be incorporated into the marker pattern for the purposes of unique marker identification.

Since all five subtargets of the marker 3400 of FIG. 34 (the four small concentric pairs 3402 and the large concentric pair 3404) comprise concentric shapes, the system is able to uniquely and/or efficiently identify and locate each of the five subtargets from an image of the marker. The system may do this in some embodiments by finding the centroids of all the objects in a given size range, and then grouping objects with the same (or sufficiently similar) centroid coordinates. All the objects with the same (or sufficiently similar) centroid coordinates may be marked as a valid subtarget that is part of the overall marker 3400. Utilizing such a design, where one or more sub targets comprise at least two concentric shapes, can be advantageous, for example, to enable quickly and/or efficiently identifying valid sub targets and ignoring other objects in an image of the marker. For example, when a marker as disclosed herein is utilized during an MRI brain scan, a detector that captures an image of the marker may also capture other non-marker features in the image. For example, the image captured by the detector may also include features of a patient's skin complexion, such as moles or other items. When processing such an image, the system may identify a facial feature, such as a mole, as being a feature having a particular centroid location. However, if there is not another feature having a same or similar centroid location, the system can confidently and efficiently filter out the mole as a potential marker sub target. Accordingly, it can be advantageous to utilize two or more concentric shapes, or shapes having a different common geometrical indicator, to, among other things, efficiently filter out parts of an image that do not contain a valid subtarget. Although in this embodiment, the subtargets each comprise a white dot and a white ring around that white dot, various other embodiments of markers may comprise various other shapes. For example, two, three, four, five, or more circles, ellipses, hexagons, octagons, and/or other shapes may be utilized. Further, within the same marker, different types of subtargets may be utilized. For example, one subtarget may comprise a different number of concentric shapes than another subtarget, which may, for example, provide context that enables tracking of in-plane rotations throughout the full 360 degrees even in a design where the subtarget centroid positions alone are rotationally symmetrical (such as the equilateral triangle design of FIG. 2A).

Since large concentric pair 3404 is larger than the small concentric pairs 3402, the system may be able to more quickly identify large concentric pair 3402 than the other concentric pairs. The position of the large concentric pair 3404 may then be used to quickly locate the remaining concentric pairs—the four small concentric pairs 3402— through a variety of methods. One method for locating the remaining concentric pairs may be taking the four closest concentric pairs that surround the large concentric pair 3402, and then grouping all five concentric pairs as a marker. Thus, the large concentric pair 3402 may be used to identify the location of the marker quickly. Otherwise, the centroids of each concentric pair can be located but the specific subtarget each concentric pair corresponds to is unknown. The concentric pairs may in some embodiments be put into local groups to determine the subtarget for each concentric pair, such as through an algorithm like perimeter edge detection, described previously herein. This may in some embodiments add undesired computational time and/or complexity to the algorithm for identifying the location of the marker or uniquely identifying subtargets. Further details on marker pattern centroid detection are provided below in the discussion associated with FIG. 37 and FIG. 38.

Figure 35:
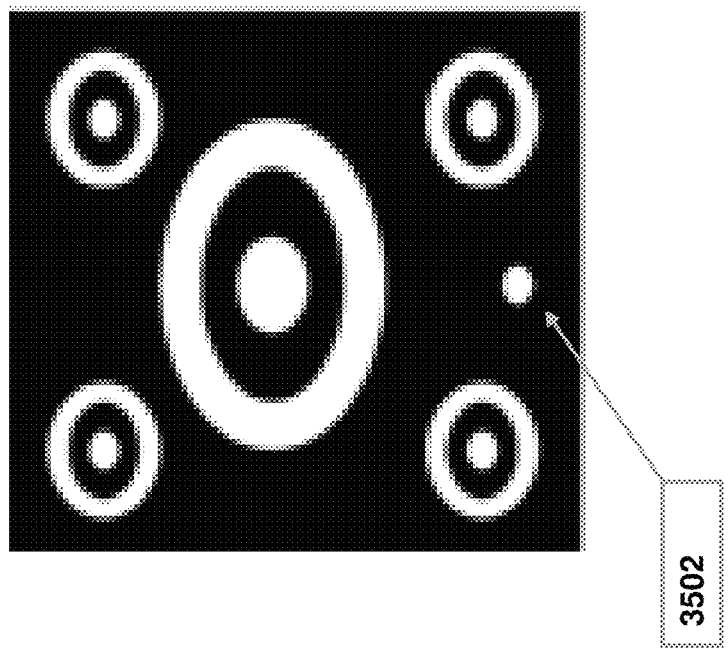
FIG. 35 illustrates an example of a marker or optical tracker that avoids rotational degeneracy, according to one embodiment.

FIG. 35 illustrates another example of a marker or optical tracker that avoids rotational degeneracy, according to one embodiment. In FIG. 35, there is an additional dot 3502 that is not a concentric pair. Additional shapes like dot 3502 may be added to the marker pattern for unique marker identification. In some embodiments of the system, multiple markers may be used simultaneously. The multiple markers may have related, rotationally asymmetric patterns with small variations, such as the number of additional shapes like dot 3502 that are included in the pattern. The number, location, or arrangement of the shapes or dots may assist the system in unique marker identification, such that the system may be able to distinguish the markers from one another. The system may separate the different markers from each other by searching for non-concentric shapes, marks, or objects such as dot 3502 in the bounding box region. The number of non-concentric shapes may be added up to determine which marker number it is. Further details on multi-marker detection are provided below in the present disclosure. Although the embodiment illustrated in FIG. 35 utilizes a dot or circle 3502 as an additional shape to enable marker unique identification and/or avoidance of rotational degeneracy, various other embodiments of markers may utilize other shapes for these purposes, such as two or more concentric shapes, a bar, a star, a square, a rectangle, and/or the like. It may be desirable to have a set of markers that are individually uniquely identifiable, such as when multiple markers are used during a same tracking procedure. For example, during an MRI brain scan, the patient may have two, three, four, five, six, or more markers simultaneously affixed to his or her head, for example, to increase accuracy, redundancy, and or efficiency of the tracking process. In some embodiments, patterns are provided that uniquely identify an individual marker with a given set of markers (e.g., a set of 2, 3, 4, 5, 6, 7, 8, 9, 10, or more markers that are intended to be used simultaneously for the same scan). In some embodiments, however, an individual marker may be uniquely identifiable with respect to a larger set of markers or all other markers, not just markers with in a specific smaller subset of markers that are intended to be used simultaneously. For example, a marker may comprise a bar code, QR code, and/or the like that can be decoded to interpret a unique identifier. In some embodiments, such an encoded unique identifier may not necessarily be decoded and/or used during a motion tracking process, but may be saved associated with motion tracking and/or scan data for later lookup and/or traceability.

FIGS. 36A and 36B each illustrate multiple embodiments of markers with variations in the amount of non-concentric dots for the purposes of unique marker identification and/or additional avoidance of rotational degeneracy. FIG. 36A illustrates multiple embodiments of markers that possess slight variations on the embodiment illustrated in FIG. 34. The leftmost marker shown in FIG. 36A is identical to the embodiment illustrated in FIG. 34. There are four small concentric pairs 3602 in the corners, with a large concentric pair 3604 near the center but slightly offset in the vertical direction. The marker immediately to the right has an additional dot 3606 at the bottom of the marker. Going from left to right in FIG. 36A, each marker possesses an additional dot over the previous marker—starting with a marker having zero non-concentric dots to a marker having five non-concentric dots. Thus, FIG. 36A shows six markers with variations in the amount of non-concentric dots, which may all be used and uniquely identified simultaneously by the system because each marker is unique.

FIG. 36B also illustrates multiple embodiments of markers that comprise variations. Each marker in FIG. 36B has five same-sized concentric pairs 3608. Four of the concentric pairs are in the corners of each of the markers, with the last concentric pair near the center of each marker but possessing a vertical offset. Going from left to right in FIG. 36B, each marker possesses an additional non-concentric dot 3608 over the previous marker. Thus, FIG. 36B also shows six markers that have variations in the amount of non-concentric dots they display, and they may all be used and uniquely identified simultaneously by the system because each marker is unique. However, the markers in FIG. 36B lack the large concentric pair 3604 that the markers in FIG. 36A possess. This may mean that the markers in FIG. 36B do not allow the system to perform the method of quickly identifying a large concentric pair from the other concentric pairs, and then using the position of the large concentric pair to locate the remaining concentric pairs in the marker. Using the markers in FIG. 36B may work as well as the markers in FIG. 36A for reducing rotational degeneracy. However, using the markers in FIG. 36B may result in a longer time for identifying the markers and centroids from images, as more calculations may be needed. However, the markers of FIG. 36B comprise larger unique identification features (e.g., dots) than the markers of FIG. 36A, which may also be beneficial to the system and the processing time required to locate and identify markers.

There may be conflicting requirements associated with the size and design of the actual marker used. Making the marker as small as possible may be beneficial for the patient's convenience, and/or to enable more markers to be used. However, the marker may need to be large enough that the system may be able to accurately determine the centroids of the marker from a pixelated image taken of the marker. Furthermore, there may be an ideal spacing associated with the subtargets in a marker. Increased distances between subtargets in a marker may result in improved tracking, since the tracking algorithm observes differences associated with the movement of the centroids of the subtargets. The larger the marker is, the larger this distance is for a given motion, and thus the better the tracking will be. Further discussion on the size of a marker is provided above in the present disclosure. In some embodiments, it can be desirable to utilize a marker comprising outer subtargets having centroid locations that define a bounding square of a 14×14 millimeter size. In other embodiments, the bounding square (or rectangle) may comprise one or more sides having a length of 5, 6, 7, 8, 9, 10, 11, 12, 13, 15, 16, 17, 18, 19, 20, or more millimeters.

Marker Pattern Centroid Detection

Since the motion tracking system tracks the relative positions of markers, it may be useful for the system to use a process that can reliably identify the centroids of the subtargets (also referred to as reference points or concentric rings, herein) in a marker. It may also be useful to quickly and uniquely identify the subtargets that comprise a market. Various processes or methods may be used to identify the subtargets and the centroids of the subtargets. The system may use different processes or methods based on the marker patterns. Some marker designs may allow the system to use more efficient processes or methods when identifying the subtargets and the centroids of the subtargets.

Figure 37:
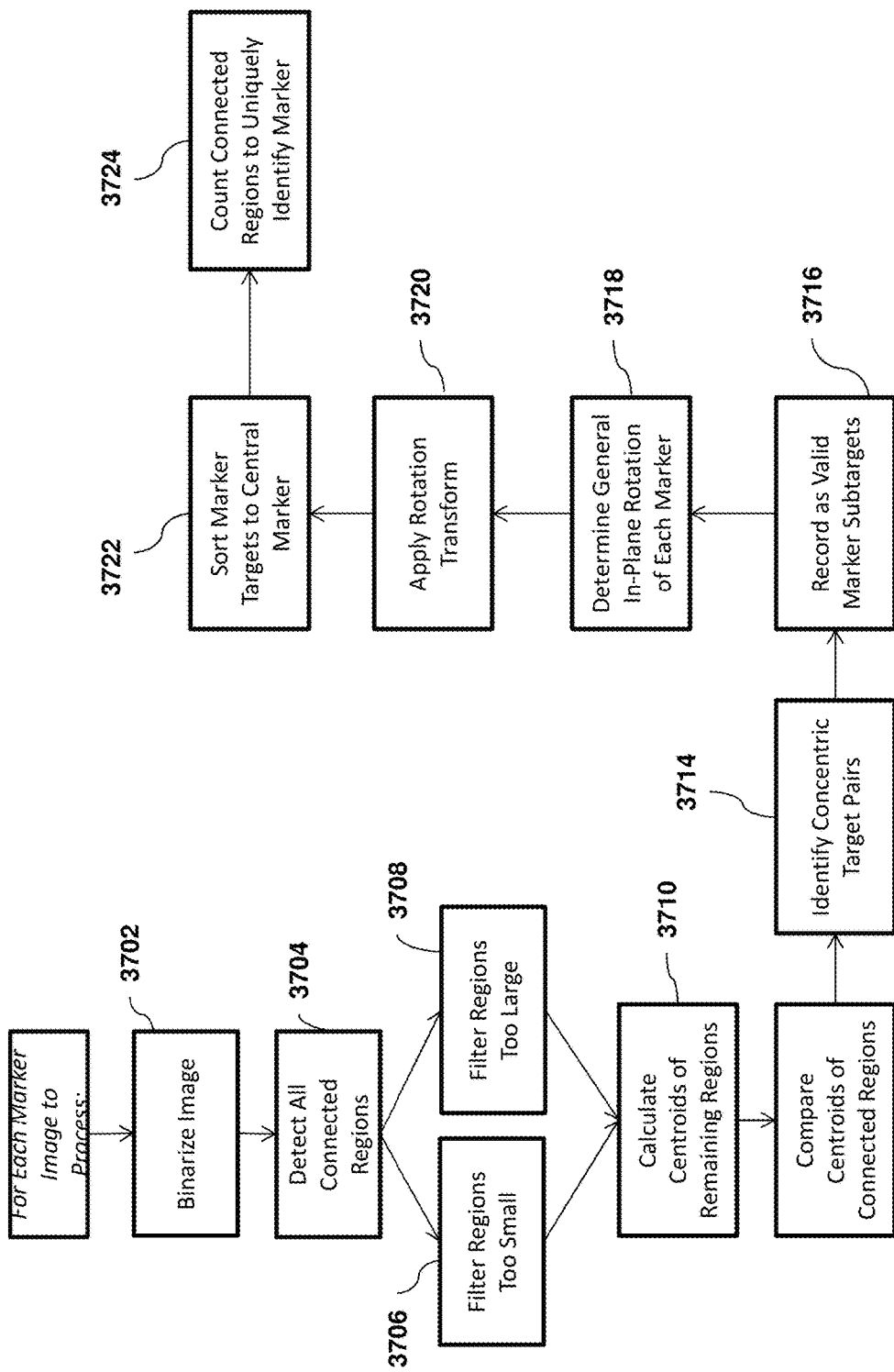
FIG. 37 is a flow chart that illustrates a marker pattern centroid detection process, according to one embodiment.

FIG. 37 is a flow chart that illustrates a marker pattern centroid detection process, according to one embodiment. This process may be applied to each marker image obtained from a detector, camera, or optical sensor (or in some embodiments only a subset of marker images, such as to increase efficiency). In some embodiments, 0 to 5 additional dots are used on the markers in order to uniquely identify up to 6 unique markers (although various other unique identification methods may be used, as described above). However, there is no technical limitation on the number of markers a system may apply this centroid extraction algorithm to. Parallel processing may be used to simultaneously perform the marker centroid extraction algorithm for all markers in the images received by all cameras present in the system. When paired with a tracking algorithm that may scale to any number of targets, the number of markers used may be limited only by space and computational resource constraints. Further discussion of multi-marker tracking is provided below.

At block 3702, the system may binarize each marker image received. The system may set all pixels above a certain threshold to be white, while setting all pixels below that threshold to be black. The system would then proceed to block 3704 to detect all connected regions within each image. The connected regions may be defined as all groups of white pixels that are touching each other. However, in some embodiments, the system may be configured to detect connected regions of all groups of black pixels, such as when the marker comprises black subtargets on a white background.

At block 3706, the system then filters out connected regions that are too small to be a marker component (such as those less than 4 pixels in some embodiments). At block 3708, the system may filter out connected regions that are too large to be a marker component (such as those greater than 2000 pixels in some embodiments). The system may perform block 3706 and block 3708 in parallel, or in some embodiments, the system may perform those two blocks sequentially. The system may perform block 3706 first and then block 3708 second, or the system may perform block 3708 first and then block 3706 second.

At block 3710, the system may calculate the centroids of the remaining connected regions. At block 3712, the system may then compare the centroids of each connected region. Those regions with centroids within 1 pixel of each other are identified as concentric subtarget pairs at block 3714. In other embodiments, other thresholds may be used, such 0, 2, 3, 4, 5, or more pixels. At block 3716, the system may then average the centroids of the regions in each concentric pair and record them as a valid marker subtarget in block 3716.

Alternatively, the system may utilize a somewhat different process if the marker has a large concentric ring, such as the marker embodiment illustrated in FIG. 34. Since the centermost subtarget is enlarged with respect to the other marker subtargets, it may be more quickly isolated based on size. The overall marker location within the image may then be identified efficiently. An algorithm may group the four subtargets or concentric rings nearest to each central subtarget, in order to isolate and group all of the subtargets comprising each marker. In such an embodiment, the system would perform these modified processes in lieu of blocks 3710, 3712, and 3714.

At block 3718, the system may then determine the general in-plane rotation of each marker by calculating the angle of the line segment connecting the overall centroid of the group of subtargets comprising the marker to the central subtarget. With the rotation angle determined, a rotation transform is applied to the marker at block 3720 to remap it to an upright position.

At block 3722, the system may then sort the subtargets comprising the marker by their relative position to the central marker. At block 3724 a system may count all of the connected regions within the bounding box of each marker to uniquely identify each observed marker.

Figure 38:
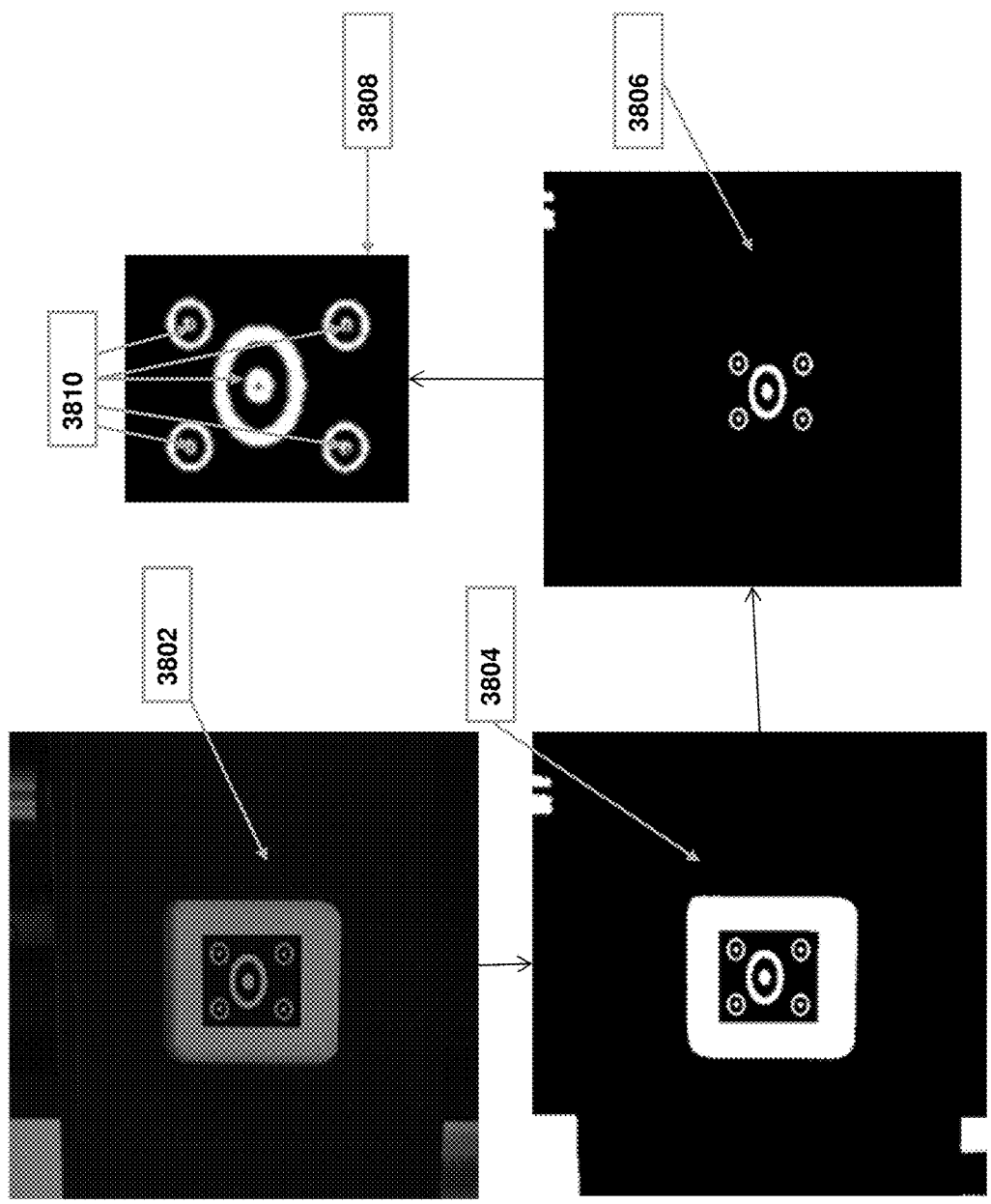
FIG. 38 illustrates how an image of a rotationally asymmetric marker may be processed in some embodiments in order to locate the centroids in the marker.

FIG. 38 illustrates how an image of a rotationally asymmetric marker may be processed in order to locate the centroids in the marker, for example, using the process flow illustrated in FIG. 37.

Image 3802 is a raw greyscale image of a marker with rotational asymmetry, such as the marker in FIG. 34. This image is similar to the image of the marker that a detector or optical camera would take.

The system then binarizes image 3802 in order to obtain image 3804 for locating all white, connected regions (e.g., block 3702 of FIG. 37). To binarize a grayscale image, a threshold for 50% of full scale is set. All pixels above this threshold are made white, and all pixels below this threshold are converted to black pixels. Connected regions are all remaining groups of white pixels that are touching either. Various connected regions can be seen in image 3804. The system then finds and evaluates all the connected regions based on their size. The regions that are way too small (such as a couple of pixels) may be noise rather than objects, and the system may discard those regions. The regions that are too big (such as greater than 2000 pixels) may be large objects in the image rather than components of the marker, and the system may discard those regions as well. These may be, for example, the processes performed at blocks 3704-3708 of FIG. 37.

The system may then be left with image 3806, which shows all the connected regions that have not been discarded, as they are within the defined size range that the system is looking for. At this point, the system may then calculate the centroids of all remaining objects in the image (e.g., block 3710 of FIG. 37). Objects with centroids occurring within 1 pixel of each other (i.e., concentric objects) may be identified as concentric pairs or a valid subtarget (e.g., block 3714 of FIG. 37). The centroids of each object in a concentric pair may be averaged, in order to determine a centroid for the concentric pair. The end result is image 3808, which illustrates the identified centroids 3810 of all five of the concentric pairs present in the marker shown in the original image 3802. These identified coordinates may be used with various algorithms disclosed herein to estimate the marker's position in six degrees of freedom, thus enabling an estimate of the patient's position in six degrees of freedom. As can be seen in the above examples, using concentric rings may be one method of uniquely identifying the subtargets that are part of the marker. By using concentric rings for the subtargets, when objects in an image are identified as having the same centroid coordinates, the probability is greatly in favor of the two objects belonging to the same subtarget pair and to the marker.

Generalized Six-Degree-of-Freedom Tracking System

Overview

This disclosure previously described some embodiments in which a MRI Head Tracker (or other motion tracking system) may take real-time input from two 2D imaging sensors and analyze the data to determine and report motions in six degrees of freedom with minimal latency. Some of those embodiments are configured to detect and measure three centroid positions on the marker and utilize those positions to determine the position of the patient's head, by combining data from the two images of the marker to generate six unique principal quantities. One example of such a process is illustrated in FIG. 20C. It can be desirable, however, to utilize a motion tracking system that can use any number of cameras, and/or any number of markers, including markers having various designs. Further, it can be desirable to have a motion tracking system that can dynamically adjust to the addition and subtraction of one or more cameras and/or markers (and/or the blocking and unblocking of one or more sight lines between cameras and markers). For example, as a patient moves, one or more sightlines may become blocked, and it can be desirable to have a motion tracking system that can dynamically and automatically adapt to the sightlines that become blocked and/or unblocked during a medical imaging scan.

In some embodiments, a generalized six-degree-of-freedom algorithm is utilized that enables any non-zero number of cameras (and/or any non-zero number of markers) to be used with the system. Such a six-degree-of-freedom tracking system may utilize 1 to n cameras with no particular restrictions on camera locations, except that the field of view of each camera covers some or the entire region of interest and that the six-degree-of-freedom position of each camera is known in a common arbitrary coordinate system. In some embodiments, an increase in the number of cameras and/or markers increases the overall tracking accuracy and/or redundancy. However, an increase in the number of cameras and/or markers may also cause an increase in processing power and/or processing time required to estimate a patient's pose. Accordingly, it can be desirable to optimize the number of cameras and/or number of markers used based on the available processing power, the available space in, on, or around the medical scanner for positioning therein of cameras, and/or the available space and/or mounting positions for markers on the patient being scanned. In some embodiments, such as in an MRI scanner where a patient is scanned within a generally cylindrical bore, the system can be configured to position a plurality of cameras about the bore, with the cameras positioned such that at least one camera (or any other number of cameras) can always see at least one marker (or any other number of markers) in any anticipated position of the patient during the scan.

In some embodiments, the system may use data from every camera that can currently see a marker (which may or may not include every camera in the system). For example, if cameras 1, 3, and 5 can see a marker, then the system may use data from just those three cameras while ignoring data from other cameras. The system may automatically determine the position of the marker based on which cameras can see the marker. In some embodiments, the system may be able to seamlessly deal with blocking or obstructing of the viewpath of one or more cameras. For example, if there are initially three cameras that can see a marker but one camera's viewpath becomes blocked, such as by the patient's arm, then the system may be able to use the other two cameras with unobstructed viewpaths to determine the marker (or markers) position. In some embodiments, more than one marker may be tracked by some or all of the cameras or detectors.

In some embodiments, the accuracy of the motion tracking system may be lower when one camera is used as compared to when more cameras are used, although the accuracy may still be sufficient to reduce or eliminate motion artifacts in the medical imaging scans. The accuracy may improve with two or more cameras, and the tracking accuracy may generally increase with additional numbers of cameras that can detect a marker (the same marker and/or other markers) at a given time. The generalized six-degree-of-freedom algorithm may allow the system to switch dynamically from camera to camera, or add and remove cameras from use.

In some embodiments, the system utilizes a generalized set of principal quantities (e.g., the principal quantities may be used with various marker designs). The principal quantities may comprise in some embodiments the sums and differences in the X and the Y coordinates between every pair of targets from every image. For example, a marker may be imaged by both camera 1 and camera 2. The principal quantities would be the sum and difference in the X coordinate and the Y coordinate between every possible combination of pairs of targets available for a given marker. The system may construct a set of principle quantities for any number of markers based on the data available. For example, if there are six cameras being utilized by the system and three of the cameras can see the centroids of that marker, then the system may generate a full set of principal quantities based on all of that combined data. In this manner, the system may adjust the principal quantities based on new data available, such as if a fourth camera was able to see the centroids in the marker (or if only one camera were able to see a marker). Additional details regarding principal quantity calculations are given below.

In some embodiments, the system may utilize six cameras. In some embodiments, the system may utilize four cameras located on the circumference of a circle on or about the body coil of an MR scanner, pointed inward with positions adjusted for best coverage of the region(s) of interest. The number of cameras used in the system may be chosen based on available processing power, space, optimum view paths, and/or the like. Additional cameras may improve accuracy and allow for redundancy, although in some embodiments additional cameras may result in additional processing power being needed for a desired processing time.

In some embodiments, the system may need to know the exact position and orientation of all the cameras in the system (or at least a position and orientation within sufficient tolerances). This information may be obtained in some embodiments as part of a separate calibration process, an example of which is further discussed below. The system may also need to know the relative positions of all the targets or subtargets within a marker. The relative positions of all the targets within a marker may in some embodiments be known before-hand based on the design of the marker.

Target Displacement Equations

In some embodiments, the marker nominal centroid positions are determined from the geometrical characteristics of the marker. The full six-degree-of-freedom translation is composed of a 3-D displacement as well as a 3-axis rotation.

The rotations are separated into roll, pitch and yaw (although other conventions may be used), and the translated position through rotation follows the Euler rotation matrix formulation as follows (using right-handed angle conventions). The x, y, and z displacement coordinates then follow the obvious independent translations:

$$\begin{pmatrix} x' \\ y' \\ z' \end{pmatrix} = \begin{pmatrix} 1 & 0 & 0 \\ 0 & \cos\varphi & -\sin\varphi \\ 0 & \sin\varphi & \cos\varphi \end{pmatrix} \begin{pmatrix} \cos\theta & 0 & \sin\theta \\ 0 & 1 & 0 \\ -\sin\theta & 0 & \cos\theta \end{pmatrix} \begin{pmatrix} \cos\psi & -\sin\psi & 0 \\ \sin\psi & \cos\psi & 0 \\ 0 & 0 & 1 \end{pmatrix} \begin{pmatrix} x \\ y \\ z \end{pmatrix} + \begin{pmatrix} \Delta x \\ \Delta y \\ \Delta z \end{pmatrix}$$

Decomposing the six independent translations from the absolute and relative displacements of the measured marker centroids is the subject of this effort. The 2D inverse problem is somewhat more difficult than the 3D problem, in that after the marker centroid projections in focal plane row and column are determined, significant degeneracies remain in the unfolding matrices for each camera. Combining the data from multiple cameras removes these degeneracies through a series of interrelated, nonlinear equations. The fastest procedure for solving this inverse problem is obtained by a variant of the Newton-Raphson method, whereby an approximate first-order solution is proposed and tested against the known (measured) centroid locations on the camera focal planes. The residual error is divided by the local derivatives with respect to each component of rotation and translation, to determine an iterative correction. The first-order solution is chosen by considering the features of the projected target pattern which are most strongly affected by a single rotation angle or displacement, and linearizing the inversion problem along these feature axes.

Six-Degree-of-Freedom Extraction Algorithm

Image Characterization and Calculation of Principal Quantities

In this embodiment, the markers each comprise 3 or more targets (plus additional identifying marks in some embodiments) and may be observed by 0 to n cameras, where n is the total number of active cameras in the system. In the case of a marker being obscured or moved outside of the field of view of all cameras, its position is unknown and not considered in any subsequent calculations until such time as the marker moves to a position where is can again be detected. In other cases, characterization of the images is achieved, in this embodiment, by calculating both the sum and difference of the column (X) and row (Y) coordinates between each target image and every other target image across all cameras. For a given marker, with targets, T and cameras, C, the set of principal quantities (PQ) characterizing each marker is given by:

$PQ_x = \{X_{T_iC_k} \pm X_{T_jC_l} | i,j \in [1:m] \wedge k,l \in [1:n] \wedge C_kC_l$ contain valid marker images$\}$ $PQ_y = \{Y_{T_iC_k} \pm Y_{T_jC_l} | i,j \in [1:m] \wedge k,l \in [1:n] \wedge C_kC_l$ contain valid marker images$\}$ $PQ = PQ_x \cup PQ_y$ In this manner, a set of principal quantities, PQ, may be constructed for each marker based on all available image data.

Characterizing Global Variation in Principal Quantities with Six-Degree-of-Freedom Motions Partial derivatives relative to subject displacements and rotations ($\varphi$, $\theta$, $\psi$, $\Delta x$, $\Delta y$, $\Delta z$), of the principal quantities described above, about the initial (non-displaced) position, are computed numerically. Here:

Roll $\varphi$ is right-handed rotation about the x-axis
Pitch $\theta$ is right-handed rotation about the y-axis
Yaw $\psi$ is right-handed rotation about the z-axis
$\Delta x$ is toe-to-head direction
$\Delta y$ is left-to-right direction
$\Delta z$ is down-to-up direction Starting from an initial marker position in 3-D world space, defined as ($\varphi$, $\theta$, $\psi$, $\Delta x$, $\Delta y$, $\Delta z$)=(0, 0, 0, 0, 0, 0), the initial world coordinates ($x_{0i}, y_{0i}, z_{0i}$) are determined for each target, i, comprising the marker based on the known geometric configuration of the marker and definition of a convenient coordinate origin.

Local partial derivatives of each of the principal quantities, with respect to each of the 6 degrees of freedom (roll, pitch, yaw, dx, dy, dz), are performed numerically by evaluating changes in these quantities for small increments in each degree of freedom. Changes in the target positions for specified motions along the six degrees of freedom are computed using the Euler rotation matrices and translation vector:

$$\begin{pmatrix} x_i \\ y_i \\ z_i \end{pmatrix} = \begin{pmatrix} 1 & 0 & 0 \\ 0 & \cos\varphi & -\sin\varphi \\ 0 & \sin\varphi & \cos\varphi \end{pmatrix} \begin{pmatrix} \cos\theta & 0 & \sin\theta \\ 0 & 1 & 0 \\ -\sin\theta & 0 & \cos\theta \end{pmatrix} \begin{pmatrix} \cos\psi & -\sin\psi & 0 \\ \sin\psi & \cos\psi & 0 \\ 0 & 0 & 1 \end{pmatrix} \begin{pmatrix} x_{0i} \\ y_{0i} \\ z_{0i} \end{pmatrix} + \begin{pmatrix} \Delta x \\ \Delta y \\ \Delta z \end{pmatrix} \quad [1A]$$

Subsequently, the normalized pinhole camera model projections of the new marker target positions are determined using a geometric projection calculation. Given accurate knowledge of camera positions, the normalized projections are given by:

$$x_{i,j} = \mp \tan\alpha_{i,j} \sin\beta_{i,j}, y_{i,j} = \pm\tan\alpha_{i,j} \cos\beta_{i,j} \quad [2A]$$

Here $x$ and $y_{i,j}$ are the horizontal and vertical pinhole camera projections for translated target i projected onto the camera j sensor, where the angles $\alpha_{i,j}$ and $\beta_{i,j}$ are the polar and azimuth angles locating target i, relative to the camera j focal axis. In order to maintain the convention of a counterclockwise sense of rotation for the azimuth angle for each of the camera boresight axes, equation 2 is divided into two mirrored functions: one for cameras to the patient's left side and the second for cameras to the patient's right side. The polar and azimuth angles are calculated from the target position world coordinates as follows:

$$\alpha_{i,j} = \sin^{-1}\left(\frac{\sqrt{(x_{\perp,j} - x_i)^2 + (y_{\perp,j} - y_i)^2 + (z_{\perp,j} - z_i)^2}}{\sqrt{(x_{cj} - x_i)^2 + (y_{cj} - y_i)^2 + (z_{cj} - z_i)^2}}\right), \quad [3A]$$

$$\beta_{i,j} = \pm\cos^{-1}\left(\frac{(x_{\perp,j} - x_i)(y_{cj} - y_0) - (y_{\perp,j} - y_i)(x_{cj} - x_0)}{\sqrt{(x_{\perp,j} - x_i)^2 + (y_{\perp,j} - y_i)^2 + (z_{\perp,j} - z_i)^2}\sqrt{(x_{cj} - x_0)^2 + (y_{cj} - y_0)^2}}\right). \quad [4A]$$

Here the point $(x_{\perp,j}, y_{\perp,j}, z_{\perp,j})$ is the point of intersection between the camera optical axis and the plane perpendicular to the optical axis which includes the translated target position $(x_i, y_i, z_i)$:

$$x_{\perp,j} = x_0 + \kappa(x_{cj} - x_0); y_{\perp,j} = y_0 + \kappa(y_{cj} - y_0); z_{\perp,j} = z_0 + \kappa(z_{cj} - z_0), \quad [5A]$$

with $(x_{cj}, y_{cj}, z_{cj})$ defining the 3-D position of camera j, $(x_0, y_0, z_0)$ defining the nominal boresight position of all cameras at the un-displaced target center and the constant $\kappa$ based on geometric projection and given by:

$$\kappa = \left\{ \frac{(x_{cj} - x_0)(x_i - x_0) + (y_{cj} - y_0)(y_i - y_0) + (z_{cj} - z_0)(z_i - z_0)}{(x_{cj} - x_0)^2 + (y_{cj} - y_0)^2 + (z_{cj} - z_0)^2} \right\}. \quad [6A]$$

In equation [4], the inverse cosine function is taken to range from 0 to $\pi$, and the appropriate sign for $\beta_{i,j}$ is given by:

$$[(z_{cj} - z_0)\{(x_{cj} - x_0)(x_{\perp,j} - x_i) + (y_{cj} - y_0)(y_{\perp,j} - y_i)\} - (z_{\perp,j} - z_i)\{(x_{cj} - x_0)^2 + (y_{cj} - y_0)^2\}]$$

To numerically evaluate the partial derivatives of the principal quantities about the initialized target position, the un-displaced 3-D target position coordinates $(x_{0i}, y_{0i}, z_{0i})$ are first projected to camera coordinates using equations [2A] through [6A] above, and initial values are computed for each of the principal quantities described above (most should be zero or near-zero at the starting position). Then small increments of roll, pitch, yaw, x-, y- and z-axis displacements are introduced one at a time; for each increment the new world coordinates and the new camera projections of the target positions are computed and the principal quantities are re-calculated. The change in each principal quantity is divided by the small angular or displacement increment to determine the partial derivative.

Radial and tangential lens distortion effects are applied to the normalized projections according to the following equation:

$$\begin{bmatrix} x_{i,j\,distorted} \\ y_{i,j\,distorted} \end{bmatrix} = (1 + ar^2 + br^4 + cr^6) \begin{bmatrix} x_{i,j} \\ y_{i,j} \end{bmatrix} + \begin{bmatrix} 2dxy + e(r^2 + 2x^2) \\ d(r^2 + 2y^2) + 2exy \end{bmatrix}$$

Where $r^2 = x^2 + y^2$, and the radial distortion coefficients, a, b, c and the tangential distortion coefficients d, e, are determined by a separate lens calibration procedure. Lastly, the distorted projection coordinates are mapped to pixel values for each camera as follows:

$$X_{i,j} = X_0 + \left(\frac{f.l.}{s_{pix}}\right) x_{i,j\,distorted}, \quad Y_{i,j} = Y_0 + \left(\frac{f.l.}{s_{pix}}\right) y_{i,j\,distorted}$$

Where f.l. and $s_{pix}$ are the lens focal length and camera pixel pitch, and $X_0$ and $Y_0$ are the pixel coordinates of the center of the pixel array (i.e. for a 1280×1024 array, $X_0 = 640.5$ and $Y_0 = 512.5$, assuming the center of the upper left corner pixel is defined as having coordinates (1,1).).

For instance, to determine the partial derivatives with respect to roll, the displacement vector $(\phi, \theta, \psi, \Delta x, \Delta y, \Delta z) = (\hat{o}\phi, 0, 0, 0, 0, 0)$ is introduced to the general displacement equation [1] to determine the translated target positions $(x_i, y_i, z_i)$: The conversion to camera coordinates $(X_{i,j}, Y_{i,j})$ is then performed using equations [2] through [6], and the principal quantities are calculated as outlined above. The difference between each principal quantity and the corresponding value of that quantity for the un-displaced calculation is divided by the small increment in roll, to give the partial derivative of each quantity with respect to roll. To determine partial derivatives with respect to pitch, the displacement vector $(\phi, \theta, \psi, \Delta x, \Delta y, \Delta z) = (0, \hat{o}\theta, 0, 0, 0, 0)$ is used to initiate the calculations, and so on for all six degrees of freedom.

Each of these six repetitions produces one column of the global partial derivative matrix:

$$\begin{pmatrix} \frac{\partial PQ_1}{\partial \varphi} & \frac{\partial PQ_1}{\partial \theta} & \frac{\partial PQ_1}{\partial \psi} & \frac{\partial PQ_1}{\partial x} & \frac{\partial PQ_1}{\partial y} & \frac{\partial PQ_1}{\partial z} \\ \vdots & \vdots & \vdots & \vdots & \vdots & \vdots \\ \frac{\partial PQ_t}{\partial \varphi} & \frac{\partial PQ_t}{\partial \theta} & \frac{\partial PQ_t}{\partial \psi} & \frac{\partial PQ_t}{\partial x} & \frac{\partial PQ_t}{\partial y} & \frac{\partial PQ_t}{\partial z} \\ \vdots & \vdots & \vdots & \vdots & \vdots & \vdots \\ \frac{\partial PQ_n}{\partial \varphi} & \frac{\partial PQ_n}{\partial \theta} & \frac{\partial PQ_n}{\partial \psi} & \frac{\partial PQ_n}{\partial x} & \frac{\partial PQ_n}{\partial y} & \frac{\partial PQ_n}{\partial z} \end{pmatrix}_{(0,0,0,0,0,0)}$$

Determining First-Order Displacement Vector

A first-order approximation to the displacement matrix is determined by multiplying the matrix of measured principal quantities, as determined above, by the inverse of the partial derivative matrix computed above:

$$\begin{pmatrix} \varphi_0 \\ \theta_0 \\ \psi_0 \\ (\Delta x)_0 \\ (\Delta y)_0 \\ (\Delta z)_0 \end{pmatrix} = \begin{pmatrix} \frac{\partial PQ_1}{\partial \varphi} & \frac{\partial PQ_1}{\partial \theta} & \frac{\partial PQ_1}{\partial \psi} & \frac{\partial PQ_1}{\partial x} & \frac{\partial PQ_1}{\partial y} & \frac{\partial PQ_1}{\partial z} \\ \vdots & \vdots & \vdots & \vdots & \vdots & \vdots \\ \frac{\partial PQ_t}{\partial \varphi} & \frac{\partial PQ_t}{\partial \theta} & \frac{\partial PQ_t}{\partial \psi} & \frac{\partial PQ_t}{\partial x} & \frac{\partial PQ_t}{\partial y} & \frac{\partial PQ_t}{\partial z} \\ \vdots & \vdots & \vdots & \vdots & \vdots & \vdots \\ \frac{\partial PQ_n}{\partial \varphi} & \frac{\partial PQ_n}{\partial \theta} & \frac{\partial PQ_n}{\partial \psi} & \frac{\partial PQ_n}{\partial x} & \frac{\partial PQ_n}{\partial y} & \frac{\partial PQ_n}{\partial z} \end{pmatrix}^{-1} \begin{pmatrix} PQ_1 \\ \vdots \\ PQ_t \\ \vdots \\ PQ_n \end{pmatrix}$$

Characterizing Local Variation in Principal Quantities with Six-Degree-of-Freedom Motions First order values for $(\phi, \theta, \psi, \Delta x, \Delta y, \Delta z)$ determined above are entered into the translation equation [1A] to determine the corresponding translated 3-D target position $(x_i, y_i, z_i)$ for each of the target positions. These world coordinates are projected to camera coordinates $(X_{i,j}, Y_{i,j})$ using equations [2A] through [6A], and the principal quantities are re-calculated. These quantities are compared against the measured values of these quantities determined above, to create a residual error matrix:

$$(\sigma_{PQ_1}, \ldots, \sigma_{PQ_i}, \ldots, \sigma_{PQ_n})$$

Local partial derivatives of the principal quantities are calculated by introducing small increments in roll, pitch, yaw, x-, y- and z-axis displacements one at a time as before, but this time the increments are relative to the first-order displacement vector. For each increment, the new world coordinates and the new camera projections of the target positions are re-computed and the principal quantities are re-calculated. The change in each principal quantity is divided by the small angular or displacement increment to determine a local partial derivative. For instance, to calculate partial derivatives with respect to roll, the first-order displacement vector $\{\phi_0, \theta_0, \psi_0, (\Delta x)_0, (\Delta y)_0, (\Delta z)_0\}$ is replaced by $\{\phi_0 + \hat{o}\phi, \theta_0, \psi_0, (\Delta x)_0, (\Delta y)_0, (\Delta z)_0\}$ and resulting changes to each of the principal quantities is divided by to determine the local derivative with respect to roll. This is repeated for each of the six degrees of freedom.

Each of these six repetitions produces one column of the new local partial derivative matrix:

$$\left(\begin{array}{cccccc} \frac{\partial PQ_1}{\partial \varphi} & \frac{\partial PQ_1}{\partial \theta} & \frac{\partial PQ_1}{\partial \psi} & \frac{\partial PQ_1}{\partial x} & \frac{\partial PQ_1}{\partial y} & \frac{\partial PQ_1}{\partial z} \\ \vdots & \vdots & \vdots & \vdots & \vdots & \vdots \\ \frac{\partial PQ_i}{\partial \varphi} & \frac{\partial PQ_i}{\partial \theta} & \frac{\partial PQ_i}{\partial \psi} & \frac{\partial PQ_i}{\partial x} & \frac{\partial PQ_i}{\partial y} & \frac{\partial PQ_i}{\partial z} \\ \vdots & \vdots & \vdots & \vdots & \vdots & \vdots \\ \frac{\partial PQ_n}{\partial \varphi} & \frac{\partial PQ_n}{\partial \theta} & \frac{\partial PQ_n}{\partial \psi} & \frac{\partial PQ_n}{\partial x} & \frac{\partial PQ_n}{\partial y} & \frac{\partial PQ_n}{\partial z} \end{array}\right)_{\{\varphi_0, \theta_0, \psi_0, (\Delta x)_0, (\Delta y)_0, (\Delta z)_0\}}$$

Determining Coarse Correction to the First-Order Displacement Vector

A coarse correction is computed to improve the first-order displacement vector and reduce residual error, by multiplying the residual error matrix determined above by the inverse of the local partial derivative matrix, also determined above:

$$\left(\begin{array}{c} \Delta\varphi \\ \Delta\theta \\ \Delta\psi \\ \Delta(\Delta x) \\ \Delta(\Delta y) \\ \Delta(\Delta z) \end{array}\right) = \left(\begin{array}{cccccc} \frac{\partial PQ_1}{\partial \varphi} & \frac{\partial PQ_1}{\partial \theta} & \frac{\partial PQ_1}{\partial \psi} & \frac{\partial PQ_1}{\partial x} & \frac{\partial PQ_1}{\partial y} & \frac{\partial PQ_1}{\partial z} \\ \vdots & \vdots & \vdots & \vdots & \vdots & \vdots \\ \frac{\partial PQ_t}{\partial \varphi} & \frac{\partial PQ_t}{\partial \theta} & \frac{\partial PQ_t}{\partial \psi} & \frac{\partial PQ_t}{\partial x} & \frac{\partial PQ_t}{\partial y} & \frac{\partial PQ_t}{\partial z} \\ \vdots & \vdots & \vdots & \vdots & \vdots & \vdots \\ \frac{\partial PQ_n}{\partial \varphi} & \frac{\partial PQ_n}{\partial \theta} & \frac{\partial PQ_n}{\partial \psi} & \frac{\partial PQ_n}{\partial x} & \frac{\partial PQ_n}{\partial y} & \frac{\partial PQ_n}{\partial z} \end{array}\right)^{-1} \left(\begin{array}{c} \sigma_{PQ_1} \\ \vdots \\ \sigma_{PQ_t} \\ \vdots \\ \sigma_{PQ_n} \end{array}\right)$$

The first-order displacement vector is incremented by the coarse correction matrix to create a better approximation to the displacement vector: $\{\varphi_0+\Delta\varphi, \theta_0+\Delta\theta, \psi_0+\Delta\psi, (\Delta x)_0+\Delta(\Delta x), (\Delta y)_0+\Delta(\Delta y), (\Delta z)_0+\Delta(\Delta z)\}$.

Iterative Fine Correction to Determine Final Six-Degree-of-Freedom Displacement Vector Characterizing Local Variation in Principal Quantities with Six-Degree-of-Freedom Motions and Determining Coarse Correction to the First-Order Displacement Vector are repeated, starting with the coarse-corrected displacement vector, to determine a fine correction to the displacement vector. After this iteration, the resultant fine correction increments are added to the coarse-corrected vector to create the new 6-DOF displacement vector. These processes are repeated iteratively until the magnitude of each of the fine corrections is less than the desired threshold (typically $10^{-6}$ mm or degrees) or the number of iterations reaches a predetermined maximum (typically 10 iterations).

One of skill in the art will recognize that the above-described six degree of freedom tracking algorithm is merely one way of implementing the tracking techniques disclosed herein, and various modifications may be made to this process without departing from the techniques disclosed herein.

Multi-Marker Tracking

Some embodiments of the motion tracking systems disclosed herein may simultaneously use multiple markers, such as to increase accuracy and/or redundancy. It may be useful for the system to be able to distinguish each marker from one another. One way of physically distinguishing markers from one another is described above, in which rotationally asymmetrical markers have varying amounts of non-concentric dots or other indicators on them. Although these markers are physically distinct, it may be desirable for the system to distinguish and uniquely identify the markers algorithmically. This algorithm may be generalized, such that the system may simultaneously handle any number of markers, including a greater amount of markers than the arrangements shown in FIG. 36A and FIG. 36B which depict six varying markers. With this multi-marker tracking algorithm, calculations may be performed separately and completely independent for each marker in parallel. Some markers may be simultaneously tracked by more than one camera. Some markers may be tracked by whichever camera is able to see or detect the marker. Further discussion of an example algorithm performed for each marker is described below in relation to the processes outlined for the six-degree-of-freedom extraction algorithm.

In addition to accuracy and redundancy benefits, the tracking of multiple markers may be helpful in determining the presence of non-rigid facial movement. A marker may undergo rigid motion and move with the skeletal structure of the patient, or the marker may undergo non-rigid motion that is not indicative of structural motion of the patient's head or other feature being tracked (e.g., from relative movement of a patient's skin, cartilage, and/or the like that is not rigidly connected to the patient's skeletal structure). It may be helpful to distinguish what kind of motion a marker is undergoing, because non-rigid motion may lead to an erroneous correction by the motion tracking system if it is detected as rigid motion.

Some embodiments of systems disclosed herein may keep track of a history of the relative positions of all the markers in the system. Once the six-degree-of-freedom coordinates for all visible markers are determined, coordinate transforms may be applied to remap the coordinate system origin sequentially to each of the markers, recording the resulting relative positions of the remaining markers in each case. In this manner, the six-degree-of-freedom relative position of each marker with respect to every other marker may be determined. A history of the relative position data over several seconds is maintained and may be used to calculate the means and standard deviations of relative positions of all markers. Each new set of relative position data may be compared to the historical mean and standard deviation, $\sigma$. If the new value is more than $\pm 3\sigma$ from the historical mean (or another value in other embodiments), then it may be flagged as a non-rigid motion.

With the use of only one marker, the marker may be subject to non-rigid motion but the system may in some embodiments be unable to determine it.

With two markers, the system may be able to look at the relative positions in space of the two markers. The system may be able to compare the latest set of coordinates for the two markers against their history. If the two markers move more than 3 sigma than their historical relative position (or another value in other embodiments), then the system may determine that there is non-rigid motion. However, with two markers it may be difficult to tell if one of them (or both of them) are undergoing non-rigid motion, only that it is happening.

With three or more visible markers, the system may be able to look at relative positions of each marker with respect to the other markers, and compare their history. The system may be able to determine that marker 2 is moving relative to other markers, but all the other markers are maintaining their relative positions to each other. This may mean that marker 2 is likely to be the non-rigid moving marker. The system may then focus on the other markers that are moving rigidly, and use data from those markers in order to enhance accuracy. As another example, if there are three visible markers and non-rigid motion flags are only raised in the relative positions between markers 1&2 and markers 2&3, then it is deduced that either marker 2 is moving non-rigidly or markers 1 &3 are moving non-rigidly with exactly the same motion (to within 3σ). Additional visible markers in the system would further reduce the already unlikely probability of the latter.

The multi-marker tracking algorithm may also allow tracking to continue in situations when camera viewpaths are obscured, or objects move out of the field of view of the cameras. More specifically, if two or more markers are determined to be moving rigidly, then their position data may be combined to further improve tracking accuracy. This may be done by specifying one marker in the system as the 'primary' marker (this may be done automatically, for example, by assigning the lowest numbered marker in the system as the primary marker), whose six-degree-of-freedom position is reported, and mapping all of the other visible, rigidly moving markers to its position using the historical relative position data. Once mapped to the same coordinate position, the six-degree-of-freedom coordinates are averaged. This method has the additional benefit that if the primary marker becomes obscured or moves outside of the field of view of all cameras, its six-degree-of-freedom position is automatically reconstructed based on the visible markers. Thus, even if the primary marker happens to be obscured at that time, mapping other markers (moving rigidly and relative to each other) to the historical relative position of the primary marker allows for the primary marker's location to be reconstructed.

Tracking System Calibration

Overview

This disclosure previously described some embodiments utilizing an example handling of the lens calibration, which involved the correction of a barrel distortion in the lens based on prior lens calibration measurements. However, a more sophisticated lens calibration method may be used in combination with the generalized, six-degree-of-freedom extraction algorithm.

In some embodiments, there may be a separate lens calibration that is performed with a checkerboard target (or in some embodiments another type of target). The checkerboard target may have a structure that comprises a set of nine marker structures arranged in a grid pattern (or a different number of marker structures). A user may reorient the checkerboard target based on where the desired zero origin should be, then the cameras may image the checkerboard target. The calibration algorithm may then be used to optimize camera positions instead of principal quantities.

In some embodiments, a radial component and a tangential component of the barrel distortion may be stored in the camera, which may be specific to a particular camera-lens combination. The system may guess a location for the target in the world coordinate system, and then project the marker, based what may be expected to be seen in the images. The previously-calculated distortion may be applied, and then the projection may be converted into pixels and paired with the actual data that was collected from the sensor.

Tracking System Calibration Setup

After each lens is assembled to a camera and a lens calibration is performed to determine its focal length and distortion coefficients, the cameras are integrated with MR system and the integrated system is calibrated as described herein. Although this example is described with respect to cameras integrated into an MR system, similar calibration concepts may be utilized with other camera setups.

Figure 39:
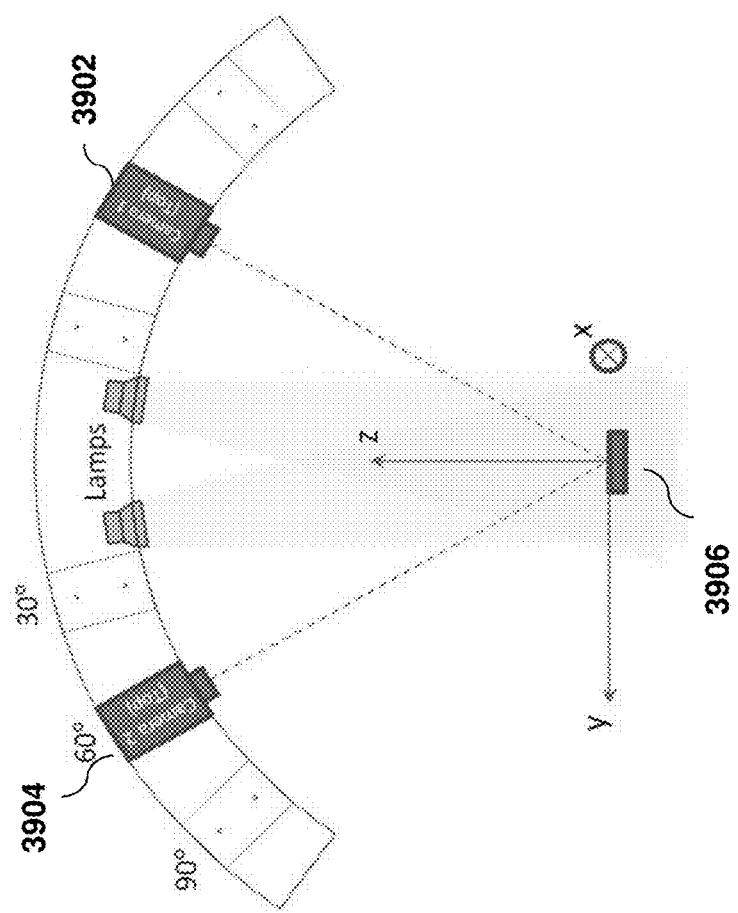
FIG. 39 illustrates the orientation and positions of components in a MR system, according to one embodiment.

FIG. 39 shows the orientation and positions of components in an embodiment of a MR system, with first camera 3902, second camera 3904, and reference target 3906.

The integrated camera positions (defined as the center of the focal planes) are taken to lie at $(x_{cj}, y_{cj}, z_{cj})$. The cameras' (3902 and 3904) optical axes are pointed at the nominal target center position, $(x_0, y_0, z_0)$, along the vectors $(x_0-x_{cj})\hat{e}_x + (y_0-y_{cj})\hat{e}_y + (z_0-z_{cj})\hat{e}_z$. The focal planes then lie in the laboratory planes $(x_0-x_{cj})(x-x_{cj}) + (y_0-y_{cj})(y-y_{cj}) + (z_0-z_{cj})(z-z_{cj}) = 0$.

Now, by convention for definition of angles, the cameras are oriented (spun as necessary about their optical axes) such that the vertical ("Y") axis of each focal plane lays in the laboratory plane $z=z_{cj}$; these vertical axes are then defined by the lines $(x_0-x_{cj})(x-x_{cj})+(y_0-y_{cj})(y-y_{cj})=0$, or equivalently
$x(x_0-x_{cj})+y(y_0-y_{cj})=x_{cj}(x_0-x_{cj})+y_{cj}(y_0-y_{cj})$.

The focal plane vertical "Y" axis unit vectors $$\hat{Y}_{cj} = \frac{(y_0 - y_{c1})\hat{e}_x - (x_0 - x_{c1})\hat{e}_y}{\sqrt{(x_0 - x_{c1})^2 + (y_0 - y_{c1})^2}} \quad \text{1B}$$

(for cameras to the patient's left side)

$$\hat{Y}_{cj} = \frac{-(y_0 - y_{c2})\hat{e}_x + (x_0 - x_{c2})\hat{e}_y}{\sqrt{(x_0 - x_{c2})^2 + (y_0 - y_{c2})^2}}$$

(for cameras to the patient's right side)

are approximately antiparallel to the laboratory x axis, in the usual case where $x_0 \approx x_{cj}$. Taking the vector cross product of the optical axis unit vectors $$\frac{(x_0 - x_{cj})\hat{e}_x + (y_0 - y_{cj})\hat{e}_y + (z_0 - z_{cj})\hat{e}_z}{\sqrt{(x_0 - x_{cj})^2 + (y_0 - y_{cj})^2 + (z_0 - z_{cj})^2}}$$

with the camera vertical axis vectors gives the camera focal plane horizontal axis vectors:

$$\hat{X}_{cj} = -\frac{(z_0 - z_{c1})(x_0 - x_{c1})\hat{e}_x + (z_0 - z_{c1})(y_0 - y_{c1})\hat{e}_y - [(x_0 - x_{c1})^2 + (y_0 - y_{c1})^2]\hat{e}_z}{\sqrt{(x_0 - x_{c1})^2 + (y_0 - y_{c1})^2 + (z_0 - z_{c1})^2} \sqrt{(x_0 - x_{c1})^2 + (y_0 - y_{c1})^2}} \quad \text{(left side)} \quad \text{2B}$$

$$\hat{X}_{cj} = \frac{(z_0 - z_{c2})(x_0 - x_{c2})\hat{e}_x + (z_0 - z_{c2})(y_0 - y_{c2})\hat{e}_y - [(x_0 - x_{c2})^2 + (y_0 - y_{c2})^2]\hat{e}_z}{\sqrt{(x_2 - x_{c2})^2 + (y_0 - y_{c2})^2 + (z_0 - z_{c2})^2} \sqrt{(x_0 - x_{c2})^2 + (y_0 - y_{c2})^2}} \quad \text{(right side)}$$

In the simple embodiment for which $x_{cj}=x_0$, the "X" and "Y" axis unit vectors reduce to $$\hat{X}_{cj} = \frac{(z_0 - z_{cj})\hat{e}_y - (y_0 - y_{cj})\hat{e}_z}{\sqrt{(y_0 - y_{cj})^2 + (z_0 - z_{cj})^2}}; \hat{Y}_{cj} = -1\hat{e}_x$$

After the cameras are mounted in the system, a reference target is placed approximately at the desired camera system origin and roughly aligned to the desired camera coordinate system x and y axes.

Figure 40:
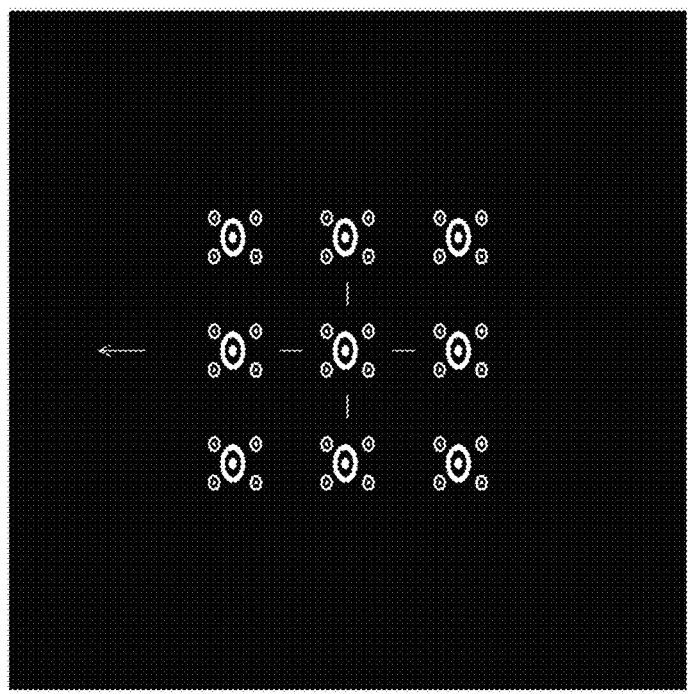
FIG. 40 illustrates one embodiment of a reference target used in tracking system calibration.

FIG. 40 illustrates one embodiment of the reference target used in tracking system calibration. The reference target pattern shown comprises 9 tracking marker patterns arranged in a 3×3 grid, spaced 25 mm apart center to center. Additional markings indicate the proper orientation and provide alignment marks for use with laser crosshairs or similar alignment tools. Various other reference target patterns may be utilized.

The camera coordinate system origin typically corresponds to a position at or near the MR system isocenter. The calibration target positioning and alignment can be easily performed using laser cross-hairs available in many MR systems. Camera parameters, aside from lens focal length and distortion coefficients, which have been measured previously, include physical location of focal plane centers and angular orientations relative to the reference target center: $(x_{cj}, y_{cj}, z_{cj}, \alpha_{cj}, \gamma_{cj}, \omega_{cj})$. Here $\alpha_{cj}$ are the polar angles of the camera optical axes relative to nadir, $\gamma_{cj}$ are the azimuth angles of these optical axes, and $\omega_{cj}$ define any further "twist" rotation of the cameras about their optical axes (relative to the nominal focal plane orientation convention described in the boxed text above).

Figure 43:
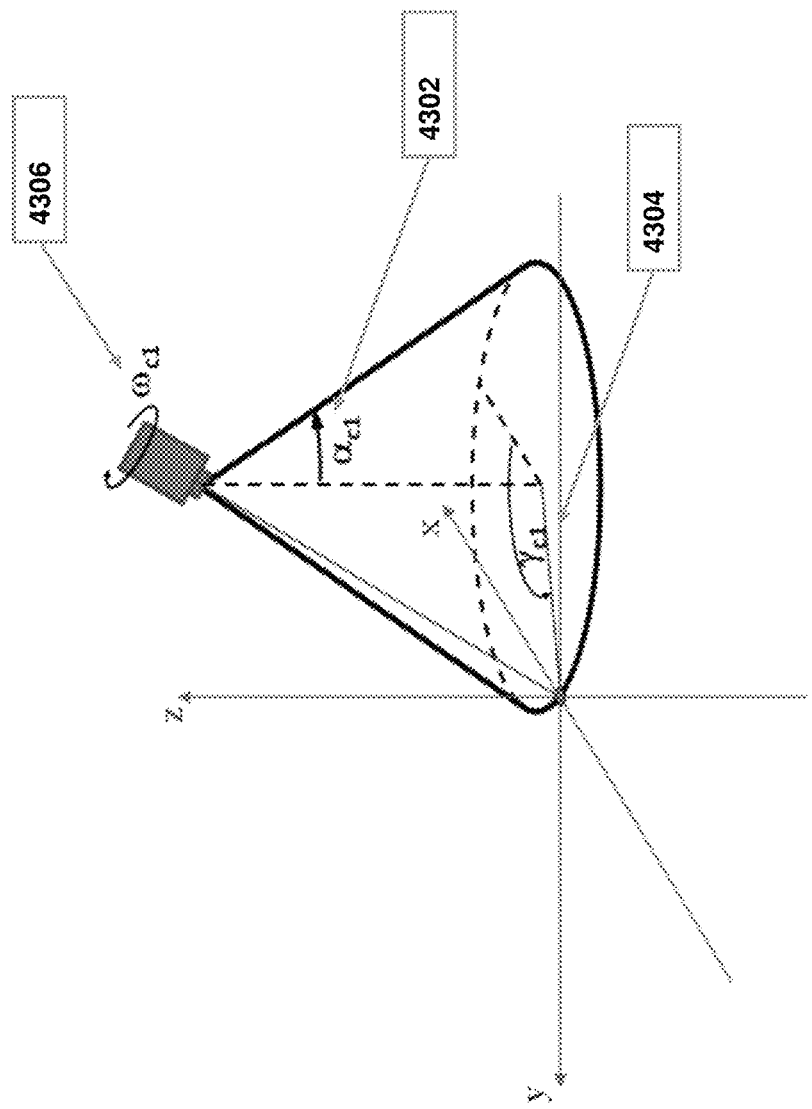
FIG. 43 illustrates nominal angles associated with camera positioning.

FIG. 43 illustrates the nominal polar angle 4302, nominal azimuth angle 4304, and the nominal twist angle 4306 of a camera.

Figure 44:
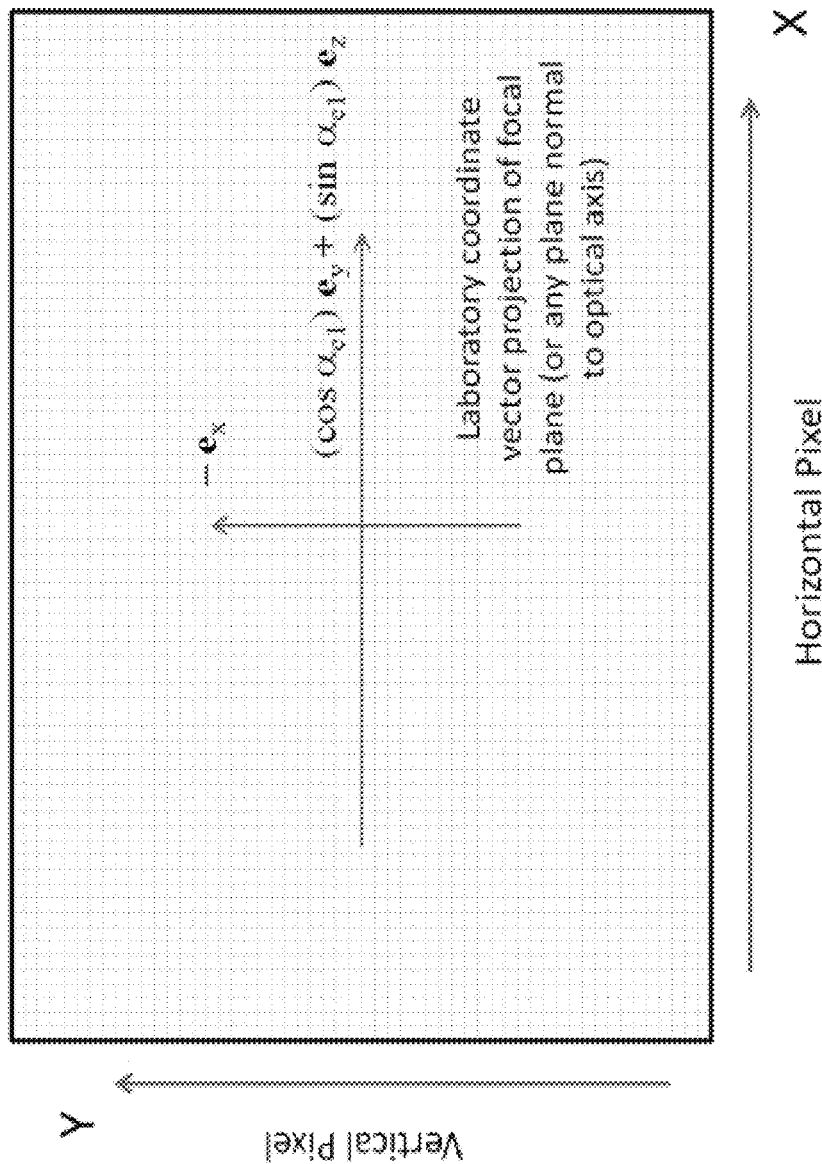
FIG. 44 illustrates the focal plane of a camera for a case when $x_{c1}=x_0$.

FIG. 44 illustrates the focal plane of a camera for a case when $x_{c1} = x_0$.

Nominal camera positions $(x_{cj}, y_{cj}, z_{cj})$ are chosen with consideration for viewing access through various models of MRI head coils. By convention, the nominal polar angle is taken to be $$\alpha_{cj} = \tan^{-1}\frac{\sqrt{(x_{cj} - x_0)^2 + (y_{cj} - y_0)^2}}{z_{cj} - z_0},$$

the nominal azimuth angle is taken to be $$\gamma_{cj} = \tan^{-1}\left(\frac{y_0 - y_{cj}}{x_0 - x_{cj}}\right),$$

(using the usual convention for the arctangent function, for which the angle falls in the first quadrant, or 0 to 90 degrees, if both numerator and denominator are positive, in the second quadrant if the numerator is positive and denominator negative, and so on), and the nominal twist angle (relative to the reference orientation described in boxed text above) is taken to be $\omega_{cj} = 0$.

Tracking System Calibration Algorithm

In some embodiments, a calibration algorithm starts by determining the point on the $z = z_c$ plane which projects to the center of the focal plane. This point is unaffected by camera twist, but depends on all other camera variables as follows:

$$x_{0,j} = x_{cj} + \frac{(z_{cj} - z_0)\cos\gamma_{cj}}{\tan\alpha_{cj}};$$

$$y_{0,j} = y_{cj} + \frac{(z_{cj} - z_0)\sin\gamma_{cj}}{\tan\alpha_{cj}}$$

3B

The point $(x_{0,j}, y_{0,j}, z_0)$ becomes the apparent coordinate origin for camera j, but the laboratory coordinates $(x_0, y_0, z_0)$ of the target center in its home position on the calibration station are fixed, by definition, at this absolute point in space. At the home position, or at any other setting for the six translation/rotation degrees of freedom, the location of the target centroids can be calculated precisely in laboratory coordinates, with the assumption of no positional error due to the confirmed accuracy of the calibration station.

Defining several vectors which are used in determining the location on the camera focal planes $(X_t, Y_t)$ of the image projection from an arbitrary reference target centroid point $(x_t, y_t, z_t)$ in laboratory coordinates:

The vector from the apparent origin of coordinates for either camera to the camera itself is:

$$\vec{R}_{0,cj} = (x_{cj} - x_{0,cj})\hat{e}_x + (y_{cj} - y_{0,cj})\hat{e}_y + (z_{cj} - z_0)\hat{e}_z$$

The vector between the apparent origin and the true target position is:

$$\vec{R}_{t,cj} = (x_t - x_{0,cj})\hat{e}_x + (y_t - y_{0,cj})\hat{e}_y + (z_t - z_0)\hat{e}_z \quad 4B$$

Figure 45:
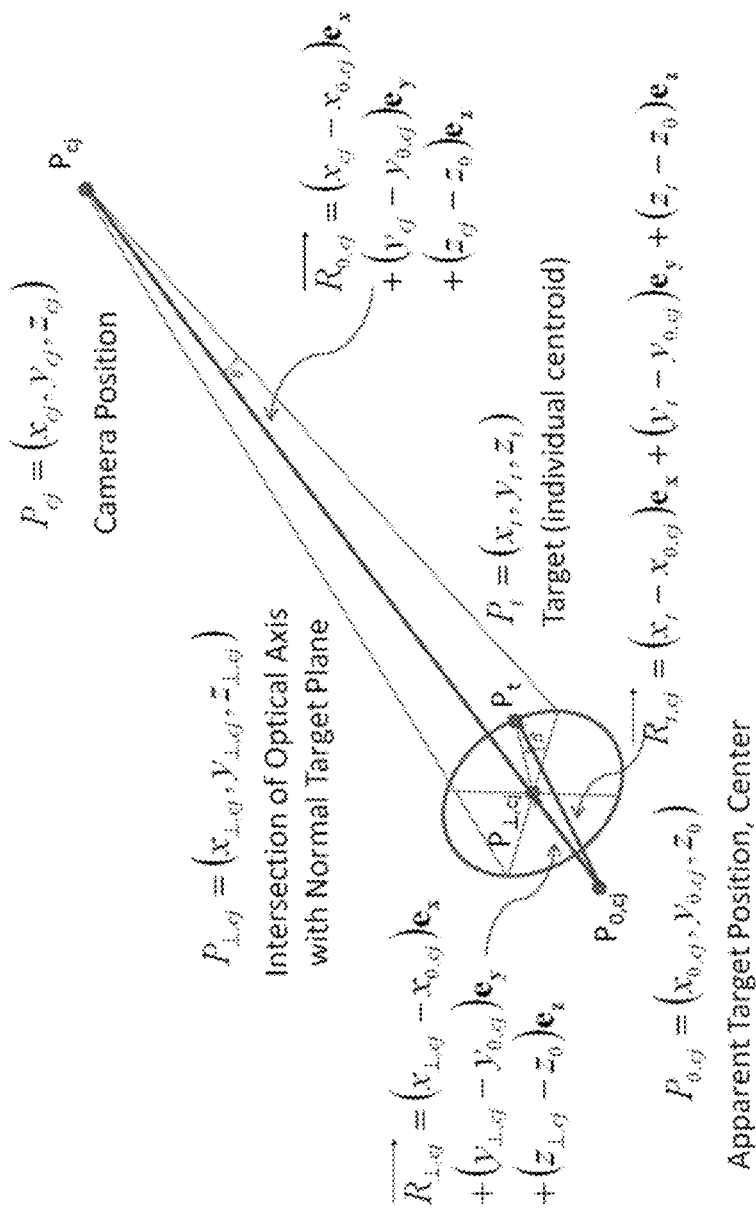
FIG. 45 illustrates a vector between the apparent origin and the point of intersection of the camera optical axis with the perpendicular plane that contains the target point.

FIG. 45 illustrates a vector between the apparent origin and the point of intersection of the camera optical axis with the perpendicular plane that contains the target point.

The vector between the apparent origin and the point of intersection of the camera optical axis with the perpendicular plane that contains the target point (see figure above) is:

$$\vec{R}_{\perp,cj} = \frac{|\vec{R}_{t,cj} \cdot \vec{R}_{0,cj}|}{|\vec{R}_{0,cj}|^2}\vec{R}_{0,cj} = \kappa[(x_{cj} - x_{0,cj})\hat{e}_x + (y_{cj} - y_{0,cj})\hat{e}_y + (z_{cj} - z_0)\hat{e}_z]$$

where $$\kappa_{cj} = \frac{(x_{cj} - x_{0,cj})(x_t - x_{0,cj}) + (y_{cj} - y_{0,cj})(y_t - y_{0,cj}) + (z_{cj} - z_0)(z_t - z_0)}{(x_{cj} - x_{0,cj})^2 + (y_{cj} - y_{0,cj})^2 + (z_{cj} - z_0)^2}$$

so that $$x_{\perp,cj} = x_{0,cj} + \kappa_{cj}(x_{cj} - x_{0,cj}); \quad y_{\perp,cj} = y_{0,cj} + \kappa_{cj}(y_{cj} - y_{0,cj});$$

$$z_{\perp,cj} = z_0 + \kappa_{cj}(z_{cj} - z_0).$$

The unit vector running from the optical axis intercept to the target centroid in the perpendicular plane is $$\hat{r}_{\perp,cj} = \frac{(x_t - x_{\perp,cj})\hat{e}_x + (y_t - y_{\perp,cj})\hat{e}_y + (z_t - z_{\perp,cj})\hat{e}_z}{\sqrt{(x_t - x_{\perp,cj})^2 + (y_t - y_{\perp,cj})^2 + (z_t - z_{\perp,cj})^2}}$$

Simple trigonometry from the figure above shows that the polar angle between the camera's optical axis and the true target point is:

$$\theta_{t,cj} = \sin^{-1}\left(\frac{\sqrt{(x_t - x_{\perp,cj})^2 + (y_t - y_{\perp,cj})^2 + (z_t - z_{\perp,cj})^2}}{\sqrt{(x_{cj} - x_t)^2 + (y_{cj} - y_t)^2 + (z_{cj} - z_t)^2}}\right)$$

The azimuth angle of the target point relative to the focal plane vertical axis is determined by projection. In any plane perpendicular to the optical axis, the focal plane principal axis ($\hat{X}$ and $\hat{Y}$) unit vectors are given by equations (2) and (1) respectively; in the absence of camera twist, the focal plane azimuth angle β is determined through the dot product of the $r_\perp$ vector with the projected vertical focal plane ($\hat{Y}$) vector. Adding the camera twist (minus sign by convention and definition only), $$\beta_{t,cj} = \pm\cos^{-1}\left(\frac{(x_t - x_{\perp,cj})(y_{0,cj} - y_{cj}) - (y_t - y_{\perp,cj})(x_{0,cj} - x_{cj})}{\sqrt{(x_t - x_{\perp,cj})^2 + (y_t - y_{\perp,cj})^2 + (z_t - z_{\perp,cj})^2}\sqrt{(x_{0,cj} - x_{cj})^2 + (y_{0,cj} - y_{cj})^2}}\right) - \omega_{cj} \quad \text{(left side)}$$

$$\beta_{t,cj} = \pm\cos^{-1}\left(-\frac{(x_t - x_{\perp,cj})(y_{0,cj} - y_{cj}) - (y_t - y_{\perp,cj})(x_{0,cj} - x_{cj})}{\sqrt{(x_t - x_{\perp,cj})^2 + (y_t - y_{\perp,cj})^2 + (z_t - z_{\perp,cj})^2}\sqrt{(x_{0,cj} - x_{cj})^2 + (y_{0,cj} - y_{cj})^2}}\right) - \omega_{cj} \quad \text{(right side)}$$

The arc-cos function is assumed to be bounded at 0 and 180 degrees, and the appropriate sign multiplier for the azimuth angle is given by the sign of the projection (dot product) of the target perpendicular on the focal plane horizontal axis vector, as $\text{sign}[\beta_{t,cj}] = \text{sign}(\hat{r}_{\perp,cj} \cdot \hat{X})$;

$$\text{sign}[\beta_{t,cj}] = \text{sign}[(z_{0j} - z_0)\{(x_{0,cj} - x_{cj})(x_t - x_{\perp,cj}) + (y_{0,cj} - y_{cj})(y_t - y_{\perp,cj})\} + (z_t - z_{\perp,cj})\{(x_{0,cj} - x_{cj})^2 + (y_{0,cj} - y_{cj})^2\}] \quad \text{(left side)}$$

$$\text{sign}[\beta_{t,cj}] = -\text{sign}[(z_{cj} - z_0)\{(x_{0,cj} - x_{cj})(x_t - x_{\perp,cj}) + (y_{0,cj} - y_{cj})(y_t - y_{\perp,cj})\} + (z_t - z_{\perp,cj})\{(x_{0,cj} - x_{cj})^2 + (y_{0,cj} - y_{cj})^2\}] \quad \text{(right side)}$$

The camera projections of these new target centroid positions are determined using a geometric projection calculation. The normalized pinhole camera projections are given by:

$$x_{t,cj} = \mp \tan \alpha_{t,cj} \sin \beta_{t,cj}, \quad y_{t,cj} = \pm \tan \alpha_{t,cj} \sin \beta_{t,cj}$$

Radial and tangential lens distortion effects are then applied to the normalized projections according to the following equation:

$$\begin{bmatrix} x_{t,cj\,distorted} \\ y_{t,cj\,distorted} \end{bmatrix} = (1 + ar^2 + br^4 + cr^6)\begin{bmatrix} x_{t,cj} \\ y_{t,cj} \end{bmatrix} + \begin{bmatrix} 2dx_{t,cj}y_{t,cj} + e(r^2 + 2x_{t,cj}^2) \\ d(r^2 + 2y_{t,cj}^2) 2ex_{t,cj}y_{t,cj} \end{bmatrix}$$

Where $r^2 = x^2 + y^2$, and the radial distortion coefficients, a, b, c and the tangential distortion coefficients d, e, are determined by a separate lens calibration procedure. Lastly, the distorted projection coordinates are mapped to pixel values for each camera as follows:

$$X_{t,cj} = X_0 + \left(\frac{f.l.}{s_{pix}}\right)x_{t,cj\,distorted}, \quad Y_{i,j} = Y_0 + \left(\frac{f.l.}{s_{pix}}\right)y_{t,cj\,distorted}$$

Where f.l. and are $s_{pix}$ the lens focal length and camera pixel pitch, and $X_0$ and $Y_0$ are the pixel coordinates of the center of the pixel array (i.e. for a 1280×1024 array, $X_0$=640.5 and $Y_0$=512.5, assuming the center of the upper left corner pixel is defined as having coordinates (1,1).).

Here $X_{0,cj}$ and $Y_{0,cj}$ are the horizontal and vertical number of the central pixel column and row of camera j (assumed to intersect the optical axis of that camera), and f.l.$_{cj}$ and $s_{pix}$ are the camera j lens focal length and pixel pitch.

Tracking System Calibration Routine

After assembly and rough system alignment, a calibration routine is run to determine residual errors in camera orientations ($\hat{o}x_{cj}, \hat{o}y_{cj}, \hat{o}z_{cj}, \hat{o}\alpha_{cj}, \hat{o}\gamma_{cj}, \hat{o}\omega_{cj}$).

A small error displacement $\hat{o}x_{cj}$ of a camera in the x-direction or a small error rotation $\hat{o}\gamma_{cj}$ of the camera optical axis about the laboratory "z" axis will result in the center of the reference target (i.e. home position) being imaged at a displaced position relative to the vertical center of the focal plane. Likewise, small error displacements $\hat{o}y_{cj}$ and/or $\hat{o}z_{cj}$ of camera position in the y- and/or z-directions will result in the center of the reference target being imaged at a position displaced relative to the horizontal center of the focal plane. By viewing multiple target features simultaneously, (e.g. the individual centroids of the reference target), image displacements corresponding to errors in camera position or orientation along six degrees of freedom can be distinguished using a similar method to that used for in the Head Tracker 6DOF extraction algorithm.

The self-calibration algorithm considers the effects of small errors in each of the camera orientation parameters on the projected centroid positions seen by each camera. The reference target center defines the origin of the camera coordinate system and its orientation defines the coordinate system axes. This becomes the basis of measurement for camera position/orientation errors. The reference target itself is assumed to provide truth data relative to size scale. Thus, by definition, the true positions of the reference target centroids are known in laboratory coordinates, and by extension, the expected locations on the camera focal planes for projections of these points are also known.

Comparison of the measured pixel positions ($X_{t,cj}, tY_{t,cj}$) of the each of the imaged centroids on each camera, with the expected projections gives 2N equations for the six unknown orientation errors ($\hat{o}x_{cj}, \hat{o}y_{cj}, \hat{o}z_{cj}, \hat{o}\alpha_{cj}, \hat{o}\gamma_{cj}, \hat{o}\omega_{cj}$) for each camera, where N is the number of unique centroids in the reference target pattern. Like the run-time head tracker software, the calibration algorithm is based on computing the local derivatives of the ($X_{t,cj}, Y_{t,cj}$) centroid projections with respect to each error axis, and then performing a matrix inversion to determine the errors themselves. The calculation is performed iteratively until convergence to within an acceptable tolerance is achieved.

The procedure outlined above only requires the end user to place and orient the reference target once and then start the calibration routine, after which all calculations are performed without additional user interaction. The resulting coordinates for all cameras are then stored in the system. Camera position calibrations need only be performed periodically or when changes to camera positions are suspected.

Additional Features

Adapting to Addition/Removal of Cameras (e.g., Camera Viewpaths being Unblocked/Blocked)

In some embodiments there may be a plurality of cameras. However, in certain situations one or more cameras in the plurality of cameras may stop working or have their viewpath obscured, or otherwise be incapable of detecting an image of a marker. It may be helpful for the system to utilize a generalized six-degree-of-freedom algorithm, as disclosed herein, that allows the system to continue performing when a camera goes down (e.g., by having its viewpath obscured).

The same method or process may also enable the seamless addition of cameras (e.g., when a viewpath becomes unobstructed) into the motion tracking compensation system. Thus, desirably the motion tracking is not disturbed when a camera goes down, and it is also not disturbed when the camera comes back online.

Figure 41:
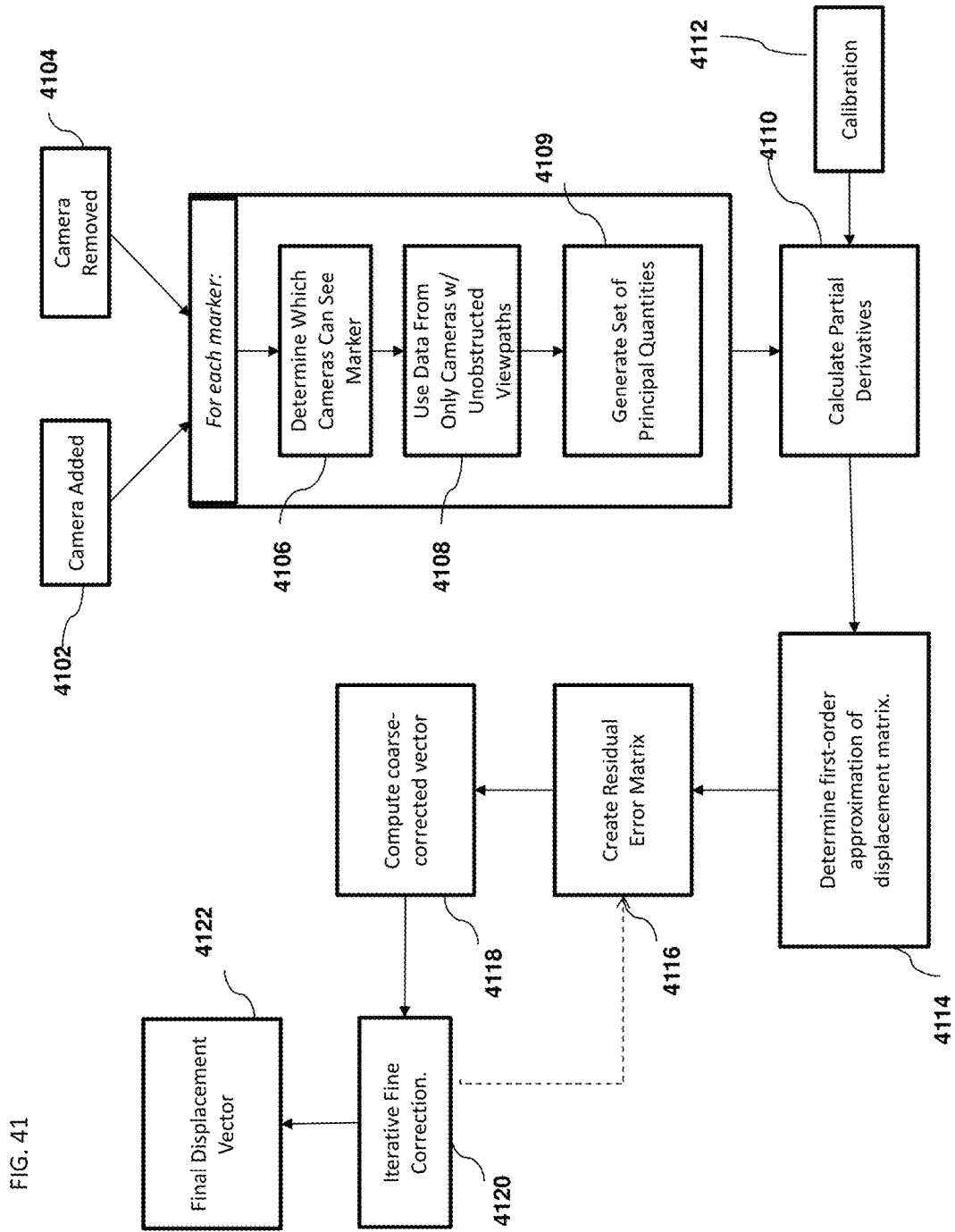
FIG. 41 is a flow chart that illustrates how the system may adapt to the addition or removal of cameras.

FIG. 41 is a flow chart that illustrates an example embodiment of how the system may adapt to the addition or removal of cameras/markers (e.g. a view path becoming unobstructed or obstructed) using the generalized six-degrees-of-freedom algorithm. As used herein, the terms adding or removing a camera may refer to a camera's view path to a marker becoming unobstructed or obstructed, respectively. These terms may also refer to a camera being activated or deactivated, physically added or removed from the system, and/or the like. At block 4102, an additional camera may be added to the system. Alternatively, at block 4104 a camera may be removed from the system. The removal may be intentional, such as if a camera is malfunctioning, or the removal may be a result of an accident or patient motion, such as if the patient raises his or her arm in front of one of the cameras, rotates his or her head, and/or the like, resulting in a blocked viewpath of that camera. Regardless of what happened, for each marker the system at block 4106 determines which remaining cameras can see that marker. At block 4108, the system then uses image data only from cameras with an unobstructed viewpath with a given marker, which was determined at block 4106.

Then, at block 4109 the system generates a set of principal quantities. The system calculates the set of principal quantities by calculating both the sum and difference of the X (column) and Y (row) coordinates between each target image and every other target image across all cameras. Thus, a set of principal quantities may be constructed for each marker based on all available image data.

The system at block 4110 numerically evaluates the partial derivatives relative to subject displacements and rotations of the principal quantities. More specifically, local partial derivatives of each of the principal quantities, with respect to each of the six degrees of freedom, are determined numerically by evaluating changes in the principal quantities for small increments in each degree of freedom. The system at block 4112 may perform a calibration procedure, and that calibration may be used to help numerically evaluate the partial derivatives of the principal quantities about the initialized target position. In some embodiments, the calibration procedure is only performed once, or only periodically. The calibration procedure does not have to be performed every time a patient is tracked. The system obtains a partial derivative matrix at the end of block 4110.

At block 4114, the system may then determine a first-order approximation of the displacement matrix by multiplying the matrix of measured principal quantities, obtained following block 4109, with the inverse of the partial derivative matrix obtained at the end of block 4110.

At block 4116, the system may then generate a residual error matrix. The residual error matrix may be obtained from taking the first-order approximations, entering them into a translation equation to determine the corresponding translated 3-D target position for each of the target positions, obtaining 3-D world coordinates that are projected to camera coordinates, and re-calculating the principal quantities. These principal quantities may be compared against the measured values of the principal quantities which were obtained after block 4109, and the differences would reside in the residual error matrix. A local partial derivative matrix can then be obtained, with respect to each of the six degrees of freedom, by calculating the effect of small increments in each of the six degrees of freedom relative to the first-order displacement vector. For each increment, the new world coordinates and the new camera projections of the target positions are re-computed and the principal quantities are re-calculated. The change in each principal quantity is divided by the small angular or displacement increment to determine a local partial derivative. Repeating this for each of the six degrees of freedom yields the six-column local partial derivative matrix, as each repetition produces one column.

At block 4118, the system may then compute a coarse correction to improve the first-order displacement vector and reduce residual error, by multiplying the residual error matrix from block 4116 with the inverse of the local partial derivative matrix from block 4116. The system may then increment the first-order displacement vector by the coarse correction matrix to create a better approximation of the displacement vector.

At block 4120, the system may then perform an interative fine correction. The system continue looping back to block 4116 to determine a fine correction to the displacement vector. With each iteration, the resultant fine correction increments are added to the coarse-corrected vector to create the new displacement vector. The steps are repeated iteratively until the magnitude of each of the fine corrections is less than some threshold, or a number of pre-defined iterations have been performed. Afterwards, at block 4122 the system arrives at a final displacement vector, which may be associated with the position of the marker.

Additional Process Flow

If a patient is sitting still, or moving very slowly, noise in the tracking data may cause uncertainty or noise in the image correction, making it possible for the image correction to do more harm than good. It may be insufficient to simply turn off the image correction and keep the patient centered on the origin, since a patient may turn his head during the procedure and end up falling asleep in a position with a large offset. Thus, it may be helpful to perform an image correction that may be able to filter out any noise if there is very little motion in the patient.

In some embodiments, prior to reporting the Six-Degree-of-Freedom marker position data (e.g., prior to sending tracking data to a controller of the scanner for compensation for motion), a noise filter or output filter may be applied to smooth the fluctuations in coordinate values when there is little to no active motion.

In some embodiments, this filter comprises an application of an adaptive Kalman filter. The Kalman filter may use a constant velocity kinematic model, in which the process noise (that represents the uncertainty of the model) is in the form of an unknown acceleration. The magnitude of the process noise may control the relative weighting of the model vs. the measured data in the filter output.

In some embodiments, the new, measured data may be compared to the average of the last 10 data points and a scale factor dependent on this difference may be applied to the process noise input of the Kalman filter. This may cause the model to be strongly preferred when the new data falls within 3σ of the recent average (of the last 10 data points), and continuously shifts preference toward the data as the difference increases beyond this range. Thus, if there is a large process noise, the filter will strongly weight the new data coming in and will hardly do any filtering at all of this data. If there is very little process noise, the filter may prefer the model over the data and perform a very strong smoothing or averaging of the data. Thus, the resulting filter strongly smooths the data when there is little to no motion by the patient, yet responds instantly to large changes in position without overshoot or lag. If the patient performs a large, instantaneous motion, the filter adapts right away and will go with the new data coming in that is associated with that large motion.

Figure 42:
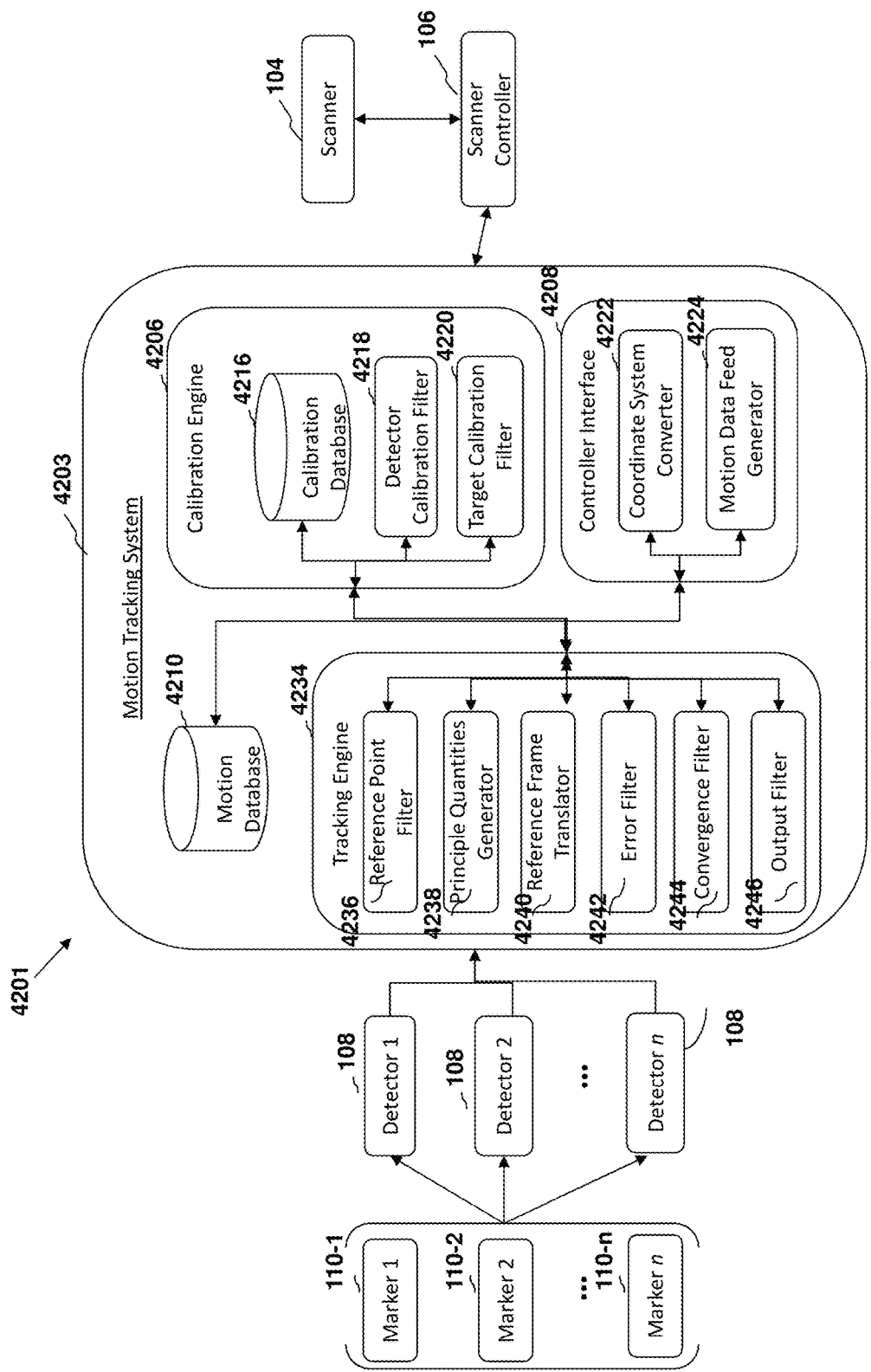
FIG. 42 is a block diagram depicting an embodiment of a motion compensation system.

FIG. 42 is a block diagram depicting another embodiment of a motion compensation system 4201. The embodiment in FIG. 42 is similar to the embodiment of the motion compensation system 300 illustrated in FIG. 3B.

Motion compensation system 4201 also utilizes one or more detectors 108. However, motion compensation 4201 is configured to use a six-degree-of-freedom algorithm that has been generalized so that motion compensation system 4201 may use any number, from 1 to n, of detectors 108. These detectors 108 may be configured to be used with any number of markers. The figure shows marker 1 (110-1), marker 2 (110-2), all the way up to marker n (110-n). These markers may have slight variations in them that allow the markers to be uniquely identifiable from one another. Each marker may at different times be imaged by zero, one, two, more than two, or all the detectors 108.

Calibration engine 4206 may comprise a calibration database 4216, a detector calibration filter 4218, and a target calibration filter 4220. In some embodiments, calibration engine 4206 may be configured to calibrate the system at the initial startup of the system. In other embodiments, calibration engine 4206 may be used for at least some calibration procedures during some or all motion tracking procedures. The detector calibration filter 4218 may be configured to calibrate the detectors 108 to the motion compensation system. In some embodiments, detector calibration filter 4218 may be configured to allow a manufacturer or assembler of a motion compensation system to input information specific to each detector 108, such as values associated with barrel distortion for the detector 108. In some embodiments, target calibration filter 4220 may be configured to calibrate the system to one or more specific targets or markers, such as a grid of nine markers having the embodiment shown in FIG. 34. This information may be stored in calibration database 4216, and may help speed up a tracking routine.

Tracking engine 4234 may comprise a reference point filter 4236, a principal quantities generator 4238, a reference frame translator 4240, an error filter 4242, a convergence filter 4244, and an output filter 4246. The components of the tracking engine 4234 may be configured to operate similarly to the process flow described in association with FIG. 7C and FIG. 41. However, there may be some slight variation.

For example, the reference point filter 4236 may be configured to analyze determine the locations of, and identify, the reference points in each marker. This information may be used to determine if any detectors 108 are not detecting or imaging a certain marker, and then exclude the image data from that detector from calculation. Principal quantitates generator 4238 may be configured to determine a set of principal quantities, which are obtained by calculating both the sum and difference of the X (column) and Y (row) coordinates between each target image and every other target image across all cameras. The principal quantities may be constructed for each marker based on all available image data.

The reference frame translator 340 may be configured to convert between the two dimensional reference frame of each detector 108 and the three dimensional frame of the motion tracking system 4203. The error filter 4242 may be configured to analyze differences in principal quantities based on the visualized reference points and based on estimates of an object's pose to determine an amount of error between the two. The convergence filter 4244 may be configured to perform an iterative process to reduce an amount of error in an object pose estimate until an object pose estimate has an acceptable amount of error.

Output filter 4246 may be the adaptive Kalman filter that was previously discussed. Output filter 4246 may be configured to detect when a patient is not moving or exhibiting little movement, and then perform a strong smoothing or averaging of the data in order to reduce the impact of noise. Output filter 4246 may also be configured to detect when a patient is making large movements, and respond the large movements without overshoot or lag. At block 4222, the coordinate system converter may remap the coordinate system to the same axes as the MR coordinate system, and convert to a quaternion representation of the angles.

Variations

Specific embodiments have been described in detail above with emphasis on medical application and in particular MRI examination of a patient's head. However, the teachings of the present invention can be utilized for other MRI examinations of other body parts where movements of up to six degrees of freedom are possible. In addition medical procedures involving imaging devices other than MRI equipment (e.g., CT, PET, ultrasound, plain radiography, and others) may benefit from the teaching of the present invention. The teachings of the present invention may be useful in many non-medical applications where tracking of a target having several degrees of freedom are possible. Some of these applications could be military applications. Furthermore, while particular algorithms are disclosed, variations, combinations, and subcombinations are also possible.

Computing System

Figure 21:
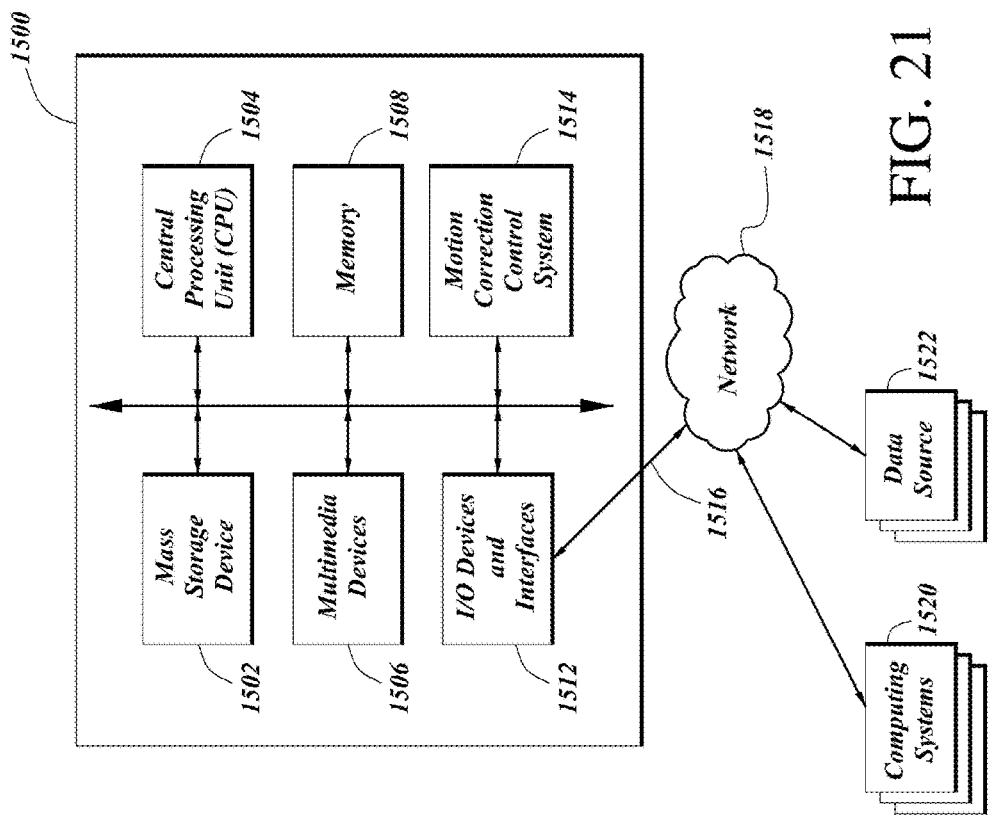
FIG. 21 is a block diagram depicting an embodiment of a computer system configured to implement one or more embodiments of the methods, devices, and systems described herein.

In some embodiments, the computer clients and/or servers described above take the form of a computing system 1500 illustrated in FIG. 21, which is a block diagram of one embodiment of a computing system that is in communication with one or more computing systems 1520 and/or one or more data sources 1522 via one or more networks 1518. The computing system 1500 may be used to implement one or more of the systems and methods described herein. In addition, in one embodiment, the computing system 1500 may be configured to apply one or more of the methods and systems described herein. While FIG. 21 illustrates an embodiment of a computing system 1500, it is recognized that the functionality provided for in the components and modules of computing system 1500 may be combined into fewer components and modules or further separated into additional components and modules.

Motion Correction Control Systems

In an embodiment, the system 700 comprises a motion correction control system module 1514 that carries out the functions described herein with reference to motion correction mechanism, including any one of the motion correction methods described above. The motion correction control system module 1514 may be executed on the computing system 1500 by a central processing unit 1504 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++ or Objective C. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

In an embodiment, the computing system 1500 also comprises a workstation or other computing devices suitable for controlling and/or communicating with large databases, performing transaction processing, and generating reports from large databases. The computing system 1500 also comprises a central processing unit ("CPU") 1504, which may comprise a conventional microprocessor. The computing system 1500 further comprises a memory 1508, such as random access memory ("RAM") for temporary storage of information and/or a read only memory ("ROM") for permanent storage of information, and a mass storage device 1502, such as a hard drive, diskette, or optical media storage device. Typically, the modules of the computing system 1500 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 1500 comprises one or more commonly available input/output (I/O) devices and interfaces 1512, such as a keyboard, mouse, touchpad, and printer. In one embodiment, the I/O devices and interfaces 1512 comprise one or more display devices, such as a monitor, that allows the visual presentation of data to a user. More particularly, a display device provides for the presentation of GUIs, application software data, and multimedia presentations, for example. In the embodiment of FIG. 21, the I/O devices and interfaces 1512 also provide a communications interface to various external devices. The computing system 1500 may also comprise one or more multimedia devices 1506, such as speakers, video cards, graphics accelerators, and microphones, for example.

Computing System Device/Operating System

The computing system 1500 may run on a variety of computing devices, such as, for example, a mobile device or a server or a desktop or a workstation, a Windows server, an Structure Query Language server, a Unix server, a personal computer, a mainframe computer, a laptop computer, a cell phone, a personal digital assistant, a kiosk, an audio player, a smartphone, a tablet computing device, and so forth. The computing system 1500 is generally controlled and coordinated by operating system software, such as iOS, z/OS, Windows 95, Windows 98, Windows NT, Windows 2000, Windows XP, Windows Vista, Windows 7, Linux, BSD, SunOS, Solaris, or other compatible operating systems. In Macintosh systems, the operating system may be any available operating system, such as MAC OS X. In other embodiments, the computing system 1500 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 21, the computing system 1500 is coupled to a network 1518, such as a LAN, WAN, or the Internet, for example, via a wired, wireless, or combination of wired and wireless, communication link 1516. The network 1518 communicates with various computing devices and/or other electronic devices via wired or wireless communication links. In the embodiment of FIG. 21, the network 1518 is communicating with one or more computing systems 1520 and/or one or more data sources 1522.

Access to the motion correction control system module 1514 of the computer system 1500 by computing systems 1520 and/or by data sources 1522 may be through a web-enabled user access point such as the computing systems' 1520 or data source's 1522 personal computer, cellular phone, laptop, or other device capable of connecting to the network 1518. Such a device may have a browser module is implemented as a module that uses text, graphics, audio, video, and other media to present data and to allow interaction with data via the network 1518.

The browser module may be implemented as a combination of an all points addressable display such as a cathode-ray tube (CRT), a liquid crystal display (LCD), a plasma display, touch screen display or other types and/or combinations of displays. In addition, the browser module may be implemented to communicate with input devices 1512 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1500 may comprise a physical or logical connection established between a remote microprocessor and a mainframe host computer for the express purpose of uploading, downloading, or viewing interactive data and databases online in real time. The remote microprocessor may be operated by an entity operating the computer system 1500, including the client server systems or the main server system, an/or may be operated by one or more of the data sources 1522 and/or one or more of the computing systems. In some embodiments, terminal emulation software may be used on the microprocessor for participating in the micro-mainframe link.

In some embodiments, computing systems 1520 that are internal to an entity operating the computer system 1500 may access the motion correction control system module 1514 internally as an application or process run by the CPU 1504.

User Access Point

In an embodiment, the computing system 1500 comprises a computing system, a smartphone, a tablet computing device, a mobile device, a personal computer, a laptop computer, a portable computing device, a server, a computer workstation, a local area network of individual computers, an interactive kiosk, a personal digital assistant, an interactive wireless communications device, a handheld computer, an embedded computing device, or the like.

Other Systems

In addition to the systems that are illustrated in FIG. 21, the network 1518 may communicate with other data sources or other computing devices. The computing system 1500 may also comprise one or more internal and/or external data sources. In some embodiments, one or more of the data repositories and the data sources may be implemented using a relational database, such as DB2, Sybase, Oracle, Code-Base and Microsoft® SQL Server as well as other types of databases such as, for example, a signal database, object-oriented database, and/or a record-based database.

Figure 23:
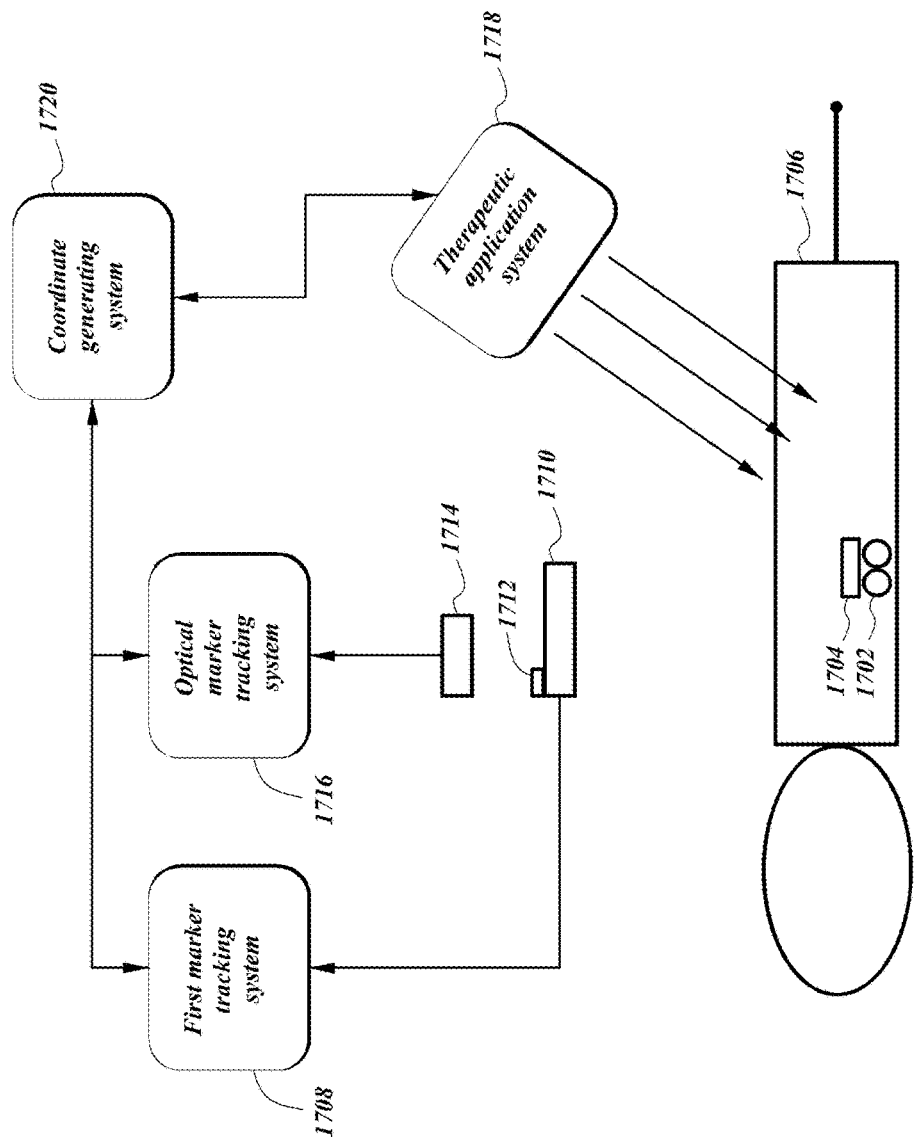
FIG. 23 is an embodiment of a schematic diagram illustrating a therapeutic applications connected to one or more marker tracking systems.

FIG. 23 is an embodiment of a schematic diagram illustrating a therapeutic application system 1718 that is connected to one or more tracking systems. In an embodiment, a patient 1706 is receiving a therapeutic therapy to treat a condition. For example, the therapeutic therapy can be radiation therapy, proton therapy, or other therapies. The therapeutic therapy can be generated from a therapeutic application system 1718. For example, the therapeutic applications systems 1718 can comprise a radiotherapy technology configured to generate a radiation beam that is transmitted to a diseased tissue 1704. In an embodiment, the system comprises fiducial markers or other markers 1702. In an embodiment, the fiducial markers or other markers 1702 are placed inside the patient 1706. The fiducial markers or other markers 1702 are configured to be detected by an electronics package 1710. The fiducial markers or other markers 1702 can be configured to identify the location of the diseased tissue to be treated with the therapeutic therapy.

The electronics package 1710 is configured to detect the location of the fiducial marker or other marker 1702 in order to determine the location of the diseased tissue 1704. In an embodiment, the electronics package 1710 is coupled to a first marker tracking system 1708. The first marker tracking system 1708 can be configured to receive tracking data from the electronics package 1710 to determine the location of the markers 1702. By determining the locations of the markers 1702, the first marker tracking system 1708 can be configured to determine the location of the diseased tissue 1704. In an embodiment, the systems and methods disclosed herein for tracking markers with 0.1 mm and 0.1 degree accuracies can be implemented or employed by the first marker tracking system 1708. In an embodiment, the electronics package 1710 comprises an optical marker 1712. The optical marker 1712 is configured to be detected by an optical scanner 1714, for example, a CCD camera. In an embodiment, the optical scanner 1714 is coupled to an optical marker tracking system 1716.

The optical marker tracking system 1716 can be configured to determine the location of the electronics package 1710 relative to the therapeutic application system 1718. In an embodiment, the systems and methods disclosed herein for tracking markers with 0.1 mm and 0.1 degree accuracies can be implemented or employed by the optical marker tracking system 1716. In an embodiment, the system can comprise a coordinate generating system 1720 that is configured to receive tracking data from the first marker tracking system 1708 and the optical marker tracking system 1716. The coordinate generating system 1720 can be configured to analyze the tracking data in order to generate coordinate data that can be used to identify the location of the diseased tissue 1704. In an embodiment, the coordinate generating system 1720 can be configured to transmit the coordinate data to the therapeutic application system 1718.

The therapeutic application system 1718 can be configured to generate a therapeutic beam based on the coordinate data. For example, the therapeutic application system 1718 can be configured to direct a radiation beam to a particular location in the patient 1706 based on the coordinate data. Further, the therapeutic application system 1718 can also be configured, for example, to generate a particular radiation beam shape based on the coordinate data. Any patient movement can be detected by the electronics package 1710 and the optical scanner 1714. The first marker tracking system 1708 and the optical marker tracking system 1716 can be configured to generate new tracking data to be inputted into the coordinate generating system 1720. The coordinate generating system 1720 can be configured to generate new coordinate data for transmission into the therapeutic application system 1718. The therapeutic application system 1718 can be configured to analyze the new coordinate data in order to redirect and/or reshape the therapeutic beam to be applied to the diseased tissue 1704 of the patient 1706.

Figure 25:
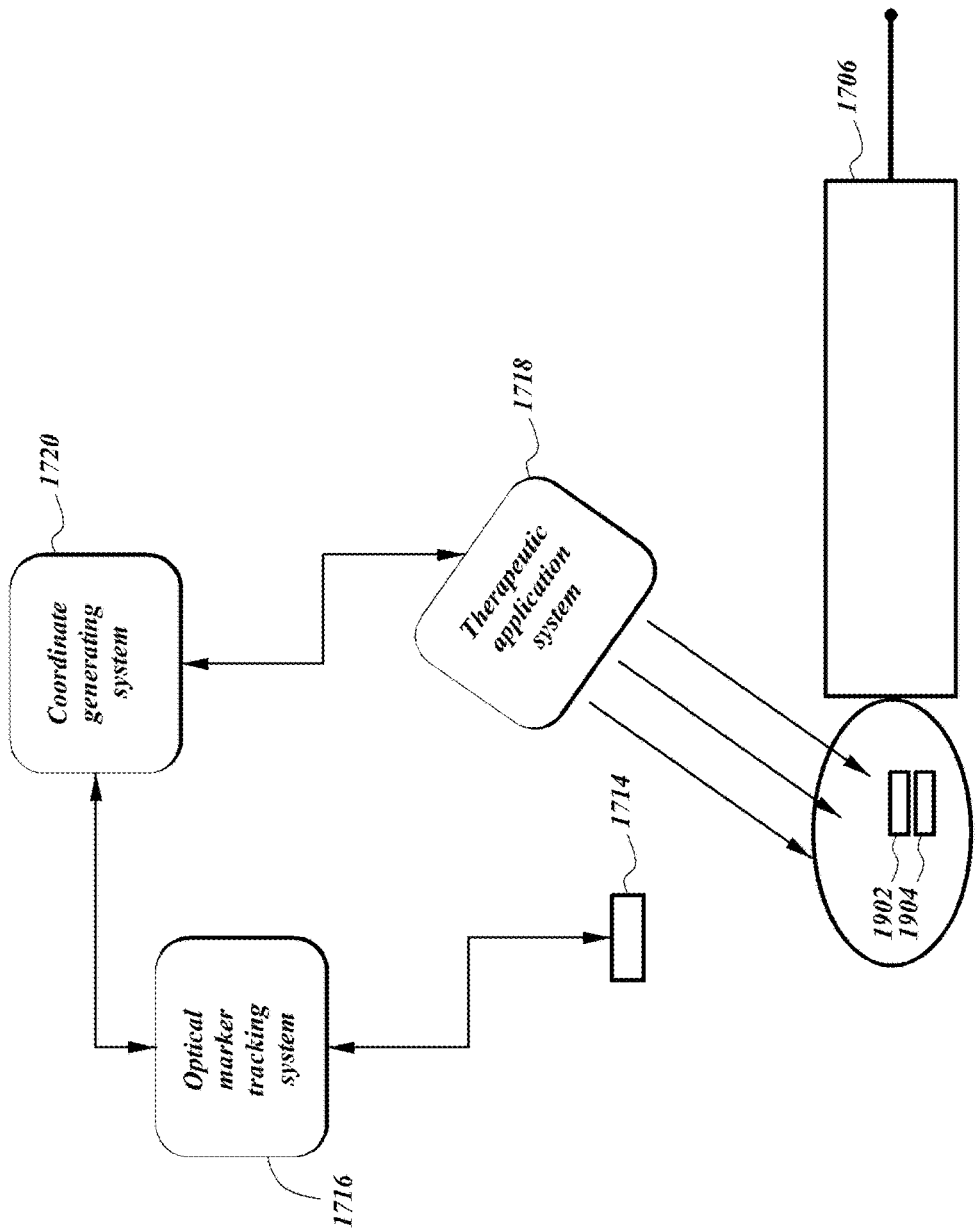
FIG. 25 is an embodiment of a schematic diagram illustrating a therapeutic applications connected to a marker tracking system.

Similar to FIG. 23, in an embodiment, the system can comprise one motion tracking system as illustrated in FIG. 25. The single motion tracking system 1716, configured to employ the techniques disclosed herein, can track marker 1902 to generate coordinate data for transmission to a therapeutic application system 1718 in order to direct a therapeutic therapy to the target tissue site 1904.

Figure 24:
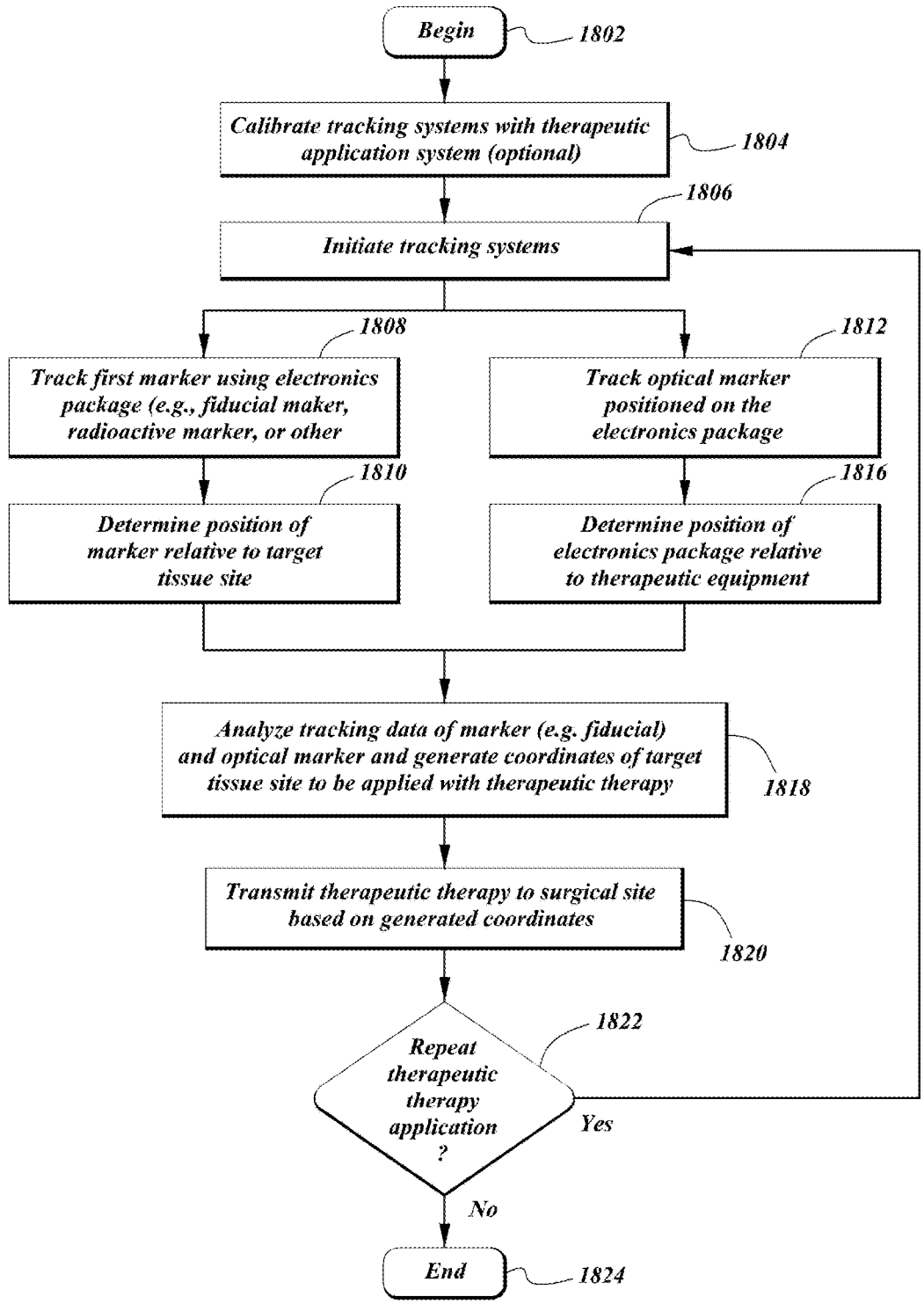
FIG. 24 is a flowchart depicting an embodiment of a process for controlling the application of a therapeutic therapy based on coordinate data generated from one or more tracking systems.

FIG. 24 is a flowchart depicting an embodiment of a process for applying a therapeutic therapy based on tracking patient movement. The process can begin at block 1802 by optionally calibrating tracking systems with the therapeutic application system at block 1804. At block 1806, the system can be configured to initiate the tracking systems. For example, the system can be configured to initiate the electronics package tracking system and the optical marker tracking system. At block 1808, the system can be configured to track the first marker using the electronics package. For example, the electronics package can be configured to track the fiducial marker that is implanted in the patient. In an embodiment, at block 1810, the system can be configured to determine the position of the marker relative to the target tissue site.

At block 1818, the system can be configured to track the optical marker position in order to determine the location of the electronics package. At block 1816, the system can be configured to determine the position of the electronics package relative to the therapeutic equipment. At block 1818, the system can be configured to analyze the tracking data of the first marker and the optical marker, and generate coordinates of the target tissue site. The coordinates of the target tissue site can be transmitted to the therapeutic therapy equipment at block 1820. The therapeutic therapy equipment can be configured to utilize the coordinate data to transmit the therapeutic therapy to the surgical site at block 1820. At decision block 1822, the system can be configured to repeat the application of the therapeutic therapy. If the therapeutic therapy application should be repeated, the system can be configured to loop back to block 1806 to initiate the tracking systems. If the therapeutic therapy application should not be repeated, the system can be configured to end the process at block 1824.

Figure 26:
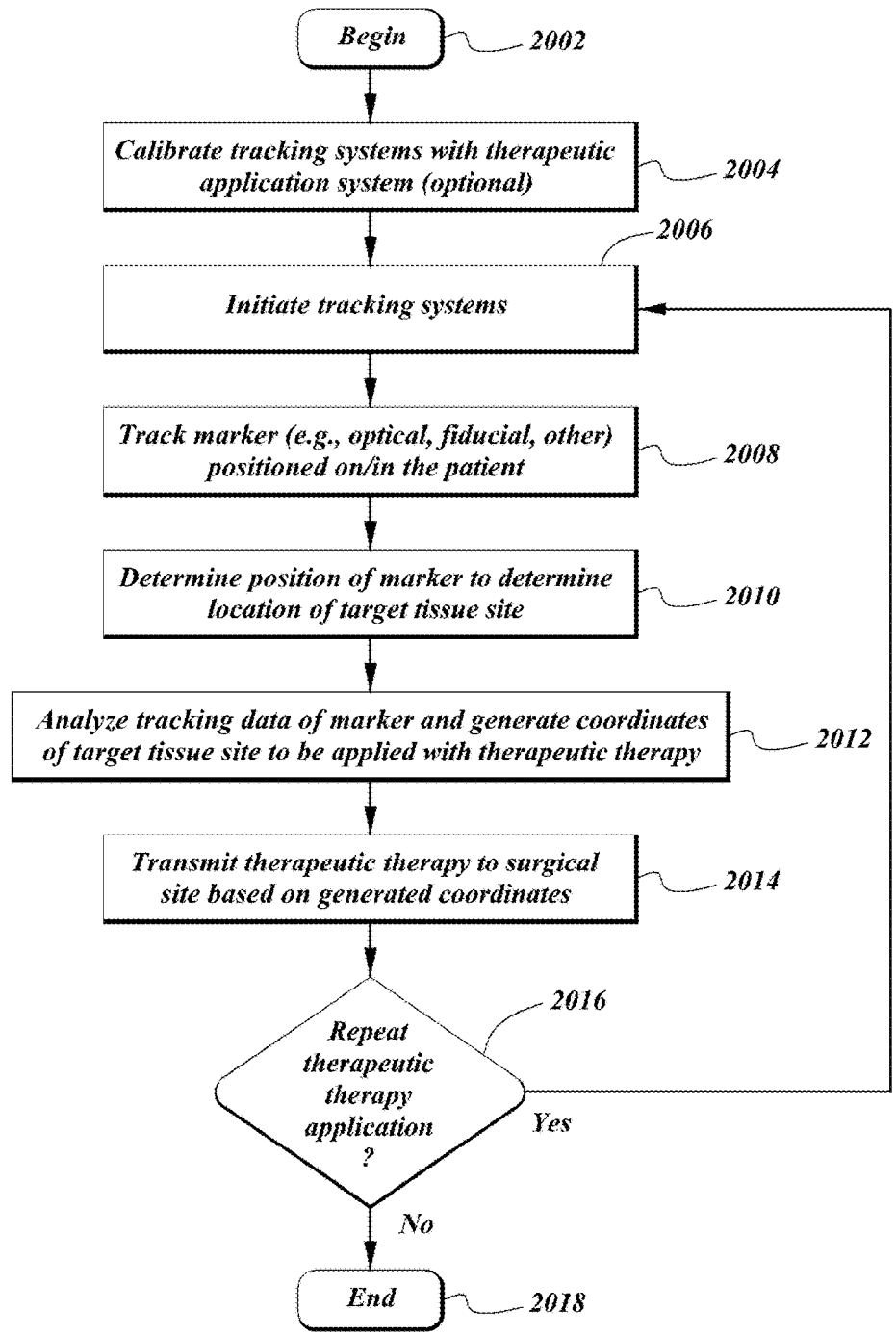
FIG. 26 a flowchart depicting an embodiment of a process for controlling the application of a therapeutic therapy based on coordinate data generated from a tracking system.

Similar to FIG. 24, in an embodiment, the system can be configured to employ an alternative method as illustrated in FIG. 26 wherein a single camera is used to track a marker in order to generate coordinate data for use by the therapeutic application system.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

What is claimed is:

1. A motion tracking system for tracking and compensating for motion of a patient during a medical imaging scan, the motion tracking system comprising:
   an optical marker configured to be attached to the patient, wherein the optical marker comprises a plurality of optically visible landmarks, the plurality of optically visible landmarks defining a plurality of reference points;
   a plurality of optical detectors, wherein each of the plurality of optical detectors is positioned to view the optical marker along a different line of sight;
   one or more computer readable storage devices configured to store a plurality of computer executable instructions; and
   one or more hardware computer processors in communication with the one or more computer readable storage devices and configured to execute the plurality of computer executable instructions in order cause the motion tracking system to:
      receive a digital image from each of the plurality of optical detectors, wherein each digital image represents a view along a different line of sight;
      determine, for each digital image, whether the digital image includes a view of the optical marker;
      determine, for each digital image that includes a view of the optical marker, positions of the plurality of reference points in the digital image;
      calculate a plurality of baseline attributes related to the plurality of reference points, the plurality of baseline attributes calculated based on the determined positions of the plurality of reference points; and
      estimate iteratively a three-dimensional pose of the patient, until a measure of error is within a threshold amount, the measure of error calculated based on the plurality of baseline attributes as compared to a plurality of comparison attributes, the plurality of comparison attributes calculated by assuming the object is in an estimated pose.

2. The motion tracking system of claim 1, wherein the motion tracking system is further caused to repeatedly estimate the three-dimensional pose of the patient at a rate of at least 100 Hz.

3. The motion tracking system of claim 1, wherein the plurality of baseline attributes comprises a set of principal quantities, the set of principal quantities comprising values associated with the relationships between the positions of reference points.

4. The motion tracking system of claim 1, wherein determining whether each digital image includes a view of the optical marker comprises:
   classifying each pixel in the digital image as one of two colors;
   grouping one or more connected regions, wherein the connected regions are comprised of adjacent pixels with the some color;
   filtering out one or more connected regions based on a size threshold;
   computing the centroid of one or more connected regions; and
   grouping together one or more connected regions by their computed centroids.

5. The motion tracking system of claim 1, wherein the motion tracking system is further caused to remap a coordinate system associated with the estimated three-dimensional pose of the patient.

6. The motion tracking system of claim 4, wherein grouping one or more connected regions comprises:
   identifying connected regions with centroids occurring within one pixel of each other; and
   calculating a centroid for each group of the one or more connected regions.

7. The motion tracking system of claim 4, wherein the motion tracking system is further caused to binarize each digital image before classifying each pixel in the digital image as one of two colors.

8. The motion tracking system of claim 6, wherein calculating a centroid for each group of the one or more connected regions comprises averaging the centroid for each connected region in the group of one or more connected regions.

9. The motion tracking system of claim 1, wherein the motion tracking system is further caused to generate tracking data based on the estimated three-dimensional pose of the patient and to transmit the tracking data to a medical imaging scanner controller to enable a medical imaging scanner to dynamically adjust the medical imaging scan to compensate for patient motion.

10. The motion tracking system of claim 9, further comprising:
    the medical imaging scanner, wherein the medical imaging scanner is configured to dynamically adjust the medical imaging scan to compensate for patient motion based on the tracking data.

11. A motion tracking system for dynamic tracking of and compensation for motion of a patient during a magnetic resonance scan, the motion tracking system comprising:
    an optical marker configured to be attached to a patient being scanned, wherein the optical marker comprises an optically visible pattern comprising a plurality of reference point locators, each reference point locator configured to define a single reference point, each reference point locator comprising alternating dark and light elliptical shapes centered on the single reference point, wherein at least one of the plurality of reference point locators is larger than at least another of the plurality of reference point locators, and wherein the optically visible pattern is rotationally asymmetrical about an axis normal to a plane of the optically visible pattern;

a first camera positioned to view the optical marker along a first line of sight;

a second camera positioned to view the optical marker along a second line of sight; and a computer system configured to analyze images generated by the first and second cameras to determine changes in position of the optical marker, and to generate tracking data for use by a magnetic resonance scanner to dynamically adjust scans to compensate for the changes in position of the optical marker, wherein the computer system is configured to dynamically determine whether the first camera, the second camera, or both cameras are currently viewing the optical marker, and wherein the computer system is configured to dynamically adapt its image analysis to utilize images from all cameras that are currently viewing the optical marker.

12. The motion tracking system of claim 11, further comprising:

one or more additional cameras each positioned to view the optical marker along a different line of sight, wherein the computer system is further configured to dynamically determine which of all of the cameras are currently viewing the optical marker.

13. The motion tracking system of claim 11, further comprising:

a third camera positioned to view the optical marker along a third line of sight; and a fourth camera positioned to view the optical marker along a fourth line of sight, wherein the computer system is further configured to dynamically determine which of all of the cameras are currently viewing the optical marker.

14. The motion tracking system of claim 11, further comprising:

one or more additional optical markers configured to be attached to the patient being scanned, wherein the computer system is configured to analyze images generated by all cameras that are currently viewing at least one optical marker to determine changes in position of the optical markers, and to generate tracking data for use by the magnetic resonance scanner to dynamically adjust scans to compensate for the changes in position of the optical markers.

15. The motion tracking system of claim 11, further comprising:

the magnetic resonance scanner, wherein the magnetic resonance scanner is configured to dynamically adjust scans to compensate for the changes in position of the optical marker based on the tracking data.

* * * * *

UNITED STATES PATENT AND TRADEMARK OFFICE
CERTIFICATE OF CORRECTION

PATENT NO. : 9,734,589 B2
APPLICATION NO. : 14/806521
DATED : August 15, 2017
INVENTOR(S) : Yu et al.

It is certified that error appears in the above-identified patent and that said Letters Patent is hereby corrected as shown below:

On the Title Page

In Column 2 (item (56)) at Line 11, Under Other Publications, change ""Hybrind" to --"Hybrid--.

In Column 1 (page 7, item (56)) at Line 18, Under Other Publications, change "Breain"," to --Brain",--.

In Column 1 (page 7, item (56)) at Line 26, Under Other Publications, change "magnetric" to --magnetic--.

In Column 1 (page 7, item (56)) at Line 52, Under Other Publications, change "Continous" to --Continuous--.

In Column 2 (page 7, item (56)) at Line 24, Under Other Publications, change "Feburary" to --February--.

In Column 2 (page 7, item (56)) at Line 55, Under Other Publications, change "NeuroImage" to --NeuroImage--.

In the Drawings

Sheet 41 of 75 (FIG. 20A) at Line 4 (approx.), Change "($X_O$, $Y_O$)" to --($X_0$, $Y_0$)--.

Sheet 41 of 75 (FIG. 20A) at Line 6 (approx.), Change "$X_O$" to --$X_0$--.

Sheet 41 of 75 (FIG. 20A) at Line 7 (approx.), Change "$Y_O$" to --$Y_0$--.

Sheet 43 of 75 (FIG. 20C) at Line 21 (approx.), Change "centoids" to --centroids--.

Signed and Sealed this
Twenty-third Day of October, 2018

Andrei Iancu
*Director of the United States Patent and Trademark Office*

CERTIFICATE OF CORRECTION (continued)
U.S. Pat. No. 9,734,589 B2

In the Specification

In Column 19 at Line 62, Change "-4.5"," to --=4.5",--.

In Column 54 at Line 51, Change "(ôφ," to --(δφ,--.

In Column 54 at Line 53, After "coordinates" insert --($X_{i,j}$, $Y_{i,j}$)--.

In Column 55 at Line 64, Change "ôφ," to --δφ,--.

In Column 55 at Line 66, Change "ôφ" to --δφ--.

In Column 64 at Line 6, Change "shoulde" to --shoulder--.

In Column 71 at Lines 48-49, Change "and or" to --and/or--.

In Column 79 at Line 63, Change "(ôφ," to --(δφ,--.

In Column 80 at Line 6, Change "ôθ," to --δθ,--.

In Column 80 at Line 66, Change "ôφ," to --δφ,--.

In Column 88 at Line 8, Change "(ô$x_{cj}$,ô$y_{cj}$,ô$z_{cj}$,ô$α_{cj}$,ô$γ_{cj}$,ô$ω_{cj}$)." to --(δ$x_{cj}$,δ$y_{cj}$,δ$z_{cj}$,δ$α_{cj}$,δ$γ_{cj}$,δ$ω_{cj}$).--.

In Column 88 at Line 9, Change "ô$x_{cj}$" to --δ$x_{cj}$--.

In Column 88 at Line 14, Change "ô$y_{cj}$" to --δ$y_{cj}$--.

In Column 88 at Line 14, Change "ô$z_{cj}$" to --δ$z_{cj}$--.

In Column 88 at Line 39, Change "(ô$x_{cj}$,ô$y_{cj}$,ô$z_{cj}$,ô$α_{cj}$,ô$γ_{cj}$,ô$ω_{cj}$)" to --(δ$x_{cj}$,δ$y_{cj}$,δ$z_{cj}$,δ$α_{cj}$,δ$γ_{cj}$,δ$ω_{cj}$)--.

In Column 94 at Line 55, Change "an/or" to --and/or--.

In the Claims

In Column 97 at Line 54, In Claim 1, after "order" insert --to--.